US012643880B2

(12) United States Patent
Zbieg et al.

(10) Patent No.: US 12,643,880 B2
(45) Date of Patent: Jun. 2, 2026

(54) HETEROBIFUNCTIONAL MOLECULES AS TEAD INHIBITORS

(71) Applicant: Genentech, Inc., South San Francisco, CA (US)

(72) Inventors: Jason Robert Zbieg, Montara, CA (US); Elisia Villemure, Oakland, CA (US); Joachim Rudolph, Burlingame, CA (US); Paul Powell Beroza, Belmont, CA (US); James John Crawford, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 796 days.

(21) Appl. No.: 17/929,644

(22) Filed: Sep. 2, 2022

(65) Prior Publication Data

US 2023/0242506 A1 Aug. 3, 2023

Related U.S. Application Data

(63) Continuation of application No. PCT/US2021/020367, filed on Mar. 2, 2021.

(60) Provisional application No. 62/985,256, filed on Mar. 4, 2020.

(51) Int. Cl.
*C07D 401/14* (2006.01)
*C07D 417/14* (2006.01)

(52) U.S. Cl.
CPC ......... *C07D 401/14* (2013.01); *C07D 417/14* (2013.01)

(58) Field of Classification Search
CPC ............................ C07D 401/14; C07D 417/14
See application file for complete search history.

(56) References Cited

U.S. PATENT DOCUMENTS

| | | | | |
|---|---|---|---|---|
| 7,244,851 | B2 | 7/2007 | Cohen et al. | |
| 9,694,084 | B2 | 7/2017 | Bradner et al. | |
| 2014/0356322 | A1 | 12/2014 | Crews et al. | |
| 2015/0291562 | A1 | 10/2015 | Crew et al. | |
| 2016/0045607 | A1 | 2/2016 | Crew et al. | |
| 2016/0058872 | A1 | 3/2016 | Crew et al. | |
| 2016/0272639 | A1 | 9/2016 | Crew et al. | |
| 2018/0169109 | A1* | 6/2018 | Bradner ............. | A61K 31/4985 |
| 2018/0179522 | A1* | 6/2018 | Buckley ............. | A61K 40/4211 |
| 2020/0038378 | A1 | 2/2020 | Crew et al. | |

FOREIGN PATENT DOCUMENTS

| | | | | |
|---|---|---|---|---|
| WO | 02/059106 | A1 | 8/2002 | |
| WO | 2012/030160 | A2 | 3/2012 | |
| WO | 2013/106643 | A2 | 7/2013 | |
| WO | 2014/063061 | A1 | 4/2014 | |
| WO | 2016/149668 | A1 | 9/2016 | |
| WO | WO-2020051099 | A1 * | 3/2020 | ........... C07D 213/81 |

OTHER PUBLICATIONS

Sun et al. Signal Transduction and Targeted Therapy 2019, 4, 64, pp. 1-33 (Year: 2019).*

Ahn, E., et al., "RASSFIA-Mediated Regulation of AREG via the Hippo Pathway in Hepatocellular Carcinoma" Mole Cancer Res 11(7):748-758 (Jul. 1, 2013).

Avruch, J., et al., "YAP oncogene overexpression supercharges colon cancer proliferation" Cell Cycle 11(6):1090-1096 (Mar. 15, 2012).

Baia, G., et al., "Yes-Associated Protein 1 Is Activated and Functions as an Oncogene in Meningiomas" Mole Cancer Res 10(7):904-913 (Jul. 1, 2012).

Bao, Y., et al., "Mammalian Hippo pathway: from development to cancer and beyond" J Biochem-Oxford 149(4):361-379 (Apr. 1, 2011).

Chan, S., et al., "A Role for TAZ in Migration, Invasion, and Tumorigenesis of Breast Cancer Cells" Cancer Res 68(8):2592-2598 (Apr. 15, 2008).

Fujii, M., et al., "TGF-β synergizes with defects in the Hippo pathway to stimulate human malignant mesothelioma growth" J Exp Med 209(3):479-494 (Mar. 12, 2012).

Gasparotto, D., et al., "Overexpression of TWIST2 correlates with poor prognosis in Head and Neck Squamous Cell Carcinomas" Oncotarget 2(12):1165-1175 (Dec. 1, 2011).

Girardini, M., et al., "Cereblon versus VHL: Hijacking E3 ligases against each other using PROTACs" Bioorg Med Chem 27(12):2466-2479 (Jun. 15, 2019).

Halder, G., et al., "Hippo signaling: growth control and beyond" Development 138(1):9-22 (Jan. 1, 2011).

Hall, C., et al., "Hippo Pathway Effector Yap Is an Ovarian Cancer Oncogene" Cancer Res 70(21):8517-8525 (Oct. 31, 2010).

Harvey, K., et al., "The Hippo pathway and human cancer" Nat Rev Cancer 13(4):246-257 (Mar. 7, 2013).

"International Preliminary Report on Patentability—PCT/EP2021/020367" (Report Issuance Date: Sep. 6, 2022; Chapter I), :pp. 1-9 (Sep. 15, 2022).

"International Search Report—PCT/US2021/020367" (w/Written Opinion), :pp. 1-15 (Jul. 29, 2021).

Jie, L., et al., "The Hippo-Yes Association Protein Pathway in Liver Cancer" Gastroenterol Res Pract 2013:187070 (1-7) (Aug. 6, 2013).

Jimenez-Velasco, A., et al., "Downregulation of the large tumor suppressor 2 (LATS2/KPM) gene is associated with poor prognosis in acute lymphoblastic leukemia" Leukemia 19(12):2347-2350 (Dec. 1, 2005).

Lamar, J., et al., "The Hippo pathway target, YAP, promotes metastasis through its TEAD-interaction domain" PNAS USA 109(37):E2441-E2450 (Sep. 11, 2012).

Lei, Q., et al., "TAZ Promotes Cell Proliferation and Epithelial-Mesenchymal Transition and Is Inhibited by the Hippo Pathway" Mol Cell Biol 28(7):2426-2436 (Apr. 1, 2008).

(Continued)

*Primary Examiner* — Matthew P Coughlin

(57) ABSTRACT

The invention relates to compounds and methods of using said compounds, as well as pharmaceutical compositions containing such compounds, for treating diseases and conditions mediated by TEAD, such as cancer.

15 Claims, No Drawings

Specification includes a Sequence Listing.

(56) References Cited

OTHER PUBLICATIONS

Liu,A., et al., "An update on targeting Hippo-YAP signaling in liver cancer" Expert Opin Ther Targets 16(3):243-247 (Feb. 16, 2012).
Mizuno, T., et al., "YAP induces malignant mesothelioma cell proliferation by upregulating transcription of cell cycle-promoting genes" Oncogene 31(49):5117-5122 (Dec. 6, 2012).
Orr, B., et al., "Yes-associated protein 1 is widely expressed in human brain tumors and promotes glioblastoma growth" J Neuropathol Exp Neurol 70(7):568-577 (Jul. 1, 2011).
Seidel, C., et al., "Frequent hypermethylation of MST1 and MST2 in soft tissue sarcoma" Mol Carcinog 46(10):865-871 (Oct. 1, 2007).
Sekido, Y., "Inactivation of Merlin in malignant mesothelioma cells and the Hippo signaling cascade dysregulation" Pathol Int 61(6):331-344 (Jun. 1, 2011).
Steinhardt, A., et al., "Expression of Yes-associated protein in common solid tumors" Human Pathol 39(11):1582-1589 (Nov. 1, 2008).
Steinmann, K., et al., "Frequent promoter hypermethylation of tumor-related genes in head and neck squamous cell carcinoma" Onco Reports 22(6):1519-1526 (Dec. 1, 2009).
Striedinger, K., et al., "The Neurofibromatosis 2 Tumor Suppressor Gene Product, Merlin, Regulates Human Meningioma Cell Growth by Signaling through YAP" Neoplasia 10(11):1204-1212 (Nov. 1, 2008).
Vassilev, A., et al., "TEAD/TEF transcription factors utilize the activation domain of YAP65, a Src/Yes-associated protein localized in the cytoplasm" Genes Development 15(10):1229-1241 (May 15, 2001).
Wang, X., et al., "Yes-associated protein promotes tumour development in luminal epithelial derived breast cancer" Eur J Cancer 48(8):1227-1284 (May 1, 2012).
Wang, Y., et al., "Overexpression of yes-associated protein contributes to progression and poor prognosis of non-small-cell lung cancer" Cancer Science 101(5):1279-1285 (May 1, 2010).
Yuen, H., et al., "TAZ expression as a prognostic indicator in colorectal cancer" PLoS One 8(1):E54211 (1-17) (Jan. 23, 2013).
Zeng, Q., et al., "The emerging role of the hippo pathway in cell contact inhibition, organ size control, and cancer development in mammals" Cancer Cell 313:188-192 (Mar. 1, 2008).
Zhao, B., et al., "Both TEAD-Binding and WW Domains Are Required for the Growth Stimulation and Oncogenic Transformation Activity of Yes-Associated Protein" Cancer Res 69(3):1089-1098 (Feb. 1, 2009).
Zhao, B., et al., "Cell detachment activates the Hippo pathway via cytoskeleton reorganization to induce anoikis" Gene Development 26(1):54-68 (Jan. 1, 2012).
Zhao, B., et al., "Hippo signaling at a glance" J Cell Science 123(23):4001-4006 (Dec. 1, 2010).
Zhao, B., et al., "Inactivation of YAP oncoprotein by the Hippo pathway is involved in cell contact inhibition and tissue growth control" Gene Develop 21(21):2747-2761 (Nov. 1, 2007).
Zhao, B., et al., "The Hippo pathway in organ size control, tissue regeneration and stem cell self-renewal" Nat Cell Biol 13(8):877-883 (Aug. 1, 2011).
Zhao, B., et al., "The Hippo-YAP pathway in organ size control and tumorigenesis: an updated version" Genes Development 24(9):862-874 (May 1, 2010)
Zhou, Z., et al., "TAZ is a novel oncogene in non-small cell lung cancer" Oncogene 30(18):2181-2186 (May 5, 2011).

* cited by examiner

HETEROBIFUNCTIONAL MOLECULES AS TEAD INHIBITORS

CROSS-REFERENCE TO RELATED APPLICATIONS

This application is a continuation of International Application No. PCT/US2021/020367 having an International filing date of Mar. 2, 2021, which claims benefit of priority to U.S. Provisional Application No. 62/985,256, filed on Mar. 4, 2020, the contents of which are incorporated herein by reference in their entirety.

SEQUENCE LISTING

This application contains a Sequence Listing submitted and is hereby incorporated by reference in its entirety. Said xml copy, created on Aug. 31, 2022, is named P35870-US-1_SequenceListing and is 23,765 bytes in size.

FIELD OF THE DISCLOSURE

The present disclosure relates to compounds useful for therapy and/or prophylaxis in a mammal, and in particular as inhibitors and/or degraders of TEAD useful for treating cancer.

BACKGROUND

The Hippo pathway is a signaling pathway that regulates cell proliferation and cell death and determines organ size. The pathway is believed to play a role as a tumor suppressor in mammals, and disorders of the pathway are often detected in human cancers. The pathway is involved in and/or may regulate the self-renewal and differentiation of stem cells and progenitor cells. In addition, the Hippo pathway may be involved in wound healing and tissue regeneration. Furthermore, it is believed that as the Hippo pathway cross-talks with other signaling pathways such as Wnt, Notch, Hedgehog, and MAPK/ERK, it may influence a wide variety of biological events, and that its dysfunction could be involved in many human diseases in addition to cancer. For reviews, see, for example, Halder et al., 2011, Development 138:9-22; Zhao et al., 2011, Nature Cell Biology 13:877-883; Bao et al., 2011, J. Biochem. 149:361-379; Zhao at al., 2010, J. Cell Sci. 123:4001-4006.

The Hippo signaling pathway is conserved from *drosophila* to mammals (Vassilev et al., Genes and Development, 2001, 15, 1229-1241; Zeng and Hong, Cancer Cell, 2008, 13, 188-192). The core of the pathway consists of a cascade of kinases (Hippo-MST1-2 being upstream of Lats 1-2 and NDRI-2) leading to the phosphorylation of two transcriptional co-activators, YAP (Yes-Associated Protein) and TAZ (Transcription co-activator with PDZ binding motif or tafazzin; Zhao et al., Cancer Res., 2009, 69, 1089-1098; Lei et al., Mol. Cell. Biol., 2008, 28, 2426-2436).

Because the Hippo signaling pathway is a regulator of animal development, organ size control and stem cell regulation, it has been implicated in cancer development (Review in Harvey et al., Nat. Rev. Cancer, 2013, 13, 246-257; Zhao et al., Genes Dev. 2010, 24, 862-874). In vitro, the overexpression of YAP or TAZ in mammary epithelial cells induces cell transformation, through interaction of both proteins with the TEAD family of transcription factors. Increased YAP/TAZ transcriptional activity induces oncogenic properties such as epithelial-mesenchymal transition and was also shown to confer stem cells properties to breast cancer cells. In vivo, in mouse liver, the overexpression of YAP or the genetic knockout of its upstream regulators MST1-2 triggers the development of hepatocellular carcinomas. Furthermore, when the tumor suppressor NF2 is inactivated in the mouse liver, the development of hepatocellular carcinomas can be blocked completely by the co-inactivation of YAP.

It is believed that deregulation of the Hippo tumor suppressor pathway is a major event in the development of a wide range of malignancies, including with no limitations, lung cancer (NSCLC; Zhou et al., Oncogene, 2011, 30, 2181-2186; Wang et al., Cancer Sci., 2010, 101, 1279-1285), breast cancer (Chan et al., Cancer Res., 2008, 68, 2592-2598; Lamar et al., Proc. Natl. Acad. Sci, USA, 2012; 109, E2441-E2250; Wang et al., Eur. J. Cancer, 2012, 48, 1227-1234), head and neck cancer (Gasparotto et al., Oncotarget., 2011, 2, 1165-1175; Steinmann et al., Oncol. Rep., 2009, 22, 1519-1526), colon cancer (Angela et al., Hum. Pathol., 2008, 39, 1582-1589; Yuen et al., PLoS One, 2013, 8, e54211; Avruch et al., Cell Cycle, 2012, 11, 1090-1096), ovarian cancer (Angela et al., Hum. Pathol., 2008, 39, 1582-1589; Chad et al., Cancer Res., 2010, 70, 8517-8525; Hall et al., Cancer Res., 2010, 70, 8517-8525), liver cancer (Jie et al., Gastroenterol. Res. Pract., 2013, 2013, 187070; Ahn et al., Mol. Cancer. Res., 2013, 11, 748-758; Liu et al., Expert. Opin. Ther. Targets, 2012, 16, 243-247), brain cancer (Orr et al., J Neuropathol. Exp. Neurol. 2011, 70, 568-577; Baia et al., Mol. Cancer Res., 2012, 10, 904-913; Striedinger et al., Neoplasia, 2008, 10, 1204-1212) and prostate cancer (Zhao et al., Genes Dev., 2012, 26, 54-68; Zhao et al., Genes Dev., 2007, 21, 2747-2761), mesotheliomas (Fujii et al., J. Exp. Med., 2012, 209, 479-494; Mizuno et al., Oncogene, 2012, 31, 5117-5122; Sekido Y., Pathol. Int., 2011, 61, 331-344), sarcomas (Seidel et al., Mol. Carcinog., 2007, 46, 865-871) and leukemia (Jimenez-Velasco et al., Leukemia, 2005, 19, 2347-2350).

Two of the core components of the mammalian Hippo pathway are Lats1 and Lats2, which are nuclear Dbf2-related (NDR) family protein kinases homologous to *Drosophila* Warts (Wts). The Lats1/2 proteins are activated by association with the scaffold proteins Mob1A/B (Mps one binder kinase activator-like 1A and 1B), which are homologous to *Drosophila* Mats. Lats1/2 proteins are also activated by phosphorylation by the STE20 family protein kinases Mst1 and Mst2, which are homologous to *Drosophila* Hippo. Lats1/2 kinases phosphorylate the downstream effectors YAP (Yes-associated protein) and TAZ (transcriptional coactivator with PDZ-binding motif, WWTR1), which are homologous to *Drosophila* Yorkie. The phosphorylation of YAP and TAZ by Lats1/2 are crucial events within the Hippo signaling pathway. Lats1/2 phosphorylates YAP at multiple sites, but phosphorylation of Ser127 is critical for YAP inhibition. Phosphorylation of YAP generates a protein-binding motif for the 14-3-3 family of proteins, which upon binding of a 14-3-3 protein, leads to retention and/or sequestration of YAP in the cell cytoplasm. Likewise, Lats1/2 phosphorylates TAZ at multiple sites, but phosphorylation of Ser89 is critical for TAZ inhibition. Phosphorylation of TAZ leads to retention and/or sequestration of TAZ in the cell cytoplasm. In addition, phosphorylation of YAP and TAZ is believed to destabilize these proteins by activating phosphorylation-dependent degradation catalyzed by YAP or TAZ ubiquitination. Thus, when the Hippo pathway is "on", YAP and/or TAZ is phosphorylated, inactive, and generally sequestered in the cytoplasm; in contrast, when the Hippo pathway is "off", YAP and/or TAZ is non-phosphorylated, active, and generally found in the nucleus.

Non-phosphorylated, activated YAP is translocated into the cell nucleus where its major target transcription factors are the four proteins of the TEAD-domain-containing family (TEAD1-TEAD4, collectively "TEAD"). YAP together with TEAD (or other transcription factors such as Smad1, RUNX, ErbB4 and p73) has been shown to induce the expression of a variety of genes, including connective tissue growth factor (CTGF), Gli2, Birc5, Birc2, fibroblast growth factor 1 (FGF1), and amphiregulin (AREG). Like YAP, non-phosphorylated TAZ is translocated into the cell nucleus where it interacts with multiple DNA-binding transcription factors, such as peroxisome proliferator-activated receptor 7 (PPART), thyroid transcription factor-1 (TTF-1), Pax3, TBX5, RUNX, TEAD1 and Smad2/3/4. Many of the genes activated by YAP/TAZ-transcription factor complexes mediate cell survival and proliferation. Therefore, under some conditions YAP and/or TAZ acts as an oncogene and the Hippo pathway acts as a tumor suppressor.

One type of targeted therapy involves heterobifunctional molecules that exploit the intracellular ubiquitin-proteasome system to selectively degrade target proteins by forming a ternary complex between the target protein, heterobifunctional molecule, and the ubiquitin ligase. This in turn enables the ubiquitin ligase to ubiquitinate the target protein, marking it for degradation by a proteasome.

There is a need in the art for improved cancer treatment options using pharmacological targeting of TEAD to provide functional alterations of the Hippo cascade. Heterobifunctional molecules may be particularly advantageous.

SUMMARY OF THE DISCLOSURE

In some aspects, provided is a compound of formula (I):

(I)

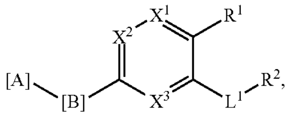

or a stereoisomer or pharmaceutically acceptable salt thereof, wherein:

[A] is a ligase ligand;

[B] is a linker moiety;

$X^1$, $X^2$, and $X^3$ are each independently N or C—$R^5$, wherein each $R^5$ is independently selected from the group consisting of H, halo, cyano, $C_{1-12}$alkyl, O—$C_{1-12}$alkyl, and $C_{1-12}$haloalkyl;

$L^1$ is a bond or is —$C_{1-12}$alkyl-, —$C_{2-12}$alkenyl-, —$C_{2-12}$alkynyl-, or —$C_{3-10}$cycloalkyl-;

$R^1$ is H, $C_{1-12}$alkyl, $C_{3-10}$cycloalkyl, $C_{1-12}$alkyl-$C_{3-10}$cycloalkyl, $C_{1-12}$haloalkyl, O—$C_{1-12}$alkyl, O—$C_{3-10}$cycloalkyl, O—$C_{1-12}$alkyl-$C_{3-10}$cycloalkyl, or O—$C_{1-12}$haloalkyl; and $R^2$ is H, $C_{3-10}$cycloalkyl, $C_{1-12}$alkyl-$C_{3-10}$cycloalkyl, 3-10 membered heterocyclyl, $C_{6-20}$aryl, 5-20 membered heteroaryl, or $C_{5-13}$spirocyclyl, wherein:

the $C_{3-10}$cycloalkyl, $C_{1-12}$alkyl-$C_{3-10}$cycloalkyl, 3-10 membered heterocyclyl, $C_{6-20}$aryl, 5-20 membered heteroaryl, or $C_{5-13}$spirocyclyl of $R^2$ is independently optionally substituted with one or more oxo, cyano, halo, $C_{1-12}$alkyl, $C_{1-12}$haloalkyl, $C_{3-10}$cycloalkyl, $C_{6-20}$aryl, $NO_2$, N($R^x$)($R^y$), and O($R^x$), wherein:

each $R^x$ and $R^y$ is independently selected from the group consisting of H, $C_{1-12}$alkyl, $C_{2-12}$alkenyl, $C_{2-12}$alkylnyl, $C_{3-10}$cycloalkyl, $C_{1-12}$alkyl-$C_{3-10}$cycloalkyl, 3-10 membered heterocyclyl, $C_{6-20}$aryl and 5-20 membered heteroaryl, wherein:

each $C_{1-12}$ alkyl, $C_{2-12}$ alkenyl, $C_{2-12}$ alkylnyl, $C_{3-10}$cycloalkyl, $C_{1-12}$alkyl-$C_{3-10}$cycloalkyl, 3-10 membered heterocyclyl, $C_{6-20}$aryl and 5-20 membered heteroaryl of $R^x$ and $R^y$ is independently optionally substituted with one or more oxo, cyano, halo, $NO_2$, $NH_2$, hydroxy, $C_{1-12}$ alkyl, $C_{1-12}$haloalkyl, or O—$C_{1-12}$alkyl.

In some embodiments, the linker moiety has a structure of formula (II):

(II)

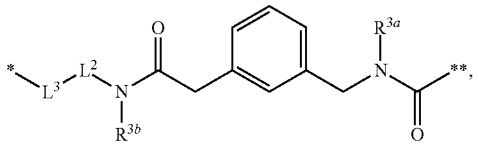

wherein:

* of the linker moiety denotes the point of attachment to the ligase ligand and ** of the linker moiety denotes the point of attachment to the remainder of the molecule;

$L^2$ is —$(CH_2)_n$— or —$(CH_2CH_2O)_n$—, wherein n is 1-12;

$L^3$ is a bond or is —C≡C—, —CH=CH—, —$(CH_2)_m$—, —O—, —NH—, or

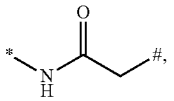

wherein # of $L^3$ denotes the point of attachment to $L^2$ and * of $L^3$ denotes the point of attachment to the ligase ligand;

each of $R^{3a}$ and $R^{3b}$ is independently H, $C_{1-12}$alkyl, $C_{2-12}$ alkenyl, $C_{2-12}$ alkynyl, $C_{3-10}$cycloalkyl, $C_{1-12}$alkyl-$C_{3-10}$cycloalkyl, $C_{1-12}$alkyl-$C_{6-20}$aryl, 3-10 membered heterocyclyl, $C_{6-20}$aryl, or 5-20 membered heteroaryl, wherein:

each $C_{1-12}$alkyl, $C_{2-12}$ alkenyl, $C_{2-12}$ alkynyl, $C_{3-10}$cycloalkyl, $C_{1-12}$alkyl-$C_{3-10}$cycloalkyl, $C_{1-12}$alkyl-$C_{6-20}$aryl, 3-10 membered heterocyclyl, $C_{6-20}$aryl, or 5-20 membered heteroaryl is independently optionally substituted with at least one of oxo, CN, $C_{1-12}$alkyl, $C_{1-12}$haloalkyl, halo, $NO_2$, N($R^e$)($R^f$), $C_{1-12}$alkyl-C(O)—N($R^e$)($R^f$), and O$R^e$, wherein:

each $R^e$ and $R^f$ is independently selected from the group consisting of H, $C_{1-12}$alkyl, $C_{2-12}$alkenyl, $C_{2-12}$alkynyl, $C_{3-10}$cycloalkyl, $C_{1-12}$alkyl-$C_{3-10}$cycloalkyl, 3-10 membered heterocyclyl, $C_{6-20}$aryl, and 5-20 membered heteroaryl, wherein each $C_{1-12}$alkyl, $C_{2-12}$alkenyl, $C_{2-12}$alkynyl, $C_{3-10}$cycloalkyl, $C_{1-12}$alkyl-$C_{3-10}$cycloalkyl, 3-10 membered heterocyclyl, $C_{6-20}$aryl, or 5-20 membered heteroaryl is independently optionally substituted with one or more oxo, CN, $C_{1-12}$alkyl, $C_{1-12}$haloalkyl, halo, $NO_2$, O—$C_{1-12}$alkyl, or OH.

In certain embodiments, the ligase ligand is an E3 ubiquitin ligase ligand.

In some embodiments, the ligase ligand is a cereblon ligand, a VHL ligand, or an XIAP ligand.

In some aspects, the compound of formula (I) is a heterobifunctional molecule.

In some aspects, a pharmaceutical composition comprising a compound of formula (I) or a pharmaceutically acceptable salt thereof, and a pharmaceutically acceptable carrier, diluent or excipient is provided.

In some aspects, a compound of formula (I) or a pharmaceutically acceptable salt thereof is provided for use in medical therapy.

In some aspects, a compound of formula (I) or a pharmaceutically acceptable salt thereof is provided for the treatment or prophylaxis of cancer, mesothelioma, sarcoma, or leukemia.

In some aspects, a compound of formula (I) or a pharmaceutically acceptable salt thereof is provided for the preparation of a medicament for the treatment or prophylaxis of cancer, mesothelioma, sarcoma, or leukemia.

In some aspects, a method for treating cancer, mesothelioma, sarcoma, or leukemia in a mammal is provided, the method comprising, administering a compound of formula (I) or a pharmaceutically acceptable salt thereof to the mammal.

In some aspects, a compound of formula (I) or a pharmaceutically acceptable salt thereof is provided for modulating TEAD activity.

In some aspects, a compound of formula (I) or a pharmaceutically acceptable salt thereof is provided for degrading a TEAD protein. In some aspects, a compound of formula (I) or a pharmaceutically acceptable salt thereof is provided for modulating TEAD activity, wherein the modulating of the TEAD activity is by degradation of a TEAD protein.

In some aspects, a compound of formula (I) or a pharmaceutically acceptable salt thereof is provided for the treatment or prophylaxis of a disease or condition mediated by TEAD activity.

In some aspects, a compound of formula (I) or a pharmaceutically acceptable salt thereof is provided for use for the preparation of a medicament for the treatment or prophylaxis of a disease or condition that is mediated by TEAD activity.

In some aspects, a method for modulating TEAD activity is provided, the method comprising contacting TEAD with a compound of formula (I) or a pharmaceutically acceptable salt thereof.

In some aspects, a method for treating a disease or condition mediated by TEAD activity in a mammal is provided, the method comprising administering a compound of formula (I) or a pharmaceutically acceptable salt thereof to the mammal.

In some aspects, provided is a ternary complex, comprising: the compound of formula (I), or a stereoisomer or pharmaceutically acceptable salt thereof, a TEAD protein; and a ubiquitin ligase.

DETAILED DESCRIPTION

Definitions

Unless otherwise indicated, the following specific terms and phrases used in the description and claims are defined as follows.

The term "moiety" refers to an atom or group of chemically bonded atoms that is attached to another atom or molecule by one or more chemical bonds thereby forming part of a molecule.

The term "substituted" refers to the fact that at least one of the hydrogen atoms of that moiety is replaced by another substituent or moiety.

The term "alkyl" refers to an aliphatic straight-chain or branched-chain saturated hydrocarbon moiety having 1 to 20 carbon atoms, such as 1 to 12 carbon atoms, or 1 to 6 carbon atoms. Alkyl groups may be optionally substituted.

The term "cycloalkyl" means a saturated or partially unsaturated carbocyclic moiety having mono- or bicyclic (including bridged bicyclic) rings and 3 to 10 carbon atoms in the ring. In particular aspects, cycloalkyl may contain from 3 to 8 carbon atoms (i.e., ($C_3$-$C_8$)cycloalkyl). In other particular aspects cycloalkyl may contain from 3 to 6 carbon atoms (i.e., ($C_3$-$C_6$)cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl). The cycloalkyl moiety can be attached in a spirocycle fashion such as spirocyclopropyl:

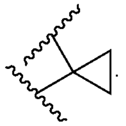 [SMILES: *C1(*)CC1]

The term "haloalkyl" refers to an alkyl group wherein one or more of the hydrogen atoms of the alkyl group has been replaced by the same or different halogen atoms, such as fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. Haloalkyl groups may be optionally substituted.

The term "alkenyl" refers to a straight or branched chain alkyl or substituted alkyl group as defined elsewhere herein having at least one carbon-carbon double bond. Alkenyl groups may be optionally substituted.

The term "alkynyl" refers to a straight or branched chain alkyl or substituted alkyl group as defined elsewhere herein having at least one carbon-carbon triple bond. Alkynyl groups may be optionally substituted.

The terms "heterocyclyl" and "heterocycle" refer to a 4, 5, 6 and 7-membered monocyclic or 7, 8, 9 and 10-membered bicyclic (including bridged bicyclic) heterocyclic moiety that is saturated or partially unsaturated, and has one or more (e.g., 1, 2, 3 or 4) heteroatoms selected from oxygen, nitrogen and sulfur in the ring with the remaining ring atoms being carbon. When used in reference to a ring atom of a heterocycle, a nitrogen or sulfur may also be in an oxidized form, and a nitrogen may be substituted. The heterocycle can be attached to its pendant group at any heteroatom or carbon atom that results in a stable structure and any of the ring atoms can be optionally substituted. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, 2-azabicyclo[2.2.1]heptanyl, octahydroindolyl, or tetrahydroquinolinyl. Heterocyclyl groups may be optionally substituted.

The term "aryl" refers to a cyclic aromatic hydrocarbon moiety having a mono-, bi- or tricyclic aromatic ring of 5 to 20 carbon ring atoms. Examples of aryl moieties include, but are not limited to, phenyl, naphthyl, benzyl, and the like. The term "aryl" also includes partially hydrogenated derivatives of the cyclic aromatic hydrocarbon moiety provided that at least one ring of the cyclic aromatic hydrocarbon moiety is aromatic, each being optionally substituted. In some aspects, monocyclic aryl rings may have 5 or 6 carbon ring atoms. Aryl groups may be optionally substituted.

The term "heteroaryl" refers an aromatic heterocyclic mono- or bicyclic ring system of 1 to 20 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Heteroaryl groups may be optionally substituted.

The terms "halo" and "halogen" refer to fluoro, chloro, bromo and iodo. In some aspects, halo is fluoro or chloro.

The term "oxo" refers to the =O moiety.

The terms "spirocycle" and "spirocyclyl" refer to carbogenic bicyclic ring systems comprising between 5 and 15 carbon atoms with both rings connected through a single atom. The rings can be different in size and nature, or identical in size and nature. Examples include spiropentane, spirohexane, spiroheptane, spirooctane, spirononane, or spirodecane. One or more of the carbon atoms in the spirocycle can be substituted with a heteroatom (e.g., O, N, S, or P), wherein in such aspects the spirocycle may comprise between 3 and 14 carbon atoms. Spirocycle groups may be optionally substituted.

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The term "prodrug" refers to those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

In some prodrug aspects, prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present disclosure. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

In some other prodrug aspects, a free carboxyl group of a compound of the disclosure can be derivatized as an amide or alkyl ester. In yet other prodrug aspects, prodrugs comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, $—P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191

(1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present disclosure provides for metabolites of compounds of the disclosure. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}C$ or $^{3}H$) isotope of a compound of the disclosure, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure can exist in multiple crystalline or amorphous forms. In general, all physical forms are equivalent for the uses contemplated by the present disclosure and are intended to be within the scope of the present disclosure.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain aspects the compound is enriched by at least about 90% by weight with a single diastereomer or enantiomer. In other aspects the compound is enriched by at least about 95%, 98%, or 99% by weight with a single diastereomer or enantiomer.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure.

The compounds of the present disclosure may also exist in different tautomeric forms, and all such forms are embraced within the scope of the disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Unless otherwise indicated, the term "a compound of the formula" or "a compound of formula" or "compounds of the formula" or "compounds of formula" refers to any compound selected from the genus of compounds as defined by the formula. In some embodiments or aspects, the term also includes a pharmaceutically acceptable salt or ester of any such compound, a stereoisomer, or a tautomer of such compound.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this disclosure can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with a compound of the disclosure, use thereof in the compositions of the disclosure is contemplated. Supplementary active compounds can also be incorporated into the compositions.

Compounds

In some aspects of the present disclosure, the compounds, or stereoisomers or pharmaceutically acceptable salts thereof, are of the following formula (I):

(I)

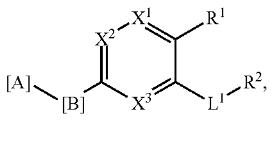

or a stereoisomer or pharmaceutically acceptable salt thereof, wherein:

[A] is a ligase ligand;

[B] is a linker moiety;

$X^1$, $X^2$, and $X^3$ are each independently N or C—$R^5$, wherein each $R^5$ is independently selected from the group consisting of H, halo, cyano, $C_{1-12}$alkyl, O—$C_{1-12}$alkyl, and $C_{1-12}$haloalkyl;

$L^1$ is a bond or is —$C_{1-12}$alkyl-, —$C_{2-12}$alkenyl-, —$C_{2-12}$alkynyl-, or —$C_{3-10}$cycloalkyl-;

$R^1$ is H, $C_{1-12}$alkyl, $C_{3-10}$cycloalkyl, $C_{1-12}$alkyl-$C_{3-10}$cycloalkyl, $C_{1-12}$haloalkyl, O—$C_{1-12}$alkyl, O—$C_{3-10}$cycloalkyl, O—$C_{1-12}$alkyl-$C_{3-10}$cycloalkyl, or O—$C_{1-12}$haloalkyl; and $R^2$ is H, $C_{3-10}$cycloalkyl, $C_{1-12}$alkyl-$C_{3-10}$cycloalkyl, 3-10 membered heterocyclyl, $C_{6-20}$aryl, 5-20 membered heteroaryl, or $C_{5-13}$spirocyclyl, wherein:

the $C_{3-10}$cycloalkyl, $C_{1-12}$alkyl-$C_{3-10}$cycloalkyl, 3-10 membered heterocyclyl, $C_{6-20}$aryl, 5-20 membered heteroaryl, or $C_{5-13}$spirocyclyl of $R^2$ is independently optionally substituted with one or more oxo, cyano, halo, $C_{1-12}$alkyl, $C_{1-12}$haloalkyl, $C_{3-10}$cycloalkyl, $C_{6-20}$aryl, $NO_2$, N($R^x$)($R^y$), and O($R^x$), wherein:

each $R^x$ and $R^y$ is independently selected from the group consisting of H, $C_{1-12}$alkyl, $C_{2-12}$alkenyl, $C_{2-12}$alkylnyl, $C_{3-10}$cycloalkyl, $C_{1-12}$alkyl-$C_{3-10}$cycloalkyl, 3-10 membered heterocyclyl, $C_{6-20}$aryl and 5-20 membered heteroaryl, wherein:

each $C_{1-12}$alkyl, $C_{2-12}$alkenyl, $C_{2-12}$alkylnyl, $C_{3-10}$cycloalkyl, $C_{1-12}$alkyl-$C_{3-10}$cycloalkyl, 3-10 membered heterocyclyl, $C_{6-20}$aryl and 5-20 membered heteroaryl of $R^x$ and $R^y$ is independently optionally substituted with one or more oxo, cyano, halo, $NO_2$, $NH_2$, hydroxy, $C_{1-12}$ alkyl, $C_{1-12}$haloalkyl, or O—$C_{1-12}$alkyl.

In some embodiments, the compound of formula (I) is a heterobifunctional molecule. It is appreciated that individual moieties described herein can be combined together with other moieties the same as if each and every combination were specifically and individually listed. For example, each description of [B] may be combined together with each description of [A] the same as if each and every combination were specifically and individually listed. Moreover, each such description or combination may be applicable to formula (I) and other related formulae as would be evident to a person of skill in the art.

A variety of linker moieties may be present in compounds of any of the formulae described herein. In some embodiments, one or more part(s) of the linker moiety may interact with the target protein and/or the ligase. In one embodiment, the part of the linker moiety that interacts with the target protein has a structure of

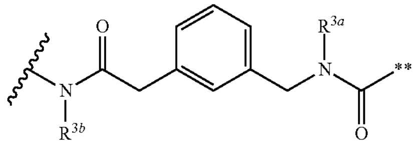

such that the portion of the compound of formula (I) that interacts with the target protein has a structure of

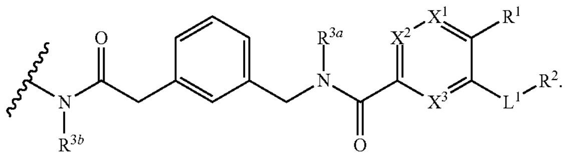

In other embodiments, the entire linker moiety may interact with the target protein and/or ligase. In some embodiments, the linker moiety has the structure of formula (II):

(II)

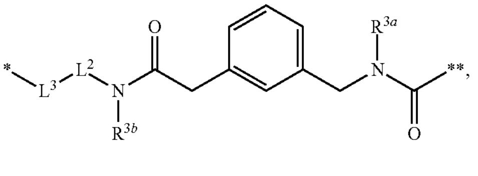

wherein * of the linker moiety denotes the point of attachment to the ligase ligand and ** of the linker moiety denotes the point of attachment to the remainder of the molecule;

$L^2$ is —$(CH_2)_n$— or —$(CH_2CH_2O)_n$—, wherein n is 1-12;

$L^3$ is a bond or is —C≡C—, —CH═CH—, —$(CH_2)_m$—, —O—, —NH—, or

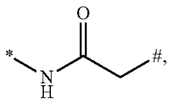

wherein # of $L^3$ denotes the point of attachment to $L^2$ and * of $L^3$ denotes the point of attachment to the ligase ligand; and each of $R^{3a}$ and $R^{3b}$ is independently H, $C_{1-12}$alkyl, $C_{2-12}$ alkenyl, $C_{2-12}$ alkynyl, $C_{3-10}$cycloalkyl, $C_{1-12}$alkyl-$C_{3-10}$cycloalkyl, $C_{1-12}$alkyl-$C_{6-20}$aryl, 3-10 membered heterocyclyl, $C_{6-20}$aryl, or 5-20 membered heteroaryl, wherein:

each $C_{1-12}$alkyl, $C_{2-12}$ alkenyl, $C_{2-12}$ alkynyl, $C_{3-10}$cycloalkyl, $C_{1-12}$alkyl-$C_{3-10}$cycloalkyl, $C_{1-12}$alkyl-$C_{6-20}$aryl, 3-10 membered heterocyclyl, $C_{6-20}$aryl, or 5-20 membered heteroaryl is independently optionally substituted with at least one of oxo, CN, $C_{1-12}$alkyl, $C_{1-12}$haloalkyl, halo, $NO_2$, N($R^e$)($R^f$), $C_{1-12}$alkyl-C(O)—N($R^e$)($R^f$), and O$R^e$, wherein:

each $R^e$ and $R^f$ is independently selected from the group consisting of H, $C_{1-12}$alkyl, $C_{2-12}$alkenyl, $C_{2-12}$alkynyl, $C_{3-10}$cycloalkyl, $C_{1-12}$alkyl-$C_{3-10}$cycloalkyl, 3-10 membered heterocyclyl, $C_{6-20}$aryl, and 5-20 membered heteroaryl, wherein each $C_{1-12}$alkyl, $C_{2-12}$alkenyl, $C_{2-12}$alkynyl, $C_{3-10}$cycloalkyl, $C_{1-12}$alkyl-$C_{3-10}$cycloalkyl, 3-10 membered heterocyclyl, $C_{6-20}$aryl, or 5-20 membered heteroaryl is independently optionally substituted with one or more oxo, CN, $C_{1-12}$alkyl, $C_{1-12}$haloalkyl, halo, $NO_2$, O—$C_{1-12}$alkyl, or OH.

In some embodiments, each of $R^{3a}$ and $R^{3b}$ is H or $C_{1-12}$alkyl. In other embodiments, each of $R^{3a}$ and $R^{3b}$ is H or methyl. In still other embodiments, each of $R^{3a}$ and $R^{3b}$ is H. In further embodiments, $R^{3a}$ is H and $R^{3b}$ is methyl.

In some embodiments, the ligase ligand is an E3 ubiquitin ligase ligand. In certain embodiments, the E3 ubiquitin ligase ligand is a cereblon ligand. In some embodiments, the cereblon ligand has a structure of formula (III):

(III)

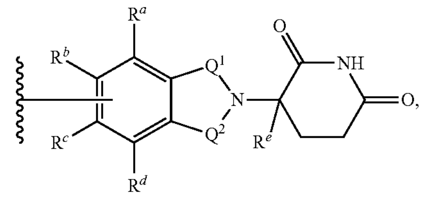

wherein: one of $Q^1$ and $Q^2$ is C═O, and the other of $Q^1$ and $Q^2$ is C═O or $CH_2$; one of $R^a$, $R^b$, $R^c$, and $R^d$ is the

bond to $L^3$ of the linker moiety, and the others of $R^a$, $R^b$, $R^c$, and $R^d$ are each independently H, halo, $C_{1-12}$alkyl, $C_{1-12}$haloalkyl, or O—$C_{1-12}$alkyl; and $R^e$ is H, halo, $C_{1-12}$alkyl, $C_{1-12}$haloalkyl, O—$C_{1-12}$alkyl, or phenyl.

In some embodiments, wherein the ligase ligand is a cereblon ligand, the compound has a structure of formula (IV):

(IV)

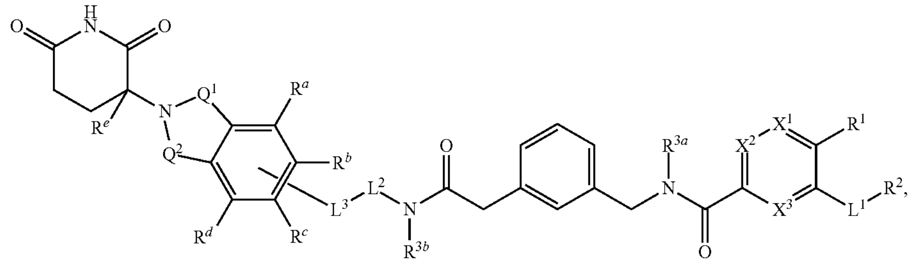

or a stereoisomer or pharmaceutically acceptable salt thereof.

In certain embodiments, the compound of formula (IV) is a compound of formula (V):

(V)

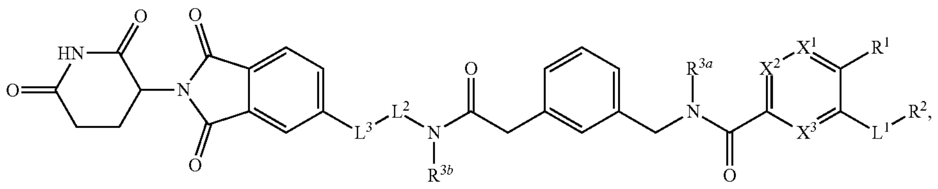

or a stereoisomer or pharmaceutically acceptable salt thereof.

In some embodiments, the compound of formula (V) is selected from the group consisting of:

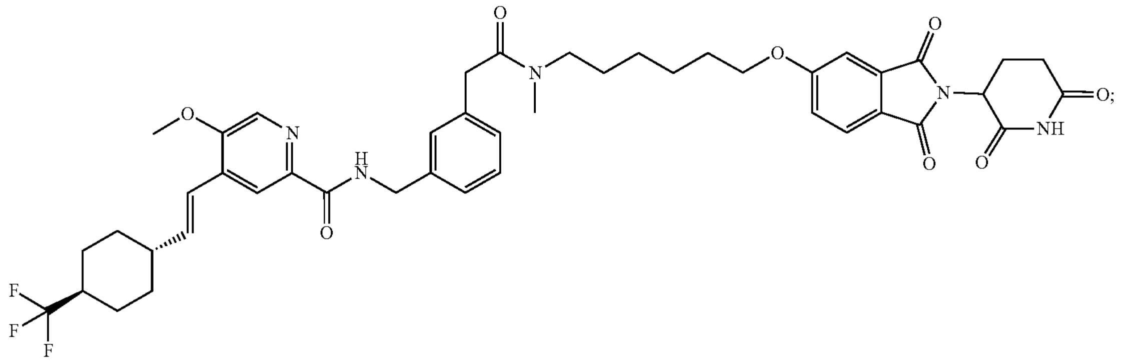

-continued
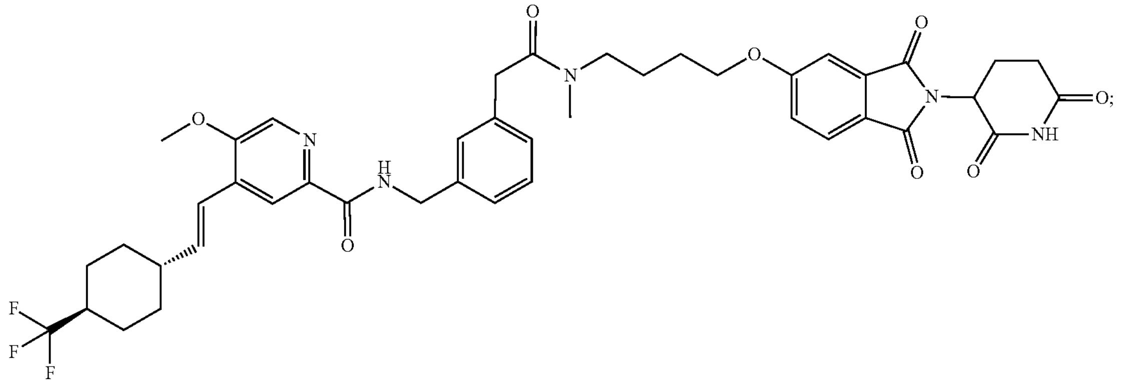
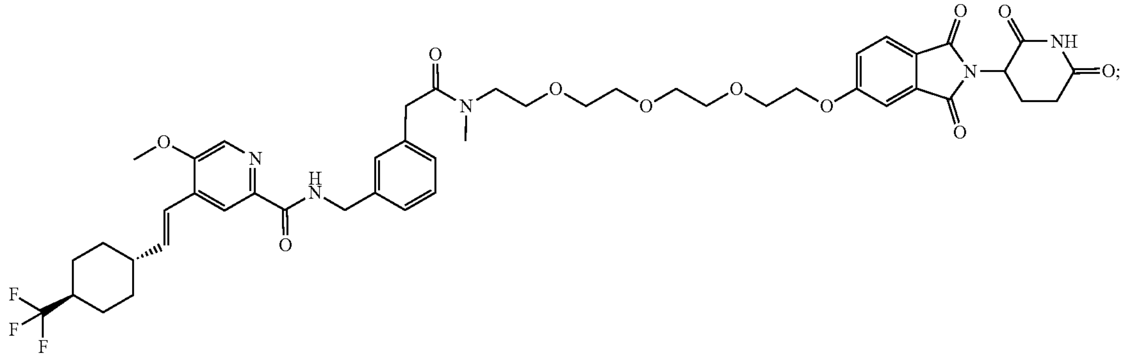
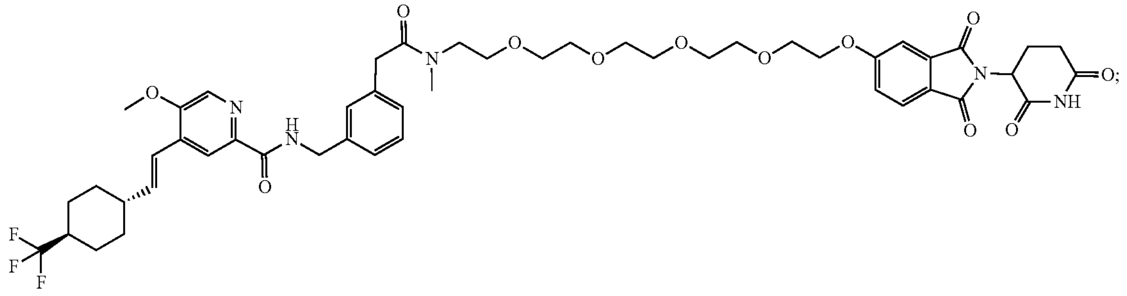
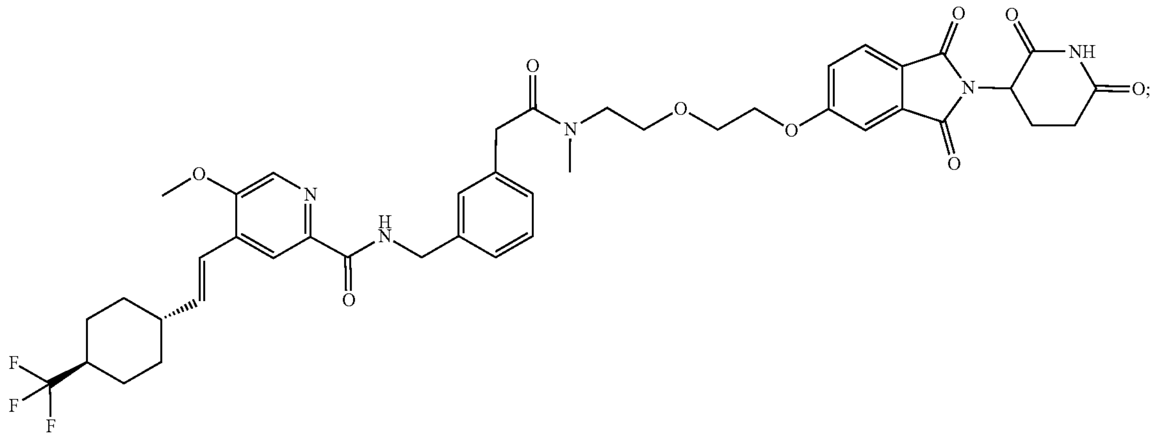

-continued
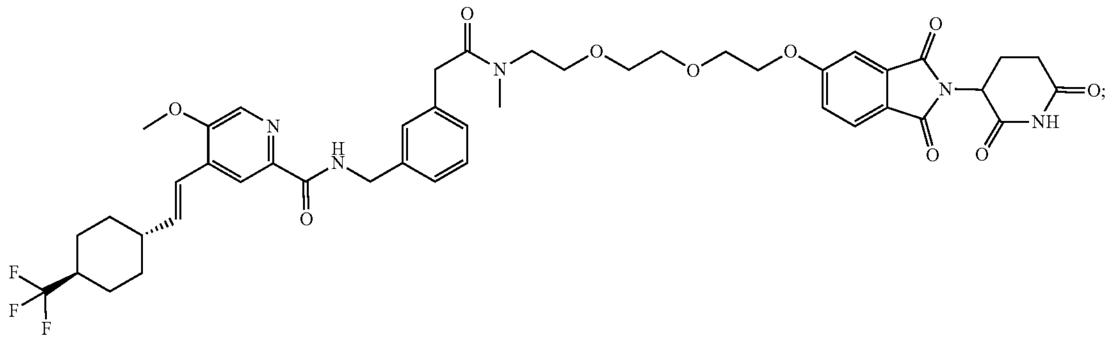
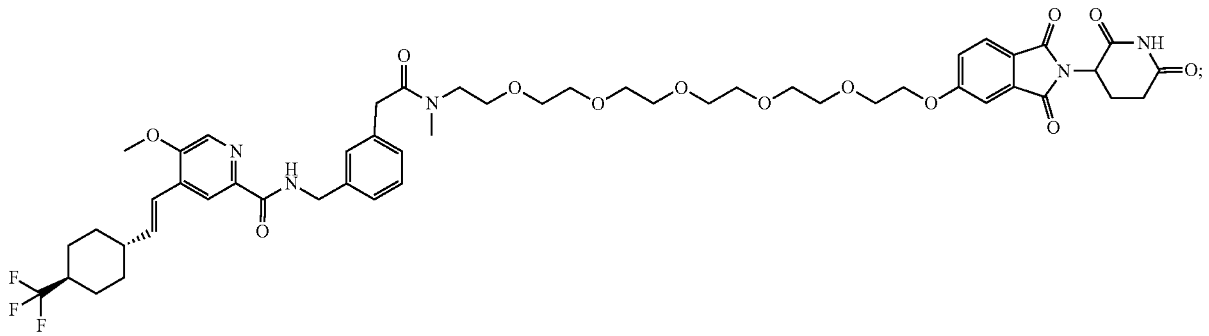
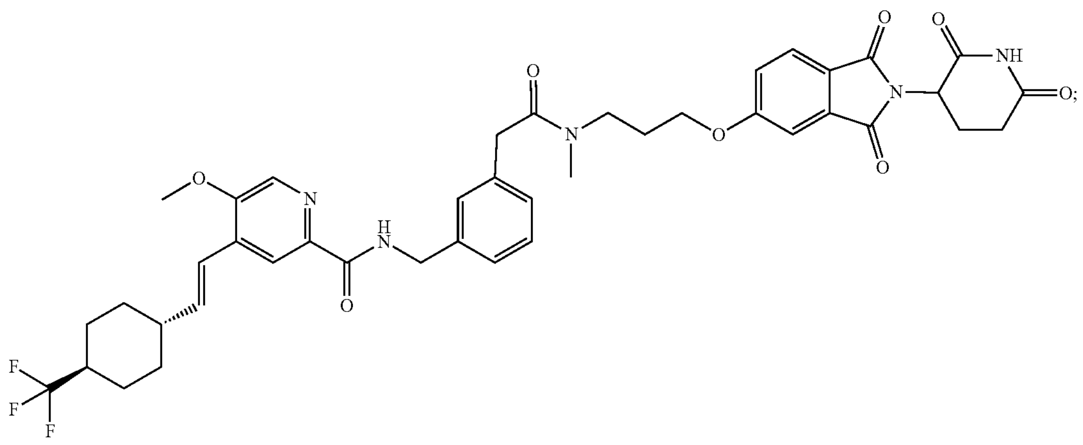
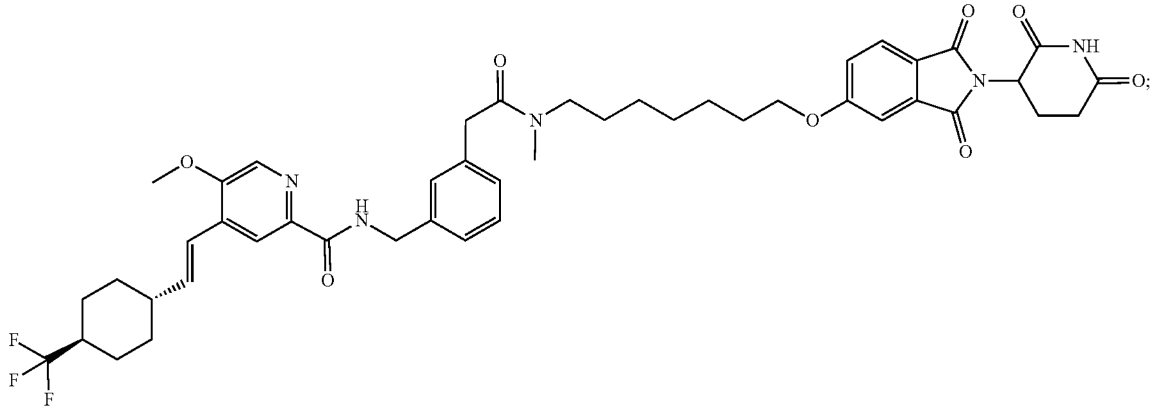
and

-continued

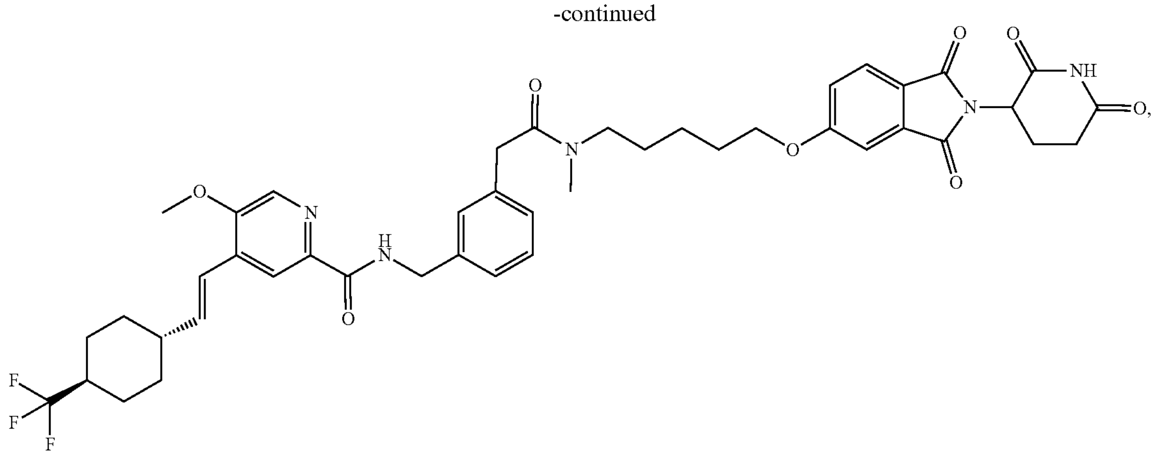

or a stereoisomer or pharmaceutically acceptable salt thereof.

In certain embodiments, the E3 ubiquitin ligase ligand is a VHL ligand. In some embodiments, the VHL ligand has a structure of formula (VI):

(VI)

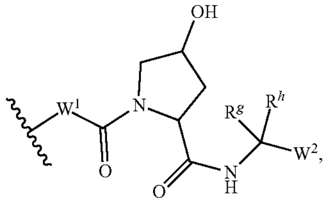

wherein: $W^1$ is CH—$C_{1-12}$alkyl, $C_{6-20}$aryl, or 5-20 membered heteroaryl; and $W^2$ is $C_{6-20}$aryl or 5-20 membered heteroaryl, wherein the $C_{6-20}$aryl or 5-20 membered heteroaryl of $W^1$ or $W^2$ is independently optionally substituted with $C_{1-12}$alkyl, $C_{3-10}$cycloalkyl, 3-10 membered heterocyclyl, $C_{6-20}$aryl, or 5-20 membered heteroaryl, each of which is further optionally substituted with one or more halo, cyano, hydroxy, $N(R^x)(R^y)$, $C_{1-12}$alkyl, $C_{1-12}$haloalkyl, O—$C_{1-12}$alkyl, $C_{3-10}$cycloalkyl, 3-10 membered heterocyclyl, $C_{6-20}$aryl, or 5-20 membered heteroaryl; and $R^g$ and $R^h$ are each independently selected from the group consisting of H, halo, cyano, hydroxy, $NH_2$, $C_{1-12}$alkyl, $C_{1-12}$haloalkyl, O—$C_{1-12}$alkyl, $C_{3-10}$cycloalkyl, 3-10 membered heterocyclyl, $C_{6-20}$aryl, and 5-20 membered heteroaryl.

In some embodiments, wherein the ligase ligand is a VHL ligand, the compound has a structure of formula (VII):

(VII)

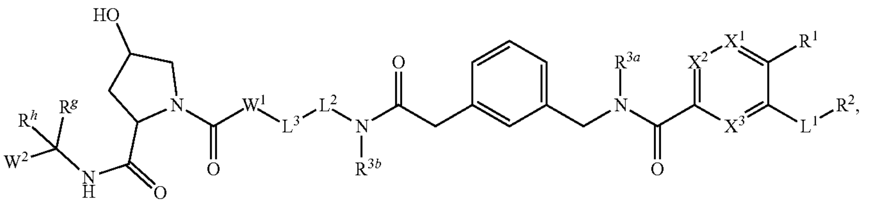

or a stereoisomer or pharmaceutically acceptable salt thereof.

In some embodiments, the compound of formula (VII) is a compound of formula (VIII)

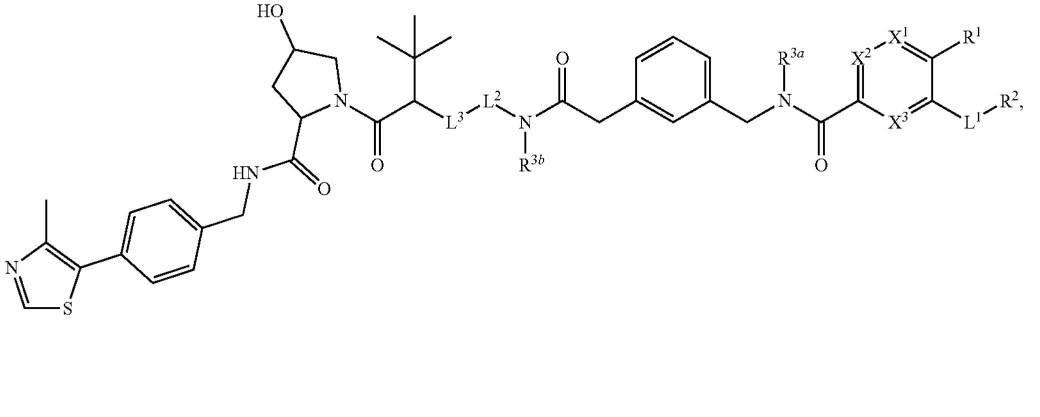

or a stereoisomer or pharmaceutically acceptable salt thereof.
In certain embodiments, the compound of formula (VIII) is selected from the group consisting of:
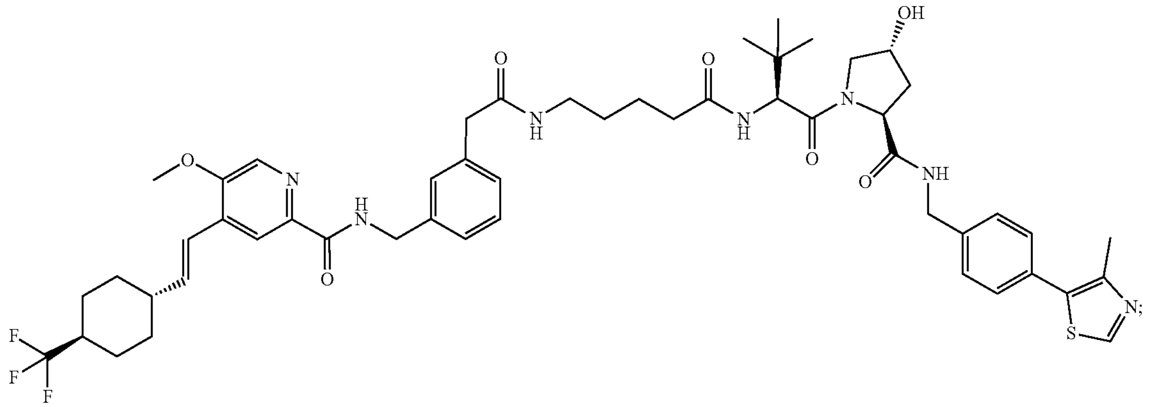
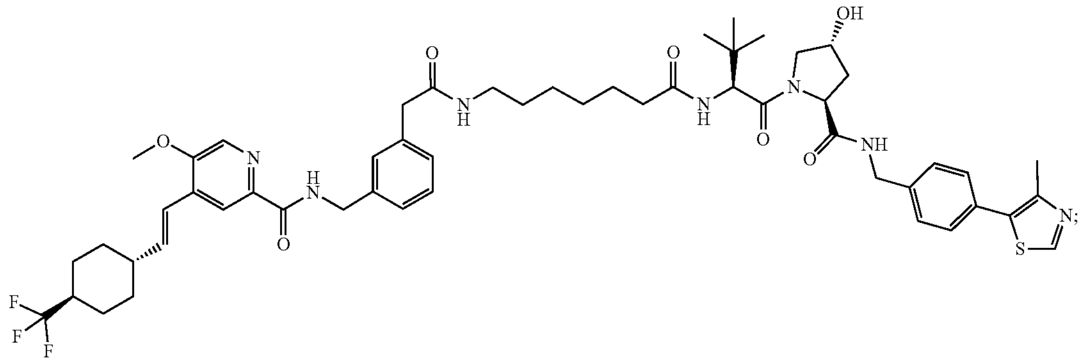
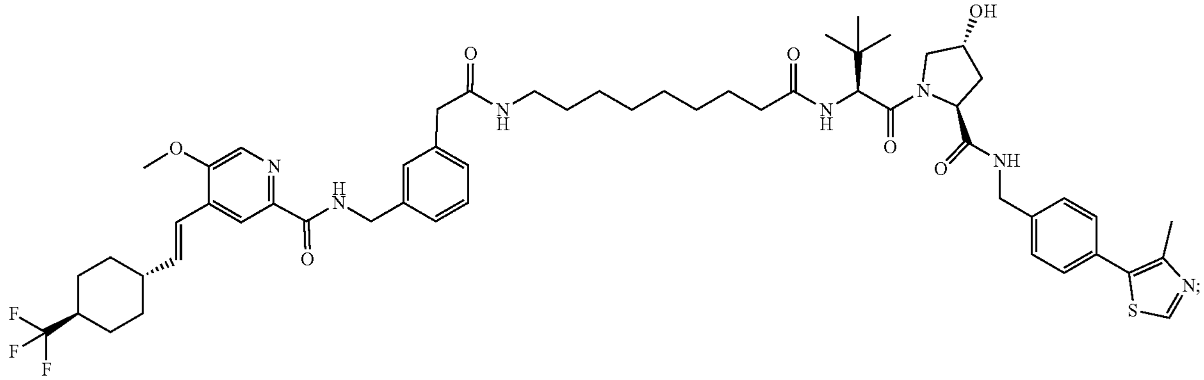
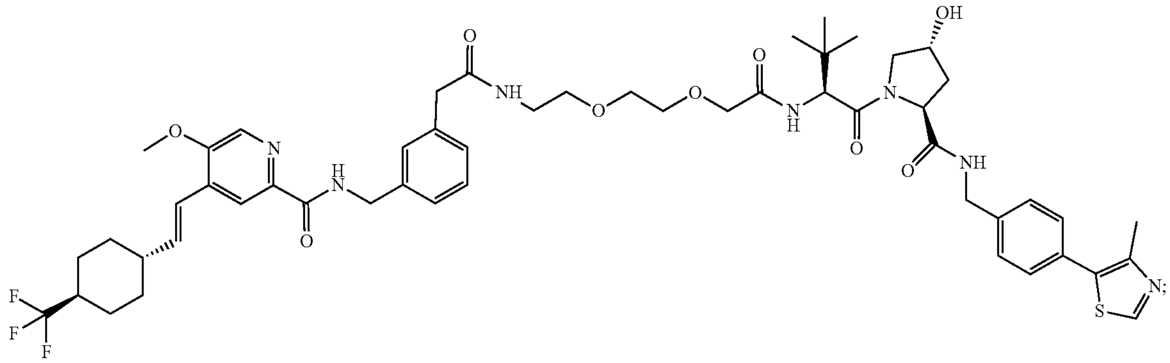

-continued

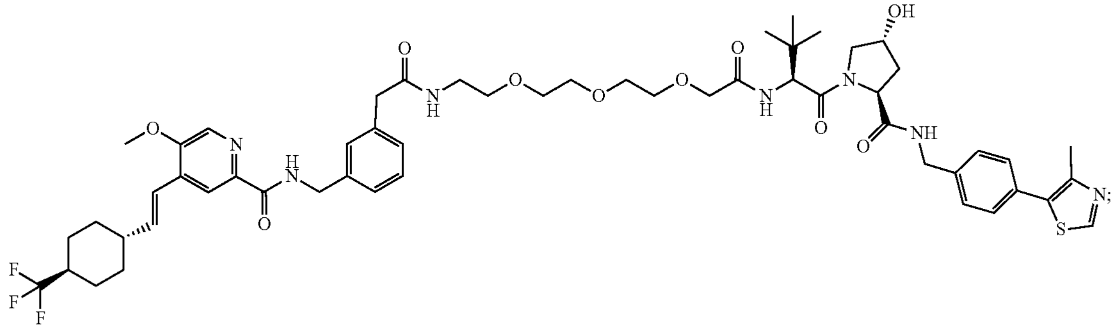

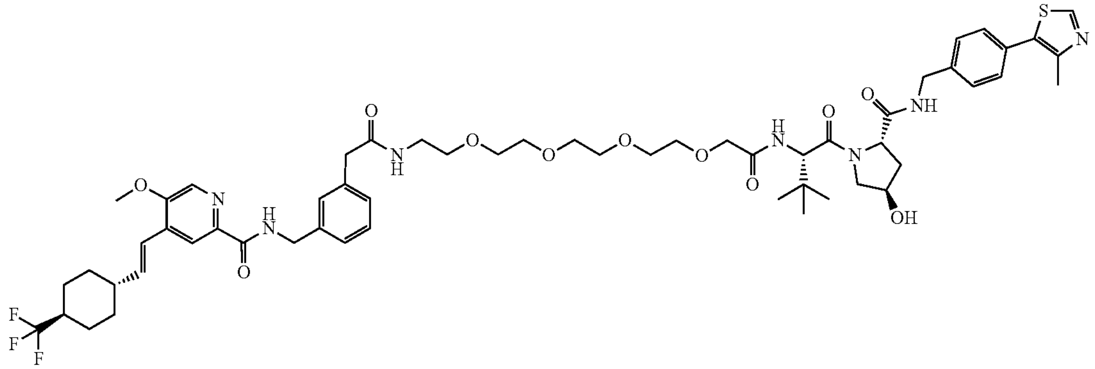

and

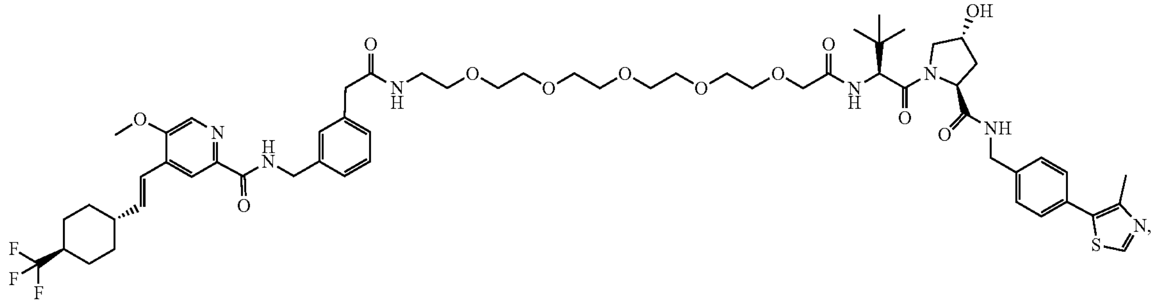

or a stereoisomer or pharmaceutically acceptable salt thereof.

In some embodiments, the E3 ubiquitin ligand is an XIAP ligand. In certain embodiments, the XIAP ligand has a structure of formula (IX):

(IX)

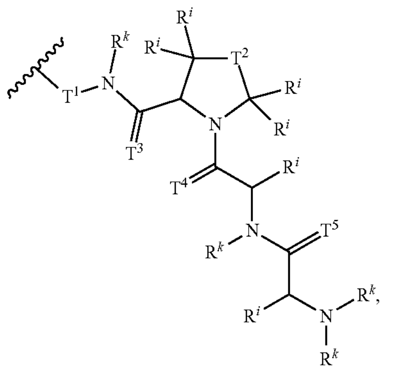

wherein: $T^1$ is a 3-10 membered heterocyclyl or 5-20 membered heteroaryl, wherein: the 3-10 membered heterocyclyl or 5-20 membered heteroaryl is independently optionally substituted with one or more halo, cyano, hydroxy, $N(R^x)(R^y)$, $C_{1-12}$alkyl, $C_{1-12}$haloalkyl, O—$C_{1-12}$alkyl, $C_{3-10}$cycloalkyl, 3-10 membered heterocyclyl, $C_{6-20}$aryl, or 5-20 membered heteroaryl; $T^2$ is $C(R^i)_2$, O, or S; $T^3$, $T^4$, and $T^5$ are each independently O or S; each $R^i$ is independently H, halo, cyano, hydroxy, $N(R^x)(R^y)$, $C_{1-12}$alkyl, $C_{1-12}$haloalkyl, O—$C_{1-12}$alkyl, $C_{3-10}$cycloalkyl, 3-10 membered heterocyclyl, $C_{6-20}$aryl, or 5-20 membered heteroaryl; and each $R^k$ is independently H, hydroxy, halo, $C_{1-12}$alkyl, $C_{1-12}$haloalkyl, $C_{3-10}$cycloalkyl, 3-10 membered heterocyclyl, $C_{6-20}$aryl, or 5-20 membered heteroaryl.

In some embodiments, wherein the ligase ligand is an XIAP ligand, the compound has a structure of formula (X):

(X)
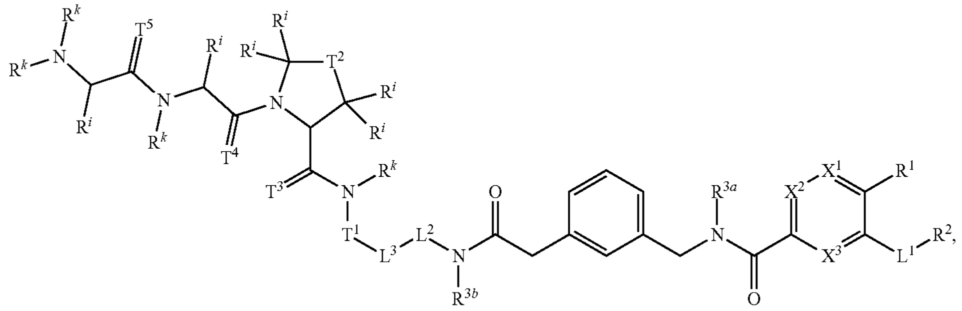
or a stereoisomer or pharmaceutically acceptable salt thereof.
In some embodiments, the compound of formula (X) is a compound of formula (XI):
(XI)
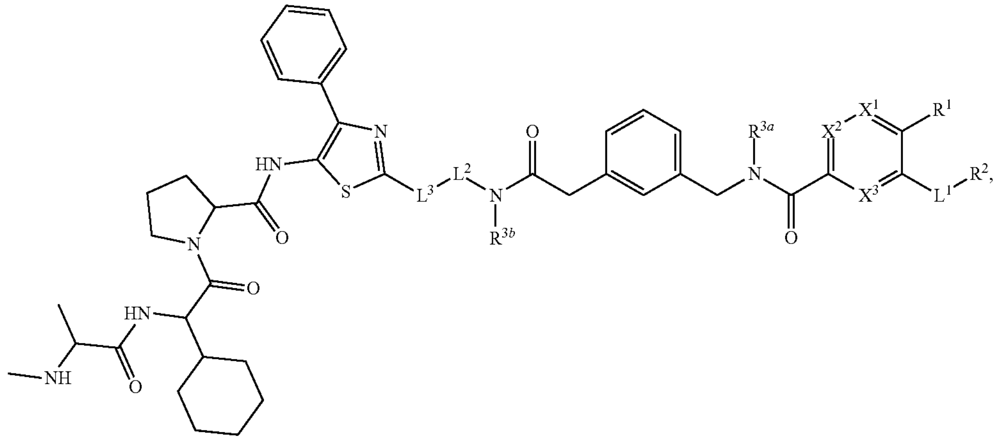
or a stereoisomer or pharmaceutically acceptable salt thereof.
In some embodiments, the compound of formula (XI) is selected from the group consisting of:
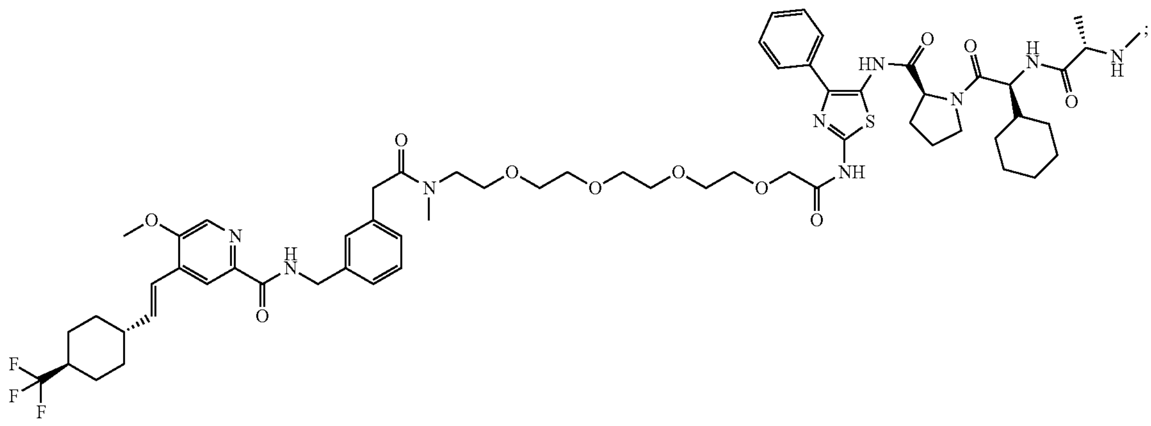
;

-continued

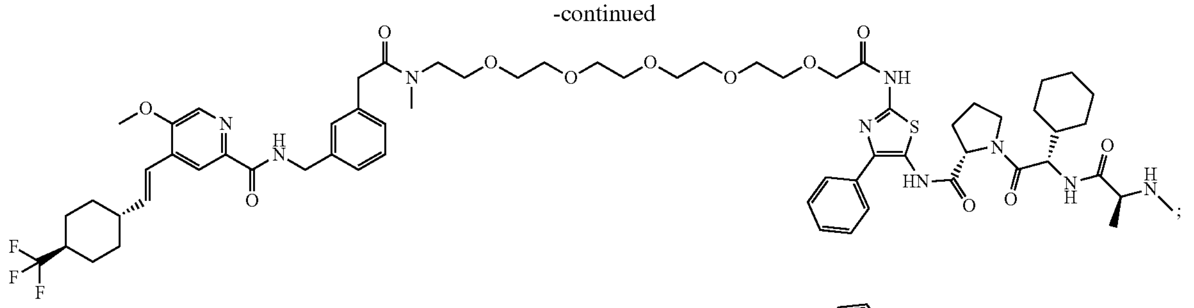

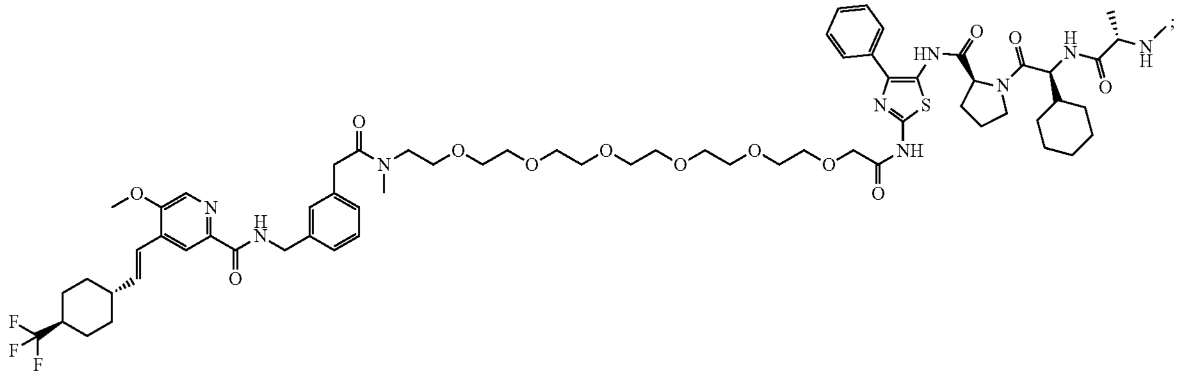

and

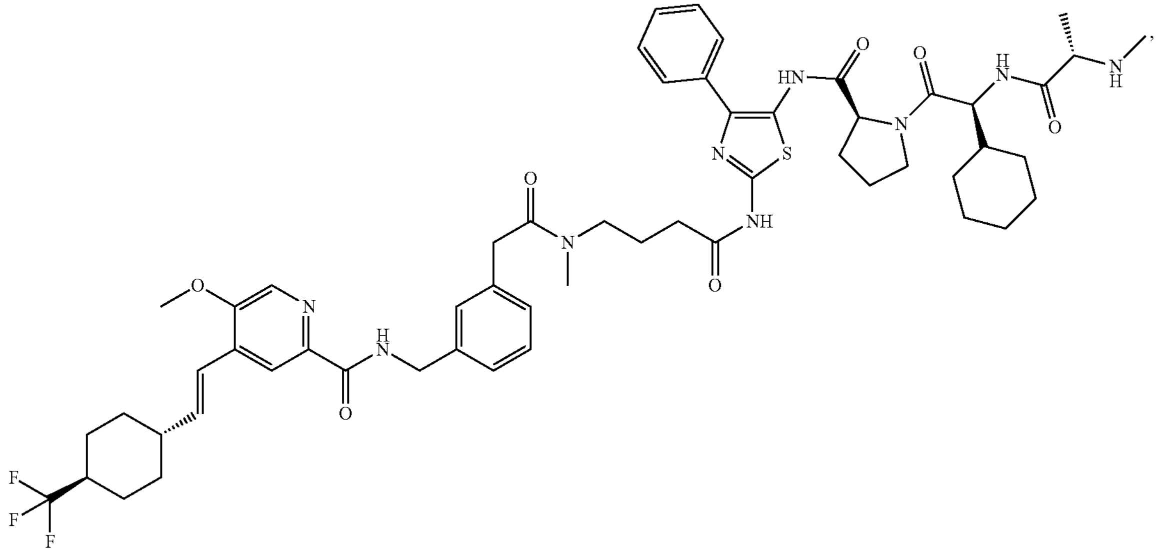

or a stereoisomer or pharmaceutically acceptable salt thereof.

Various ligase ligands can be used in accordance with the invention. In some embodiments, the ligase ligand is an E3 ubiquitin ligase ligand. In certain embodiments, the ligase ligand is a cereblon ligand. In other embodiments, the ligase ligand is a VHL ligand. In still other embodiments, the ligase ligand is an XIAP ligand.

It is to be understood that the scope of the ligase ligands encompassed in this specification is inclusive of, but is not limited to, the particular embodiments and aspects described herein. To that end, variations of the particular embodiments and aspects disclosed may be made which still fall within the scope of the appended claims. For additional embodiments and aspects of the ligase ligands, see, for example, U.S. Pat. Nos. 7,244,851 and 9,694,084 and U.S. Patent Application Publication No. US2016/0272639, each of which is incorporated herein in its entirety.

In some embodiments, provided is a compound of any one of the formulae described herein, or a stereoisomer or pharmaceutically acceptable salt thereof, wherein $L^2$ of the linker moiety is $-(CH_2)_n-$, wherein n is 1-12. In other embodiments, n is 1-10. In still other embodiments, n is 1-8. In further embodiments, n is 1-6. In still further embodiments, n is 1-4. In other embodiments, n is 1-2.

In some embodiments, provided is a compound of any one of the formulae provided herein, or a stereoisomer or pharmaceutically acceptable salt thereof, wherein $L^2$ is $-(CH_2CH_2O)_n-$, wherein n is 1-12. In other embodiments, n is 1-10. In still other embodiments, n is 1-8. In further embodiments, n is 1-6. In still further embodiments, n is 1-4. In other embodiments, n is 1-2.

In certain embodiments, $L^2$ is a group comprising one or more covalently connected structural units of Y wherein each Y unit is coupled to at least one of a ligase ligand, a $L^3$, a

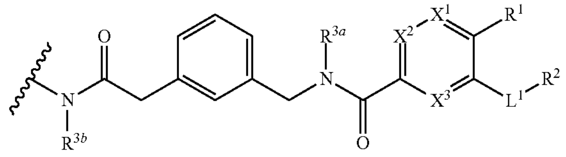

moiety, another Y unit, or a combination thereof. In certain embodiments, a Y unit links a ligase ligand, a $L^3$, a

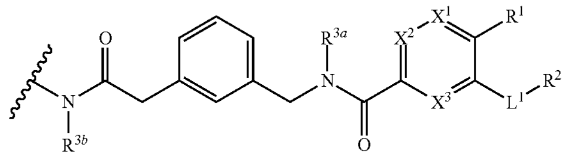

moiety, or a combination thereof, directly to another ligase ligand, $L^3$,

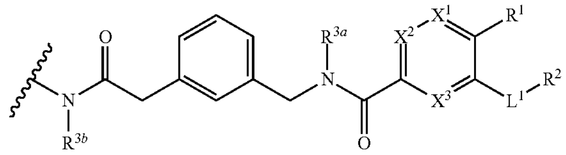

moiety, or a combination thereof. In other embodiments, a Y unit links a ligase ligand, a $L^3$, a

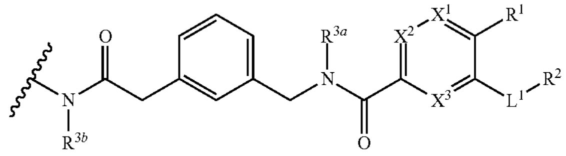

moiety, or a combination thereof, indirectly to another ligase ligand, $L^3$, a

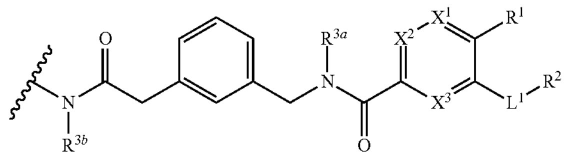

moiety, or a combination thereof, through one or more different Y unit(s). In any of the embodiments disclosed herein, one or more covalently connected structural units of Y may be coupled to $L^3$ or to a ligase ligand. In certain embodiments, the structural units of Y may be connected to the $L^3$ or the ligase ligand at one or more points of connection. In other embodiments, one or more covalently connected structural units of Y may be coupled to a

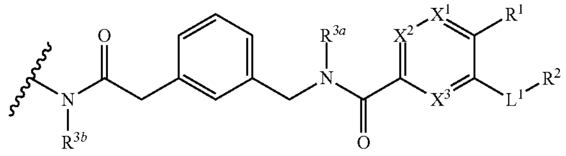

moiety and also to a $L^3$ or a ligase ligand of the present disclosure to form a heterobifunctional molecule.

In certain embodiments, $L^2$ is $(Y)_q$, and each Y unit is independently selected from the group consisting of a bond, $CR^{La}R^{Lb}$, O, S, SO, $SO_2$, $NR^{Lc}$, $SO_2NR^{Lc}$, $SONR^{Lc}$, $CONR^{Lc}$, $NR^{Lc}CONR^{Ld}$, $NR^{Lc}SO_2NR^{Ld}$, CO, $CR^{La}{=}CR^{Lb}$, C≡C, $SiR^{La}R^{Lb}$, $P(O)R^{La}$, $P(O)OR^{La}$, $NR^{Lc}C({=}NCN)NR^{Ld}$, $NR^{Lc}C({=}NCN)$, $NR^{Lc}C({=}CNO_2)NR^{Ld}$, $C_{3-10}$ cycloalkylene, $C_{3-10}$ heterocyclylene, arylene, and heteroarylene, wherein the $C_{3-10}$ cycloalkylene, $C_{3-10}$ heteocyclylene, arylene, and heteroarylene are independently either unsubstituted or substituted with 1, 2, 3, 4, 5, or 6 substituents selected from the group consisting of $R^{La}$, $R^{Lb}$, and combinations thereof, where $R^{La}$ or $R^{Lb}$, each independently, can be linked to other Y groups to form cycloalkylene and/or heterocyclylene moiety, wherein the cycloalkylene and heterocyclylene moieties are independently unsubstituted or substituted with 1, 2, 3, or 4 $R^{Le}$ groups; wherein $R^{La}$, $R^{Lb}$, $R^{Lc}$, $R^{Ld}$ and $R^{Le}$ are, each independently, selected from the group consisting of H, halogen, $R^{Lf}$, $—OR^{Lh}$, $—SR^{Lh}$, $—NHR^{Lh}$, $—N(R^{Lh})_2$, $C_3$-$C_{10}$cycloalkyl, aryl, heteroaryl, $C_3$-$C_{11}$heterocyclyl, $—N(R^{Lg})(R^{Lf})$, —OH, $—NH_2$, —SH, $—SO_2R^{Lf}$, $P(O)(OR^{Lf})(R^{Lf})$, $—P(O)(OR^{Lf})_2$, $—C{\equiv}C—R^{Lf}$, —C≡CH, $—CH{=}CH(R^{Lf})$, $—C(R^{Lf}){=}CH(R^{Lf})$, $—C(R^{Lf}){=}C(R^{Lf})_2$, $—Si(OH)_3$, $—Si(R^{Lf})_3$, $—Si(OH)(R^{Lf})_2$, $—COR^{Lf}$, $—CO_2H$, -halogen, —CN, $—CF_3$, $—CHF_2$, $—CH_2F$, $—NO_2$, $—SF_5$, $—SO_2NHR^{Lf}$, $—SO_2N(R^{Lf})_2$, $—SONHR^{Lf}$, $—SON(R^{Lf})_2$, $—CONHR^{Lf}$, $—CON(R^{Lf})_2$, $—N(R^{Lf})CONH(R^{Lf})$, $—N(R^{Lf})CON(R^{Lf})_2$, $—NHCONH(R^{Lf})$, $—NHCON(R^{Lf})_2$, $—NHCONH_2$, $—N(R^{Lf})SO_2NH(R^{Lf})$, $—N(R^{Lf})SO_2N(R^{Lf})_2$, $—NHSO_2NH(R^{Lf})$, $—NHSO_2N(R^{Lf})_2$, and $—NHSO_2NH_2$, wherein $R^{Lf}$ is a substituted or unsubstituted $C_{1-12}$alkyl; $R^{Lg}$ is a substituted or unsubstituted $C_{3-10}$cycloalkyl; and $R^{L}h$ is $R^{Lf}$ or $R^{Lg}$.

In certain embodiments, q is an integer greater than or equal to 1.

In certain embodiments, q is greater than 2.

In certain embodiments, q is 2.

In certain embodiments, q is 1. In some embodiments, q is 1 and Y is a group that is connected to a ligase ligand or a $L^3$ and to a

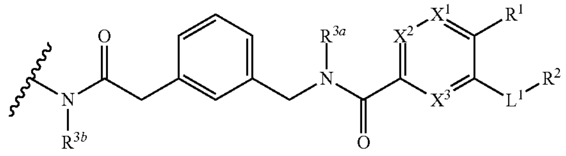

moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, $L^2$ is selected from the group consisting of:

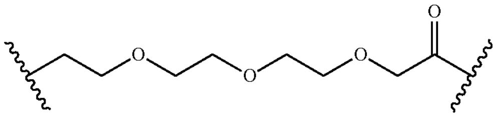
;
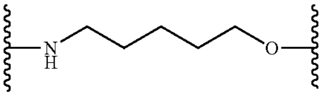
;
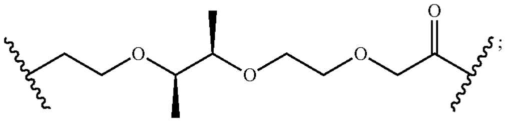
;
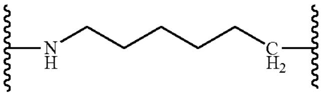
;
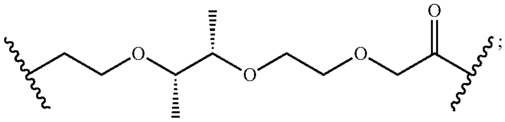
;
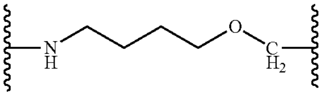
;
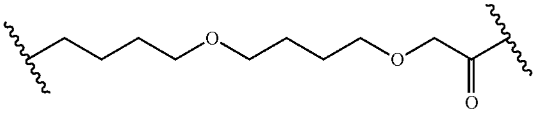
;
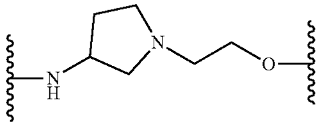
;
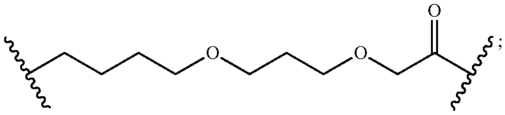
;
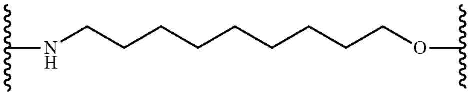
;
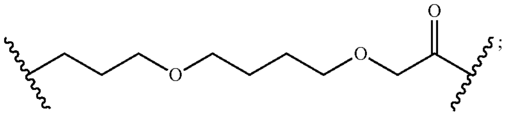
;
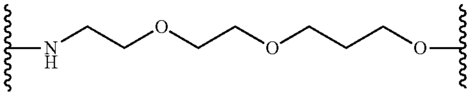
;
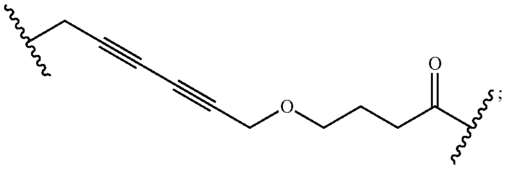
;
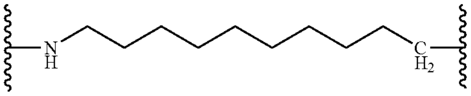
;
-continued
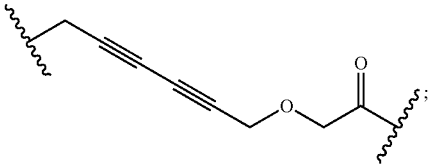
;
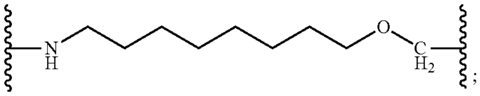
;
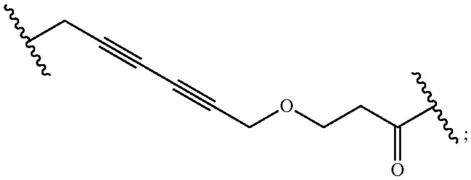
;
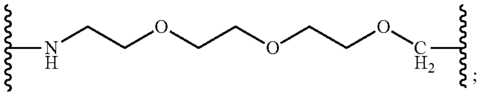
;
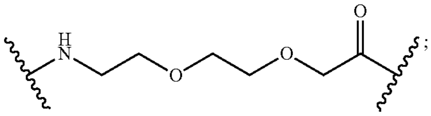
;
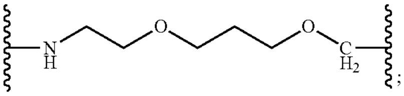
;
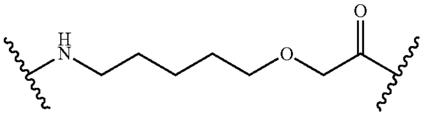
;
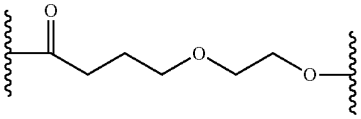
;
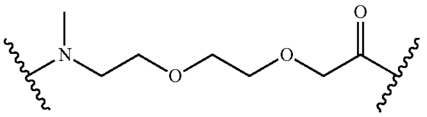
;
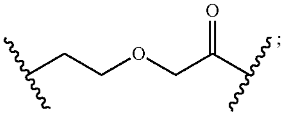
;
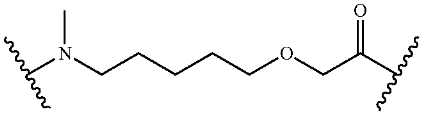
;
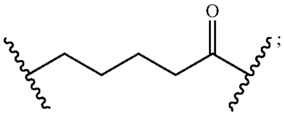
;
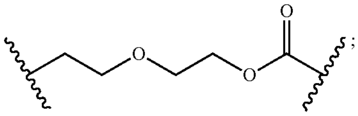
;
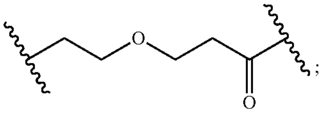
;

-continued
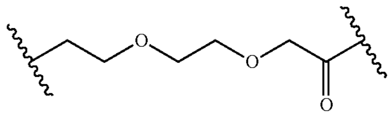
;
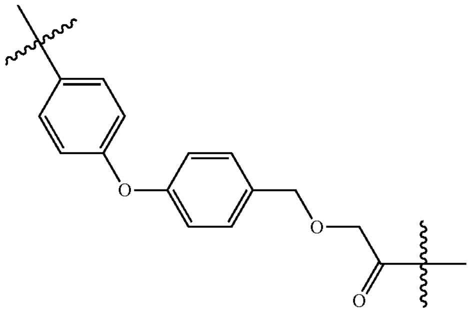
;
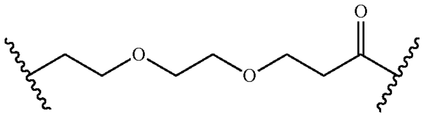
;
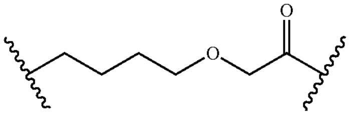
;
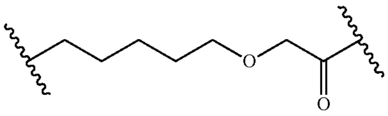
;
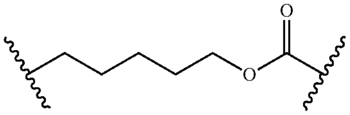
;
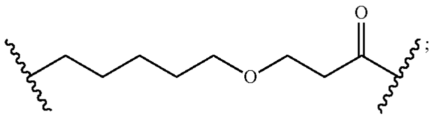
;
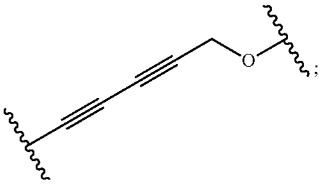
;
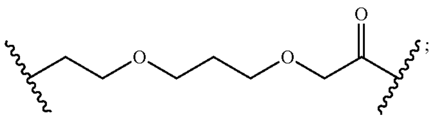
;
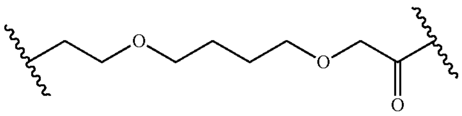
;
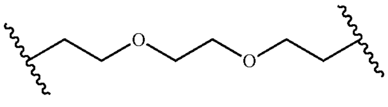
;
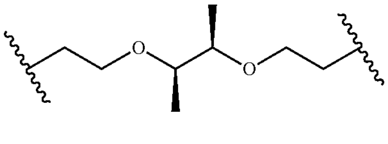
;
-continued
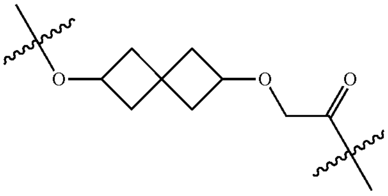
;
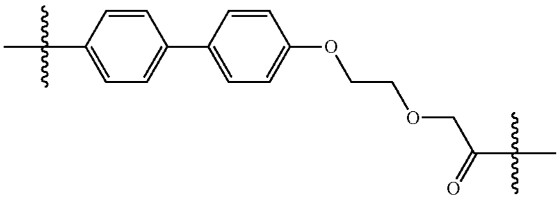
;
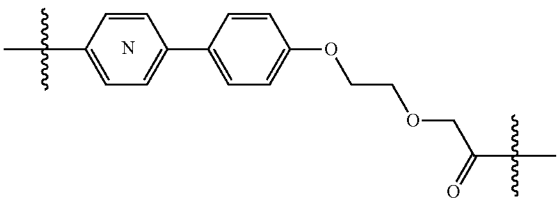
;
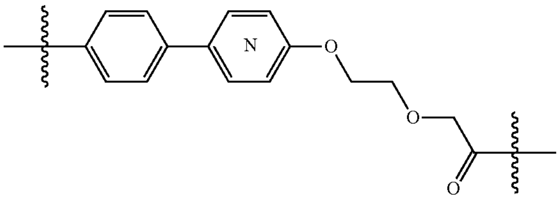
;
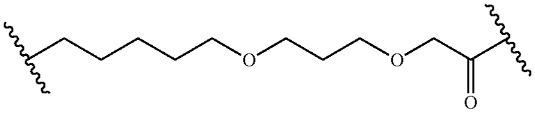
;
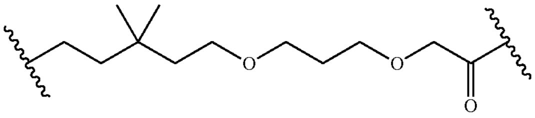
;
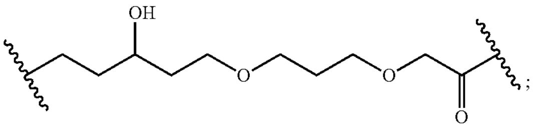
; and
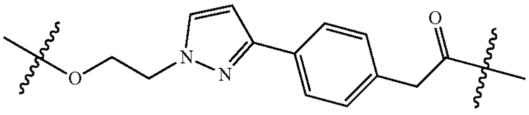
.
In one embodiment, $L^2$ is selected from the group consisting of
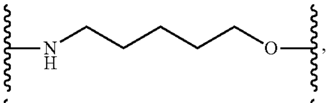
,
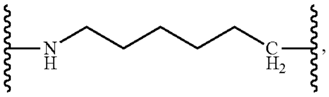
,
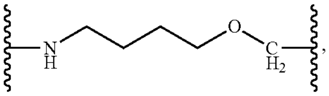
, -continued

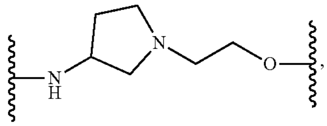

,

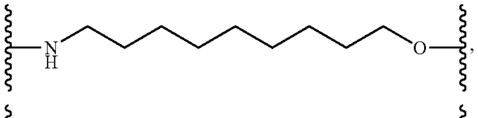

,

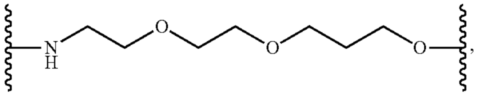

,

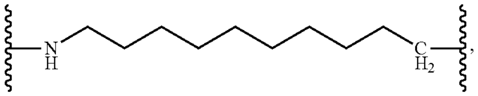

,

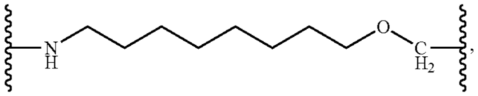

,

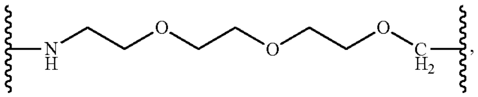

,

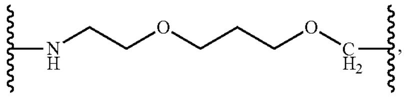

,

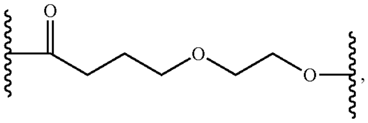

, and

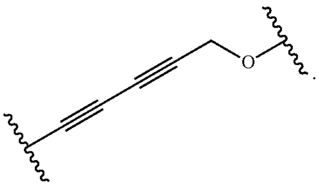

.

In additional embodiments, the $L^2$ is an optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the $L^2$ is substituted with an aryl, phenyl, benzyl, alkyl, alkylene, or heterocycle group. In certain embodiments, the $L^2$ may be asymmetric or symmetrical.

In any of the embodiments of the compounds described herein, the $L^2$ may be any suitable moiety as described herein. In one embodiment, the $L^2$ is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

The ligase ligand or the $L^3$ and the

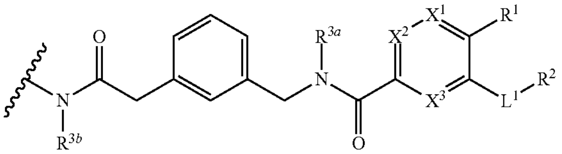

moiety may be covalently linked to the $L^2$ through any group which is appropriate and stable to the chemistry of the linker moiety, [B]. The $L^2$ is independently covalently bonded to the ligase ligand or the $L^3$ and the

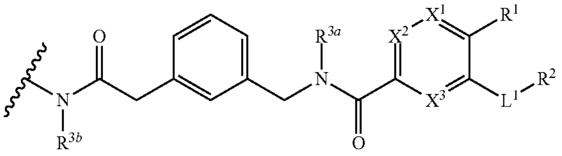

moiety preferably through an amide, ester, thioester, keto group, carbamate (urethane), carbon or ether, each of which groups may be inserted anywhere on the ligase ligand or the $L^3$ and the

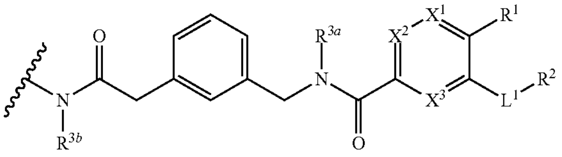

moiety to provide maximum binding of the ligase ligand on the ligase and of the

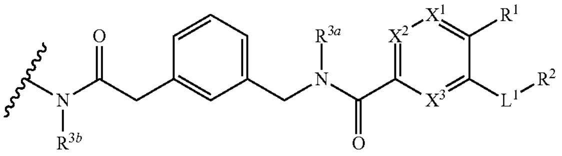

moiety on the target protein to be degraded. In certain aspects wherein the

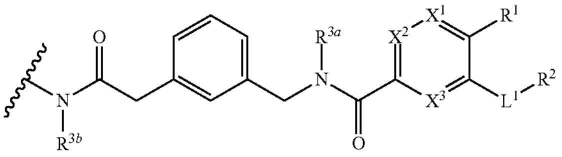

moiety is a ligase ligand, the target protein for degradation may be the ligase itself. In certain aspects, the $L^2$ may be linked to an optionally substituted alkyl, alkylene, alkene or alkyne group, an aryl group or a heterocyclic group on the ligase ligand and/or the $L^3$ and/or on the

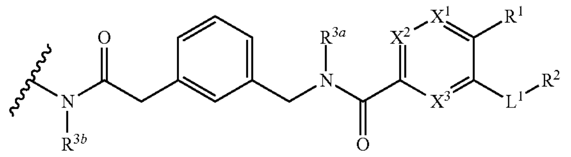

moiety. It is noted that a ligase ligand and/or a $L^3$ and/or a

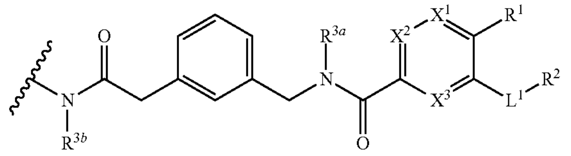

moiety may need to be derivatized to make a chemical functional group that is reactive with a chemical functional group on $L^2$. Alternatively, the $L^2$ may need to be derivatized to include a chemical functional group that can react with a functional group found on the ligase ligand and/or the $L^3$ and/or the

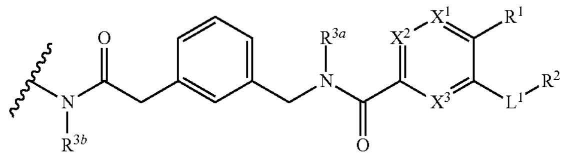

moiety.

In some embodiments, $L^2$ can also be represented by the formula:

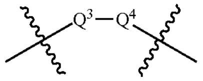

wherein $Q^3$ is a group which links the ligase ligand or the $L^3$ to $Q^4$; and $Q^4$ is a group linking $Q^3$ to the

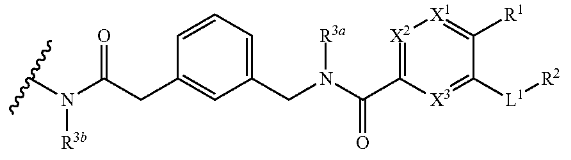

moiety.

In some embodiments, $Q^3$ is absent, such that it is a bond. In other embodiments, $Q^3$ is $—(CH_2)_j—O$, $—(CHR^{15})_j—O$, $—[C(R^{15})_2]_j—O$, $—(CH_2)_j—S$, $—(CH_2)_j—N—R^{15}$, $—S$, $—S(O)$, $—S(O)_2$, $—OP(O)OR^{15}$, $—Si(R^{15})_2$, or a $(CH_2)_j$-$Q^5Q^6$ group wherein $Q^5Q^6$ forms an amide group, or a urethane group, ester or thioester group, or a

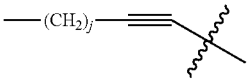

or

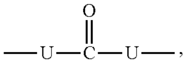

, where, each $R^{15}$ is H, or a $C_1$-$C_3$ alkyl, an alkanol group or a heterocycle (including a water soluble heterocycle, preferably, a morpholino, piperidine or piperazine group to promote water solubility of the linker group); each U is independently a bond, O, S or $N—R^{15}$; and each j is independently 0 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5.

In embodiments, $Q^4$ is a

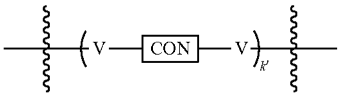

where each V is independently a bond,

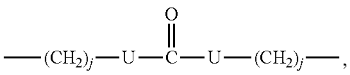

, $—(CH_2)_{m'}—$, or

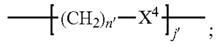

;

j' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

k' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; preferably k is 1, 2, 3, 4, or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

$X^4$ is O, S or $N—R^{15}$, preferably O;

U is the same as above;

and CON is a connector group (which may be a bond) which connects $Q^3$ to $Q^4$, when present in $L^2$.

In embodiments, CON is a bond or is a heterocycle, including a water soluble heterocycle, such as a piperazinyl or other group, or a group selected from:

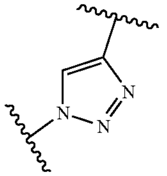

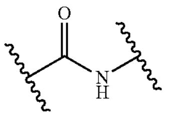

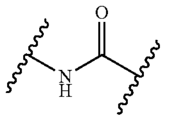

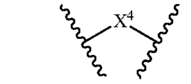

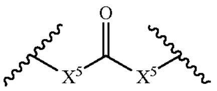

or

-continued

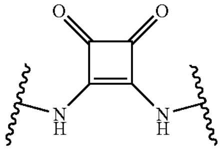

wherein $X^4$ is cycloalkyl, heterocyclyl, O, S, $NR^{12}$, S(O), $S(O)_2$, $-S(O)_2O$, $-OS(O)_2$, $OP(O)OR^{15}$, $Si(R^{15})_2$, or $OS(O)_2O$;

$X^5$ is O, S, $CHR^{12}$, $NR^{12}$;

$R^{12}$ is H or a $C_1$-$C_3$ alkyl group optionally substituted with one or two hydroxyl groups, or a pharmaceutically acceptable salt, enantiomer or stereoisomer thereof, and $R^{15}$ is as defined above.

In some embodiments, provided is a compound of any one of the formulae described herein, or a stereoisomer or pharmaceutically acceptable salt thereof, wherein, in combination with any of the foregoing $L^2$, $L^3$ is a bond. In other embodiments, in combination with any of the foregoing $L^2$, $L^3$ is —O—. In still other embodiments, in combination with any of the foregoing $L^2$, $L^3$ is

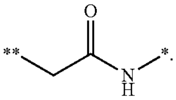

In some embodiments, provided is a compound of any one of the formulae described herein, or a stereoisomer or pharmaceutically acceptable salt thereof, wherein $L^2$ of the linker moiety is $-(CH_2)_n-$, wherein n is 1-12, and $L^3$ is a bond. In other embodiments, $L^2$ of the linker moiety is $-(CH_2)_n-$, wherein n is 1-12, and $L^3$ is —O—. In still other embodiments, $L^2$ of the linker moiety is $-(CH_2)_n-$, wherein n is 1-12, and $L^3$ is

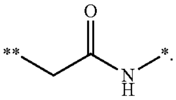

In some embodiments, provided is a compound of any one of the formulae described herein, or a stereoisomer or pharmaceutically acceptable salt thereof, wherein $L^2$ of the linker moiety is $-(CH_2)_n-$, wherein n is 1-6, and $L^3$ is a bond. In other embodiments, $L^2$ of the linker moiety is $-(CH_2)_n-$, wherein n is 1-6, and $L^3$ is —O—. In still other embodiments, $L^2$ of the linker moiety is $-(CH_2)_n-$, wherein n is 1-6, and $L^3$ is

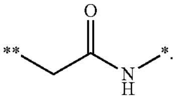

In some embodiments, provided is a compound of any one of the formulae provided herein, or a stereoisomer or pharmaceutically acceptable salt thereof, wherein $L^2$ is $-(CH_2CH_2O)_n-$, wherein n is 1-12, and $L^3$ is a bond. In other embodiments, $L^2$ of the linker moiety is $-(CH_2CH_2O)_n-$, wherein n is 1-12, and $L^3$ is —O—. In still other embodiments, $L^2$ of the linker moiety is $-(CH_2CH_2O)_n-$, wherein n is 1-12, and $L^3$ is

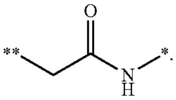

In some embodiments, provided is a compound of any one of the formulae provided herein, or a stereoisomer or pharmaceutically acceptable salt thereof, wherein $L^2$ is $-(CH_2CH_2O)_n-$, wherein n is 1-6, and $L^3$ is a bond. In other embodiments, $L^2$ of the linker moiety is $-(CH_2CH_2O)_n-$, wherein n is 1-6, and $L^3$ is —O—. In still other embodiments, $L^2$ of the linker moiety is $-(CH_2CH_2O)_n-$, wherein n is 1-6, and $L^3$ is

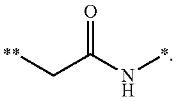

In certain embodiments, the linker moiety, [B], is a group comprising one or more covalently connected structural units of Y, wherein each Y unit is coupled to at least one of a ligase ligand, a

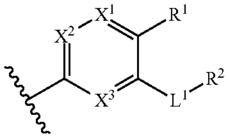

moiety, another Y unit, or a combination thereof. In certain embodiments, a Y unit links a ligase ligand, a

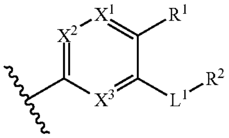

moiety, or a combination thereof, directly to another ligase ligand

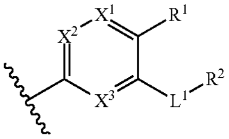

moiety, or combination thereof. In other embodiments, a Y unit links a ligase ligand moiety, a

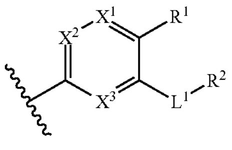

moiety, or a combination thereof, indirectly to another ligase ligand moiety, a

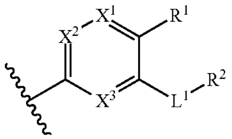

moiety, or a combination thereof, through one or more different Y unit(s). In any of the embodiments disclosed herein, one or more covalently connected structural units of Y may be coupled to the ligase ligand. In certain embodiments, the structural units of Y may be connected to the ligase ligand at one or more points of connection. In other embodiments, one or more covalently connected structural units of Y may be coupled to a

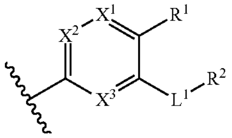

and also to a ligase ligand of the present disclosure to form a heterobifunctional molecule.

In certain embodiments, the linker moiety is $(Y)_q$, and each Y unit is independently selected from the group consisting of a bond, $CR^{La}R^{Lb}$, O, S, SO, $SO_2$, $NR^{Lc}$, $SO_2NR^{Lc}$, $SONR^{Lc}$, $CONR^{Lc}$, $NR^{Lc}CONR^{Ld}$, $NR^{Lc}SO_2NR^{Ld}$, CO, $CR^{La}{=}CR^{Lb}$, C≡C, $SiR^{La}R^{Lb}$, $P(O)R^{La}$, $P(O)OR^{La}$ $NR^{Lc}C({=}NCN)NR^{Ld}$, $NR^{Lc}C({=}NCN)$, $NR^{Lc}C({=}CNO_2)NR^{Ld}$, $C_{3-10}$ cycloalkylene, $C_{3-10}$ heterocyclylene, arylene, and heteroarylene, wherein the $C_{3-10}$ cycloalkylene, $C_{3-10}$ heteocyclylene, arylene, and heteroarylene are independently either unsubstituted or substituted with 1, 2, 3, 4, 5, or 6 substituents selected from the group consisting of $R^{La}$, $R^{Lb}$, and combinations thereof, where $R^{La}$ or $R^{Lb}$, each independently, can be linked to other Y groups to form cycloalkylene and/or heterocyclylene moiety, wherein the cycloalkylene and heterocyclylene moieties are independently unsubstituted or substituted with 1, 2, 3, or 4 $R^{Le}$ groups; wherein $R^{La}$, $R^{Lb}$, $R^{Lc}$, $R^{Ld}$ and $R^{Le}$ are, each independently, selected from the group consisting of H, halogen, $R^{Lf}$, $—OR^{Lh}$, $—SR^{Lh}$, $—NHR^{Lh}$, $—N(R^{Lh})_2$, $C_3$-$C_{10}$cycloalkyl, aryl, heteroaryl, $C_3$-$C_{11}$heterocyclyl, $—N(R^{Lg})(R^{Lf})$, —OH, $—NH_2$, —SH, $—SO_2R^{Lf}$, $P(O)(OR^{Lf})(R^{Lf})$, $—P(O)(OR^{Lf})_2$, $—C{≡}C—R^{Lf}$, —C≡CH, $—CH{=}CH(R^{Lf})$, $—C(R^{Lf}){=}CH(R^{Lf})$, $—C(R^{Lf}){=}C(R^{Lf})_2$, $—Si(OH)_3$, $—Si(R^{Lf})_3$, $—Si(OH)(R^{Lf})_2$, $—COR^{Lf}$, $—CO_2H$, -halogen, —CN, $—CF_3$, $—CHF_2$, $—CH_2F$, $—NO_2$, $—SF_5$, $—SO_2NHR^{Lf}$, $—SO_2N(R^{Lf})_2$, $—SONHR^{Lf}$, $—SON(R^{Lf})_2$, $—CONHR^{Lf}$, $—CON(R^{Lf})_2$, $—N(R^{Lf})CONH(R^{Lf})$, $—N(R^{Lf})CON(R^{Lf})_2$, $—NHCONH(R^{Lf})$, $—NHCON(R^{Lf})_2$, $—NHCONH_2$, $—N(R^{Lf})SO_2NH(R^{Lf})$, $—N(R^{Lf})SO_2N(R^{Lf})_2$, $—NHSO_2NH(R^{Lf})$, $—NHSO_2N(R^{Lf})_2$, and $—NHSO_2NH_2$, wherein $R^{Lf}$ is a substituted or unsubstituted $C_{1-12}$alkyl; $R^{Lg}$ is a substituted or unsubstituted $C_{3-10}$cycloalkyl; and $R^{Lh}$ is $R^{Lf}$ or $R^{Lg}$.

In certain embodiments, q is an integer greater than or equal to 1.

In certain embodiments, q is greater than 2.

In certain embodiments, q is 2.

In certain embodiments, q is 1. In some embodiments, q is 1 and Y is a group that is connected to a ligase ligand and to a

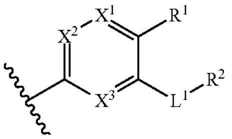

moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, the linker moiety is selected from the group consisting of:

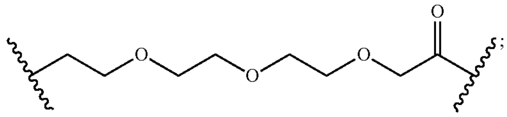;

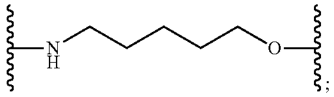;

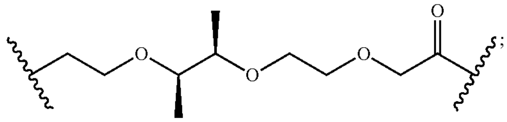;

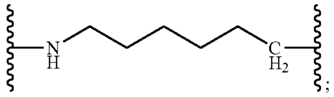;

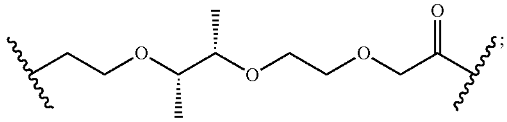;

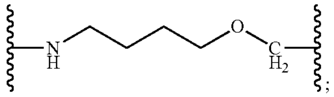;

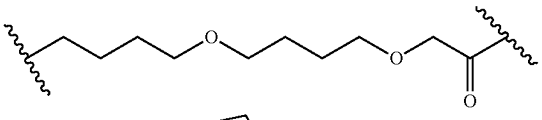;

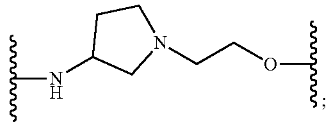;

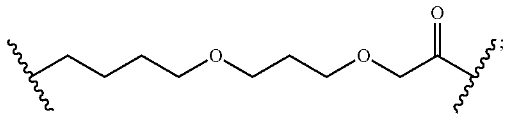;

-continued
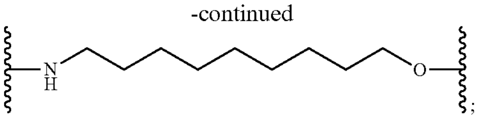
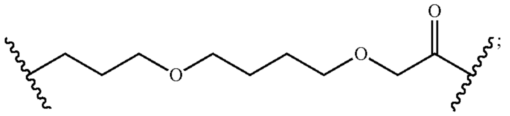
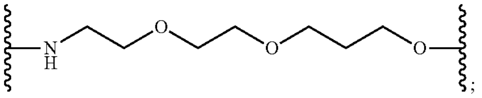
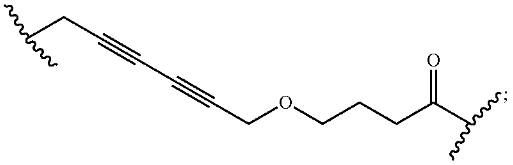
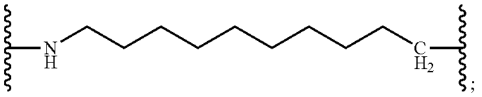
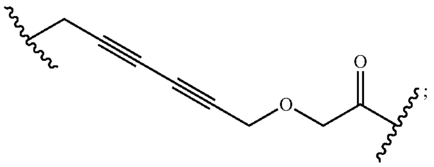
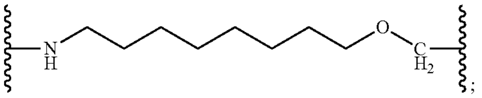
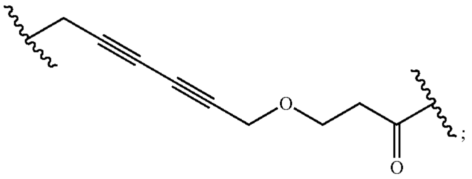
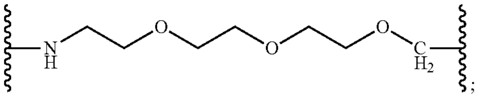
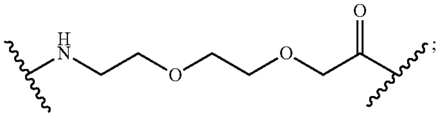
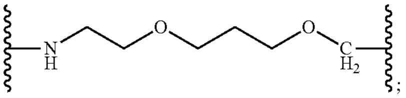
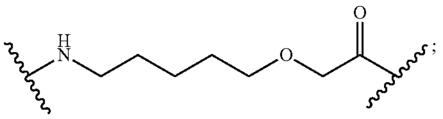
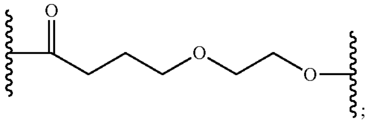
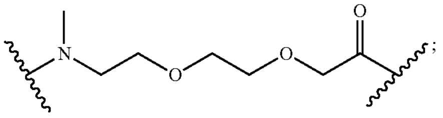
-continued
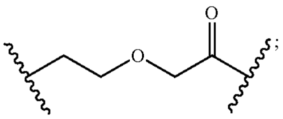
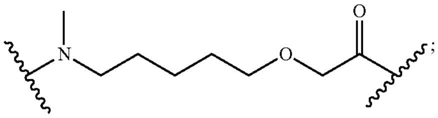
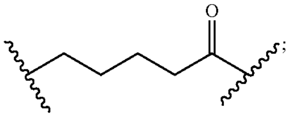
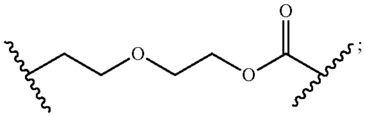
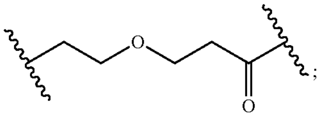
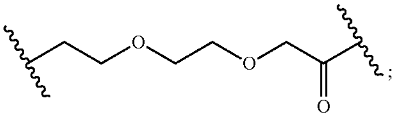
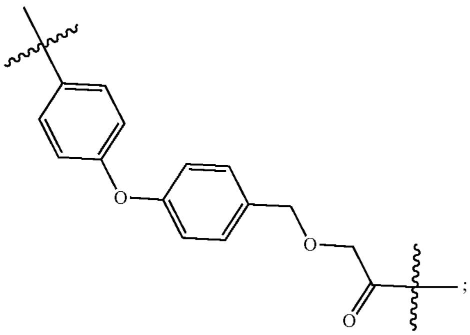
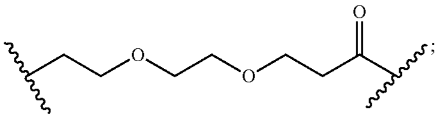
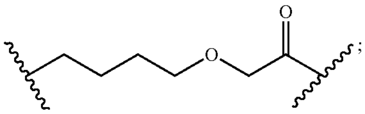
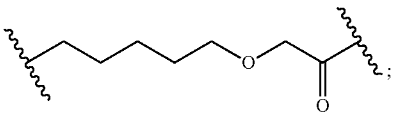
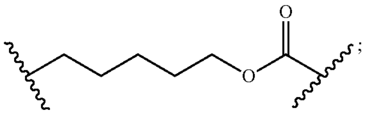
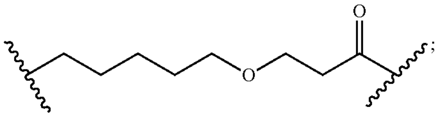

-continued
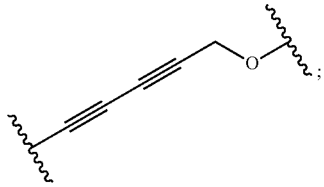;
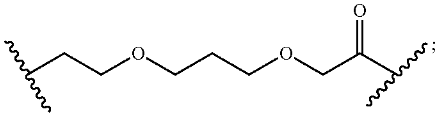;
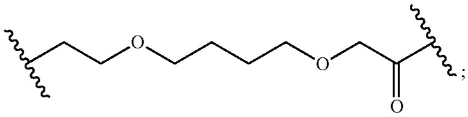;
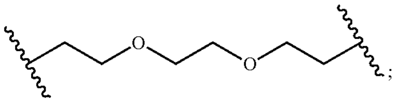;
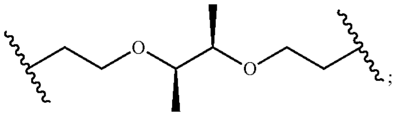;
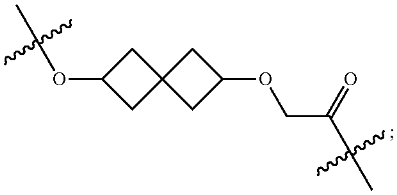;
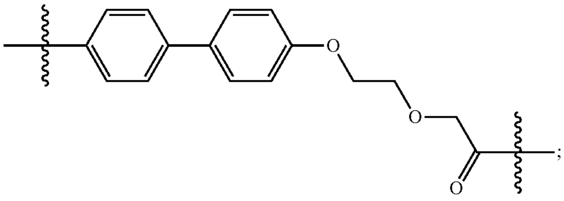;
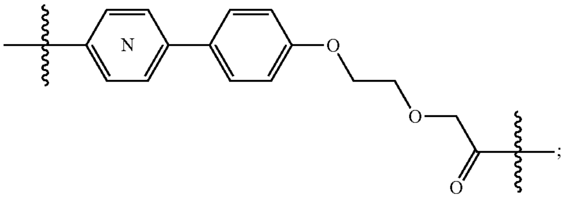;
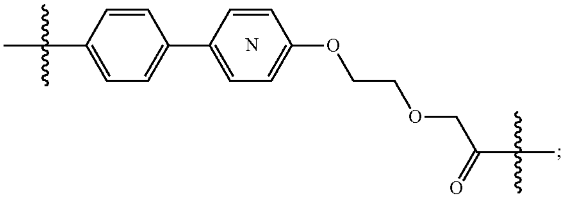;
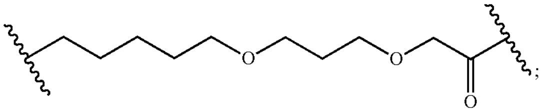;
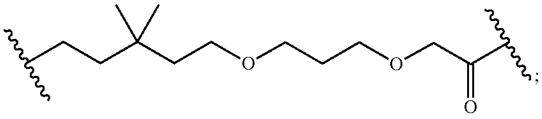;
-continued
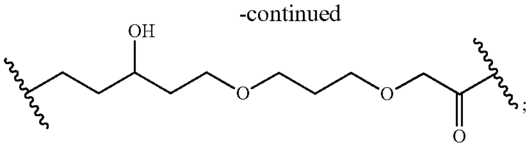; and
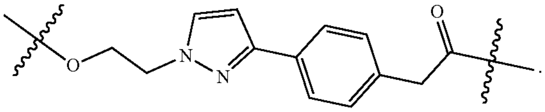.
In one embodiment, the linker is selected from the group consisting of
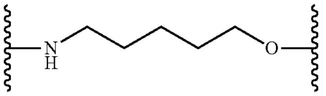,
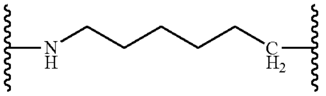,
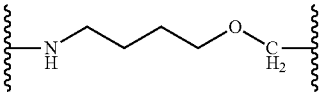,
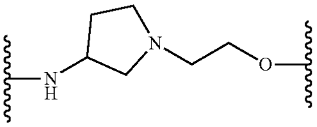,
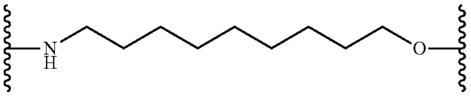,
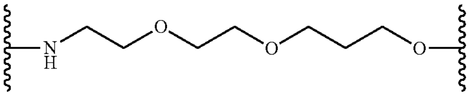,
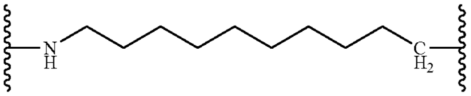,
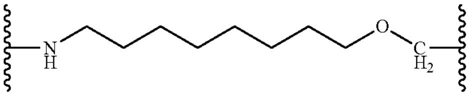,
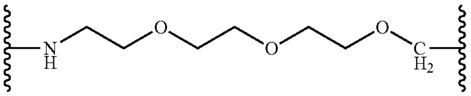,
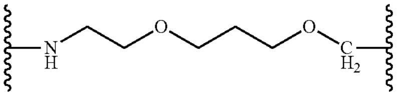,
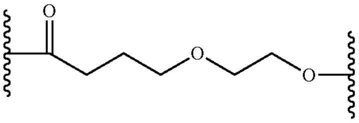, and
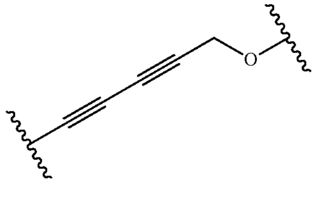.
In additional embodiments, the linker group is an optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

The ligase ligand and the

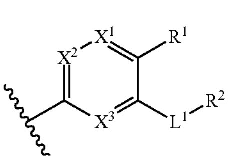

moiety may be covalently linked to the linker group through any group which is appropriate and stable to the chemistry of the linker. The linker is independently covalently bonded to the ligase ligand and the

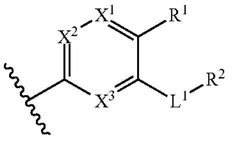

moiety preferably through an amide, ester, thioester, keto group, carbamate (urethane), carbon or ether, each of which groups may be inserted anywhere on the ligase ligand and

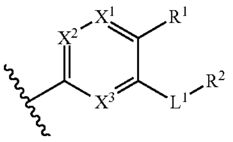

moiety to provide maximum binding of the ligase ligand on the ligase and of the

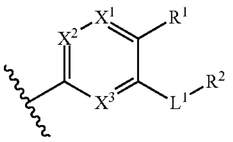

moiety on the target protein to be degraded. In certain aspects where the

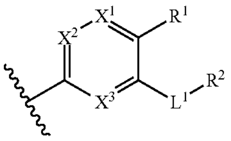

moiety is a ligase ligand, the target protein for degradation may be the ligase itself. In certain aspects, the linker may be linked to an optionally substituted alkyl, alkylene, alkene or alkyne group, an aryl group or a heterocyclic group on the ligase ligand and/or on the

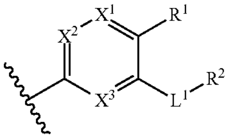

moiety. It is noted that a ligase ligand or a

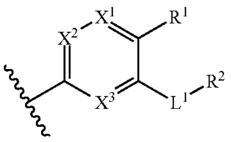

moiety may need to be derivatized to make a chemical functional group that is reactive with a chemical functional group on the linker. Alternatively, the linker may need to be derivatized to include a chemical functional group that can react with a functional group found on the ligase ligand and/or

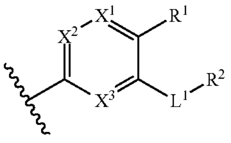

moiety.

The linker moiety can also be represented by the formula:

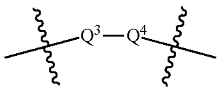

where $Q^3$ is a group which links the ligase ligand to $Q^4$; and $Q^4$ is a group linking $Q^3$ to the

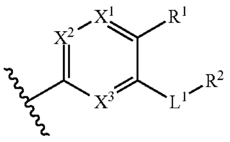

moiety.

In some embodiments, $Q^3$ is absent, such that it is a bond. In other embodiments, $Q^3$ is $-(CH_2)_j-O$, $-(CHR^{15})_j-O$, $-[C(R^{15})_2]_j-O$, $-(CH_2)_j-S$, $-(CH_2)_j-N-R^{15}$, $-S$, $-S(O)$, $-S(O)_2$, $-OP(O)OR^{15}$, $-Si(R^{15})_2$, or a $(CH_2)_j$-$Q^5Q^6$ group wherein $Q^5Q^6$ forms an amide group, or a urethane group, ester or thioester group, or a

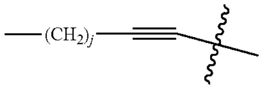

or

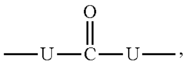

where, each $R^{15}$ is H, or a $C_1$-$C_3$ alkyl, an alkanol group or a heterocycle (including a water soluble heterocycle, preferably, a morpholino, piperidine or piperazine group to promote water solubility of the linker group); each U is independently a bond, O, S or N—$R^{15}$; and each j is independently 0 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5.

In embodiments, $Q^4$ is a

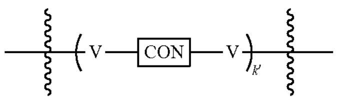

where each V is independently a bond,

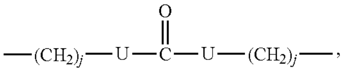

$-(CH_2)_{m'}-$, or $-[(CH_2)_{n'}-X^4]_{j'}-$;

j' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

k' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; preferably k is 1, 2, 3, 4, or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

$X^4$ is O, S or N—$R^{15}$, preferably O;

U is the same as above;

and CON is a connector group (which may be a bond) which connects $Q^3$ to $Q^4$, when present in the linker group.

In embodiments, CON is a bond or is a heterocycle, including a water soluble heterocycle, such as a piperazinyl or other group, or a group selected from:

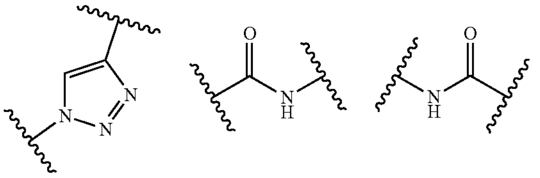

-continued

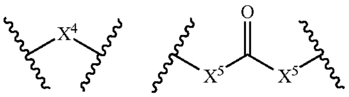

or

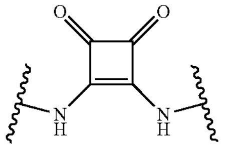

wherein $X^4$ is cycloalkyl, heterocyclyl, O, S, $NR^{12}$, S(O), $S(O)_2$, $-S(O)_2O$, $-OS(O)_2$, $OP(O)OR^{15}$, $Si(R^{15})_2$, or $OS(O)_2O$;

$X^5$ is O, S, $CHR^{12}$, $NR^{12}$;

$R^{12}$ is H or a $C_1$-$C_3$ alkyl group optionally substituted with one or two hydroxyl groups, or a pharmaceutically acceptable salt, enantiomer or stereoisomer thereof, and $R^{15}$ is as defined above.

In alternative preferred aspects, the linker moiety is a (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units. In certain embodiments, the linker is optionally substituted; i.e., comprises chemical groups interdispersed within or on the PEG linker. In certain embodiments, the PEG linker is substituted with an alkyl, alkylene, aromatic group, or aryl group, e.g., phenyl, benzyl, or heterocyclyl group, or amino acid side chain and is optionally interdispersed with optionally substituted O, N, S, P, or Si atoms.

In embodiments, CON is

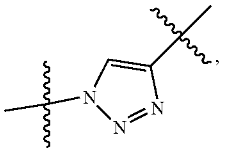 [SMILES: *c1cn(*)nn1]

or an amide group.

In some embodiments, the linker is asymmetrical. In other embodiments, the linker moiety is symmetrical.

Although the ligase ligand and the

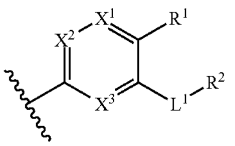

moiety may be covalently linked to the linker group through any group which is appropriate and stable to the chemistry of the linker, in preferred aspects, the linker is independently covalently bonded to the ligase ligand and the

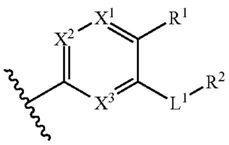

moiety through an amide, ester, thioester, keto group, carbamate (urethane) or ether, each of which groups may be inserted anywhere on the ligase ligand moiety and

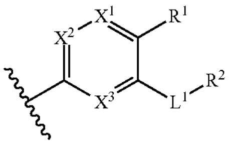

moiety to allow binding of the ligase ligand to the ligase and the

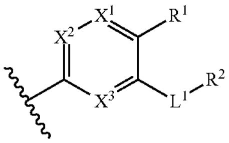

moiety to the target protein to be degraded. In other words, as shown herein, the linker can be designed and connected to ligase ligand and

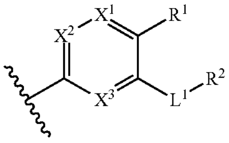

moiety to minimize, eliminate, or neutralize any impact its presence might have on the binding of the ligase ligand and the

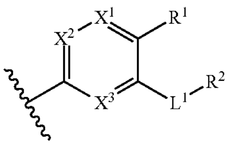

moiety to their respective binding partners. In certain aspects, the targeted protein for degradation may be an ubiquitin ligase. In some embodiments, the linker moiety may be linked to an optionally substituted alkyl, alkylene, alkene, or alkyne group, an aryl group, or a heterocyclic group on the ligase ligand and/or

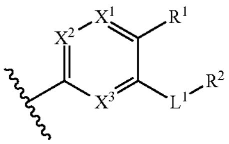

moiety.

Additional linker moeities are disclosed in U.S. Patent Application Publication Nos. 2016/0058872, 2016/0045607, 2014/0356322, 2015/0291562, and 2020/0038378; and in WO2014/063061, each of which is incorporated herein in its entirety.

In some embodiments, provided is a compound of any one of the formulae described herein, wherein $X^1$ is C—$R^5$, wherein $R^5$ is H; $X^2$ is N; $X^3$ is C—$R^5$, wherein $R^5$ is H; and $R^1$ is O—$C_{1-12}$alkyl. In some embodiments, $R^1$ is methoxy. In certain embodiments, the compound has a structure of formula (XII):

(XII)

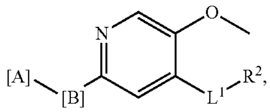

or a stereoisomer or pharmaceutically acceptable salt thereof.

In certain embodiments, $L^1$ is —CH═CH—. In other embodiments, $L^1$ is —$C_{1-12}$alkyl-. In further embodiments, $L^1$ is —$C_{1-6}$alkyl-. In still other embodiments, $L^1$ is a bond.

In some embodiments, $L^1$ is —CH═CH— and $R^2$ is $C_{3-10}$cycloalkyl, wherein the $C_{3-10}$cycloalkyl is substituted with one $C_{1-12}$haloalkyl. In certain embodiments, the compound has a structure of formula (XIII):

(XIII)

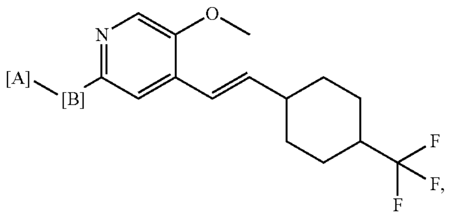

or a stereoisomer or pharmaceutically acceptable salt thereof.

In other embodiments, $L^1$ is —CH═CH— and $R^2$ is $C_{3-10}$cycloalkyl, wherein the $C_{3-10}$cycloalkyl is substituted with one or more halo. In some embodiments, the halo is fluoro. In certain embodiments, the compound has a structure of formula (XIV):

(XIV)

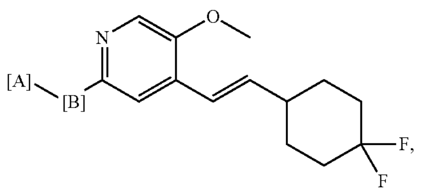

or a stereoisomer or pharmaceutically acceptable salt thereof.

In some embodiments, some embodiments, $L^1$ is —CH═CH— and $R^2$ is $C_{3-10}$cycloalkyl, wherein the $C_{3-10}$cycloalkyl is spiro. In certain embodiments, the compound has a structure of formula (XV):

(XV)

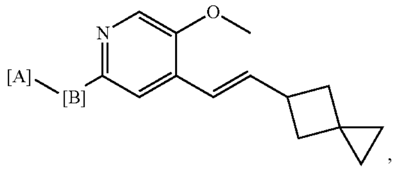

, or a stereoisomer or pharmaceutically acceptable salt thereof.

In some embodiments, $L^1$ is —CH═CH— and $R^2$ is $C_{6-20}$aryl, wherein the $C_{6-20}$aryl is substituted with one or more halo. In some embodiments, the halo is chloro. In certain embodiments, the compound has a structure of formula (XVI):

(XVI)

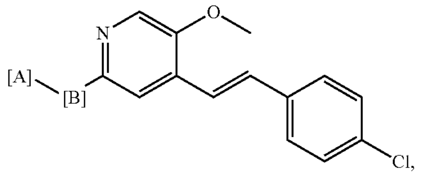

or a stereoisomer or pharmaceutically acceptable salt thereof.

In some embodiments, $L^1$ is a bond, and $R^2$ is $C_{3-10}$cycloalkyl, wherein the $C_{3-10}$cycloalkyl is substituted with $C_{6-20}$aryl, wherein the $C_{6-20}$aryl is further substituted with one or more halo. In some embodiments, the halo is chloro. In certain embodiments, the compound has a structure of formula (XVII):

(XVII)

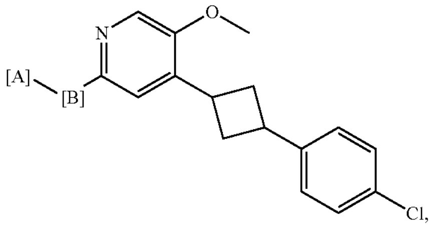

or a stereoisomer or pharmaceutically acceptable salt thereof.

In some embodiments, the compound of any one of the formulae described herein, or a stereoisomer or pharmaceutically acceptable salt thereof, is selected from the compounds listed in Table 1 below, including racemic mixtures and resolved stereoisomers:

TABLE 1

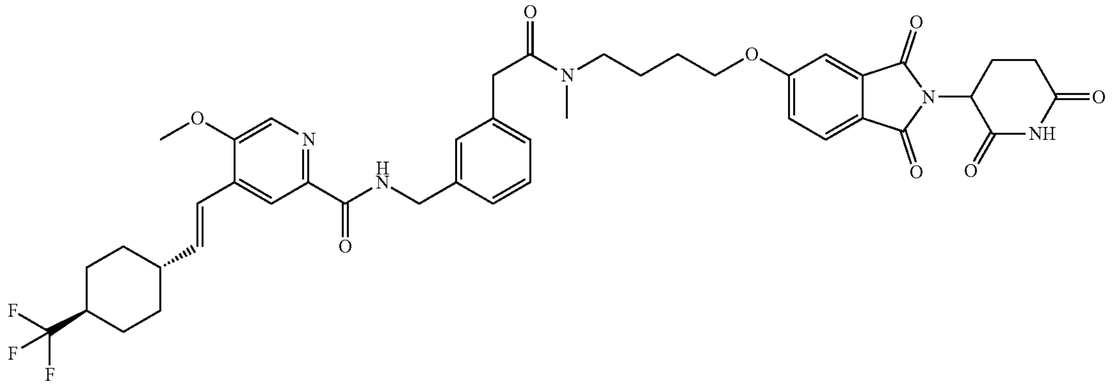 [SMILES: COc1cnc(C(=O)NCc2cccc(CC(=O)N(C)CCCCOc3ccc4c(c3)C(=O)N(C3CCC(=O)NC3=O)C4=O)c2)cc1/C=C/[C@H]1CC[C@H](C(F)(F)F)CC1]

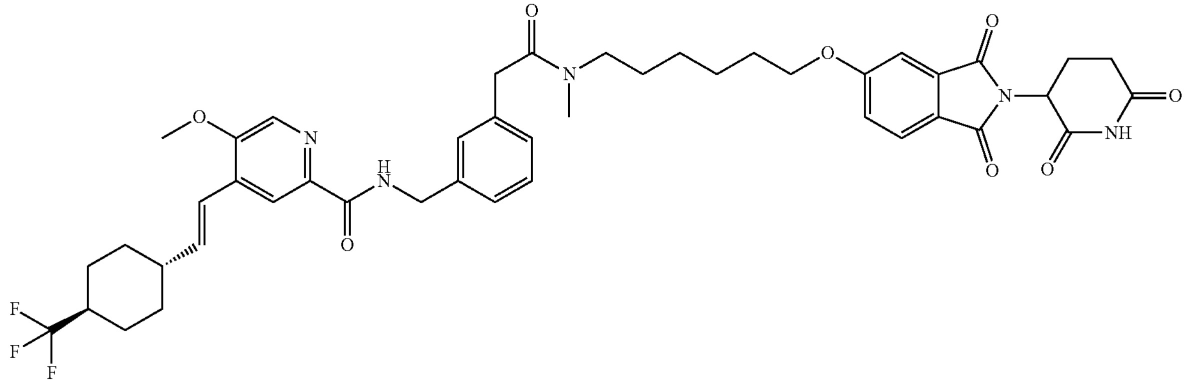 [SMILES: COc1cnc(C(=O)NCc2cccc(CC(=O)N(C)CCCCCCOc3ccc4c(c3)C(=O)N(C3CCC(=O)NC3=O)C4=O)c2)cc1/C=C/[C@H]1CC[C@H](C(F)(F)F)CC1]

TABLE 1-continued
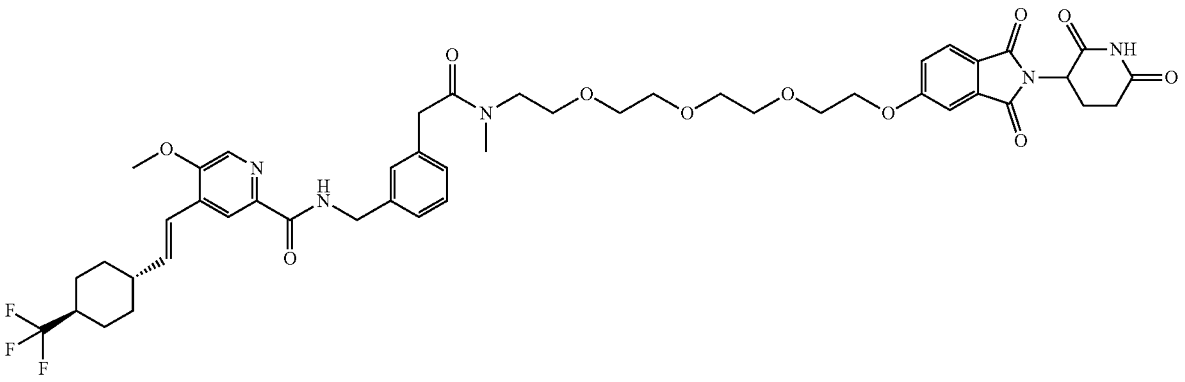 [SMILES: COc1cnc(C(=O)NCc2cccc(CC(=O)N(C)CCOCCOCCOCCOc3ccc4c(c3)C(=O)N(C3CCC(=O)NC3=O)C4=O)c2)cc1/C=C/[C@H]1CC[C@H](C(F)(F)F)CC1]
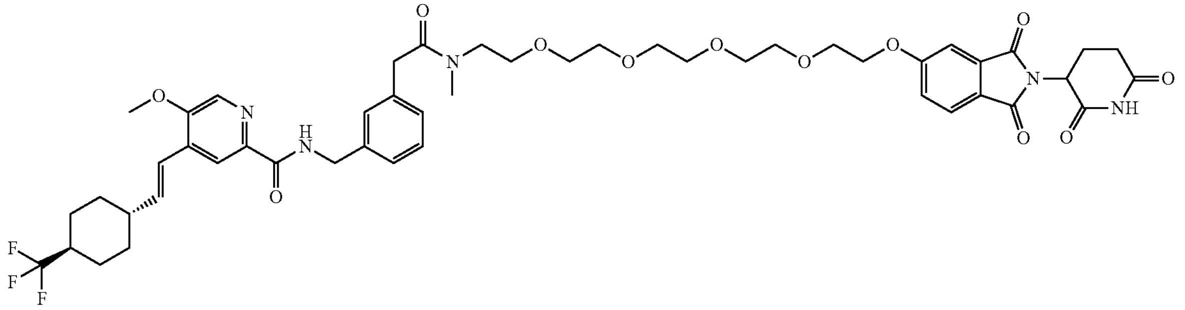 [SMILES: COc1cnc(C(=O)NCc2cccc(CC(=O)N(C)CCOCCOCCOCCOCCOc3ccc4c(c3)C(=O)N(C3CCC(=O)NC3=O)C4=O)c2)cc1/C=C/[C@H]1CC[C@H](C(F)(F)F)CC1]
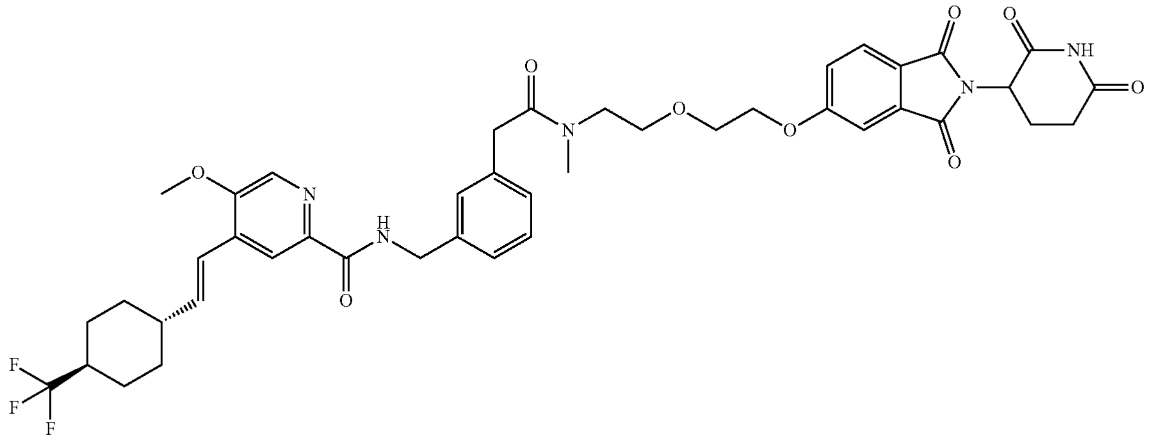
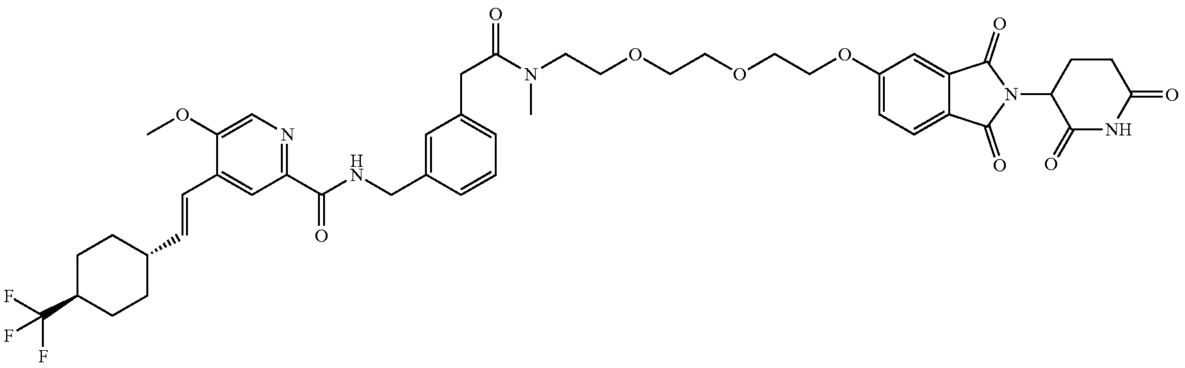 [SMILES: COc1cnc(C(=O)NCc2cccc(CC(=O)N(C)CCOCCOCCOc3ccc4c(c3)C(=O)N(C3CCC(=O)NC3=O)C4=O)c2)cc1/C=C/[C@H]1CC[C@H](C(F)(F)F)CC1]

TABLE 1-continued
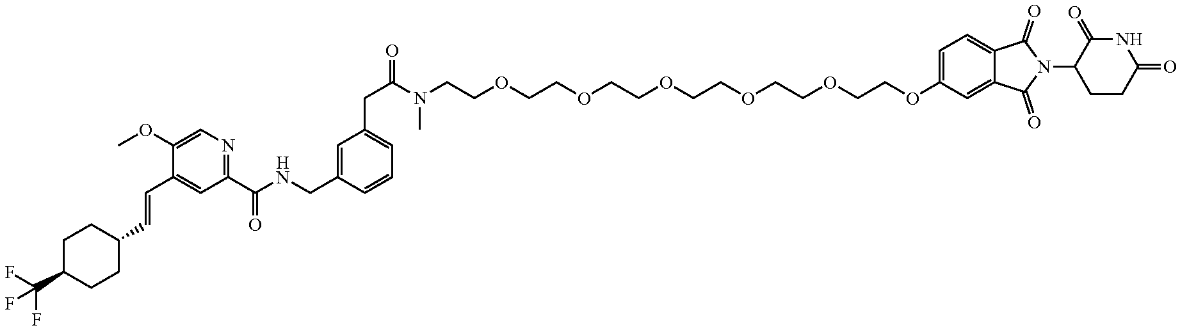 [SMILES: COc1cnc(C(=O)NCc2cccc(CC(=O)N(C)CCOCCOCCOCCOCCOCCOc3ccc4c(c3)C(=O)N(C3CCC(=O)NC3=O)C4=O)c2)cc1/C=C/[C@H]1CC[C@H](C(F)(F)F)CC1]
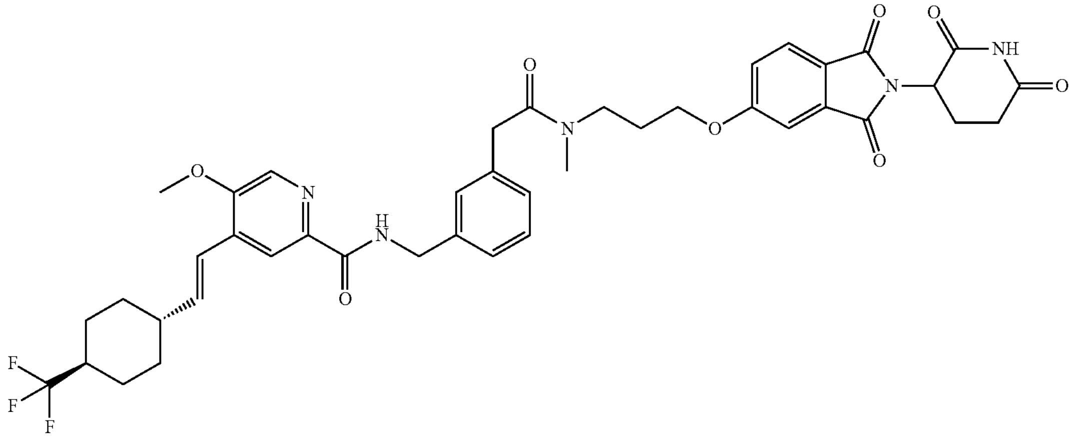 [SMILES: COc1cnc(C(=O)NCc2cccc(CC(=O)N(C)CCCOc3ccc4c(c3)C(=O)N(C3CCC(=O)NC3=O)C4=O)c2)cc1/C=C/[C@H]1CC[C@H](C(F)(F)F)CC1]
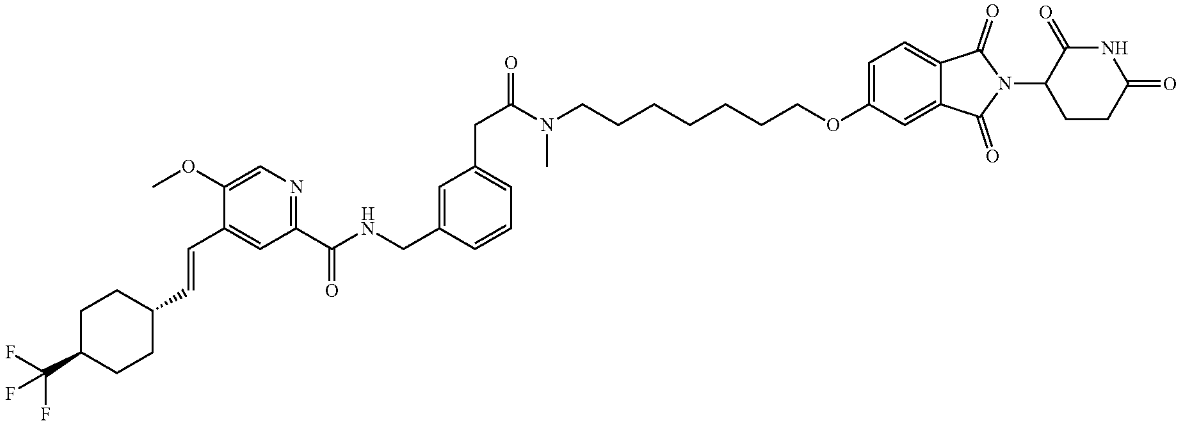 [SMILES: COc1cnc(C(=O)NCc2cccc(CC(=O)N(C)CCCCCCCOc3ccc4c(c3)C(=O)N(C3CCC(=O)NC3=O)C4=O)c2)cc1/C=C/[C@H]1CC[C@H](C(F)(F)F)CC1]
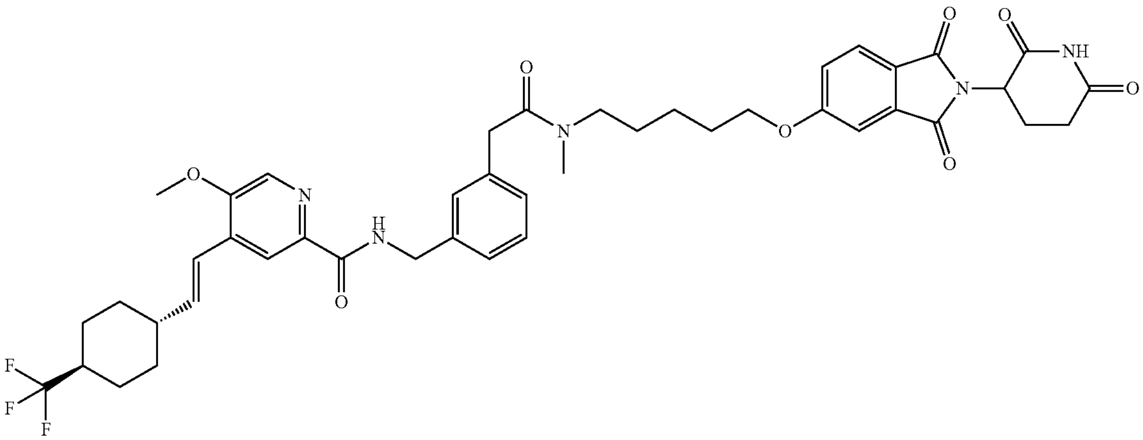 [SMILES: COc1cnc(C(=O)NCc2cccc(CC(=O)N(C)CCCCCOc3ccc4c(c3)C(=O)N(C3CCC(=O)NC3=O)C4=O)c2)cc1/C=C/[C@H]1CC[C@H](C(F)(F)F)CC1]

TABLE 1-continued
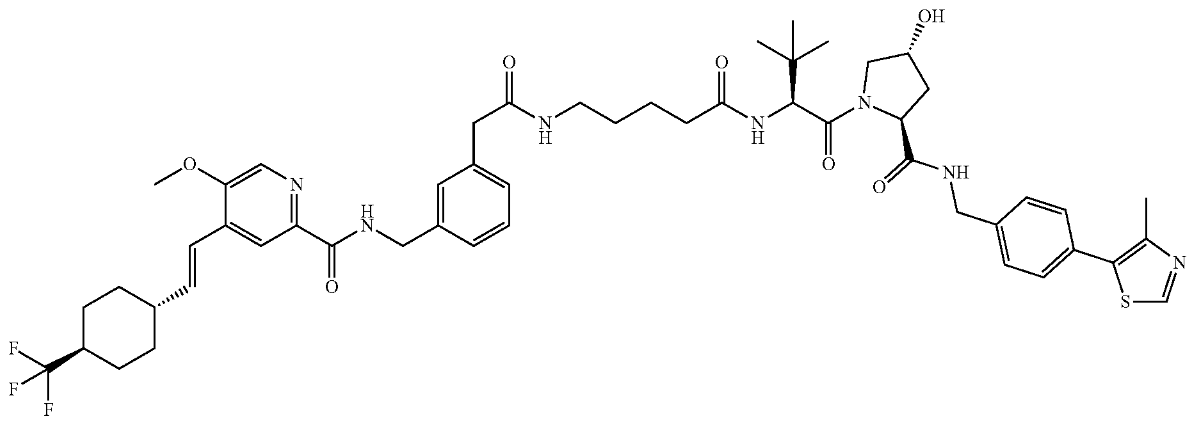 [SMILES: COc1cnc(C(=O)NCc2cccc(CC(=O)NCCCCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]
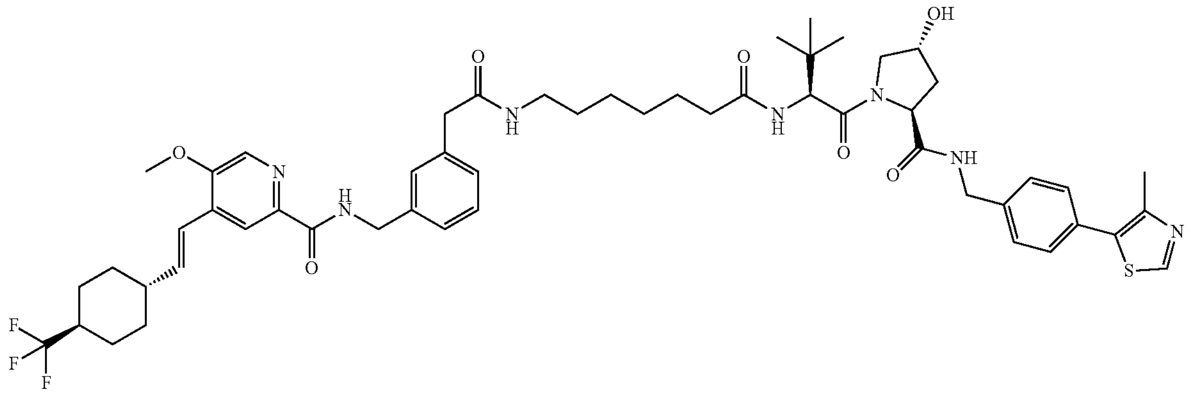 [SMILES: COc1cnc(C(=O)NCc2cccc(CC(=O)NCCCCCCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]
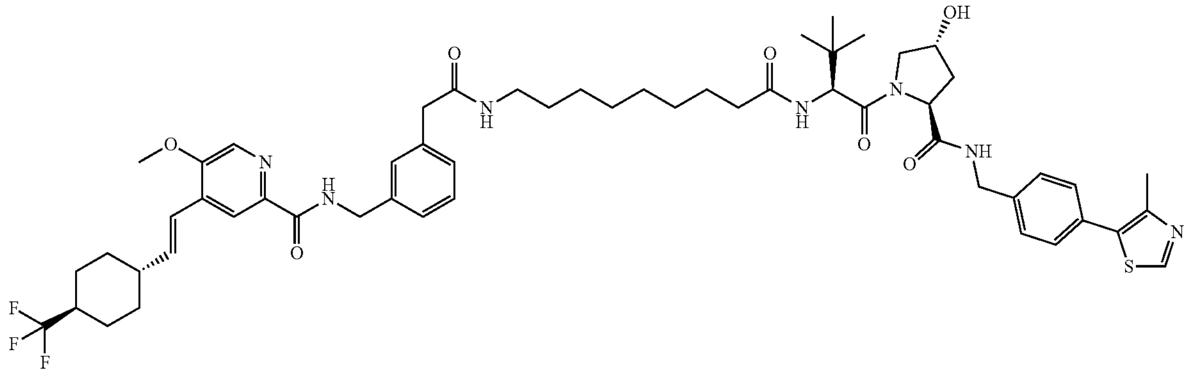 [SMILES: COc1cnc(C(=O)NCc2cccc(CC(=O)NCCCCCCCCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]
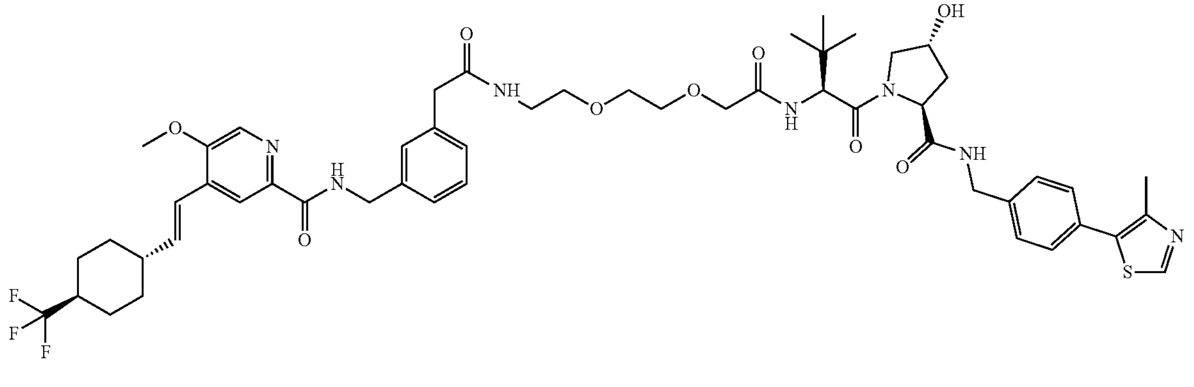 [SMILES: COc1cnc(C(=O)NCc2cccc(CC(=O)NCCOCCOCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]

TABLE 1-continued
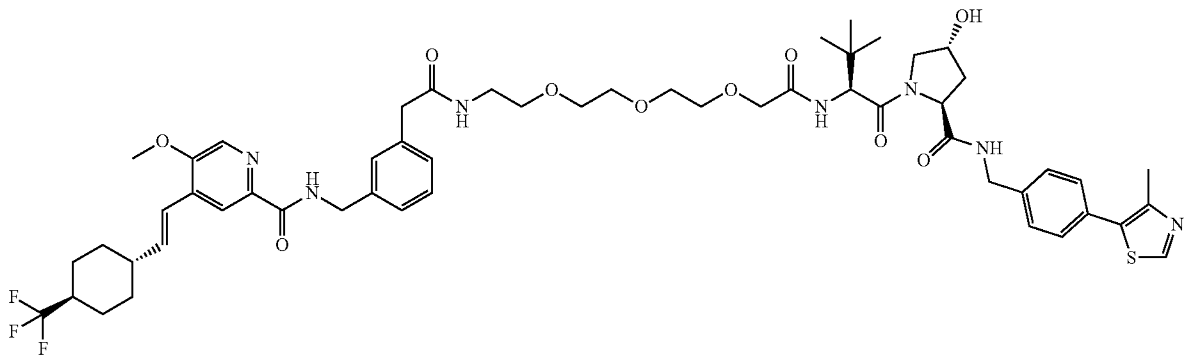 [SMILES: COc1cnc(C(=O)NCc2cccc(CC(=O)NCCOCCOCCOCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]
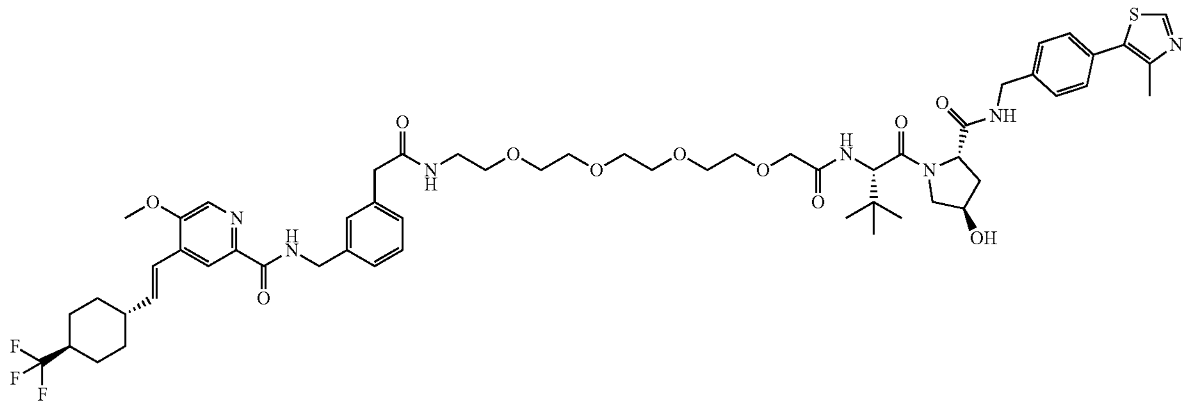 [SMILES: COc1cnc(C(=O)NCc2cccc(CC(=O)NCCOCCOCCOCCOCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]
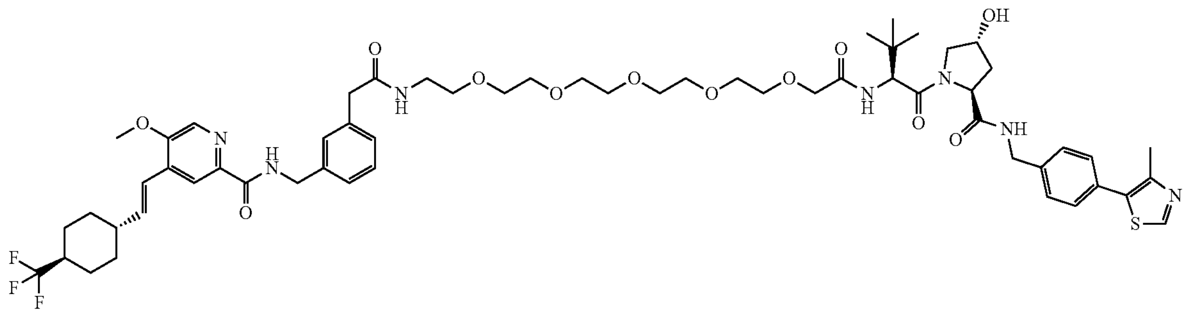 [SMILES: COc1cnc(C(=O)NCc2cccc(CC(=O)NCCOCCOCCOCCOCCOCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]
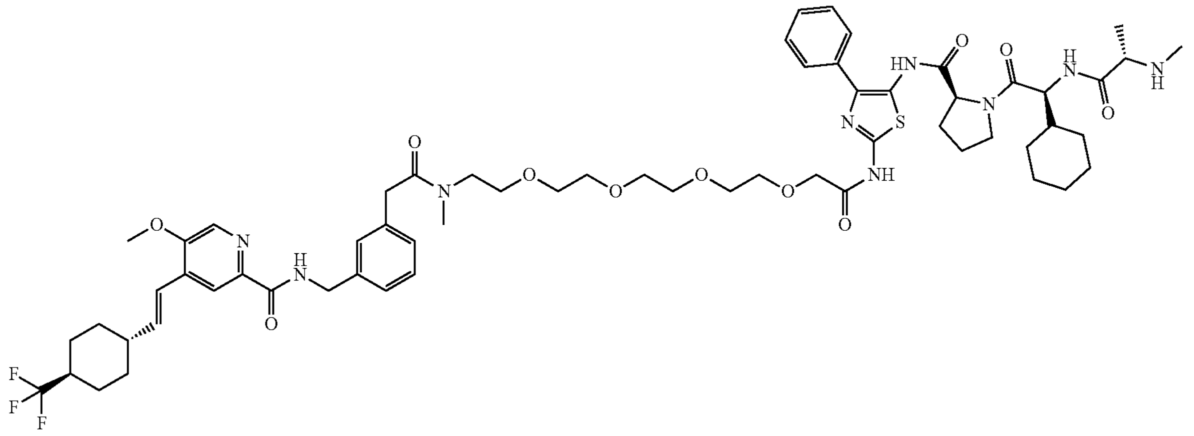 [SMILES: CN[C@@H](C)C(=O)N[C@H](C(=O)N1CCC[C@H]1C(=O)Nc1sc(NC(=O)COCCOCCOCCOCCN(C)C(=O)Cc2cccc(CNC(=O)c3cc(/C=C/[C@H]4CC[C@H](C(F)(F)F)CC4)c(OC)cn3)c2)nc1-c1ccccc1)C1CCCCC1]

TABLE 1-continued
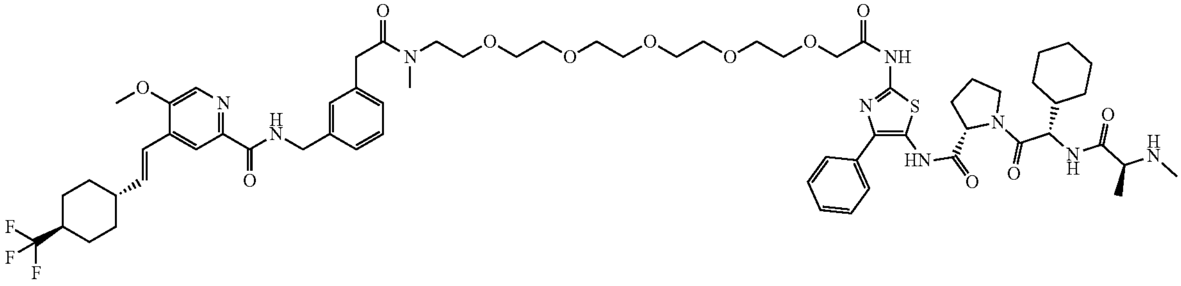 [SMILES: CN[C@@H](C)C(=O)N[C@H](C(=O)N1CCC[C@H]1C(=O)Nc1sc(NC(=O)COCCOCCOCCOCCOCCN(C)C(=O)Cc2cccc(CNC(=O)c3cc(/C=C/[C@H]4CC[C@H](C(F)(F)F)CC4)c(OC)cn3)c2)nc1-c1ccccc1)C1CCCCC1]
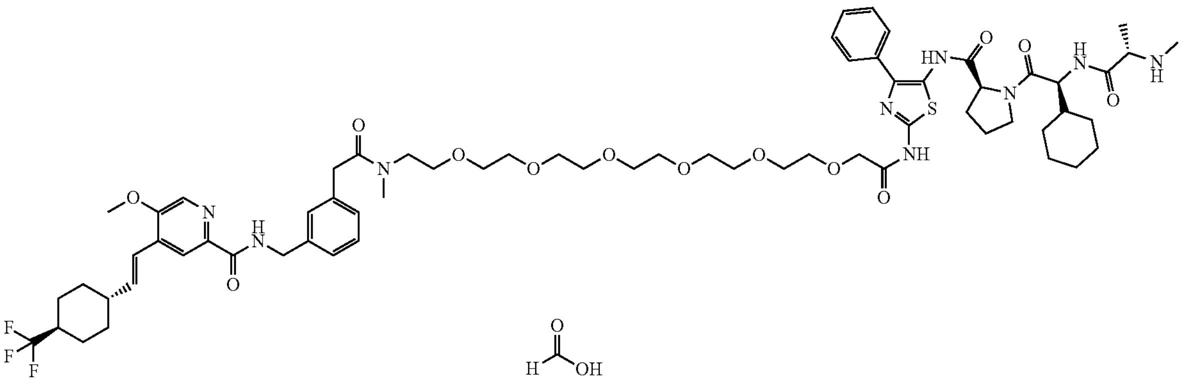 [SMILES: CN[C@@H](C)C(=O)N[C@H](C(=O)N1CCC[C@H]1C(=O)Nc1sc(NC(=O)COCCOCCOCCOCCOCCOCCN(C)C(=O)Cc2cccc(CNC(=O)c3cc(/C=C/[C@H]4CC[C@H](C(F)(F)F)CC4)c(OC)cn3)c2)nc1-c1ccccc1)C1CCCCC1 ; O=CO]
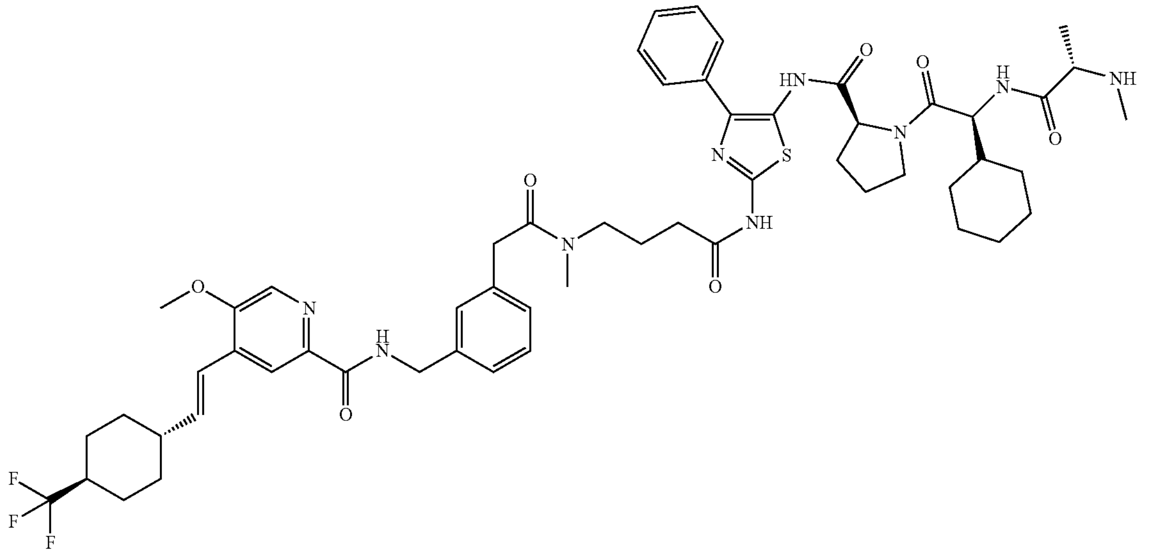 [SMILES: CN[C@@H](C)C(=O)N[C@H](C(=O)N1CCC[C@H]1C(=O)Nc1sc(NC(=O)CCCN(C)C(=O)Cc2cccc(CNC(=O)c3cc(/C=C/[C@H]4CC[C@H](C(F)(F)F)CC4)c(OC)cn3)c2)nc1-c1ccccc1)C1CCCCC1]
In some embodiments, the compound of any one of the formulae described herein, or a stereoisomer or pharmaceutically acceptable salt thereof, is selected from the compounds listed in Table 2 below, including racemic mixtures and resolved isomers:

TABLE 2
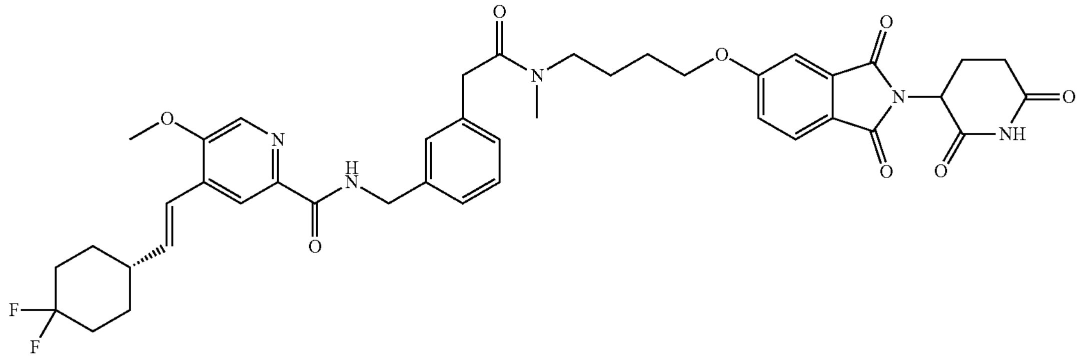
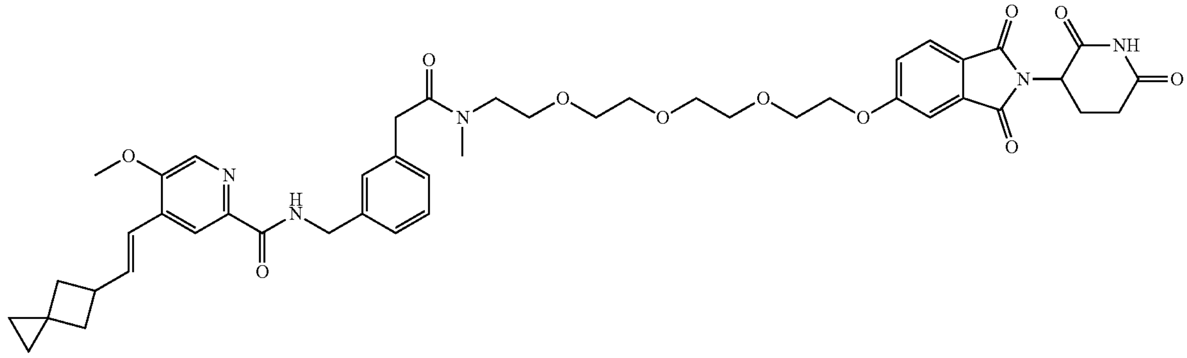 [SMILES: COc1cnc(C(=O)NCc2cccc(CC(=O)N(C)CCOCCOCCOCCOc3ccc4c(c3)C(=O)N(C3CCC(=O)NC3=O)C4=O)c2)cc1/C=C/C1CC2(CC2)C1]
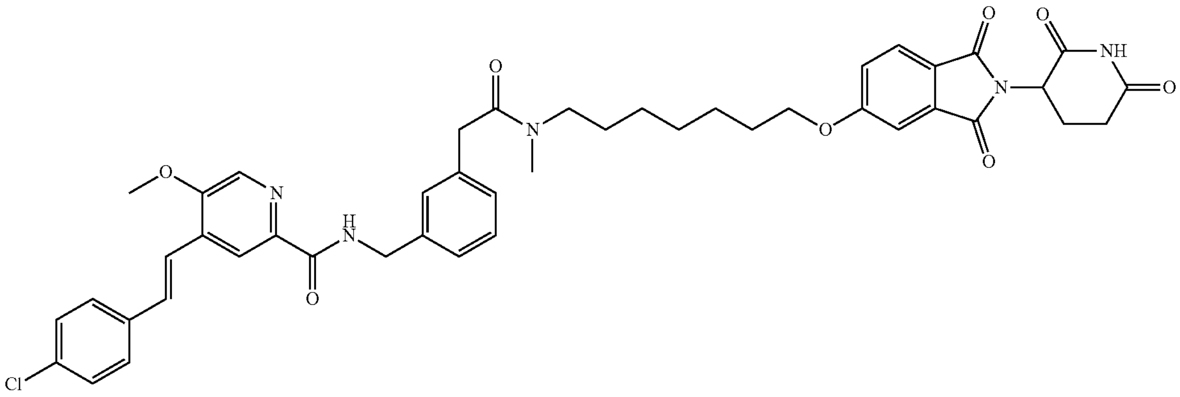 [SMILES: COc1cnc(C(=O)NCc2cccc(CC(=O)N(C)CCCCCCCOc3ccc4c(c3)C(=O)N(C3CCC(=O)NC3=O)C4=O)c2)cc1/C=C/c1ccc(Cl)cc1]
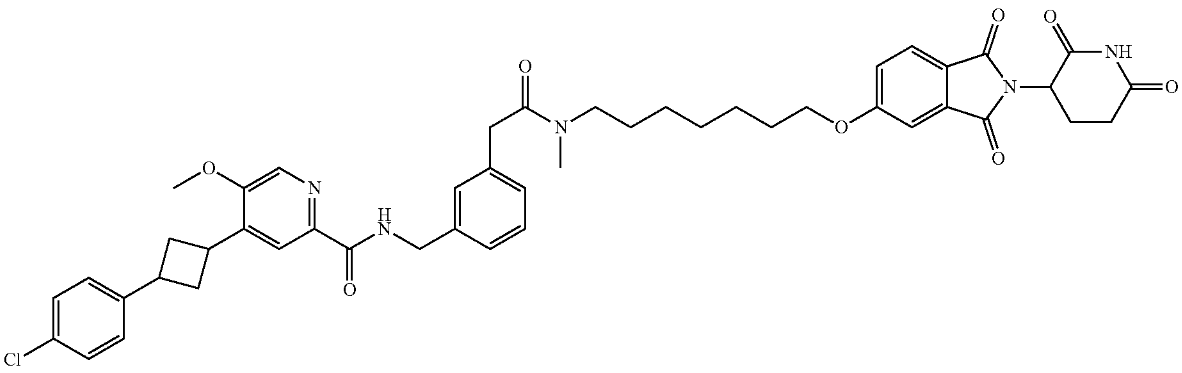 [SMILES: COc1cnc(C(=O)NCc2cccc(CC(=O)N(C)CCCCCCCOc3ccc4c(c3)C(=O)N(C3CCC(=O)NC3=O)C4=O)c2)cc1C1CC(c2ccc(Cl)cc2)C1]

TABLE 2-continued
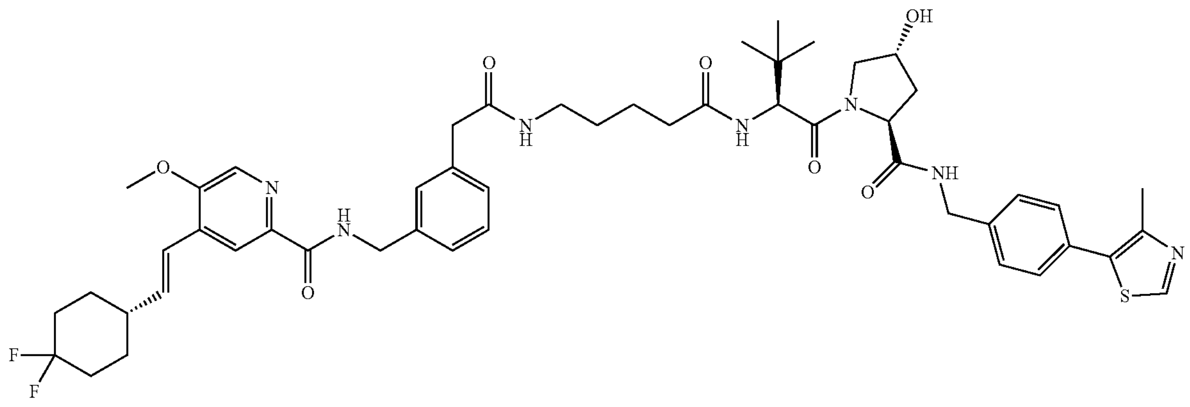
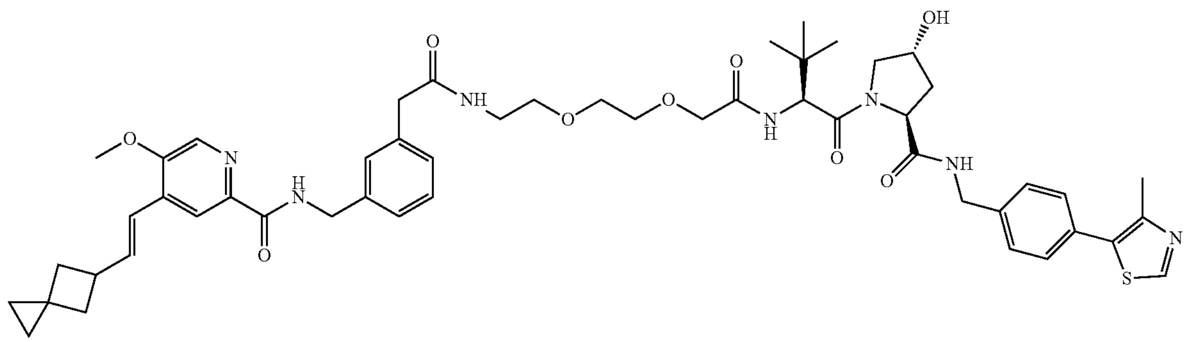 [SMILES: COc1cnc(C(=O)NCc2cccc(CC(=O)NCCOCCOCC(=O)N[C@H](C(=O)N3C[C@H](O)C[C@H]3C(=O)NCc3ccc(-c4scnc4C)cc3)C(C)(C)C)c2)cc1/C=C/C1CC2(CC2)C1]
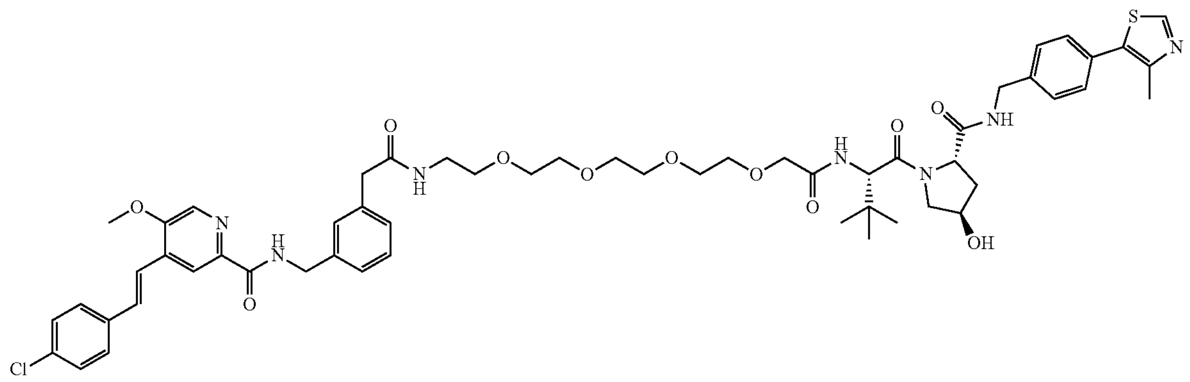 [SMILES: COc1cnc(C(=O)NCc2cccc(CC(=O)NCCOCCOCCOCCOCC(=O)N[C@H](C(=O)N3C[C@H](O)C[C@H]3C(=O)NCc3ccc(-c4scnc4C)cc3)C(C)(C)C)c2)cc1/C=C/c1ccc(Cl)cc1]
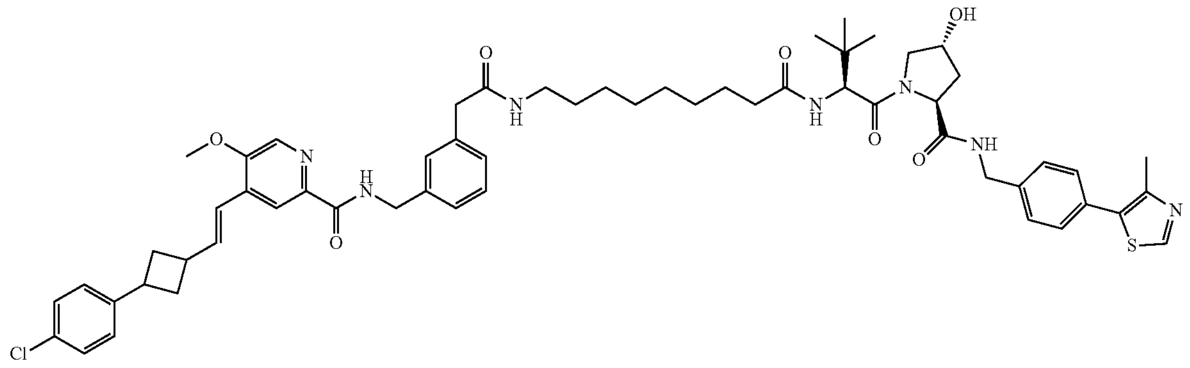 [SMILES: COc1cnc(C(=O)NCc2cccc(CC(=O)NCCCCCCCCC(=O)N[C@H](C(=O)N3C[C@H](O)C[C@H]3C(=O)NCc3ccc(-c4scnc4C)cc3)C(C)(C)C)c2)cc1/C=C/C1CC(c2ccc(Cl)cc2)C1]

TABLE 2-continued
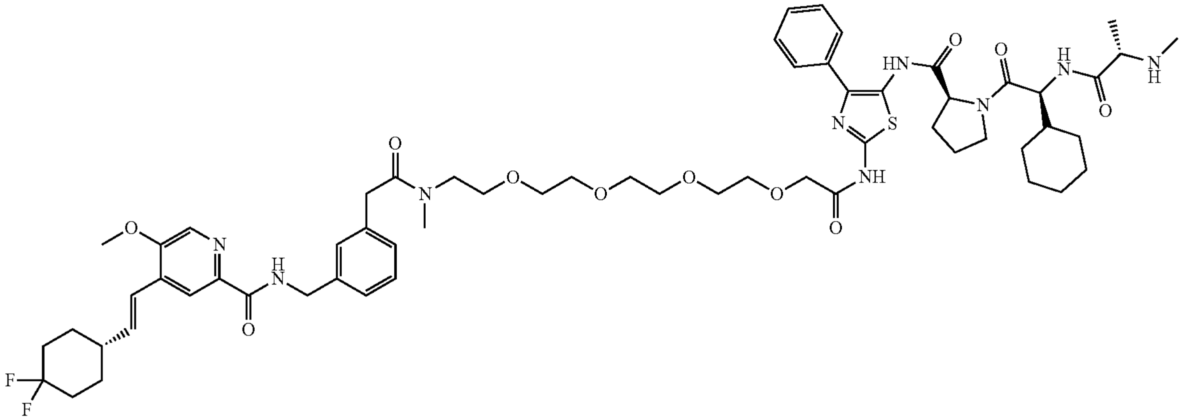
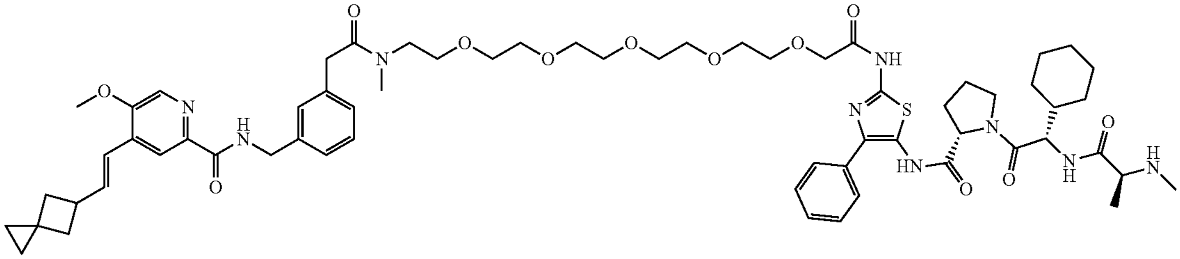 [SMILES: CN[C@@H](C)C(=O)N[C@H](C(=O)N1CCC[C@H]1C(=O)Nc1sc(NC(=O)COCCOCCOCCOCCOCCN(C)C(=O)Cc2cccc(CNC(=O)c3cc(/C=C/C4CC5(CC5)C4)c(OC)cn3)c2)nc1-c1ccccc1)C1CCCCC1]
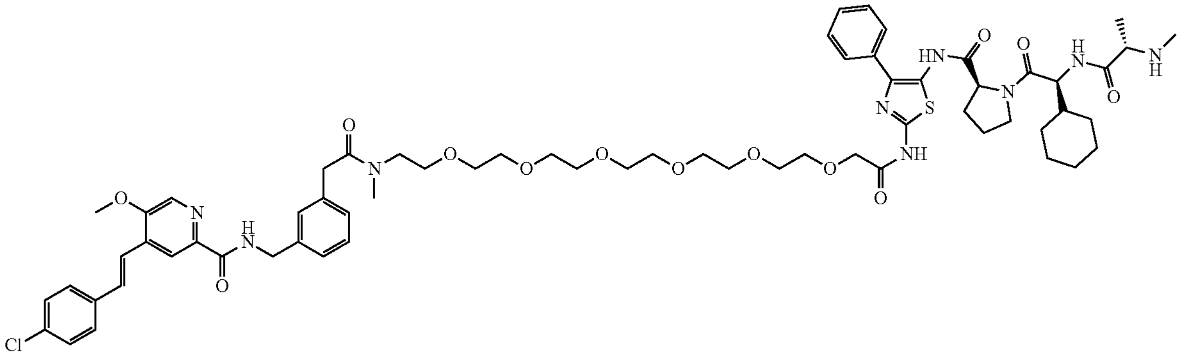 [SMILES: CN[C@@H](C)C(=O)N[C@H](C(=O)N1CCC[C@H]1C(=O)Nc1sc(NC(=O)COCCOCCOCCOCCOCCOCCN(C)C(=O)Cc2cccc(CNC(=O)c3cc(/C=C/c4ccc(Cl)cc4)c(OC)cn3)c2)nc1-c1ccccc1)C1CCCCC1]
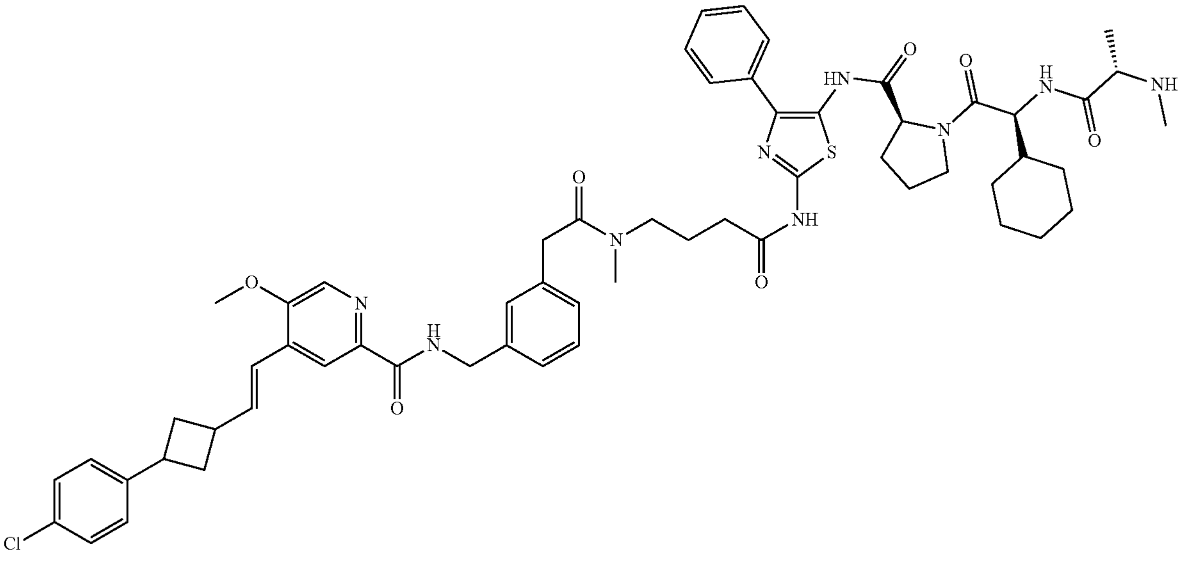 [SMILES: CN[C@@H](C)C(=O)N[C@H](C(=O)N1CCC[C@H]1C(=O)Nc1sc(NC(=O)CCCN(C)C(=O)Cc2cccc(CNC(=O)c3cc(/C=C/C4CC(c5ccc(Cl)cc5)C4)c(OC)cn3)c2)nc1-c1ccccc1)C1CCCCC1]

TABLE 2-continued
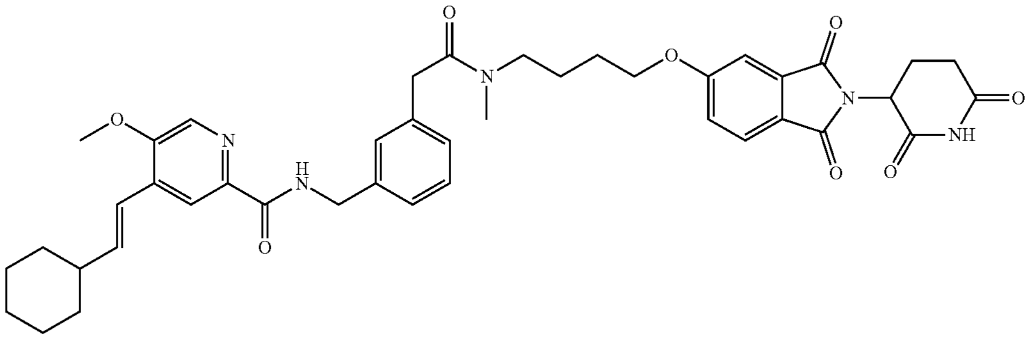 [SMILES: COc1cnc(C(=O)NCc2cccc(CC(=O)N(C)CCCCOc3ccc4c(c3)C(=O)N(C3CCC(=O)NC3=O)C4=O)c2)cc1/C=C/C1CCCCC1]
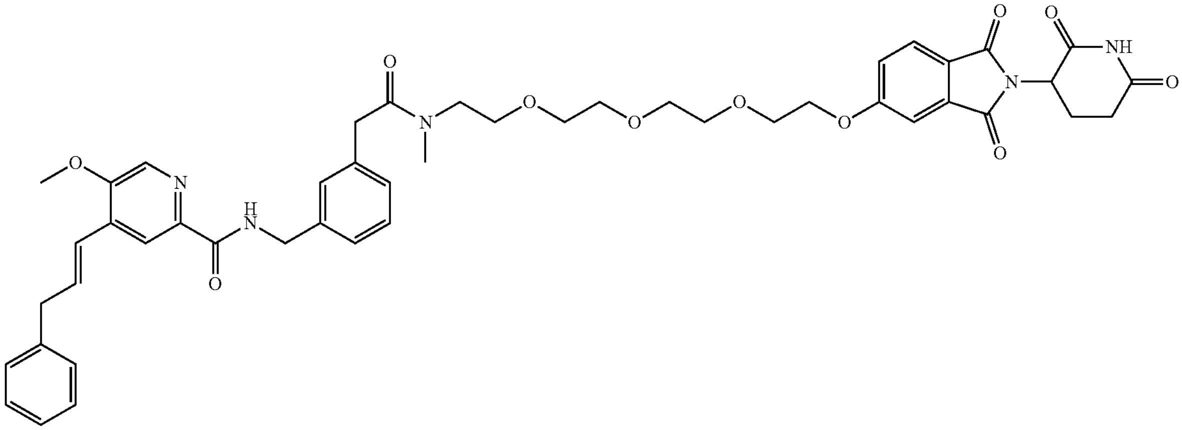 [SMILES: COc1cnc(C(=O)NCc2cccc(CC(=O)N(C)CCOCCOCCOCCOc3ccc4c(c3)C(=O)N(C3CCC(=O)NC3=O)C4=O)c2)cc1/C=C/Cc1ccccc1]
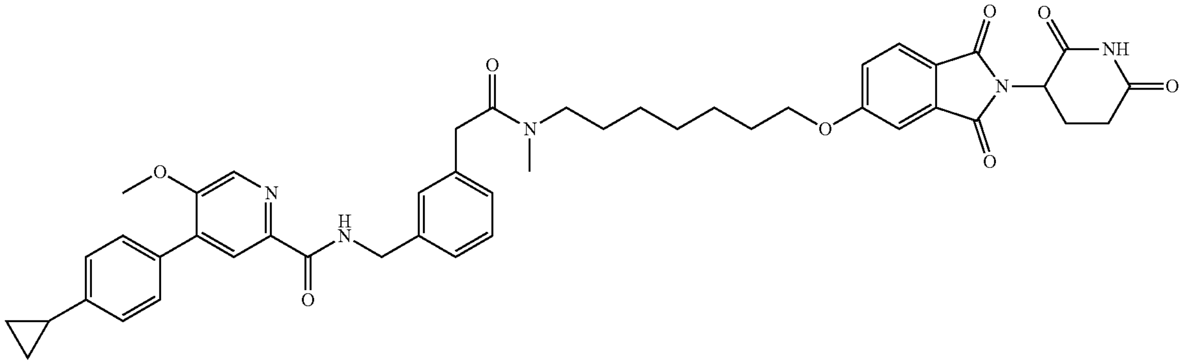 [SMILES: COc1cnc(C(=O)NCc2cccc(CC(=O)N(C)CCCCCCCOc3ccc4c(c3)C(=O)N(C3CCC(=O)NC3=O)C4=O)c2)cc1-c1ccc(C2CC2)cc1]
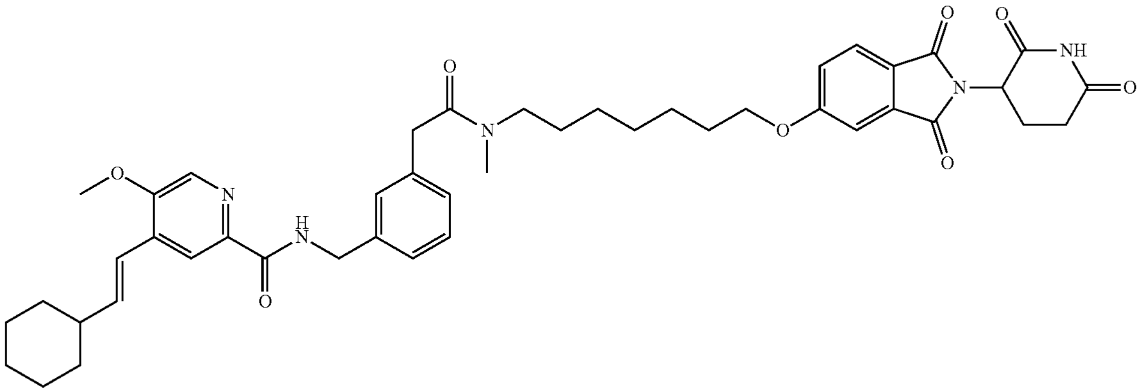 [SMILES: COc1cnc(C(=O)NCc2cccc(CC(=O)N(C)CCCCCCCOc3ccc4c(c3)C(=O)N(C3CCC(=O)NC3=O)C4=O)c2)cc1/C=C/C1CCCCC1]

TABLE 2-continued
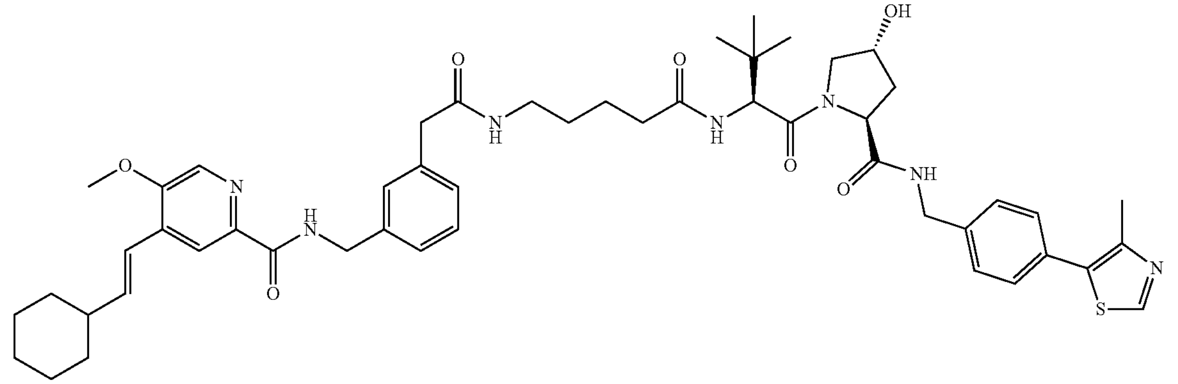 [SMILES: COc1cnc(C(=O)NCc2cccc(CC(=O)NCCCCC(=O)N[C@H](C(=O)N3C[C@H](O)C[C@H]3C(=O)NCc3ccc(-c4scnc4C)cc3)C(C)(C)C)c2)cc1/C=C/C1CCCCC1]
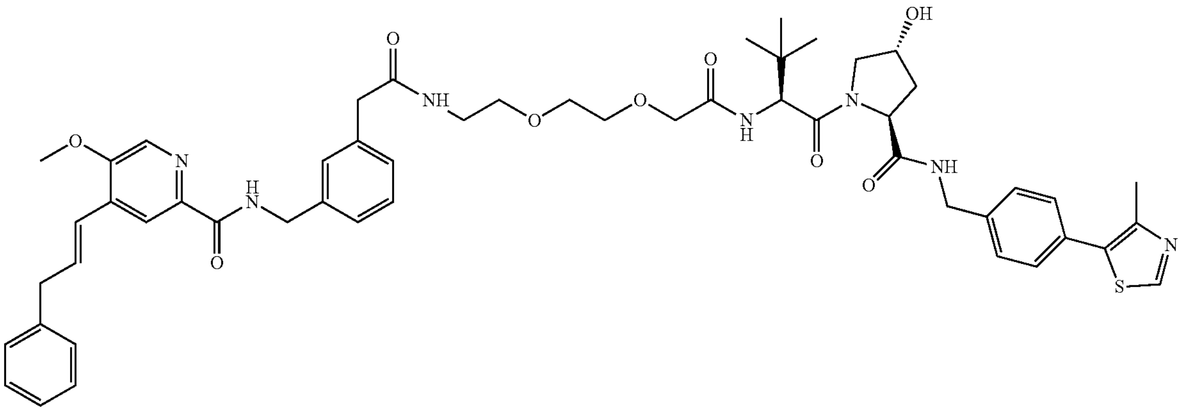 [SMILES: COc1cnc(C(=O)NCc2cccc(CC(=O)NCCOCCOCC(=O)N[C@H](C(=O)N3C[C@H](O)C[C@H]3C(=O)NCc3ccc(-c4scnc4C)cc3)C(C)(C)C)c2)cc1/C=C/Cc1ccccc1]
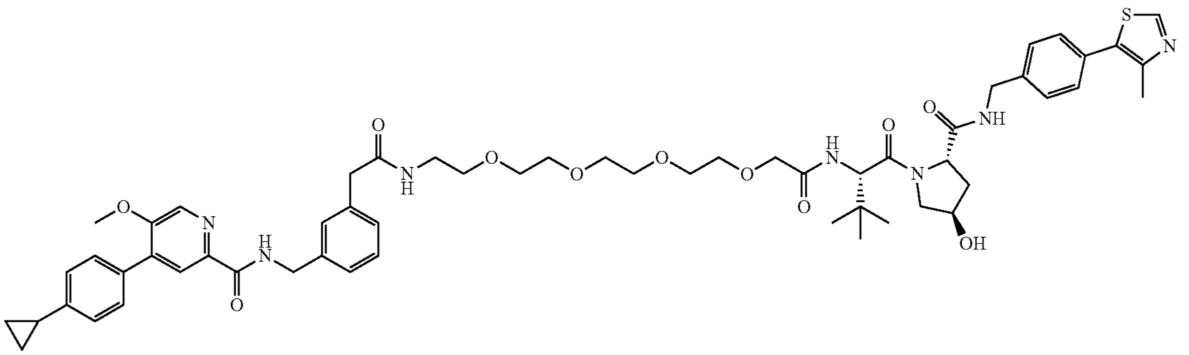 [SMILES: COc1cnc(C(=O)NCc2cccc(CC(=O)NCCOCCOCCOCCOCC(=O)N[C@H](C(=O)N3C[C@H](O)C[C@H]3C(=O)NCc3ccc(-c4scnc4C)cc3)C(C)(C)C)c2)cc1-c1ccc(C2CC2)cc1]
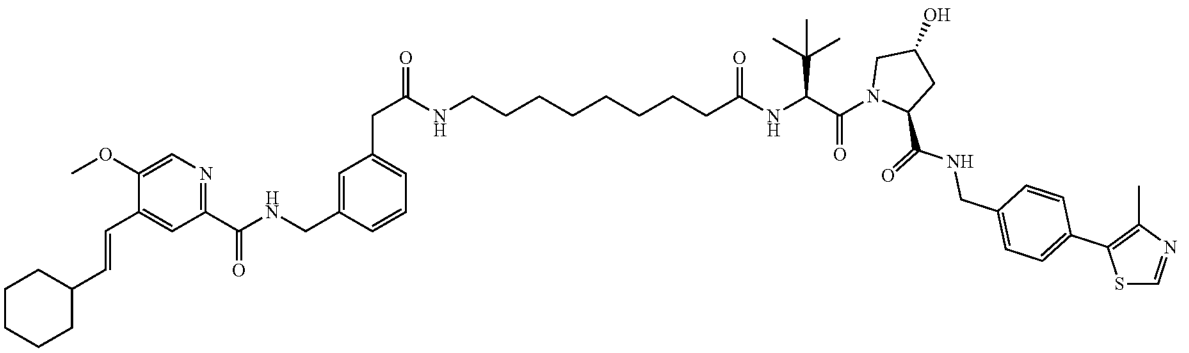 [SMILES: COc1cnc(C(=O)NCc2cccc(CC(=O)NCCCCCCCCC(=O)N[C@H](C(=O)N3C[C@H](O)C[C@H]3C(=O)NCc3ccc(-c4scnc4C)cc3)C(C)(C)C)c2)cc1/C=C/C1CCCCC1]

TABLE 2-continued
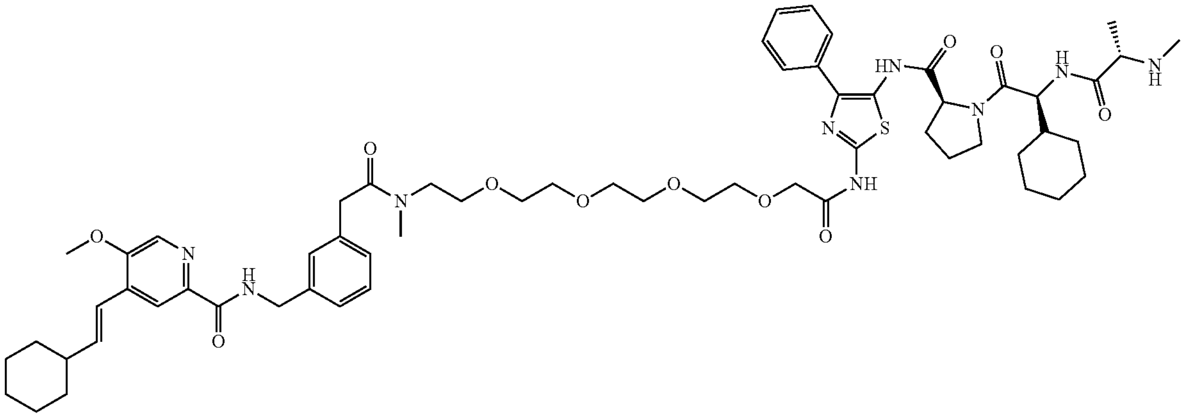 [SMILES: CN[C@@H](C)C(=O)N[C@H](C(=O)N1CCC[C@H]1C(=O)Nc1sc(NC(=O)COCCOCCOCCOCCN(C)C(=O)Cc2cccc(CNC(=O)c3cc(/C=C/C4CCCCC4)c(OC)cn3)c2)nc1-c1ccccc1)C1CCCCC1]
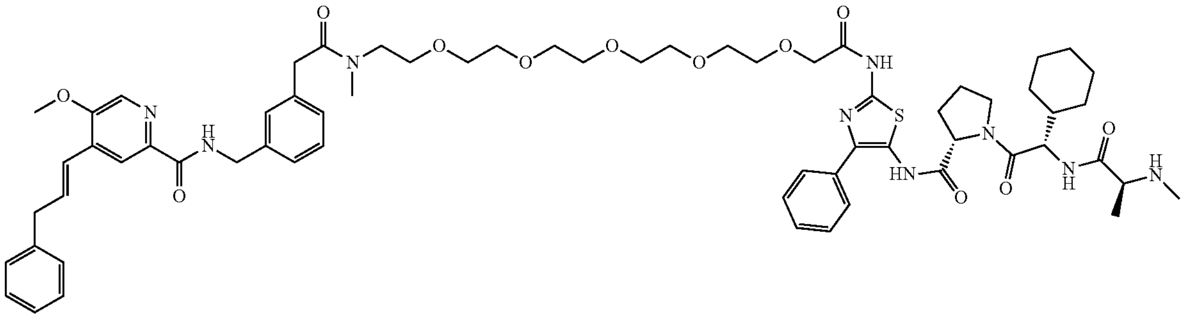 [SMILES: CN[C@@H](C)C(=O)N[C@H](C(=O)N1CCC[C@H]1C(=O)Nc1sc(NC(=O)COCCOCCOCCOCCOCCN(C)C(=O)Cc2cccc(CNC(=O)c3cc(/C=C/Cc4ccccc4)c(OC)cn3)c2)nc1-c1ccccc1)C1CCCCC1]
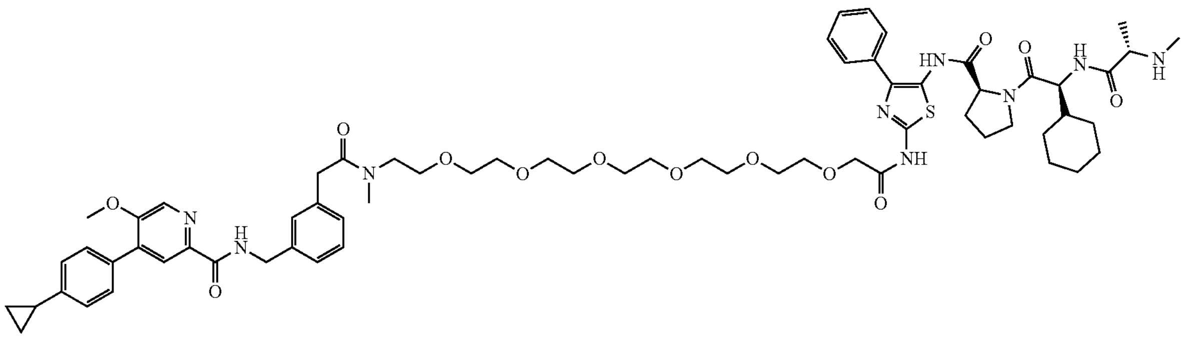 [SMILES: CN[C@@H](C)C(=O)N[C@H](C(=O)N1CCC[C@H]1C(=O)Nc1sc(NC(=O)COCCOCCOCCOCCOCCOCCN(C)C(=O)Cc2cccc(CNC(=O)c3cc(-c4ccc(C5CC5)cc4)c(OC)cn3)c2)nc1-c1ccccc1)C1CCCCC1]
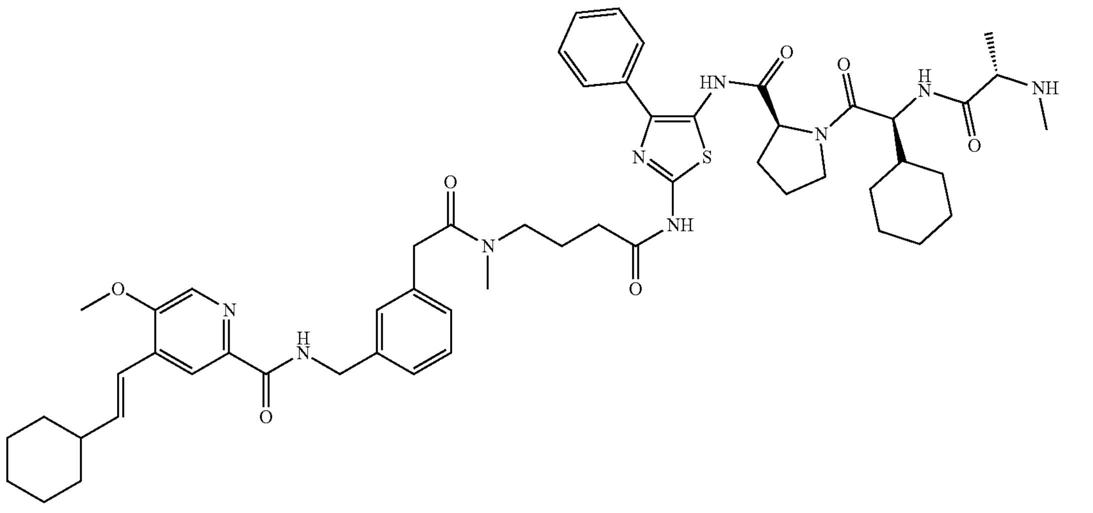 [SMILES: CN[C@@H](C)C(=O)N[C@H](C(=O)N1CCC[C@H]1C(=O)Nc1sc(NC(=O)CCCN(C)C(=O)Cc2cccc(CNC(=O)c3cc(/C=C/C4CCCCC4)c(OC)cn3)c2)nc1-c1ccccc1)C1CCCCC1]

Provided herein is a compound selected from the group consisting of:

N-(3-(2-((4-((2-(2,6-dioxopiperidin-3-yl)-1,3-dioxoisoindolin-5-yl)oxy)butyl)(methyl)amino)-2-oxoethyl)benzyl)-5-methoxy-4-(2-(4-(trifluoromethyl)cyclohexyl)vinyl)picolinamide;

N-(3-(2-((6-((2-(2,6-Dioxopiperidin-3-yl)-1,3-dioxoisoindolin-5-yl)oxy)hexyl)(methyl)amino)-2-oxoethyl)benzyl)-5-methoxy-4-(2-(4-(trifluoromethyl)cyclohexyl)vinyl)picolinamide;

N-(3-(14-((2-(2,6-Dioxopiperidin-3-yl)-1,3-dioxoisoindolin-5-yl)oxy)-3-methyl-2-oxo-6,9,12-trioxa-3-azatetradecyl)benzyl)-5-methoxy-4-(2-(4-(trifluoromethyl)cyclohexyl)vinyl)picolinamide;

N-(3-(17-((2-(2,6-Dioxopiperidin-3-yl)-1,3-dioxoisoindolin-5-yl)oxy)-3-methyl-2-oxo-6,9,12,15-tetraoxa-3-azaheptadecyl)benzyl)-5-methoxy-4-(2-(4-(trifluoromethyl)cyclohexyl)vinyl)picolinamide;

N-(3-(2-((2-(2-((2-(2,6-Dioxopiperidin-3-yl)-1,3-dioxoisoindolin-5-yl)oxy)ethoxy)ethyl)(methyl)amino)-2-oxoethyl)benzyl)-5-methoxy-4-(2-(4-(trifluoromethyl)cyclohexyl)vinyl)picolinamide;

N-(3-(2-((2-(2-(2-((2-(2,6-Dioxopiperidin-3-yl)-1,3-dioxoisoindolin-5-yl)oxy)ethoxy)ethoxy)ethyl)(methyl)amino)-2-oxoethyl)benzyl)-5-methoxy-4-(2-(4-(trifluoromethyl)cyclohexyl)vinyl)picolinamide;

N-(3-(20-((2-(2,6-Dioxopiperidin-3-yl)-1,3-dioxoisoindolin-5-yl)oxy)-3-methyl-2-oxo-6,9,12,15,18-pentaoxa-3-azaicosyl)benzyl)-5-methoxy-4-(2-(4-(trifluoromethyl)cyclohexyl)vinyl)picolinamide;

N-(3-(2-((3-((2-(2,6-Dioxopiperidin-3-yl)-1,3-dioxoisoindolin-5-yl)oxy)propyl)(methyl)amino)-2-oxoethyl)benzyl)-5-methoxy-4-(2-(4-(trifluoromethyl)cyclohexyl)vinyl)picolinamide;

N-(3-(2-((7-((2-(2,6-Dioxopiperidin-3-yl)-1,3-dioxoisoindolin-5-yl)oxy)heptyl)(methyl)amino)-2-oxoethyl)benzyl)-5-methoxy-4-(2-(4-(trifluoromethyl)cyclohexyl)vinyl)picolinamide;

N-(3-(2-((5-((2-(2,6-Dioxopiperidin-3-yl)-1,3-dioxoisoindolin-5-yl)oxy)pentyl)(methyl)amino)-2-oxoethyl)benzyl)-5-methoxy-4-(2-(4-(trifluoromethyl)cyclohexyl)vinyl)picolinamide;

N-(3-(2-((5-((1-(4-Hydroxy-2-((4-(4-methylthiazol-5-yl)benzyl)carbamoyl)pyrrolidin-1-yl)-3,3-dimethyl-1-oxobutan-2-yl)amino)-5-oxopentyl)amino)-2-oxoethyl)benzyl)-5-methoxy-4-(2-(4-(trifluoromethyl)cyclohexyl)vinyl)picolinamide;

N-(3-(2-((7-((1-(4-Hydroxy-2-((4-(4-methylthiazol-5-yl)benzyl)carbamoyl)pyrrolidin-1-yl)-3,3-dimethyl-1-oxobutan-2-yl)amino)-7-oxoheptyl)amino)-2-oxoethyl)benzyl)-5-methoxy-4-(2-(4-(trifluoromethyl)cyclohexyl)vinyl)picolinamide;

N-(3-(2-((9-((1-(4-Hydroxy-2-((4-(4-methylthiazol-5-yl)benzyl)carbamoyl)pyrrolidin-1-yl)-3,3-dimethyl-1-oxobutan-2-yl)amino)-9-oxononyl)amino)-2-oxoethyl)benzyl)-5-methoxy-4-(2-(4-(trifluoromethyl)cyclohexyl)vinyl)picolinamide;

N-(3-(13-(4-Hydroxy-2-((4-(4-methylthiazol-5-yl)benzyl)carbamoyl)pyrrolidine-1-carbonyl)-14,14-dimethyl-2,11-dioxo-6,9-dioxa-3,12-diazapentadecyl)benzyl)-5-methoxy-4-(2-(4-(trifluoromethyl)cyclohexyl)vinyl)picolinamide;

N-(3-(16-(4-Hydroxy-2-((4-(4-methylthiazol-5-yl)benzyl)carbamoyl)pyrrolidine-1-carbonyl)-17,17-dimethyl-2,14-dioxo-6,9,12-trioxa-3,15-diazaoctadecyl)benzyl)-5-methoxy-4-(2-(4-(trifluoromethyl)cyclohexyl)vinyl)picolinamide;

N-(3-(19-(4-Hydroxy-2-((4-(4-methylthiazol-5-yl)benzyl)carbamoyl)pyrrolidine-1-carbonyl)-20,20-dimethyl-2,17-dioxo-6,9,12,15-tetraoxa-3,18-diazahenicosyl)benzyl)-5-methoxy-4-(2-(4-(trifluoromethyl)cyclohexyl)vinyl)picolinamide;

N-(3-(22-(4-Hydroxy-2-((4-(4-methylthiazol-5-yl)benzyl)carbamoyl)pyrrolidine-1-carbonyl)-23,23-dimethyl-2,20-dioxo-6,9,12,15,18-pentaoxa-3,21-diazatetracosyl)benzyl)-5-methoxy-4-(2-(4-(trifluoromethyl)cyclohexyl)vinyl)picolinamide;

N-(3-(17-((5-(1-(2-Cyclohexyl-2-(2-(methylamino)propanamido)acetyl)pyrrolidine-2-carboxamido)-4-phenylthiazol-2-yl)amino)-3-methyl-2,17-dioxo-6,9,12,15-tetraoxa-3-azaheptadecyl)benzyl)-5-methoxy-4-(2-(4-(trifluoromethyl)cyclohexyl)vinyl)picolinamide;

N-(3-(20-((5-(1-(2-Cyclohexyl-2-(2-(methylamino)propanamido)acetyl)pyrrolidine-2-carboxamido)-4-phenylthiazol-2-yl)amino)-3-methyl-2,20-dioxo-6,9,12,15,18-pentaoxa-3-azaicosyl)benzyl)-5-methoxy-4-(2-(4-(trifluoromethyl)cyclohexyl)vinyl)picolinamide;

N-(3-(23-((5-(1-(2-Cyclohexyl-2-(2-(methylamino)propanamido)acetyl)pyrrolidine-2-carboxamido)-4-phenylthiazol-2-yl)amino)-3-methyl-2,23-dioxo-6,9,12,15,18,21-hexaoxa-3-azatricosyl)benzyl)-5-methoxy-4-(2-(4-(trifluoromethyl)cyclohexyl)vinyl)picolinamide;

N-(3-(2-((4-((5-(1-(2-Cyclohexyl-2-(2-(methylamino)propanamido)acetyl)pyrrolidine-2-carboxamido)-4-phenylthiazol-2-yl)amino)-4-oxobutyl)(methyl)amino)-2-oxoethyl)benzyl)-5-methoxy-4-(2-(4-(trifluoromethyl)cyclohexyl)vinyl)picolinamide;

4-(2-(4,4-difluorocyclohexyl)vinyl)-N-(3-(2-((4-((2-(2,6-dioxopiperidin-3-yl)-1,3-dioxoisoindolin-5-yl)oxy)butyl)(methyl)amino)-2-oxoethyl)benzyl)-5-methoxypicolinamide;

N-(3-(14-((2-(2,6-dioxopiperidin-3-yl)-1,3-dioxoisoindolin-5-yl)oxy)-3-methyl-2-oxo-6,9,12-trioxa-3-azatetradecyl)benzyl)-5-methoxy-4-(2-(spiro[2.3]hexan-5-yl)vinyl)picolinamide;

4-(4-chlorostyryl)-N-(3-(2-((7-((2-(2,6-dioxopiperidin-3-yl)-1,3-dioxoisoindolin-5-yl)oxy)heptyl)(methyl)amino)-2-oxoethyl)benzyl)-5-methoxypicolinamide;

4-(3-(4-chlorophenyl)cyclobutyl)-N-(3-(2-((7-((2-(2,6-dioxopiperidin-3-yl)-1,3-dioxoisoindolin-5-yl)oxy)heptyl)(methyl)amino)-2-oxoethyl)benzyl)-5-methoxypicolinamide;

4-(2-(4,4-difluorocyclohexyl)vinyl)-N-(3-(2-((5-((1-(4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)amino)-2-oxoethyl)benzyl)-5-methoxypicolinamide;

(3-(13-(4-hydroxy-2-((4-(4-methylthiazol-5-yl)benzyl)carbamoyl)pyrrolidine-1-carbonyl)-14,14-dimethyl-2,11-dioxo-6,9-dioxa-3,12-diazapentadecyl)benzyl)-5-methoxy-4-(2-(spiro[2.3]hexan-5-yl)vinyl)picolinamide;

4-(4-chlorostyryl)-N-(3-(19-(4-hydroxy-2-((4-(4-methylthiazol-5-yl)benzyl)carbamoyl)pyrrolidine-1-carbonyl)-20,20-dimethyl-2,17-dioxo-6,9,12,15-tetraoxa-3,18-diazahenicosyl)benzyl)-5-methoxypicolinamide;

4-(2-(3-(4-chlorophenyl)cyclobutyl)vinyl)-N-(3-(2-((9-((1-(4-hydroxy-2-((4-(4-methylthiazol-5-yl)benzyl)carbamoyl)pyrrolidin-1-yl)-3,3-dimethyl-1-oxobutan-2-yl)amino)-9-oxononyl)amino)-2-oxoethyl)benzyl)-5-methoxypicolinamide;

N-(3-(17-((5-(1-(2-cyclohexyl-2-(2-(methylamino)propanamido)acetyl)pyrrolidine-2-carboxamido)-4-phenylthiazol-2-yl)amino)-3-methyl-2,17-dioxo-6,9,12,15-tetraoxa-3-azaheptadecyl)benzyl)-4-(2-(4,4-difluorocyclohexyl)vinyl)-5-methoxypicolinamide;

N-(3-(20-((5-(1-(2-cyclohexyl-2-(2-(methylamino)propanamido)acetyl)pyrrolidine-2-carboxamido)-4-phenylthiazol-2-yl)amino)-3-methyl-2,20-dioxo-6,9,12,15,18-pentaoxa-3-azaicosyl)benzyl)-5-methoxy-4-(2-(spiro[2.3]hexan-5-yl)vinyl)picolinamide;

4-(4-chlorostyryl)-N-(3-(23-((5-(1-(2-cyclohexyl-2-(2-(methylamino)propanamido)acetyl)pyrrolidine-2-carboxamido)-4-phenylthiazol-2-yl)amino)-3-methyl-2,23-dioxo-6,9,12,15,18,21-hexaoxa-3-azatricosyl)benzyl)-5-methoxypicolinamide;

4-(2-(3-(4-chlorophenyl)cyclobutyl)vinyl)-N-(3-(2-((4-((5-(1-(2-cyclohexyl-2-(2-(methylamino)propanamido)acetyl)pyrrolidine-2-carboxamido)-4-phenylthiazol-2-yl)amino)-4-oxobutyl)(methyl)amino)-2-oxoethyl)benzyl)-5-methoxypicolinamide;

(E)-4-(2-cyclohexylvinyl)-N-(3-(2-((4-((2-(2,6-dioxopiperidin-3-yl)-1,3-dioxoisoindolin-5-yl)oxy)butyl)(methyl)amino)-2-oxoethyl)benzyl)-5-methoxypicolinamide;

(E)-N-(3-(14-((2-(2,6-dioxopiperidin-3-yl)-1,3-dioxoisoindolin-5-yl)oxy)-3-methyl-2-oxo-6,9,12-trioxa-3-azatetradecyl)benzyl)-5-methoxy-4-(3-phenylprop-1-en-1-yl)picolinamide;

4-(4-cyclopropylphenyl)-N-(3-(2-((7-((2-(2,6-dioxopiperidin-3-yl)-1,3-dioxoisoindolin-5-yl)oxy)heptyl)(methyl)amino)-2-oxoethyl)benzyl)-5-methoxypicolinamide;

(E)-4-(2-cyclohexylvinyl)-N-(3-(2-((7-((2-(2,6-dioxopiperidin-3-yl)-1,3-dioxoisoindolin-5-yl)oxy)heptyl)(methyl)amino)-2-oxoethyl)benzyl)-5-methoxypicolinamide;

4-((E)-2-cyclohexylvinyl)-N-(3-(2-((5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)amino)-2-oxoethyl)benzyl)-5-methoxypicolinamide;

N-(3-((S)-13-((2S,4R)-4-hydroxy-2-((4-(4-methylthiazol-5-yl)benzyl)carbamoyl)pyrrolidine-1-carbonyl)-14,14-dimethyl-2,11-dioxo-6,9-dioxa-3,12-diazapentadecyl)benzyl)-5-methoxy-4-((E)-3-phenylprop-1-en-1-yl)picolinamide;

4-(4-cyclopropylphenyl)-N-(3-((S)-19-((2S,4R)-4-hydroxy-2-((4-(4-methylthiazol-5-yl)benzyl)carbamoyl)pyrrolidine-1-carbonyl)-20,20-dimethyl-2,17-dioxo-6,9,12,15-tetraoxa-3,18-diazahenicosyl)benzyl)-5-methoxypicolinamide;

4-((E)-2-cyclohexylvinyl)-N-(3-(2-((9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononyl)amino)-2-oxoethyl)benzyl)-5-methoxypicolinamide;

N-(3-(17-((5-((S)-1-((S)-2-cyclohexyl-2-((S)-2-(methylamino)propanamido)acetyl)pyrrolidine-2-carboxamido)-4-phenylthiazol-2-yl)amino)-3-methyl-2,17-dioxo-6,9,12,15-tetraoxa-3-azaheptadecyl)benzyl)-4-((E)-2-cyclohexylvinyl)-5-methoxypicolinamide;

N-(3-(20-((5-((S)-1-((S)-2-cyclohexyl-2-((S)-2-(methylamino)propanamido)acetyl)pyrrolidine-2-carboxamido)-4-phenylthiazol-2-yl)amino)-3-methyl-2,20-dioxo-6,9,12,15,18-pentaoxa-3-azaicosyl)benzyl)-5-methoxy-4-((E)-3-phenylprop-1-en-1-yl)picolinamide;

N-(3-(23-((5-((S)-1-((S)-2-cyclohexyl-2-((S)-2-(methylamino)propanamido)acetyl)pyrrolidine-2-carboxamido)-4-phenylthiazol-2-yl)amino)-3-methyl-2,23-dioxo-6,9,12,15,18,21-hexaoxa-3-azatricosyl)benzyl)-4-(4-cyclopropylphenyl)-5-methoxypicolinamide; and N-(3-(2-((4-((5-((S)-1-((S)-2-cyclohexyl-2-((S)-2-(methylamino)propanamido)acetyl)pyrrolidine-2-carboxamido)-4-phenylthiazol-2-yl)amino)-4-oxobutyl)(methyl)amino)-2-oxoethyl)benzyl)-4-((E)-2-cyclohexylvinyl)-5-methoxypicolinamide, or a pharmaceutically acceptable salt thereof. Chemical names for compounds of Tables 1 and 2 were generated using ChemDraw version 18.2. Also provided herein are, where applicable, any and all stereoisomers of the compounds depicted herein, including geometric isomers (e.g., cis/trans isomers or E/Z isomers), enantiomers, diastereomers, or mixtures thereof in any ratio, including racemic mixtures.

In some aspects, the compounds of the disclosure are isotopically labeled by having one or more atoms therein replaced by an atom having a different atomic mass or mass number. Such isotopically-labeled (i.e., radiolabeled) compounds of any one of the formulae described herein are considered to be within the scope of this disclosure. Examples of isotopes that can be incorporated into the compounds of any one of the formulae described herein include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively. These isotopically-labeled compounds would be useful to help determine or measure the effectiveness of the compounds, by characterizing, for example, the site or mode of action, or binding affinity to TEAD. Certain isotopically-labeled compounds of any one of the formulae described herein, for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of any one of the formulae described herein can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of any one of the formulae described herein can generally be prepared by conventional techniques known to those skilled in the art or by processes analogous to those described in the Examples as set out below using an appropriate isotopically-labeled reagent in place of the non-labeled reagent previously employed.

Also provided herein is a pharmaceutically acceptable salt or ester of any compound provided herein, as well as a stereoisomer, a geometric isomer, a tautomer, a solvate, a metabolite, an isotope or a prodrug of such compound or a pharmaceutically acceptable salt of such compound.

Pharmaceutical Compositions and Administration

In addition to one or more of the compounds provided above (including stereoisomers, geometric isomers, tautomers, solvates, metabolites, isotopes, pharmaceutically acceptable salts, or prodrugs thereof), the disclosure also provides for compositions and medicaments comprising a compound of the present disclosure or an embodiment or aspect thereof and at least one pharmaceutically acceptable carrier. The compositions of the disclosure can be used to selectively inhibit TEAD in patients (e.g., humans).

In one aspect, the disclosure provides for pharmaceutical compositions or medicaments comprising a compound of the disclosure (or embodiments and aspects thereof including stereoisomers, geometric isomers, tautomers, solvates, metabolites, isotopes, pharmaceutically acceptable salts, and prodrugs) and a pharmaceutically acceptable carrier, diluent or excipient. In another aspect, the disclosure provides for preparing compositions (or medicaments) comprising compounds of the disclosure. In another aspect, the disclosure provides for administering compounds of the disclosure and compositions comprising compounds of the disclosure to a patient (e.g., a human patient) in need thereof.

The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of a compound of the disclosure which are prepared by dissolving solid compounds of the disclosure in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of a compound of the disclosure together with a suitable carrier so as to prepare the proper dosage form for proper administration to the recipient.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TEAD activity as required to prevent or treat the undesired disease or disorder, such as for example, pain. For example, such amount may be below the amount that is toxic to normal cells, or the mammal as a whole.

In one example, the therapeutically effective amount of the compound of the disclosure administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain aspects, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present disclosure may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compositions comprising compounds of the disclosure (or embodiments or aspects thereof including stereoisomers, geometric isomers, tautomers, solvates, metabolites, isotopes, pharmaceutically acceptable salts, and prodrugs thereof) are normally formulated in accordance with standard pharmaceutical practice as a pharmaceutical composition. A typical formulation is prepared by mixing a compound of the present disclosure and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present disclosure or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). An active pharmaceutical ingredient of the disclosure (e.g., a compound of any one of the formulae described herein, or an embodiment or aspect thereof) can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, PA. The particular carrier, diluent or excipient used will depend upon the means and purpose for which a compound of the present disclosure is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof.

Sustained-release preparations of a compound of the disclosure (e.g., compound of any one of the formulae described herein, or an embodiment or aspect thereof) can be prepared. Suitable examples of sustained-release preparations include semipermeable matrices of solid hydrophobic polymers containing a compound of any one of the formulae described herein, or an embodiment or aspect thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of the disclosure or an embodiment or aspect thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of the disclosure (or an embodiment or aspect thereof) is formulated in an acetate buffer, at pH 5. In another aspect, the compounds of the disclosure or an embodiment thereof are sterile. The compound may be stored, for example, as a solid or amorphous composition, as a lyophilized formulation or as an aqueous solution Formulations of a compound of the disclosure suitable for oral administration can be prepared as discrete units such as pills, capsules, cachets or tablets each containing a predetermined amount of a compound of the disclosure.

Compressed tablets can be prepared by compressing in a suitable machine a compound of the disclosure in a free-flowing form such as a powder or granules, optionally mixed with a binder, lubricant, inert diluent, preservative, surface active or dispersing agent. Molded tablets can be made by molding in a suitable machine a mixture of a powdered compound of the disclosure moistened with an inert liquid diluent. The tablets can optionally be coated or scored and optionally are formulated so as to provide slow or controlled release of a compound of the disclosure therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the disclosure intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing a compound of the disclosure in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 0.1 mg, about 1 mg, about 5 mg, about 10 mg, about 25 mg, about 30 mg, about 50 mg, about 80 mg, about 100 mg, about 150 mg, about 250 mg, about 300 mg and about 500 mg of the compounds (or an embodiment or aspect thereof) of the disclosure compounded with a filler (e.g., lactose, such as about 90-30 mg anhydrous lactose), a disintegrant (e.g, croscarmellose, such as about 5-40 mg sodium croscarmellose), a polymer (e.g. polyvinylpyrrolidone (PVP), a cellulose (e.g., hydroxypropylmethyl cellulose (HPMC), and/or copovidone, such as about 5-30 mg PVP, IPMC or copovidone), and a lubricant (e.g., magnesium stearate, such as about 1-10 mg). Wet granulation, dry granulation or dry blending may be used. In one wet granulation aspect, powdered ingredients are first mixed together and then mixed with a solution or suspension of the polymer (e.g., PVP). The resulting composition can be dried, granulated, mixed with lubricant and compressed to tablet form using conventional equipment. An example of an aerosol formulation can be prepared by dissolving the compound, for example 5-400 mg, of the disclosure in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the compounds of the disclosure in an amount of, for example, 0.075 to 20% w/w. When formulated in an ointment, the compounds of the disclosure can be employed with either a paraffinic or a water-miscible ointment base. Alternatively, the compounds of the disclosure can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of a compound of the disclosure through the skin or other affected areas. Examples of such dermal penetration enhancers include dimethyl sulfoxide and related analogs.

For topical formulations, it is desired to administer an effective amount of a pharmaceutical composition according to the disclosure to target area, e.g., skin surfaces, mucous membranes, and the like, which are adjacent to peripheral neurons which are to be treated. This amount will generally range from about 0.0001 mg to about 1 g of a compound of the disclosure (or an embodiment or aspect thereof) per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of a compound of the disclosure is used per cc of ointment base. The pharmaceutical composition can be formulated as transdermal compositions or transdermal delivery devices ("patches"). Such compositions include, for example, a backing, compound of the disclosure reservoir, a control membrane, liner and contact adhesive. Such transdermal patches may be used to provide continuous pulsatile, or on demand delivery of the compounds of the present disclosure as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of a compound of the disclosure.

When the binding target is located in the brain, certain aspects of the disclosure provide for a compound of the disclosure (or an embodiment or aspect thereof) to traverse the blood-brain barrier. Certain neurodegenerative diseases are associated with an increase in permeability of the blood-brain barrier, such that a compound of the disclosure (or an embodiment or aspect thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of the disclosure (or an embodiment or aspect thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford Pharmaceutical).

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula of the disclosure (or an embodiment or aspect thereof) across the blood-brain barrier include, but are not limited to, encapsulating the a compound of the disclosure (or an embodiment or aspect thereof) in liposomes that are coupled to antibody binding fragments that bind to receptors on the vascular endothelium of the blood-brain barrier (see, e.g., U.S. Patent Application Publication No. 2002/0025313), and coating a compound of the disclosure (or an embodiment or aspect thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of the disclosure (or an embodiment or aspect thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of the disclosure (or an embodiment or aspect thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain aspects, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic mini pumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

In some embodiments, a compound that modulates TEAD activity is a compound of any one of the formulae described herein, as defined above, or a stereoisomer or pharmaceutically acceptable salt thereof.

In some embodiments, the compound that modulates TEAD activity is a degrader of TEAD.

The compounds of the disclosure (or an embodiment or aspect thereof) are useful as a medical therapy for treating diseases and conditions mediated by TEAD activity. Such diseases and conditions include but are not limited to cancers including acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In a specific embodiment, compounds of the disclosure (or an embodiment or aspect thereof) can be administered as a medical therapy to treat proliferative disorders including acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstom's macroglobulinemia, testicular tumors, uterine cancer and Wilms' tumor.

In one specific aspect, compounds of the disclosure (or an embodiment or aspect thereof) are administered as a medical therapy to treat acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In another aspect, the disclosure provides for a method for treating acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor, comprising the step of administering a therapeutically effective amount of a compound according to any one of the formulae described herein (or an embodiment or aspect thereof) as described elsewhere herein to a subject in need thereof.

In another aspect, the disclosure provides for a compound of any one of the formulae described herein as described elsewhere herein or (or an embodiment or aspect thereof) for modulating TEAD activity. In some embodiments, the disclosure provides for a pharmaceutically acceptable salt of compound of any one of the formulae described herein for modulating TEAD activity.

In another aspect, the disclosure provides for a compound of any one of the formulae described herein, or an embodiment or aspect thereof, such as a pharmaceutically acceptable salt thereof for use in medical therapy.

In another aspect, the disclosure provides for a method for treatment or prophylaxis of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor, comprising the step of administering a therapeutically effective amount of a compound according to any one of the formulae described herein (or an embodiment or aspect thereof) as described elsewhere herein to a subject in need thereof.

In another aspect, the disclosure provides for a compound of any one of the formulae described herein or an embodiment or aspect thereof such as a pharmaceutically acceptable salt thereof for the treatment or prophylaxis of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In another aspect, the disclosure provides for the use of a compound of any one of the formulae described herein or an embodiment or aspect thereof such as a pharmaceutically acceptable salt thereof for the preparation of a medicament for the treatment or prophylaxis of acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In another aspect, the disclosure provides for a method for treating acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor in a mammal (e.g., a human) comprising administering a compound of any one of the formulae described herein or an embodiment or aspect thereof such as a pharmaceutically acceptable salt thereof to the mammal.

In another aspect, the disclosure provides for a method for modulating TEAD activity, comprising contacting TEAD with a compound of any one of the formulae described herein or an embodiment or aspect thereof such as a pharmaceutically acceptable salt thereof.

In another aspect, the disclosure provides for a compound of any one of the formulae described herein or an embodiment or aspect thereof such as a pharmaceutically acceptable salt thereof for the treatment or prophylaxis of a disease or condition mediated by TEAD activity. Within aspects of this embodiment, the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In another aspect, the disclosure provides for the use of a compound of any one of the formulae described herein or an embodiment or aspect thereof such as a pharmaceutically acceptable salt thereof for the preparation of a medicament for the treatment or prophylaxis of a disease or condition that is mediated by TEAD activity. Within aspects of this embodiment, the disease or condition is acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In one aspect, compounds of the disclosure demonstrate higher potency as compared to other analogues.

Combination Therapy

The compounds of any one of the formulae described herein, or stereoisomers or pharmaceutically acceptable salts thereof, may be employed alone or in combination with other agents for treatment. For example, the second agent of the pharmaceutical combination formulation or dosing regimen may have complementary activities to the compound of any one of the formulae described herein such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of any one of the formulae described herein, or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of any one of the formulae provided herein, such as a compound of any of the formulae described herein, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

Typically, any agent that has activity against a disease or condition being treated may be co-administered. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of any one of the formulae described herein, or a pharmaceutically acceptable salt thereof, and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2,2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc.); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3-fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc.); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-$OCH_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof, autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound of the present invention is administered in combination with a biologic agent, such as bevacizumab or panitumumab.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

In another embodiment, provided are methods of using a compound of any one of the formulae described herein, or a pharmaceutically acceptable salt thereof as described elsewhere herein, or an embodiment or aspect thereof, to treat cancer in combination with a PD-1 axis binding antagonist.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. Specific examples of PD-1 binding antagonists are provided infra.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. Specific examples of PD-L1 binding antagonists are provided infra.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

PD-1 Axis Binding Antagonists

Provided herein are methods for treating cancer in an individual comprising administering to the individual an effective amount of a PD-1 axis binding antagonist and a compound of any one of the formulae described herein, or a pharmaceutically acceptable salt thereof. Also provided herein are methods of enhancing immune function or response in an individual (e.g., an individual having cancer) comprising administering to the individual an effective amount of a PD-1 axis binding antagonist and a compound of any one of the formulae described herein, or a pharmaceutically acceptable salt thereof.

In such methods, the PD-1 axis binding antagonist includes a PD-1 binding antagonist, a PDL1 binding antagonist, and/or a PDL2 binding antagonist. Alternative names for "PD-1" include CD279 and SLEB2. Alternative names for "PDL1" include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the PD-1 binding antagonist is a molecule that inhibits the binding of PD-1 to its ligand binding partner(s). In a specific aspect the PD-1 ligand binding partners are PDL1 and/or PDL2. In another embodiment, a PDL1 binding antagonist is a molecule that inhibits the binding of PDL1 to its binding partner(s). In a specific aspect, PDL1 binding partner(s) are PD-1 and/or B7-1. In another embodiment, the PDL2 binding antagonist is a molecule that inhibits the binding of PDL2 to its binding partner(s). In a specific aspect, a PDL2 binding partner is PD-1. The antagonist may be an antibody, an antigen binding fragment thereof, an immunoadhesin, a fusion protein, an oligopeptide or a small molecule. If the antagonist is an antibody, in some embodiments the antibody comprises a human constant region selected from the group consisting of IgG1, IgG2, IgG3 and IgG4

Anti-PD-1 Antibodies

In some embodiments, the PD-1 binding antagonist is an anti-PD-1 antibody. A variety of anti-PDL1 antibodies can be utilized in the methods disclosed herein. In any of the embodiments herein, the PD-1 antibody can bind to a human PD-1 or a variant thereof. In some embodiments the anti-PD-1 antibody is a monoclonal antibody. In some embodiments, the anti-PD-1 antibody is an antibody fragment selected from the group consisting of Fab, Fab', Fab'-SH, Fv, scFv, and $(Fab')_2$ fragments. In some embodiments, the anti-PD-1 antibody is a chimeric or humanized antibody. In other embodiments, the anti-PD-1 antibody is a human antibody.

In some embodiments, the anti-PD-1 antibody is nivolumab (CAS Registry Number: 946414-94-4). Nivolumab (Bristol-Myers Squibb/Ono), also known as MDX-1106-04, MDX-1106, ONO-4538, BMS-936558, and OPDIVO®, is an anti-PD-1 antibody described in WO2006/121168. Nivolumab comprises a heavy chain and a light chain sequence, wherein:

```
(a) the heavy chain comprises the
amino acid sequence.
                                   (SEQ ID NO: 1)
QVQLVESGGGVVQPGRSLRLDCKASGITFSNSGMH

WVRQAPGKGLEWVAVIWY DGSKRYYADSVKGRFT

ISRDNSKNTLFLQMNSLRAEDTAVYYCATNDDYWG

QGTLVTVSSASTKGPSVFPLAPCSRSTSESTAALG

CLVKDYFPEPVTVSWNSGALTSGVHTFPAVLQSSG

LYSLSSVVTVPSSSLGTKTYTCNVDHKPSNTKVDK

RVESKYGPPCPPCPAPEFLGGPSVFLFPPKPKDTL

MISRTPEVTCVVVDVSQEDPEVQFNWYVDGVEVHN

AKTKPREEQFNSTYRVVSVLTVLHQDWLNGKEYKC

KVSNKGLPSSIEKTISKAKGQPREPQVYTLPPSQE

EMTKNQVSLTCLVKGFYPSDIAVEWESNGQPENNY
```

-continued

```
KTTPPVLDSDGSFFLYSRLTVDKSRWQEGNVFSCS

VMHEALHNHYTQKSLSLSLGK,
and

(b) the light chain comprises the
amino acid sequence:
                                   (SEQ ID NO: 2)
EIVLTQSPATLSLSPGERATLSCRASQSVSSYLAW

YQQKPGQAPRLLIYDASNRAT GIPARFSGSGSGT

DFTLTISSLEPEDFAVYYCQQSSNWPRTFGQGTKV

EIKRTVAAPSVFIFPPSDEQLKSGTASVVCLLNNF

YPREAKVQWKVDNALQSGNSQESVTEQDSKDSTYS

LSSTLTLSKADYEKHKVYACEVTHQGLSSPVTKSF

NRGEC.
```

In some embodiments, the anti-PD-1 antibody comprises the six HVR sequences from SEQ ID NO:1 and SEQ ID NO:2 (e.g., the three heavy chain HVRs from SEQ ID NO:1 and the three light chain HVRs from SEQ ID NO:2). In some embodiments, the anti-PD-1 antibody comprises the heavy chain variable domain from SEQ ID NO:1 and the light chain variable domain from SEQ ID NO:2.

In some embodiments, the anti-PD-1 antibody is pembrolizumab (CAS Registry Number: 1374853-91-4). Pembrolizumab (Merck), also known as MK-3475, Merck 3475, lambrolizumab, SCH-900475, and KEYTRUDA® is an anti-PD-1 antibody described in WO2009/114335. Pembrolizumab comprises a heavy chain and a light chain sequence, wherein:

```
(a) the heavy chain comprises the
amino acid sequence:
                                   (SEQ ID NO: 3)
QVQLVQSGVEVKKPGASVKVSCKASGYTFTNYYMY

WVRQAPGQGLEWMGG INPSNGGTNFNEKFKNRVT

LTTDSSTTTAYMELKSLQFDDTAVYYCARRDYRFD

MGFDYW GQGTTVTVSSASTKGPSVFPLAPCSRST

SESTAALGCLVKDYFPEPVTVSWNSGALTSGV HT

FPAVLQSSGLYSLSSVVTVPSSSLGTKTYTCNVDH

KPSNTKVDKRVESKYGPPCPPCP APEFLGGPSVF

LFPPKPKDTLMISRTPEVTCVVVDVSQEDPEVQFN

WYVDGVEVHNAKTK PREEQFNSTYRVVSVLTVLH

QDWLNGKEYKCKVSNKGLPSSIEKTISKAK GQPR

EPQVYTLPPSQEEMTKNQVSLTCLVKGFYPSDIAV

EWESNGQPENN YKTTPPVLDSDGSFFLYSRLTVD

KSRWQEGNVFSCSVMHEALHNHYTQKSLSLSLGK,
and

(b) the light chain comprises the
amino acid sequence:
                                   (SEQ ID NO: 4)
EIVLTQSPAT LSLSPGERATLSCRASKGVSTSGY

SYLHWYQQKPGQAPRLLIYLASYLES GVPARFSG

SGSGTDFTLTISSLEPEDFAVYYCQHSRDLPLTFG
```

-continued

```
GGTKVEIKRTVAAPSVF IFPPSDEQLKSGTASVV

CLLNNFYPREAKVQWKVDNALQSGNSQESVTEQ D

SKDSTYSLSSTLTLSKADYEKHKVYACEVTHQGLS

SPVTKSFNRGEC.
```

In some embodiments, the anti-PD-1 antibody comprises the six HVR sequences from SEQ ID NO:3 and SEQ ID NO:4 (e.g., the three heavy chain HVRs from SEQ ID NO:3 and the three light chain HVRs from SEQ ID NO:4). In some embodiments, the anti-PD-1 antibody comprises the heavy chain variable domain from SEQ ID NO:3 and the light chain variable domain from SEQ ID NO:4.

In some embodiments, the anti-PD-1 antibody is MEDI-0680 (AMP-514; AstraZeneca). MEDI-0680 is a humanized IgG4 anti-PD-1 antibody.

In some embodiments, the anti-PD-1 antibody is PDR001 (CAS Registry No. 1859072-53-9; Novartis). PDR001 is a humanized IgG4 anti-PD1 antibody that blocks the binding of PDL1 and PDL2 to PD-1.

In some embodiments, the anti-PD-1 antibody is REGN2810 (Regeneron). REGN2810 is a human anti-PD1 antibody.

In some embodiments, the anti-PD-1 antibody is BGB-108 (BeiGene). In some embodiments, the anti-PD-1 antibody is BGB-A317 (BeiGene).

In some embodiments, the anti-PD-1 antibody is JS-001 (Shanghai Junshi). JS-001 is a humanized anti-PD1 antibody.

In some embodiments, the anti-PD-1 antibody is STI-A1110 (Sorrento). STI-A1110 is a human anti-PD1 antibody.

In some embodiments, the anti-PD-1 antibody is INCSHR-1210 (Incyte). INCSHR-1210 is a human IgG4 anti-PD1 antibody.

In some embodiments, the anti-PD-1 antibody is PF-06801591 (Pfizer).

In some embodiments, the anti-PD-1 antibody is TSR-042 (also known as ANB011; Tesaro/AnaptysBio).

In some embodiments, the anti-PD-1 antibody is AM0001 (ARMO Biosciences).

In some embodiments, the anti-PD-1 antibody is ENUM 244C8 (Enumeral Biomedical Holdings). ENUM 244C8 is an anti-PD1 antibody that inhibits PD-1 function without blocking binding of PDL1 to PD-1.

In some embodiments, the anti-PD-1 antibody is ENUM 388D4 (Enumeral Biomedical Holdings). ENUM 388D4 is an anti-PD1 antibody that competitively inhibits binding of PDL1 to PD-1.

In some embodiments, the PD-1 antibody comprises the six HVR sequences (e.g., the three heavy chain HVRs and the three light chain HVRs) and/or the heavy chain variable domain and light chain variable domain from a PD-1 antibody described in WO2015/112800 (Applicant: Regeneron), WO2015/112805 (Applicant: Regeneron), WO2015/112900 (Applicant: Novartis), US20150210769 (Assigned to Novartis), WO2016/089873 (Applicant: Celgene), WO2015/035606 (Applicant: Beigene), WO2015/085847 (Applicants: Shanghai Hengrui Pharmaceutical/Jiangsu Hengrui Medicine), WO2014/206107 (Applicants: Shanghai Junshi Biosciences/Junmeng Biosciences), WO2012/145493 (Applicant: Amplimmune), U.S. Pat. No. 9,205,148 (Assigned to MedImmune), WO2015/119930 (Applicants: Pfizer/Merck), WO2015/119923 (Applicants: Pfizer/Merck), WO2016/032927 (Applicants: Pfizer/Merck), WO2014/179664 (Applicant: AnaptysBio), WO2016/106160 (Applicant: Enumeral), and WO2014/194302 (Applicant: Sorrento).

Anti-PDL1 Antibodies

In some embodiments, the PD-1 axis binding antagonist is an anti-PDL1 antibody. A variety of anti-PDL1 antibodies are contemplated and described herein. In any of the embodiments herein, the isolated anti-PDL1 antibody can bind to a human PDL1, for example a human PDL1 as shown in UniProtKB/Swiss-Prot Accession No. Q9NZQ7.1, or a variant thereof. In some embodiments, the anti-PDL1 antibody is capable of inhibiting binding between PDL1 and PD-1 and/or between PDL1 and B7-1. In some embodiments, the anti-PDL1 antibody is a monoclonal antibody. In some embodiments, the anti-PDL1 antibody is an antibody fragment selected from the group consisting of Fab, Fab'-SH, Fv, scFv, and $(Fab')_2$ fragments. In some embodiments, the anti-PDL1 antibody is a chimeric or humanized antibody. In some embodiments, the anti-PDL1 antibody is a human antibody. Examples of anti-PDL1 antibodies useful in the methods of this invention and methods of making them are described in PCT patent application WO 2010/077634 and U.S. Pat. No. 8,217,149, both of which are incorporated herein.

In some embodiments, the anti-PDL1 antibody is atezolizumab (CAS Registry Number: 1422185-06-5). Atezolizumab (Genentech), also known as MPDL3280A, is an anti-PDL1 antibody.

Atezolizumab comprises:

(a) an HVR—H1, HVR—H2, and HVR—H3 sequence of GFTFSDSWIH (SEQ ID NO:5), AWISPYGGSTYYADSVKG (SEQ ID NO:6) and RHWPGGFDY (SEQ ID NO:7), respectively, and (b) an HVR-L1, HVR-L2, and HVR-L3 sequence of RASQDVSTAVA (SEQ ID NO:8), SASFLYS (SEQ ID NO:9) and QQYLYHPAT (SEQ ID NO:10), respectively.

Atezolizumab comprises a heavy chain and a light chain sequence, wherein:

```
(a) the heavy chain variable
region sequence comprises the
amino acid sequence:
                              (SEQ ID NO: 11
EVQLVESGGGLVQPGGSLRLSCAASGFTFSDSWIH

WVRQAPGKGLEWVAWISPYGGSTYYADSVKGRFTI

SADTSKNTAYLQMNSLRAEDTAVYYCARRHWPGGF

DYWGQGTLVTVSS,
and

(b) the light chain variable
region sequence comprises the
amino acid sequence:
                              (SEQ ID NO: 12)
DIQMTQSPSSLSASVGDRVTITCRASQDVSTAVAW

YQQKPGKAPKLLIY SASFLYSGVPSRFSGSGSGT

DFTLTISSLQPEDFATYYCQQYLYHPATFGQGTKV

EIKR.
```

Atezolizumab comprises a heavy chain and a light chain sequence, wherein:

(a) the heavy chain comprises the amino acid sequence:

(SEQ ID NO: 13)

EVQLVESGGGLVQPGGSLRLSCAASGFTFSDSWIH

WVRQAPGKGLEWVAWISPYGGSTYYADSVKGRFTI

SADTSKNTAYLQMNSLRAEDTAVYYCARRHWPGGF

DYWGQGTLVTVSSASTKGPSVFPLAPSSKSTSGGT

AALGCLVKDYFPEPVTVSWNSGALTSGVHTFPAVL

QSSGLYSLSSVVTVPSSSLGTQTYICNVNHKPSNT

KVDKKVEPKSCDKTHTCPPCPAPELLGGPSVFLFP

PKPKDTLMISRTPEVTCVVVDVSHEDPEVKFNWYV

DGVEVHNAKTKPREEQYASTYRVVSVLTVLHQDWL

NGKEYKCKVSNKALPAPIEKTISKAKGQPREPQVY

TLPPSREEMTKNQVSLTCLVKGFYPSDIAVEWESN

GQPENNYKTTPPVLDSDGSFFLYSKLTVDKSRWQQ

GNVFSCSVMHEALHNHYTQKSLSLSPG, and (b) the light chain comprises the amino acid sequence:

(SEQ ID NO: 14)

DIQMTQSPSSLSASVGDRVTITCRASQDVSTAVAW

YQQKPGKAPKLLIYSASFLYSGVPSRFSGSGSGTD

FTLTISSLQPEDFATYYCQQYLYHPATFGQGTKVE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC.

In some embodiments, the anti-PDL1 antibody is avelumab (CAS Registry Number: 1537032-82-8). Avelumab, also known as MSB0010718C, is a human monoclonal IgG1 anti-PDL1 antibody (Merck KGaA, Pfizer). Avelumab comprises a heavy chain and a light chain sequence, wherein:

(a) the heavy chain comprises the amino acid sequence:

(SEQ ID NO: 15)

EVQLLESGGGLVQPGGSLRLSCAASGFTFSSYIMM

WVRQAPGKGLEWVSSIYPSGGITFYADTVKGRFTI

SRDNSKNTLYLQMNSLRAEDTAVYYCARIKLGTVT

TVDYWGQGTLVTVSSASTKGPSVFPLAPSSKSTSG

GTAALGCLVKDYFPEPVTVSWNSGALTSGVHTFPA

VLQSSGLYSLSSVVTVPSSSLGTQTYICNVNHKPS

NTKVDKKVEPKSCDKTHTCPPCPAPELLGGPSVFL

FPPKPKDTLMISRTPEVTCVVVDVSHEDPEVKFNW

YVDGVEVHNAKTKPREEQYNSTYRVVSVLTVLHQD

WLNGKEYKCKVSNKALPAPIEKTISKAKGQPREPQ

VYTLPPSRDELTKNQVSLTCLVKGFYPSDIAVEWE

-continued

SNGQPENNYKTTPPVLDSDGSFFLYSKLTVDKSRW

QQGNVFSCSVMHEALHNHYTQKSLSLSPG, and (b) the light chain comprises the amino acid sequence:

(SEQ ID NO: 16)

QSALTQPASVSGSPGQSITISCTGTSSDVGGYNYV

SWYQQHPGKAPKLMIYDVSNRPSGVSNRFSGSKSG

NTASLTISGLQAEDEADYYCSSYTSSSTRVFGTGT

KVTVLGQPKANPTVTLFPPSSEELQANKATLVCLI

SDFYPGAVTVAWKADGSPVKAGVETTKPSKQSNNK

YAASSYLSLTPEQWKSHRSYSCQVTHEGSTVEKTV

APTECS.

In some embodiments, the anti-PDL1 antibody comprises the six HVR sequences from SEQ ID NO:15 and SEQ ID NO:16 (e.g., the three heavy chain HVRs from SEQ ID NO:15 and the three light chain HVRs from SEQ ID NO:16). In some embodiments, the anti-PDL1 antibody comprises the heavy chain variable domain from SEQ ID NO: 15 and the light chain variable domain from SEQ ID NO:16.

In some embodiments, the anti-PDL1 antibody is durvalumab (CAS Registry Number: 1428935-60-7). Durvalumab, also known as MEDI4736, is an Fc-optimized human monoclonal IgG1 kappa anti-PDL1 antibody (MedImmune, AstraZeneca) described in WO2011/066389 and US2013/034559. Durvalumab comprises a heavy chain and a light chain sequence, wherein:

(a) the heavy chain comprises the amino acid sequence:

(SEQ ID NO: 17)

EVQLVESGGGLVQPGGSLRLSCAASGFTFSRYWMS

WVRQAPGKGLEWVANIKQDGSEKYYVDSVKGRFTI

SRDNAKNSLYLQMNSLRAEDTAVYYCAREGGWFGE

LAFDYWGQGTLVTVSSASTKGPSVFPLAPSSKSTS

GGTAALGCLVKDYFPEPVTVSWNSGALTSGVHTFP

AVLQSSGLYSLSSVVTVPSSSLGTQTYICNVNHKP

SNTKVDKRVEPKSCDKTHTCPPCPAPEFEGGPSVF

LFPPKPKDTLMISRTPEVTCVVVDVSHEDPEVKFN

WYVDGVEVHNAKTKPREEQYNSTYRVVSVLTVLHQ

DWLNGKEYKCKVSNKALPASIEKTISKAKGQPREP

QVYTLPPSREEMTKNQVSLTCLVKGFYPSDIAVEW

ESNGQPENNYKTTPPVLDSDGSFFLYSKLTVDKSR

WQQGNVFSCSVMHEALHNHYTQKSLSLSPG, and (b) the light chain comprises the amino acid sequence:

(SEQ ID NO: 18)

EIVLTQSPGTLSLSPGERATLSCRASQRVSSSYLA

WYQQKPGQAPRLLIYDASSRATGIPDRFSGSGSGT

DFTLTISRLEPEDFAVYYCQQYGSLPWTFGQGTKV

-continued

```
EIKRTVAAPSVFIFPPSDEQLKSGTASVVCLLNNF

YPREAKVQWKVDNALQSGNSQESVTEQDSKDSTYS

LSSTLTLSKADYEKHKVYACEVTHQGLSSPVTKSF

NRGEC.
```

In some embodiments, the anti-PDL1 antibody comprises the six HVR sequences from SEQ ID NO:17 and SEQ ID NO:18 (e.g., the three heavy chain HVRs from SEQ ID NO:17 and the three light chain HVRs from SEQ ID NO:18). In some embodiments, the anti-PDL1 antibody comprises the heavy chain variable domain from SEQ ID NO: 17 and the light chain variable domain from SEQ ID NO:18.

In some embodiments, the anti-PDL1 antibody is MDX-1105 (Bristol Myers Squibb). MDX-1105, also known as BMS-936559, is an anti-PDL1 antibody described in WO2007/005874.

In some embodiments, the anti-PDL1 antibody is LY3300054 (Eli Lilly).

In some embodiments, the anti-PDL1 antibody is STI-A1014 (Sorrento). STI-A1014 is a human anti-PDL1 antibody.

In some embodiments, the anti-PDL1 antibody is KN035 (Suzhou Alphamab). KN035 is single-domain antibody (dAB) generated from a camel phage display library.

In some embodiments, the anti-PDL1 antibody comprises a cleavable moiety or linker that, when cleaved (e.g., by a protease in the tumor microenvironment), activates an antibody antigen binding domain to allow it to bind its antigen, e.g., by removing a non-binding steric moiety. In some embodiments, the anti-PDL1 antibody is CX-072 (CytomX Therapeutics).

In some embodiments, the PDL1 antibody comprises the six HVR sequences (e.g., the three heavy chain HVRs and the three light chain HVRs) and/or the heavy chain variable domain and light chain variable domain from a PDL1 antibody described in US20160108123 (Assigned to Novartis), WO2016/000619 (Applicant: Beigene), WO2012/145493 (Applicant: Amplimmune), U.S. Pat. No. 9,205,148 (Assigned to MedImmune), WO2013/181634 (Applicant: Sorrento), and WO2016/061142 (Applicant: Novartis).

In a still further specific aspect, the PD-1 or PDL1 antibody has reduced or minimal effector function. In a still further specific aspect the minimal effector function results from an "effector-less Fc mutation" or aglycosylation mutation. In still a further embodiment, the effector-less Fc mutation is an N297A or D265A/N297A substitution in the constant region. In some embodiments, the isolated anti-PDL1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

Other PD-1 Antagonists

In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. AMP-224 (CAS Registry No. 1422184-00-6; GlaxoSmithKline/MedImmune), also known as B7-DCIg, is a PDL2-Fc fusion soluble receptor described in WO2010/027827 and WO2011/066342.

In some embodiments, the PD-1 binding antagonist is a peptide or small molecule compound. In some embodiments, the PD-1 binding antagonist is AUNP-12 (PierreFabre/Aurigene). See, e.g., WO2012/168944, WO2015/036927, WO2015/044900, WO2015/033303, WO2013/144704, WO2013/132317, and WO2011/161699.

In some embodiments, the PDL1 binding antagonist is a small molecule that inhibits PD-1. In some embodiments, the PDL1 binding antagonist is a small molecule that inhibits PDL1. In some embodiments, the PDL1 binding antagonist is a small molecule that inhibits PDL1 and VISTA. In some embodiments, the PDL1 binding antagonist is CA-170 (also known as AUPM-170). In some embodiments, the PDL1 binding antagonist is a small molecule that inhibits PDL1 and TIM3. In some embodiments, the small molecule is a compound described in WO2015/033301 and WO2015/033299.

As used herein "combination" refers to any mixture or permutation of one or more compounds of the disclosure (or an embodiment or aspect thereof) and one or more other compounds of the disclosure or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the disclosure with another therapeutic agent. Unless the context makes clear otherwise, "combination" may include routes of administration of a compound of the disclosure with another therapeutic agent. Unless the context makes clear otherwise, "combination" may include formulations of a compound of the disclosure with another therapeutic agent. Dosage forms, routes of administration and pharmaceutical compositions include, but are not limited to, those described herein.

Preparation of Compounds

The following synthetic reaction schemes detailed in the General Schemes and Examples are merely illustrative of some of the methods by which the compounds of the present disclosure (or an embodiment or aspect thereof) can be synthesized. Various modifications to these synthetic reaction schemes can be made and will be suggested to one skilled in the art having referred to the disclosure contained in this Application.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Car-*

*bon Compounds*, Elsevier Science Publishers, 1989, Volumes 1-5 and Supplementals; and *Organic Reactions*, Wiley & Sons: New York, 1991, Volumes 1-40.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C.

Although certain exemplary embodiments are depicted and described herein, the compounds of the present disclosure (or an embodiment or aspect thereof) can be prepared using appropriate starting materials according to the methods described generally herein and/or by methods available to one of ordinary skill in the art.

Intermediates and final compounds were purified by either flash chromatography, and/or by reverse-phase preparative HPLC (high performance liquid chromatography), and/or by supercritical fluid chromatography, and/or by Preparative Thin Layer Chromatography (Prep TLC).

Mass spectrometry (MS) was performed using a (1) Sciex 15 mass spectrometer in ES+ mode, or (2) Shimadzu liquid chromatography-mass spectrometry (LCMS) 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) was performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

The following generalized schemes are used to prepare the disclosed compounds, intermediates, and pharmaceutically acceptable salts thereof. Disclosed compounds and intermediates may be prepared using standard organic synthetic techniques and from commerically available starting materials and reagents. It will be appreciated that synthetic procedures employed in the preparation of disclosed compounds and intermediates will depend on the particular substituents present in the compound or intermediate and that various protection, deprotection, and conversion steps that are standard in organic synthesis may be required, but may not be illustrated in the general scheme. It is also to be understood that any of the steps shown in the following general schemes may be omitted or used in any combination and in any order that is chemically feasible to achieve a desired intermediate or disclosed compound. Furthermore, it is appreciated that methods are included and described herein, and find basis in the general schemes and specific examples, the same as if each and every method were specifically and individually listed for each and every general scheme and example.

SCHEME 1

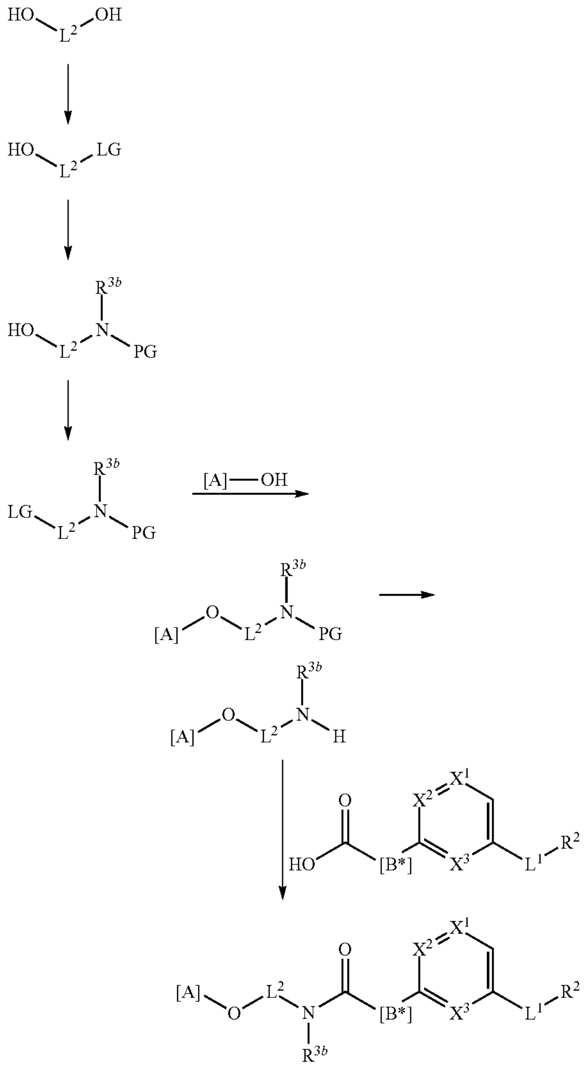

SCHEME 2

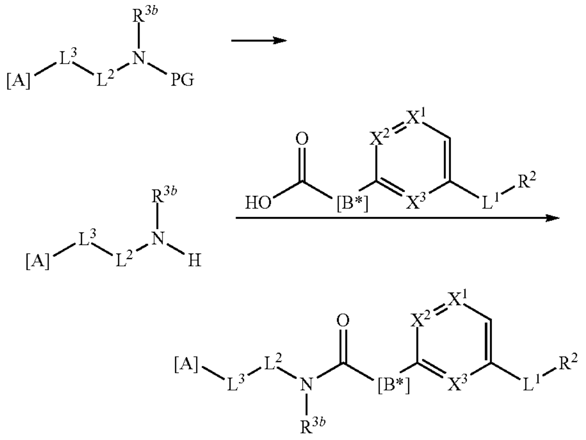

SCHEME 3

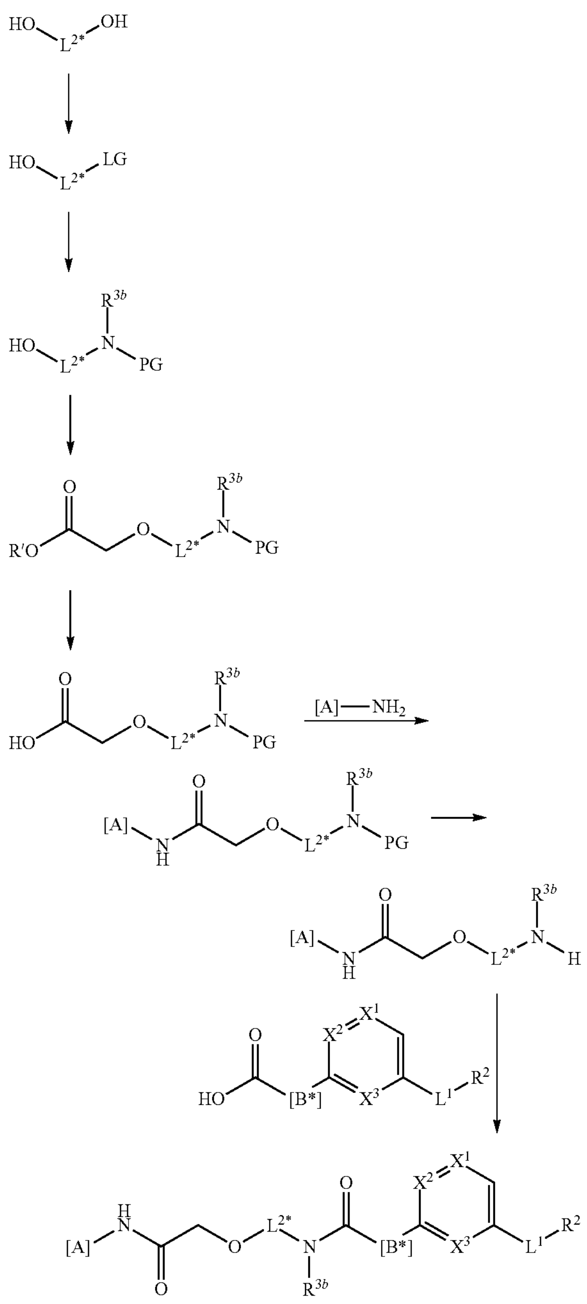

SCHEME 4

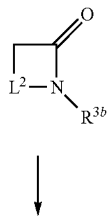

-continued

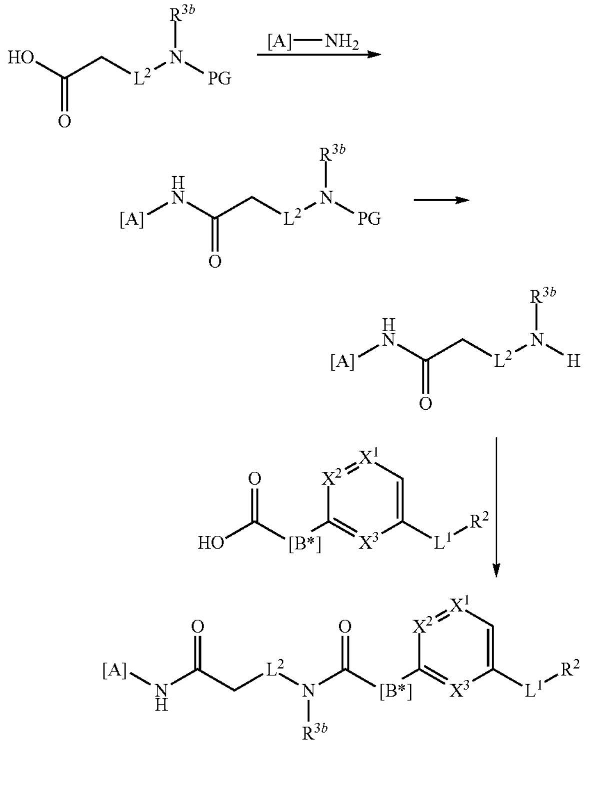

Schemes 1, 2, 3, and 4 describe general synthetic routes for the synthesis of a compound of any one of the formulae described herein. [A], $L^1$, $L^2$, $L^3$, $R^2$, $R^{3b}$, $X^1$, $X^2$, and $X^3$ are as defined above. Each LG is independently any suitable leaving group, including, for example, OTs ($O—SO_2C_6H_4CH_3$). Each PG is independently any suitable protecting group, including, for example, Boc (C(O)O-$^t$Bu) or Cbz ($C(O)OCH_2C_6H_4$). In Scheme 3, R' is any suitable moiety, including, for example, $C_{1-12}$alkyl. [B*] is the remaining portion of the [B] moiety, defined above, that is not depicted in Scheme 1, 2, 3, or 4, as the case may be. In some embodiments, [B*] is

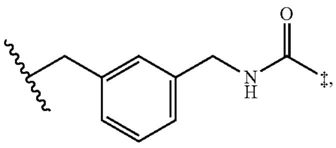

wherein ‡ denotes the point of attachment to the

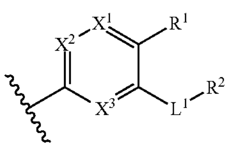

moiety. $L^{2*}$ is the portion of the $L^2$ moiety, as defined above, that is not depicted in Scheme 1, 2, 3, or 4, as the case may be.

Example 1

Preparation of N-(3-(2-((4-((2-(2,6-dioxopiperidin-3-yl)-1,3-dioxoisoindolin-5-yl)oxy)butyl)(methyl)amino)-2-oxoethyl)benzyl)-5-methoxy-4-((E)-2-(trans-4-(trifluoromethyl)cyclohexyl)vinyl)picolinamide (Compound 1)

The general reaction scheme was as follows:

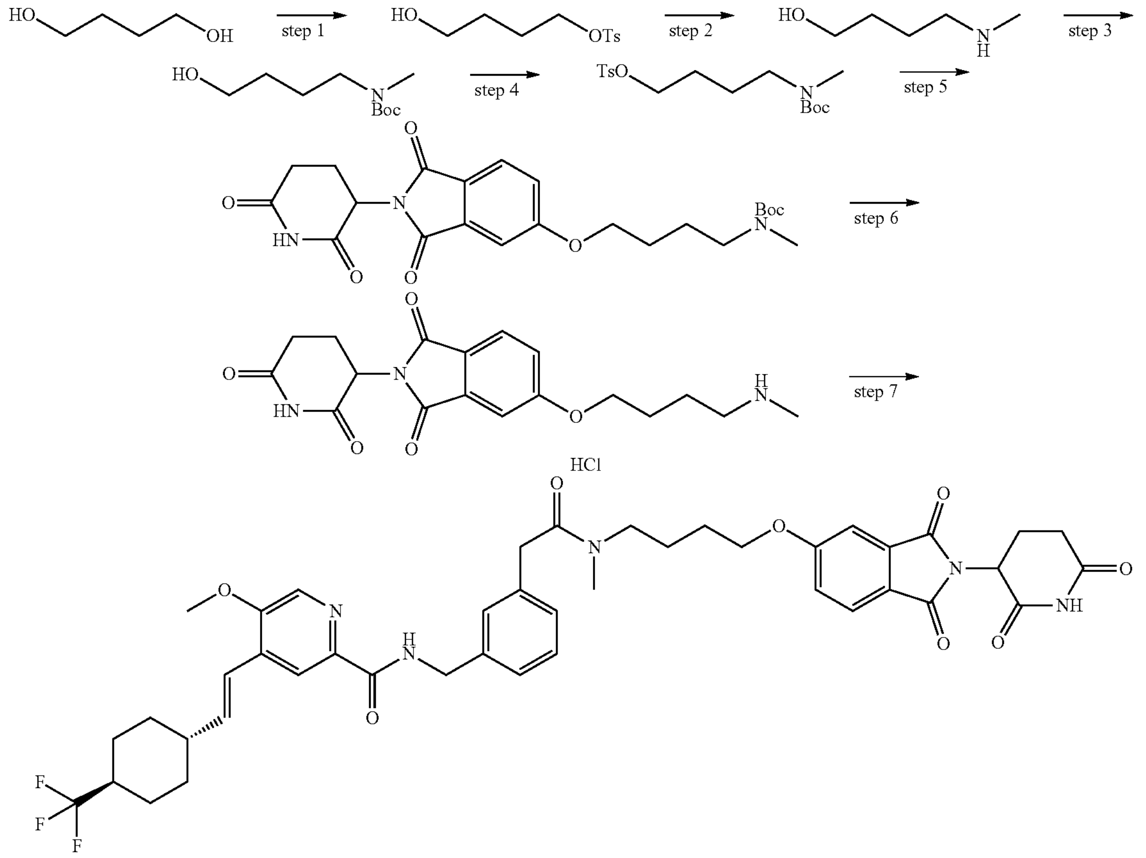

Step 1: 4-Hydroxybutyl 4-methylbenzenesulfonate

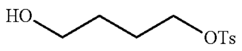 [SMILES: Cc1ccc(S(=O)(=O)OCCCCO)cc1]

To a solution of butane-1,4-diol (2.0 g, 22.19 mmol) in DCM (20 mL) was added KI (921 mg, 5.55 mmol) and $Ag_2O$ (6.17 g, 26.63 mmol) at 0° C. Then a solution of TsCl (5.08 g, 26.63 mmol) in DCM (20 mL) was added dropwise at 0° C. The resulting mixture was stirred at room temperature for 16 hours. Then the reaction mixture was filtered, the filtrate was concentrated. The residue was purified by column chromatography on silica gel (0-2% MeOH in DCM) to afford the title compound (2.3 g, 42%) as a colorless oil. $^1H$ NMR (400 MHz, $CDCl_3$): δ 7.80 (d, J=8.4 Hz, 2H), 7.36 (d, J=8.0 Hz, 2H), 4.08 (t, J=6.4 Hz, 2H), 3.63 (t, J=6.4 Hz, 2H), 2.46 (s, 3H), 1.78-1.73 (m, 2H), 1.64-1.57 (m, 2H).

Step 2: 4-(Methylamino)butan-1-ol

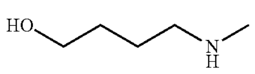

To a solution of 4-hydroxybutyl 4-methylbenzenesulfonate (2.1 g, 8.6 mmol) in EtOH (5 mL) was added 33% $MeNH_2$ in EtOH (5 mL, 102.54 mmol) at room temperature. The resulting mixture was stirred at 60° C. for 16 hours. Then the reaction mixture was cooled to room temperature and concentrated. The residue was purified by column chromatography on silica gel (0-5% MeOH in DCM) to afford the title compound (886 mg, quant.) as a colorless oil. $^1H$ NMR (400 MHz, $CD_3OD$): δ 3.59 (t, J=6.0 Hz, 2H), 3.03-2.98 (m, 2H), 2.69 (s, 3H), 1.77-1.71 (m, 2H), 1.63-1.58 (m, 2H).

Step 3: tert-Butyl (4-hydroxybutyl)(methyl)carbamate

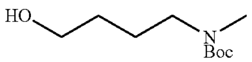

To a mixture of $Et_3N$ (3.23 mL, 23.26 mmol) and 4-(methylamino)butan-1-ol (800 mg, 7.75 mmol) in DCM (7.5 mL) was added $Boc_2O$ (2.54 g, 11.63 mmol) at room temperature. After stirring at room temperature for 16 hours the reaction mixture was concentrated. The residue was purified by column chromatography on silica gel (0-5% MeOH in DCM) to afford the title compound (260 mg, 16%) as a colorless oil. $^1H$ NMR (400 MHz, $CDCl_3$): δ 3.69-3.66 (m, 2H), 3.25 (br s, 2H), 2.81 (s, 3H), 1.56-1.53 (m, 4H), 1.45 (s, 9H).

Step 4: 4-[tert-Butoxycarbonyl(methyl)amino]butyl 4-methylbenzenesulfonate

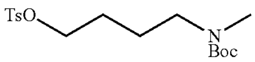 [SMILES: Cc1ccc(S(=O)(=O)OCCCCN(C)C(=O)OC(C)(C)C)cc1]

To a solution of tert-butyl (4-hydroxybutyl)(methyl)carbamate (180 mg, 0.89 mmol) in DCM (1 mL) was added $Et_3N$ (0.37 mL, 2.66 mmol) at 0° C. Then a solution of TsCl (338 mg, 1.77 mmol) in DCM (5 mL) was added dropwise at 0° C. The resulting mixture was stirred at room temperature for 16 hours and then was concentrated. The residue was purified by column chromatography on silica gel (50% EtOAc in petroleum ether) to afford the title compound (200 mg, 63%) as a colorless oil. $^1H$ NMR (400 MHz, $CDCl_3$) δ 7.80 (d, J=8.4 Hz, 2H), 7.36 (d, J=8.0 Hz, 2H), 4.05 (t, J=6.0 Hz, 2H), 3.18 (t, J=6.4 Hz, 2H), 2.80 (s, 3H), 2.46 (s, 3H), 1.65-1.61 (m, 2H), 1.57-1.50 (m, 2H), 1.44 (s, 9H).

Step 5: tert-Butyl(4-((2-(2,6-dioxopiperidin-3-yl)-1,3-dioxoisoindolin-5-yl)oxy)butyl)(methyl)carbamate

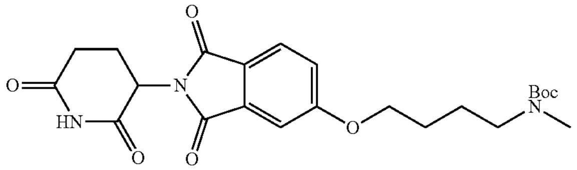 [SMILES: CN(CCCCOc1ccc2c(c1)C(=O)N(C1CCC(=O)NC1=O)C2=O)C(=O)OC(C)(C)C]

To a mixture of KI (19.5 mg, 0.12 mmol), 2-(2,6-dioxopiperidin-3-yl)-5-hydroxyisoindoline-1,3-dione (161 mg, 0.59 mmol) and $Na_2CO_3$ (125 mg, 1.17 mmol) in DMF (5 mL) was added 4-[tert-butoxycarbonyl(methyl)amino]butyl 4-methylbenzenesulfonate (210 mg, 0.59 mmol) at room temperature. The resulting mixture was stirred at 80° C. for 16 hours. Then the reaction mixture was cooled to room temperature, diluted with EtOAc (30 mL) and washed with brine (15 mL×2). The organic layer was dried over $Na_2SO_4$, filtered and concentrated. The residue was purified by column chromatography on silica gel (0-50% EtOAc in petroleum ether) to afford the title compound (180 mg, 67%) as a yellow oil. LCMS (ESI): m/z 482.1 $(M+Na)^+$.

Step 6: 2-(2,6-Dioxopiperidin-3-yl)-5-(4-(methylamino)butoxy)isoindoline-1,3-dione hydrochloride

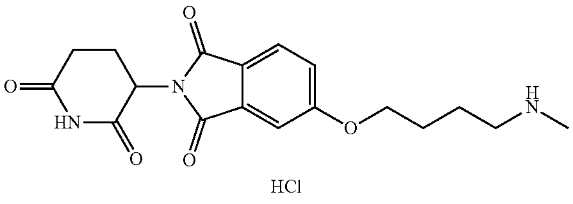 [SMILES: CNCCCCOc1ccc2c(c1)C(=O)N(C1CCC(=O)NC1=O)C2=O ; Cl]

To a solution of tert-butyl (4-((2-(2,6-dioxopiperidin-3-yl)-1,3-dioxoisoindolin-5-yl) oxy)butyl)(methyl)carbamate (180 mg, 0.39 mmol) in 1,4-dioxane (1 mL) was added 4M HCl in 1,4-dioxane (6 mL, 24 mmol) at room temperature. The resulting mixture was stirred at room temperature for 2 hours. Then the reaction mixture was concentrated to afford the title compound (120 mg, 77%) as a yellow oil. LCMS (ESI): m/z 360.1 $(M+H)^+$.

Step 7: N-(3-(2-((4-((2-(2,6-dioxopiperidin-3-yl)-1,3-dioxoisoindolin-5-yl)oxy)butyl)(methyl)amino)-2-oxoethyl)benzyl)-5-methoxy-4-((E)-2-(trans-4-(trifluoromethyl)cyclohexyl)vinyl)picolinamide

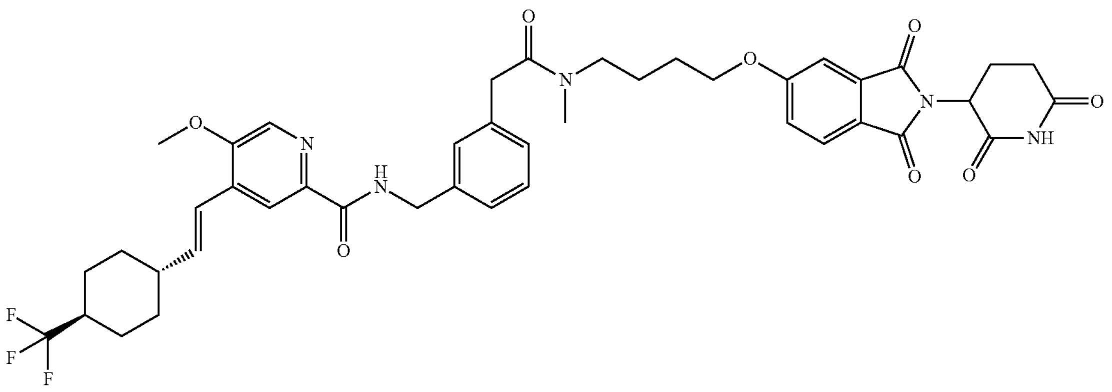 [SMILES: COc1cnc(C(=O)NCc2cccc(CC(=O)N(C)CCCCOc3ccc4c(c3)C(=O)N(C3CCC(=O)NC3=O)C4=O)c2)cc1/C=C/[C@H]1CC[C@H](C(F)(F)F)CC1]

To a mixture of 2-(3-((5-methoxy-4-((E)-2-(trans-4-(trifluoromethyl)cyclohexyl)vinyl) picolinamido)methyl)phenyl)acetic acid (50 mg, 0.10 mmol) in DMF (2 mL) was added DIPEA (68 mg, 0.52 mmol) and HATU (100 mg, 0.26 mmol) at room temperature. The resulting mixture was stirred at room temperature for 10 minutes. Then 2-(2,6-dioxopiperidin-3-yl)-5-(4-(methylamino)butoxy)isoindoline-1,3-dione hydrochloride (45.7 mg, 0.12 mmol) was added at room temperature. The reaction mixture was stirred at room temperature for another 2 hours. After that, the reaction mixture was concentrated. The residue was purified by prep-HPLC (YMC Triart C18 150*25 mm*5 um, water (10 mM $NH_4HCO_3$)-ACN, 67-97%) to afford the title compound (24.1 mg, 26%) as a white solid. $^1H$ NMR (400 MHz, DMSO-$d_6$): δ 8.76 (s, 1H), 8.30 (s, 1H), 8.03 (s, 1H), 7.79 (d, J=8.0 Hz, 1H), 7.35 (s, 1H), 7.30 (d, J=8.0 Hz, 1H), 7.25-7.21 (m, 1H), 7.19-7.17 (m, 2H), 7.10 (d, J=7.2 Hz, 1H), 6.61 (d, J=16.0 Hz, 2H), 6.53 (dd, J=16.0, 6.4 Hz, 1H), 5.09-5.04 (m, 1H), 4.48 (d, J=6.0 Hz, 2H), 4.14 (s, 2H), 3.98 (s, 3H), 3.66 (s, 2H), 3.36 (t, J=6.4 Hz, 2H), 3.34-3.14 (m, 3H), 2.96-2.83 (m, 2H), 2.64-2.57 (m, 2H), 2.22-2.19 (m, 1H), 2.08-2.04 (m, 1H), 1.95-1.88 (m, 4H), 1.70-1.59 (m, 4H), 1.37-1.26 (m, 4H). LCMS (ESI): m/z 818.4 $(M+H)^+$.

Example 2

Preparation of N-(3-(2-((6-((2-(2,6-Dioxopiperidin-3-yl)-1,3-dioxoisoindolin-5-yl)oxy)hexyl)(methyl)amino)-2-oxoethyl)benzyl)-5-methoxy-4-((E)-2-(trans-4-(trifluoromethyl)cyclohexyl)vinyl) picolinamide The general reaction scheme was as follows:

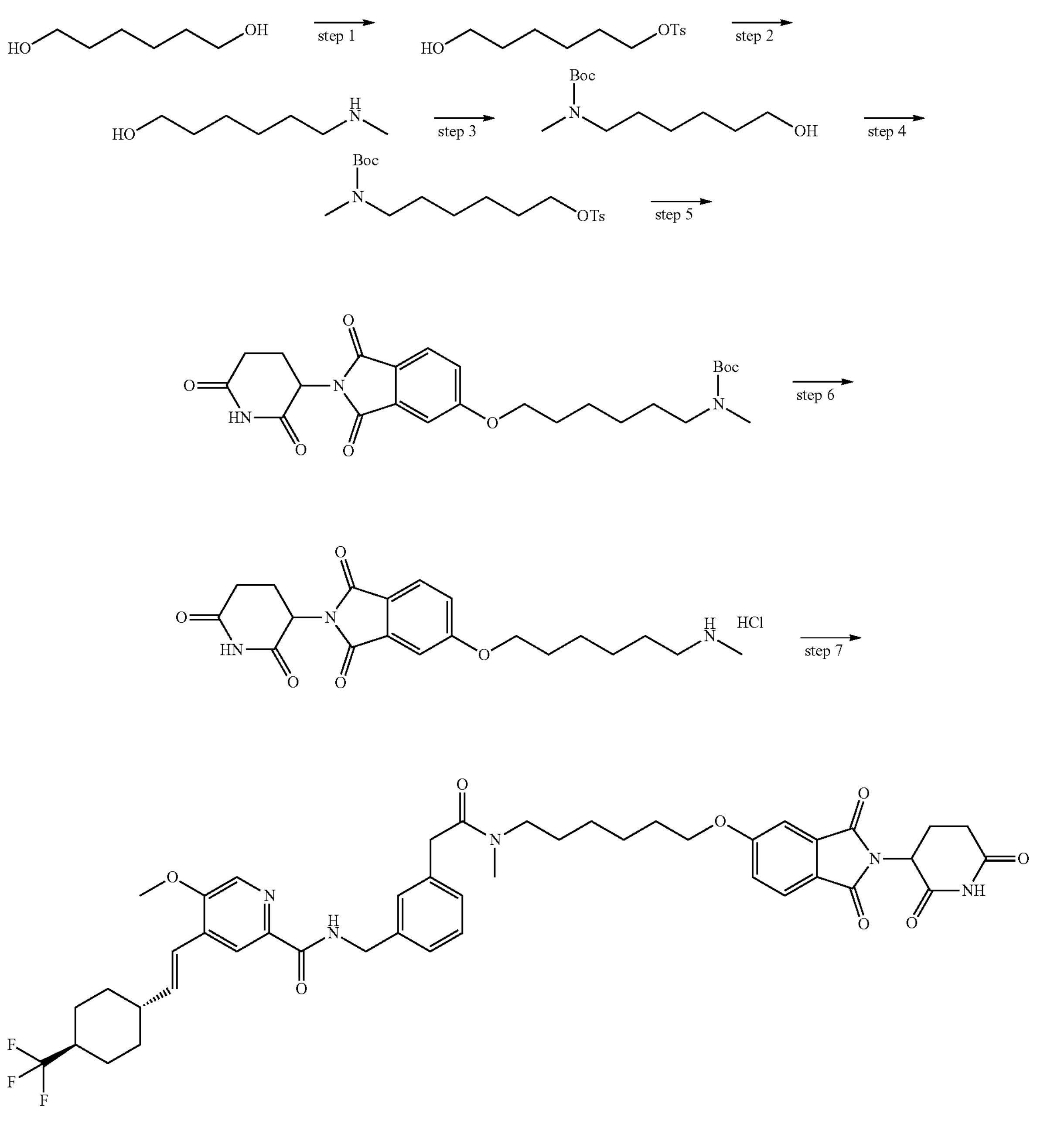

Step 1: 6-Hydroxyhexyl 4-methylbenzenesulfonate

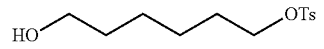 [SMILES: Cc1ccc(S(=O)(=O)OCCCCCCO)cc1]

To a solution of hexane-1,6-diol (10.0 g, 8.46 mmol) in DCM (20 mL) was added $Et_3N$ (1.76 mL, 12.69 mmol) at room temperature. Then a solution of TsCl (1.77 g, 9.31 mmol) in DCM (5 mL) was added dropwise at 0° C. The resulting mixture was stirred at room temperature for 16 hours. Then the reaction mixture was diluted with water (30 mL), extracted with DCM (30 mL×3). The combined organic layer was washed with brine (30 mL×2), dried over $Na_2SO_4$ and concentrated. The residue was purified by column chromatography on silica gel (25% EtOAc in petroleum ether) to afford the title compound (800 mg, 35%) as a colorless oil. $^1H$ NMR (400 MHz, $CDCl_3$): δ 7.78 (d, J=8.4 Hz, 2H), 7.34 (d, J=8.0 Hz, 2H), 4.02 (t, J=6.4 Hz, 2H), 3.60 (t, J=6.4 Hz, 2H), 2.45 (s, 3H), 1.65-1.62 (m, 2H), 1.55-1.49 (m, 3H), 1.35-1.30 (m, 3H).

Step 2: 6-(Methylamino)hexan-1-ol

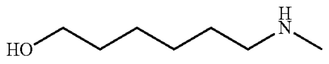

The title compound (385 mg, quant.) was furnished as a colorless oil. It was prepared from 6-hydroxyhexyl 4-methylbenzenesulfonate (800 mg, 2.94 mmol) following the procedure outlined for Example 1, Step 2.

Step 3: tert-Butyl (6-hydroxyhexyl)(methyl)carbamate

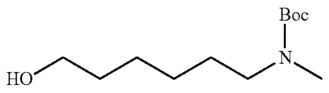 [SMILES: CN(CCCCCCO)C(=O)OC(C)(C)C]

The title compound (400 mg, 59%) was furnished as a colorless oil. It was prepared from 6-(methylamino)hexan-1-ol (385 mg, 2.94 mmol) following the procedure outlined for Example 1, Step 3. $^1H$ NMR (400 MHz, $CDCl_3$): δ 3.64 (t, J=6.4 Hz, 2H), 3.21 (m, 2H), 2.83 (s, 3H), 1.63-1.50 (m, 6H), 1.46 (s, 9H), 1.42-1.36 (m, 2H).

Step 4: 6-((tert-Butoxycarbonyl)(methyl)amino)hexyl 4-methylbenzenesulfonate

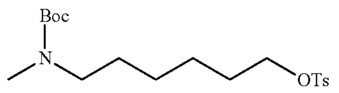 [SMILES: Cc1ccc(S(=O)(=O)OCCCCCCN(C)C(=O)OC(C)(C)C)cc1]

The title compound (350 mg, 52%) was furnished as a colorless oil. It was prepared from tert-butyl (6-hydroxyhexyl)(methyl)carbamate (400 mg, 1.73 mmol) following the procedure outlined for Example 1, Step 4. $^1H$ NMR (400 MHz, $CDCl_3$): δ 7.79 (d, J=8.4 Hz, 2H), 7.35 (d, J=8.0 Hz, 2H), 4.02 (t, J=6.4 Hz, 2H), 3.16 (t, J=7.2 Hz, 2H), 2.81 (s, 3H), 2.46 (s, 3H), 1.69-1.59 (m, 4H), 1.45 (s, 9H), 1.39-1.30 (m, 2H), 1.28-1.19 (m, 2H).

Step 5: tert-Butyl (6-((2-(2,6-dioxopiperidin-3-yl)-1,3-dioxoisoindolin-5-yl)oxy)hexyl)(methyl)carbamate

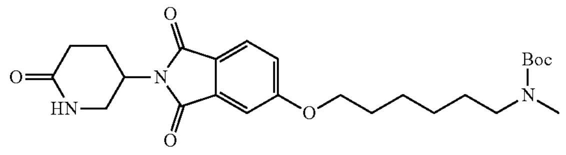 [SMILES: CN(CCCCCCOc1ccc2c(c1)C(=O)N(C1CCC(=O)NC1)C2=O)C(=O)OC(C)(C)C]

The title compound (340 mg, 77%) was furnished as a yellow oil. It was prepared from 6-[tert-butoxycarbonyl (methyl)amino]hexyl 4-methylbenzenesulfonate (350 mg, 0.91 mmol) following the procedure outlined for Example 1, Step 5. LCMS (ESI): m/z 432.1 $(M+H-56)^+$.

Step 6: 2-(2,6-Dioxopiperidin-3-yl)-5-((6-(methylamino)hexyl)oxy)isoindoline-1,3-dione hydrochloride

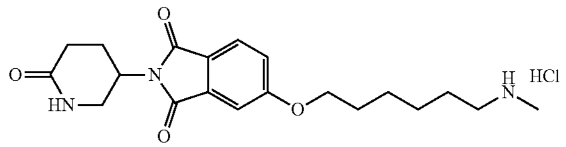 [SMILES: CNCCCCCCOc1ccc2c(c1)C(=O)N(C1CCC(=O)NC1)C2=O ; Cl]

The title compound (174 mg, quant.) was furnished as a yellow oil. It was prepared from tert-butyl(6-((2-(2,6-dioxopiperidin-3-yl)-1,3-dioxoisoindolin-5-yl)oxy)hexyl) (methyl)carbamate (200 mg, 0.41 mmol) following the procedure outlined for Example 1, Step 6. LCMS (ESI): m/z 388.1 $(M+H)^+$.

Step 7: N-(3-(2-((6-((2-(2,6-Dioxopiperidin-3-yl)-1,3-dioxoisoindolin-5-yl)oxy)hexyl)(methyl)amino)-2-oxoethyl)benzyl)-5-methoxy-4-((E)-2-(trans-4-(trifluoromethyl)cyclohexyl)vinyl)picolinamide

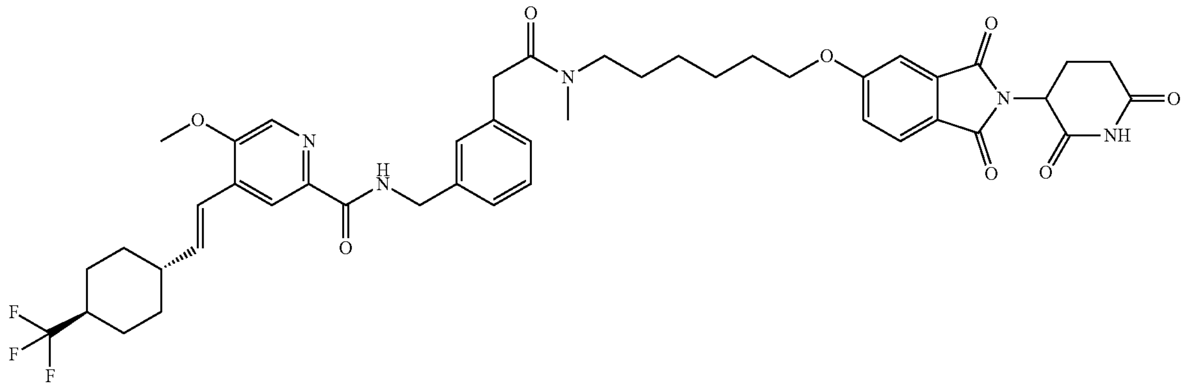 [SMILES: COc1cnc(C(=O)NCc2cccc(CC(=O)N(C)CCCCCCOc3ccc4c(c3)C(=O)N(C3CCC(=O)NC3=O)C4=O)c2)cc1/C=C/[C@H]1CC[C@H](C(F)(F)F)CC1]

The title compound (23.7 mg, 26%) was furnished as a white solid. It was prepared from 2-(2,6-dioxopiperidin-3-yl)-5-((6-(methylamino)hexyl)oxy)isoindoline-1,3-dione hydrochloride (49 mg, 0.12 mmol) following the procedure outlined for Example 1, Step 7. It was purified by prep-HPLC (Welch Xtimate C18 150*30 mm*5 um, water (0.225% FA)-CAN, 55-85%). $^{1}$H NMR (400 MHz, DMSO-$d_6$): δ 11.13 (s, 1H), 9.10 (t, J=6.4 Hz, 1H), 8.33 (d, J=3.2 Hz, 1H), 8.05 (d, J=2.4 Hz, 1H), 7.82 (d, J=8.4 Hz, 1H), 7.40-7.39 (m, 1H), 7.34-7.30 (m, 1H), 7.26-7.20 (m, 1H), 7.15 (d, J=9.6 Hz, 2H), 7.08 (t, J=6.8 Hz, 1H), 6.61-6.55 (m, 2H), 5.13-5.09 (m, 1H), 4.45 (d, J=6.0 Hz, 2H), 4.16-4.06 (m, 2H), 3.98 (d, J=3.6 Hz, 3H), 3.64 (d, J=3.2 Hz, 2H), 3.25-3.24 (m, 1H), 2.95, 2.77 (s, 3H total), 2.94-2.92 (m, 1H), 2.68-2.55 (m, 3H), 2.22-2.20 (m, 2H), 2.09-2.00 (m, 1H), 1.91-1.88 (m, 4H), 1.71-1.64 (m, 2H), 1.43-1.18 (m, 10H). LCMS (ESI): m/z 846.4 $(M+H)^+$.

Example 3

Preparation of N-(3-(14-((2-(2,6-Dioxopiperidin-3-yl)-1,3-dioxoisoindolin-5-yl)oxy)-3-methyl-2-oxo-6,9,12-trioxa-3-azatetradecyl)benzyl)-5-methoxy-4-((E)-2-(trans-4-(trifluoromethyl)cyclohexyl)vinyl)picolinamide The general reaction scheme was as follows:

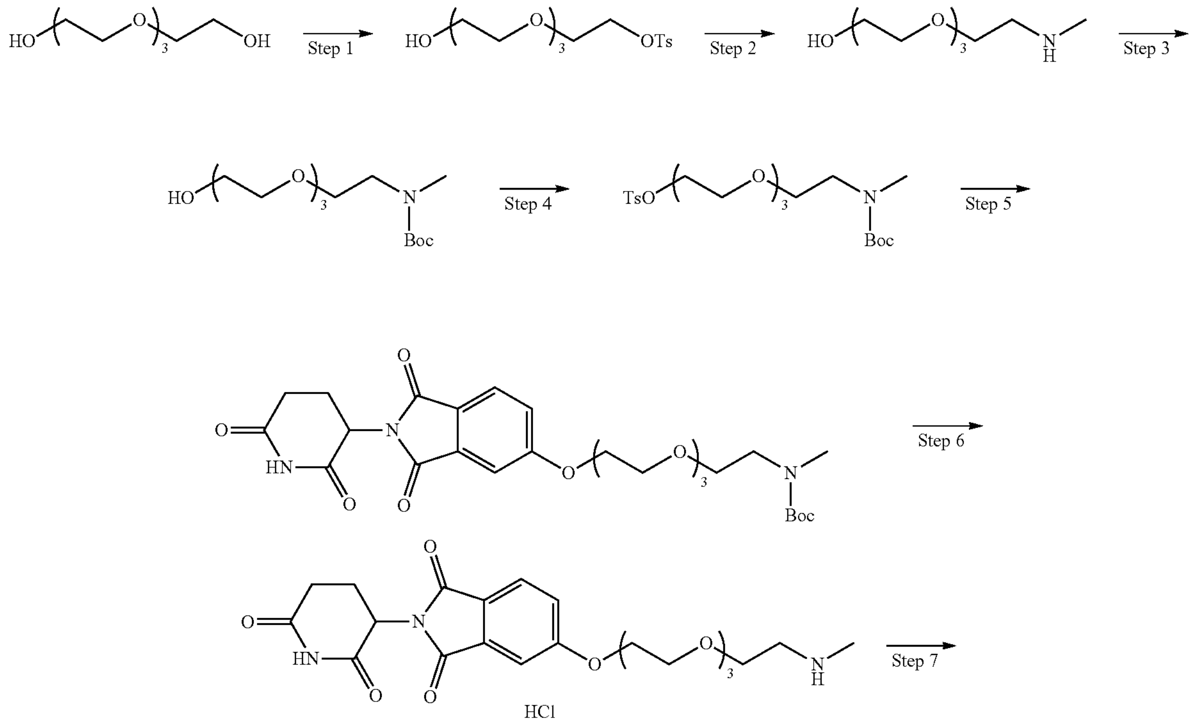

HCl

-continued

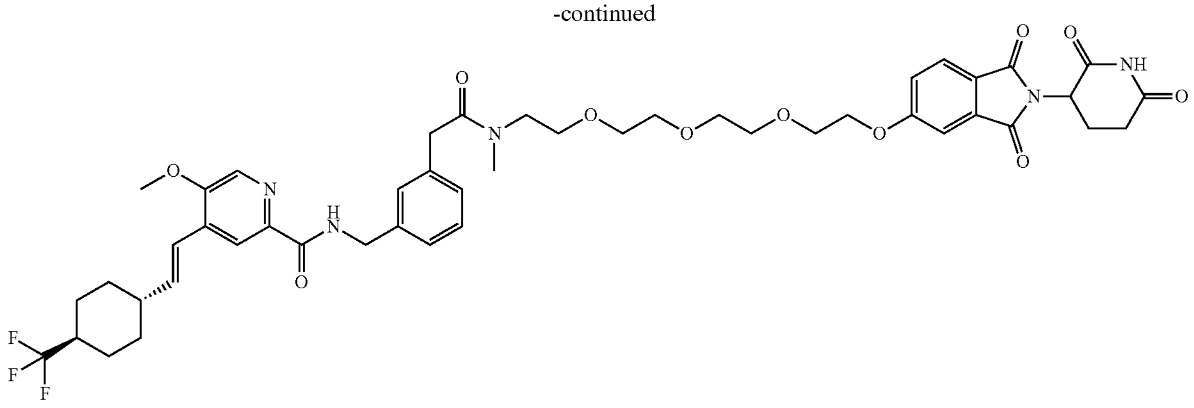

Step 1: 2-(2-(2-(2-Hydroxyethoxy)ethoxy)ethoxy) ethyl 4-methylbenzenesulfonate

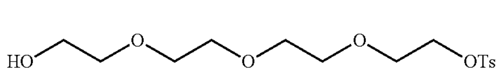 [SMILES: Cc1ccc(S(=O)(=O)OCCOCCOCCOCCO)cc1]

The title compound (2.1 g, 23%) was furnished as a colorless oil. It was prepared from 2,2'-((oxybis(ethane-2,1-diyl))bis(oxy))diethanol (5.0 g, 25.74 mmol) following the procedure outlined for Example 2, Step 1. $^1$H NMR (400 MHz, $CDCl_3$): δ 7.78 (d, J=8.0 Hz, 2H), 7.33 (d, J=8.0 Hz, 2H), 4.16-4.11 (m, 2H), 3.69-3.58 (m, 14H), 2.43 (s, 3H).

Step 2: 5,8,11-Trioxa-2-azatridecan-13-ol

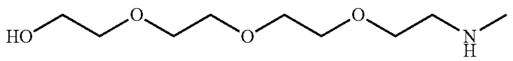

The title compound (2.97 g, 99%) was furnished as a colorless oil. It was prepared from 2-(2-(2-(2-hydroxyethoxy)ethoxy)ethoxy)ethyl 4-methylbenzenesulfonate (5.0 g, 14.35 mmol) following the procedure outlined for Example 1, Step 2.

Step 3: tert-Butyl (2-(2-(2-(2-hydroxyethoxy) ethoxy)ethoxy)ethyl)(methyl)carbamate

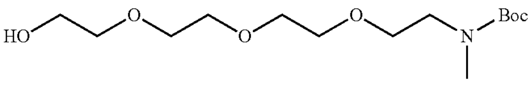 [SMILES: CN(CCOCCOCCOCCO)C(=O)OC(C)(C)C]

The title compound (2.1 g, 48%) was furnished as a colorless oil. It was prepared from 5,8,11-trioxa-2-azatridecan-13-ol (2.95 g, 14.22 mmol) following the procedure outlined for Example 1, Step 3. $^1$H NMR (400 MHz, $CDCl_3$): δ 3.68-3.67 (m, 2H), 3.62-3.55 (m, 12H), 3.34 (br, 2H), 2.86 (s, 3H), 2.67 (br, 1H), 1.40 (s, 9H).

Step 4: 2,2,5-Trimethyl-4-oxo-3,8,11,14-tetraoxa-5-azahexadecan-16-yl 4-methylbenzenesulfonate

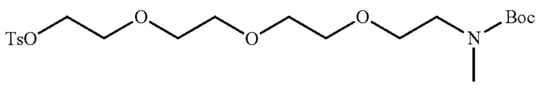 [SMILES: Cc1ccc(S(=O)(=O)OCCOCCOCCOCCN(C)C(=O)OC(C)(C)C)cc1]

The title compound (2.0 g, 63%) was furnished as a colorless oil. It was prepared from tert-butyl (2-(2-(2-(2-hydroxyethoxy)ethoxy)ethoxy)ethyl)(methyl)carbamate (2.1 g, 6.83 mmol) following the procedure outlined for Example 1, Step 4. $^1$H NMR (400 MHz, $CDCl_3$): δ 7.79 (d, J=8.4 Hz, 2H), 7.33 (d, J=8.0 Hz, 2H), 4.16-4.12 (m, 2H), 3.69-3.66 (m, 2H), 3.58-3.57 (m, 10H), 3.37 (br, 2H), 2.89 (s, 3H), 2.44 (s, 3H), 1.44 (s, 9H).

Step 5: tert-Butyl (2-(2-(2-(2-((2-(2,6-dioxopiperidin-3-yl)-1,3-dioxoisoindolin-5-yl)oxy)ethoxy) ethoxy)ethoxy)ethyl)(methyl)carbamate

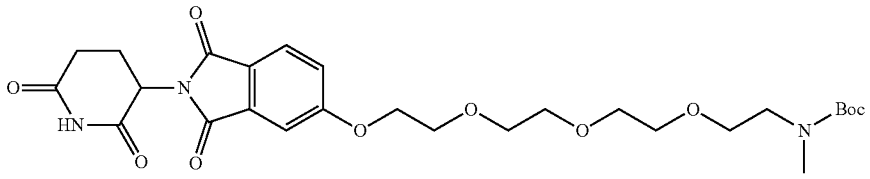 [SMILES: CN(CCOCCOCCOCCOc1ccc2c(c1)C(=O)N(C1CCC(=O)NC1=O)C2=O)C(=O)OC(C)(C)C]

The title compound (100 mg, 41%) was furnished as a colorless oil. It was prepared from 2,2,5-trimethyl-4-oxo-3,8,11,14-tetraoxa-5-azahexadecan-16-yl-4-methylbenzene-sulfonate (200 mg, 0.43 mmol) following the procedure outlined for Example 1, Step 5. LCMS (ESI): m/z 586.1 $(M+Na)^+$.

Step 6: 5-(5,8,11-Trioxa-2-azatridecan-13-yloxy)-2-(2,6-dioxopiperidin-3-yl)isoindoline-1,3-dione hydrochloride

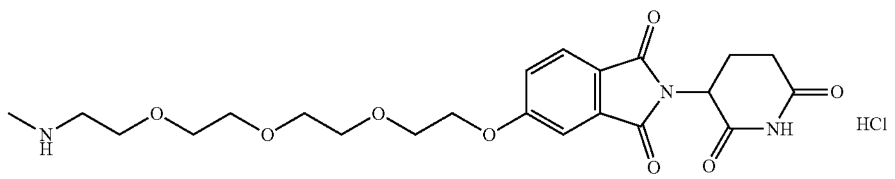 [SMILES: CNCCOCCOCCOCCOc1ccc2c(c1)C(=O)N(C1CCC(=O)NC1=O)C2=O ; Cl]

The title compound (75 mg, 99.5%) was furnished as a white solid. It was prepared from tert-butyl(2-(2-(2-(2-((2-(2,6-dioxopiperidin-3-yl)-1,3-dioxoisoindolin-5-yl)oxy)ethoxy)ethoxy)ethoxy)ethyl)(methyl)carbamate (85 mg, 0.15 mmol) following the procedure outlined for Example 1, Step 6. LCMS (ESI): m/z 464.5 $(M+H)^+$.

Step 7: N-(3-(14-((2-(2,6-Dioxopiperidin-3-yl)-1,3-dioxoisoindolin-5-yl)oxy)-3-methyl-2-oxo-6,9,12-trioxa-3-azatetradecyl)benzyl)-5-methoxy-4-((E)-2-(trans-4-(trifluoromethyl)cyclohexyl)vinyl)picolinamide

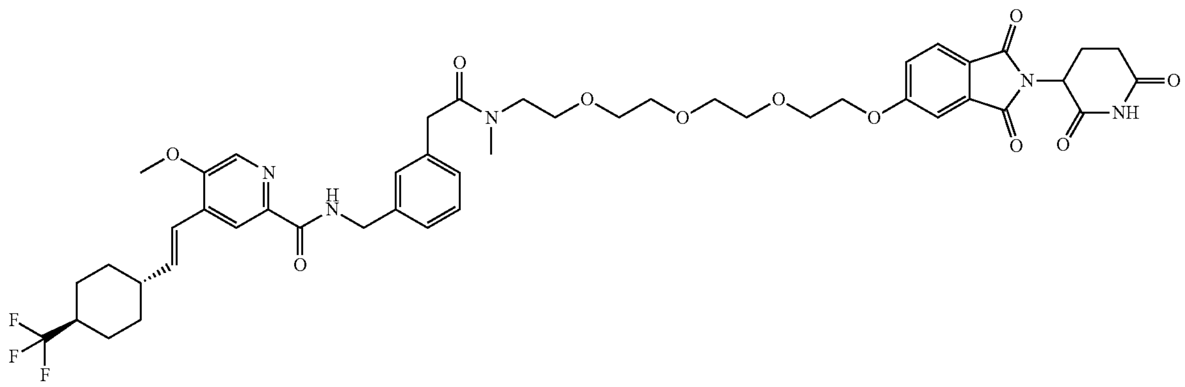 [SMILES: COc1cnc(C(=O)NCc2cccc(CC(=O)N(C)CCOCCOCCOCCOc3ccc4c(c3)C(=O)N(C3CCC(=O)NC3=O)C4=O)c2)cc1/C=C/[C@H]1CC[C@H](C(F)(F)F)CC1]

The title compound (17 mg, 17%) was furnished as a white solid. It was prepared from 5-(5,8,11-trioxa-2-azatridecan-13-yloxy)-2-(2,6-dioxopiperidin-3-yl)isoindoline-1,3-dione hydrochloride (57.7 mg, 0.12 mmol) following the procedure outlined for Example 1, Step 7. It was purified by prep-HPLC (Xtimate C18 150*40 mm*10 um, water (0.225% FA)-ACN, 60-90%). $^1H$ NMR (400 MHz, $CD_3OD$): δ 8.26 (s, 1H), 8.11 (d, J=2.8 Hz, 1H), 7.75-7.71 (m, 1H), 7.34 (dd, J=2.0, 12.4 Hz, 1H), 7.29-7.23 (m, 4H), 7.13-7.12 (m, 1H), 6.68 (d, J=16.4 Hz, 1H), 6.53 (dd, J=16.4, 6.8 Hz, 1H), 5.10-5.09 (m, 1H), 4.57 (d, J=3.2 Hz, 2H), 4.22-4.20 (m, 2H), 4.00 (s, 3H), 3.87-3.77 (m, 3H), 3.72 (s, 1H), 3.69-3.48 (m, 12H), 3.05, 2.92 (s, 3H total), 2.89-2.80 (m, 1H), 2.78-2.64 (m, 2H), 2.22-2.07 (m, 3H), 2.05-1.92 (m, 4H), 1.48-1.22 (m, 5H). LCMS (ESI): m/z 922.5 $(M+H)^+$.

Example 4

Preparation of N-(3-(17-((2-(2,6-Dioxopiperidin-3-yl)-1,3-dioxoisoindolin-5-yl)oxy)-3-methyl-2-oxo-6,9,12,15-tetraoxa-3-azaheptadecyl)benzyl)-5-methoxy-4-((E)-2-(trans-4-(trifluoromethyl)cyclohexyl)vinyl)picolinamide The general reaction scheme was as follows:

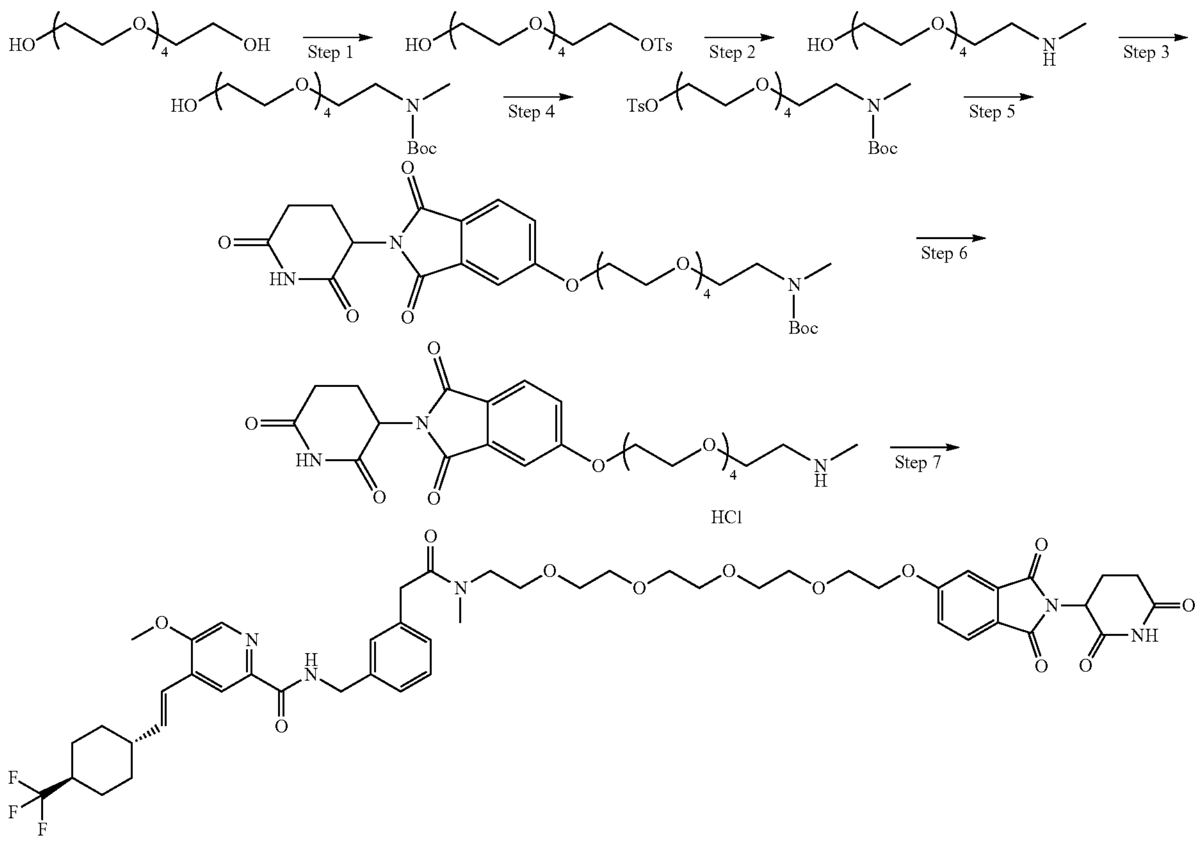

Step 1: 14-Hydroxy-3,6,9,12-tetraoxatetradecyl 4-methylbenzenesulfonate

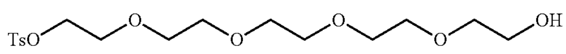 [SMILES: Cc1ccc(S(=O)(=O)OCCOCCOCCOCCOCCO)cc1]

The title compound (6.1 g, 46%) was furnished as a colorless oil. It was prepared from 3,6,9,12-tetraoxatetradecane-1,14-diol (8.0 g, 33.57 mmol) following the procedure outlined for Example 2, Step 1. $^1H$ NMR (400 MHz, $CDCl_3$): δ 7.80 (d, J=8.0 Hz, 2H), 7.35 (d, J=8.0 Hz, 2H), 4.16 (t, J=4.8 Hz, 2H), 3.72-3.58 (m, 18H), 2.45 (s, 3H).

Step 2: 5,8,11,14-Tetraoxa-2-azahexadecan-16-ol

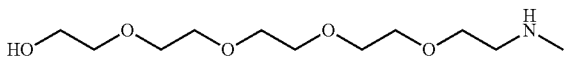 [SMILES: CNCCOCCOCCOCCOCCO]

The title compound (3.9 g, quant.) was furnished as a colorless oil. It was prepared from 14-hydroxy-3,6,9,12-tetraoxatetradecyl 4-methylbenzenesulfonate (6.1 g, 15.54 mmol) following the procedure outlined for Example 1, Step 2. $^1H$ NMR (400 MHz, $CDCl_3$): δ 3.78-3.73 (m, 4H), 3.65-3.60 (m, 12H), 3.58-3.55 (m, 4H), 3.27-3.25 (m, 2H), 2.76 (s, 3H).

Step 3: tert-Butyl (14-Hydroxy-3,6,9,12-tetraoxatetradecyl)(methyl)carbamate

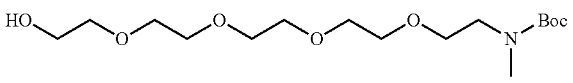 [SMILES: CN(CCOCCOCCOCCOCCO)C(=O)OC(C)(C)C]

The title compound (2.1 g, 39%) was furnished as a colorless oil. It was prepared from 5,8,11,14-tetraoxa-2-azahexadecan-16-ol (3.9 g, 15.52 mmol) following the procedure outlined for Example 1, Step 3. $^1H$ NMR (400 MHz, $CDCl_3$): δ 3.69-3.64 (m, 2H), 3.62-3.46 (m, 16H), 3.33 (br, 2H), 2.84 (s, 3H), 1.39 (s, 9H).

Step 4: 2,2,5-Trimethyl-4-oxo-3,8,11,14,17-pentaoxa-5-azanonadecan-19-yl 4-methylbenzenesulfonate

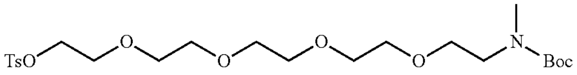 [SMILES: Cc1ccc(S(=O)(=O)OCCOCCOCCOCCOCCN(C)C(=O)OC(C)(C)C)cc1]

The title compound (2.0 g, 70%) was furnished as a colorless oil. It was prepared from tert-butyl (14-hydroxy-3,6,9,12-tetraoxatetradecyl)(methyl)carbamate (2.0 g, 5.69 mmol) following the procedure outlined for Example 1, Step 4. LCMS (ESI): m/z 528.1 $(M+Na)^+$.

Step 5: tert-Butyl (14-((2-(2,6-dioxopiperidin-3-yl)-1,3-dioxoisoindolin-5-yl)oxy)-3,6,9,12-tetraoxatetradecyl)(methyl)carbamate

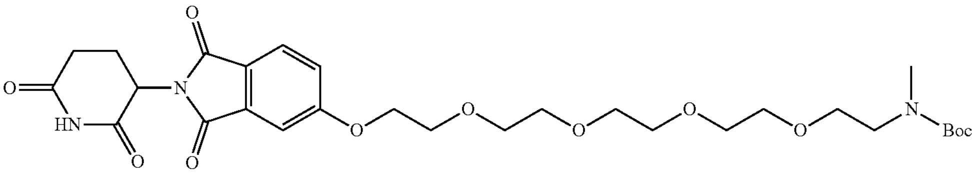 [SMILES: CN(CCOCCOCCOCCOCCOc1ccc2c(c1)C(=O)N(C1CCC(=O)NC1=O)C2=O)C(=O)OC(C)(C)C]

The title compound (120 mg, 46%) was furnished as a colorless oil. It was prepared from 2,2,5-trimethyl-4-oxo-3,8,11,14,17-pentaoxa-5-azanonadecan-19-yl 4-methylbenzenesulfonate (200 mg, 0.43 mmol) following the procedure outlined for Example 1, Step 5. LCMS (ESI): m/z 630.3 $(M+Na)^+$.

Step 6: 5-(5,8,11,14-Tetraoxa-2-azahexadecan-16-yloxy)-2-(2,6-dioxopiperidin-3-yl)isoindoline-1,3-dione hydrochloride

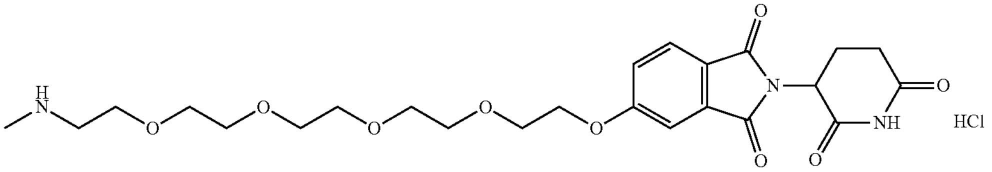 [SMILES: CNCCOCCOCCOCCOCCOc1ccc2c(c1)C(=O)N(C1CCC(=O)NC1=O)C2=O ; Cl]

The title compound (89 mg, 99%) was furnished as a white solid. It was prepared from tert-butyl(14-((2-(2,6-dioxopiperidin-3-yl)-1,3-dioxoisoindolin-5-yl)oxy)-3,6,9,12-tetraoxatetradecyl)(methyl)carbamate (100 mg, 0.16 mmol) following the procedure outlined for Example 1, Step 6. LCMS (ESI): m/z 508.2 $(M+H)^+$.

Step 7: N-(3-(17-((2-(2,6-Dioxopiperidin-3-yl)-1,3-dioxoisoindolin-5-yl)oxy)-3-methyl-2-oxo-6,9,12,15-tetraoxa-3-azaheptadecyl)benzyl)-5-methoxy-4-((E)-2-(trans-4-(trifluoromethyl)cyclohexyl)vinyl)picolinamide

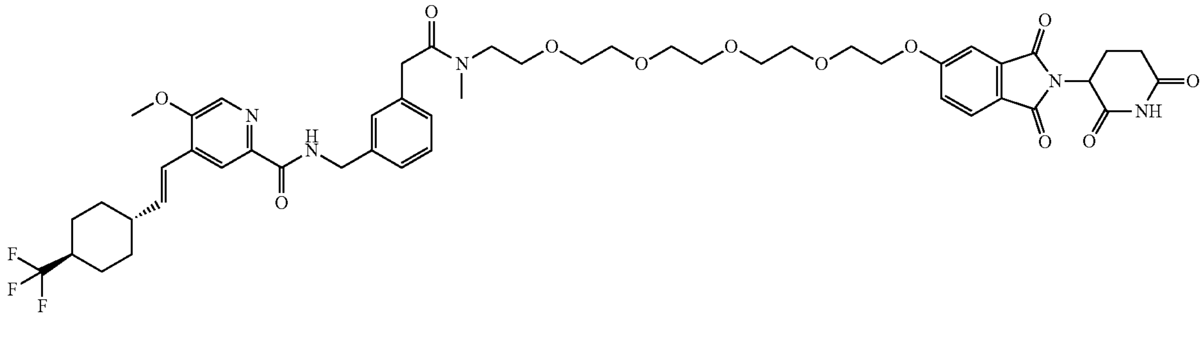 [SMILES: COc1cnc(C(=O)NCc2cccc(CC(=O)N(C)CCOCCOCCOCCOCCOc3ccc4c(c3)C(=O)N(C3CCC(=O)NC3=O)C4=O)c2)cc1/C=C/[C@H]1CC[C@H](C(F)(F)F)CC1]

The title compound (28 mg, 20%) was furnished as a white solid. It was prepared from 5-(5,8,11,14-tetraoxa-2-azahexadecan-16-yloxy)-2-(2,6-dioxopiperidin-3-yl)isoindoline-1,3-dione hydrochloride (88 mg, 0.16 mmol) following the procedure outlined for Example 1, Step 7. It was purified by prep-HPLC (Xtimate C18 150*40 mm*10 um, water (0.225% FA)-ACN, 60-90%). $^1$H NMR (400 MHz, $CD_3OD$): δ 8.26 (s, 1H), 8.11 (s, 1H), 7.75 (dd, J=2.8, 8.4 Hz, 1H), 7.37-7.35 (m, 1H), 7.29-7.24 (m, 4H), 7.14 (m, 1H), 6.68 (d, J=16.4 Hz, 1H), 6.53 (dd, J=16.4, 6.8 Hz, 1H), 5.11-5.06 (m, 1H), 4.58 (s, 3H), 4.26-4.24 (m, 2H), 4.00 (s, 3H), 3.87-3.79 (m, 3H), 3.74 (s, 1H), 3.69-3.47 (m, 15H), 3.06-2.92 (s, 3H total), 2.87-2.79 (m, 1H), 2.78-2.65 (m, 2H), 2.23-2.08 (m, 3H), 2.04-1.91 (m, 4H), 1.48-1.21 (m, 5H). LCMS (ESI): m/z 966.5 (M+H)$^+$.

Example 5

Preparation of N-(3-(2-((2-(2-((2-(2,6-Dioxopiperidin-3-yl)-1,3-dioxoisoindolin-5-yl)oxy)ethoxy)ethyl)(methyl)amino)-2-oxoethyl)benzyl)-5-methoxy-4-((E)-2-(trans-4-(trifluoromethyl)cyclohexyl)vinyl)picolinamide The general reaction scheme was as follows:

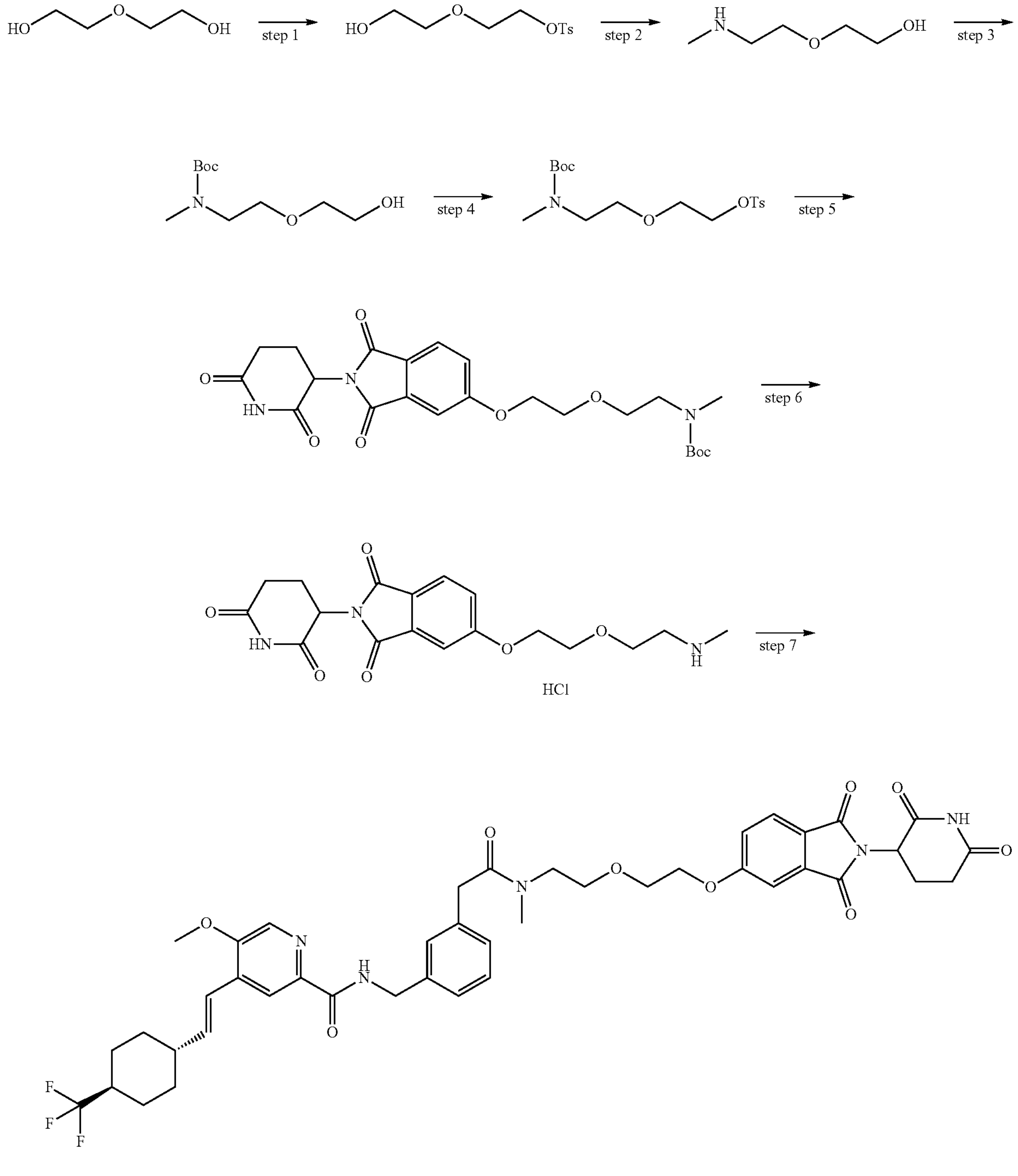

Step 1: 2-(2-Hydroxyethoxy)ethyl 4-methylbenzenesulfonate

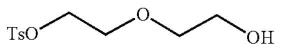 [SMILES: Cc1ccc(S(=O)(=O)OCCOCCO)cc1]

The title compound (7.5 g, 61%) was furnished as a colorless oil. It was prepared from 2,2'-oxydiethanol (5.0 g, 47.12 mmol) following the procedure outlined for Example 1, Step 1. LCMS (ESI): m/z 261.1 $(M+H)^+$.

Step 2: 2-[2-(Methylamino)ethoxy]ethanol

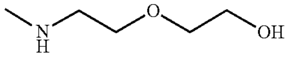

The title compound (63.2 g, 93%) was furnished as a colorless oil. It was prepared from 2-(2-hydroxyethoxy) ethyl 4-methylbenzenesulfonate (7.5 g, 28.81 mmol) following the procedure outlined for Example 1, Step 2. $^1H$ NMR (400 MHz, $CDCl_3$): δ 3.78-3.73 (m, 2H), 3.69-3.67 (m, 2H), 3.58-3.57 (m, 2H), 3.18-3.12 (m, 2H), 2.72 (s, 3H).

Step 3: tert-Butyl (2-(2-hydroxyethoxy)ethyl)(methyl)carbamate

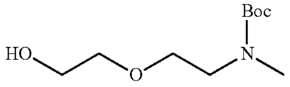

The title compound (800 mg, 15%) was furnished as a yellow oil. It was prepared from 2-[2-(methylamino)ethoxy] ethanol (3.0 g, 25.18 mmol) following the procedure outlined for Example 1, Step 3. $^1H$ NMR (400 MHz, $CDCl_3$): δ 3.71-3.70 (m, 2H), 3.58-3.57 (m, 4H), 3.41-3.40 (m, 2H), 2.90 (s, 3H), 1.45 (s, 9H).

Step 4: 2-(2-((tert-Butoxycarbonyl)(methyl)amino) ethoxy)ethyl 4-methylbenzenesulfonate

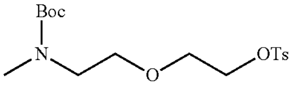 [SMILES: Cc1ccc(S(=O)(=O)OCCOCCN(C)C(=O)OC(C)(C)C)cc1]

The title compound (353 mg, 69%) was furnished as a colorless oil. It was prepared from tert-butyl (2-(2-hydroxyethoxy)ethyl)(methyl)carbamate (300 mg, 1.37 mmol) following the procedure outlined for Example 1, Step 4. $^1H$ NMR (400 MHz, $CDCl_3$): δ 7.78 (d, J=8.4 Hz, 2H), 7.43 (d, J=8.4 Hz, 2H), 4.14-4.10 (m, 2H), 3.65-3.57 (m, 2H), 3.49-3.48 (m, 2H), 3.33-3.29 (m, 3H), 2.83-2.82 (m, 2H), 2.44 (s, 3H), 1.43 (s, 9H). LCMS (ESI): m/z 274.4 $(M-100+H)^+$.

Step 5: tert-Butyl (2-(2-((2-(2,6-dioxopiperidin-3-yl)-1,3-dioxoisoindolin-5-yl)oxy)ethoxy)ethyl) (methyl)carbamate

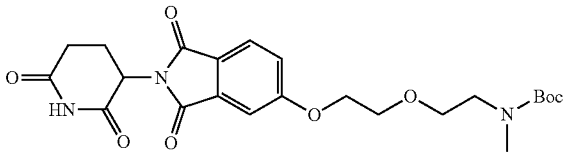 [SMILES: CN(CCOCCOc1ccc2c(c1)C(=O)N(C1CCC(=O)NC1=O)C2=O)C(=O)OC(C)(C)C]

The title compound (65 mg, 34%) was furnished as a yellow oil. It was prepared from 2-(2-((tert-butoxycarbonyl) (methyl)amino)ethoxy)ethyl 4-methylbenzenesulfonate (150 mg, 0.40 mmol) following the procedure outlined for Example 1, Step 5. LCMS (ESI): m/z 498.2 $(M+Na)^+$.

Step 6: 2-(2,6-Dioxopiperidin-3-yl)-5-(2-(2-(methylamino)ethoxy)ethoxy)isoindoline-1,3-dione hydrochloride

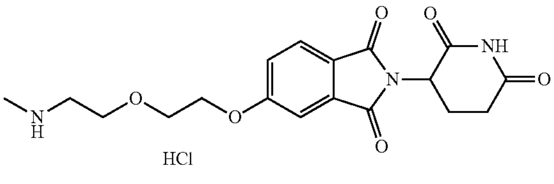 [SMILES: CNCCOCCOc1ccc2c(c1)C(=O)N(C1CCC(=O)NC1=O)C2=O ; Cl]

The title compound (51 mg, 91%) was furnished as a white oil. It was prepared from tert-butyl (2-(2-((2-(2,6-dioxopiperidin-3-yl)-1,3-dioxoisoindolin-5-yl)oxy)ethoxy) ethyl)(methyl)carbamate (65 mg, 0.14 mmol) following the procedure outlined for Example 1, Step 6. LCMS (ESI): m/z 376.1 $(M+H)^+$.

Step 7: N-(3-(2-((2-(2-((2-(2,6-dioxopiperidin-3-yl)-1,3-dioxoisoindolin-5-yl)oxy)ethoxy)ethyl)(methyl)amino)-2-oxoethyl)benzyl)-5-methoxy-4-((E)-2-(trans-4-(trifluoromethyl)cyclohexyl)vinyl)picolinamide

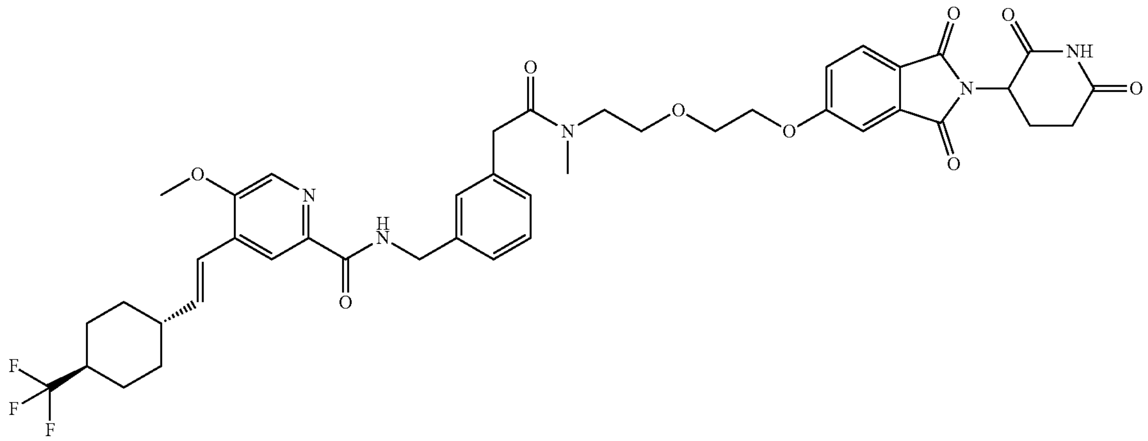

The title compound (26 mg, 18%) was furnished as a white solid. It was prepared from 2-(2,6-dioxopiperidin-3-yl)-5-(2-(2-(methylamino)ethoxy)ethoxy)isoindoline-1,3-dione hydrochloride (65 mg, 0.17 mmol) following the procedure outlined for Example 1, Step 7. It was purified by prep-HPLC (Xtimate C18 150*40 mm*10 um, water (0.225% FA)-ACN, 60-80%). $^1$H NMR (400 MHz, DMSO-$d_6$): δ 11.12 (s, 1H), 9.08-9.06 (m, 1H), 8.31 (d, J=4.4 Hz, 1H), 8.03 (d, J=4.4 Hz, 1H), 7.83-7.78 (m, 1H), 7.41 (d, J=2.0 Hz, 1H), 7.34-7.31 (m, 1H), 7.30-7.10 (m, 4H), 6.59-6.54 (m, 2H), 5.11-5.10 (m, 1H), 4.45-4.41 (m, 2H), 4.26-4.25 (m, 2H), 3.98 (d, J=3.2 Hz, 3H), 3.78-3.51 (m, 6H), 2.98, 2.81 (s, 3H total), 2.85-2.81 (m, 1H), 2.62-2.55 (m, 4H), 2.19-2.18 (m, 2H), 2.02-2.00 (m, 1H), 1.94-1.81 (m, 4H), 1.38-1.22 (m, 4H). LCMS (ESI): m/z 834.5 $(M+H)^+$.

Example 6

Preparation of N-(3-(2-((2-(2-(2-((2-(2,6-Dioxopiperidin-3-yl)-1,3-dioxoisoindolin-5-yl)oxy)ethoxy)ethoxy)ethyl)(methyl)amino)-2-oxoethyl)benzyl)-5-methoxy-4-((E)-2-(trans-4-(trifluoromethyl)cyclohexyl)vinyl)picolinamide The general reaction scheme was as follows:

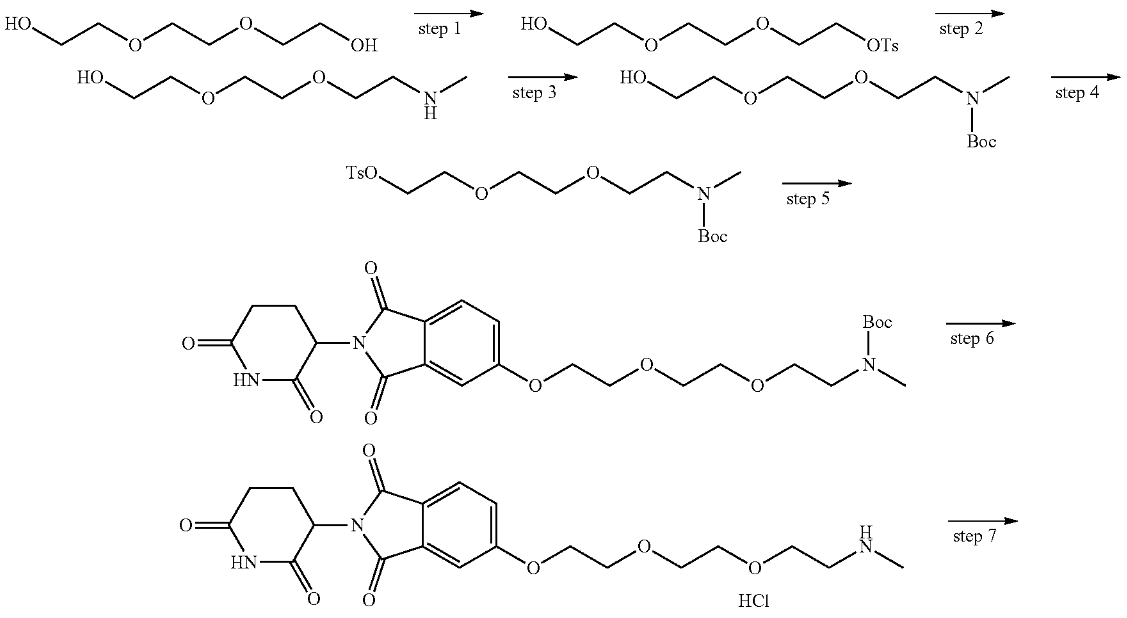

-continued

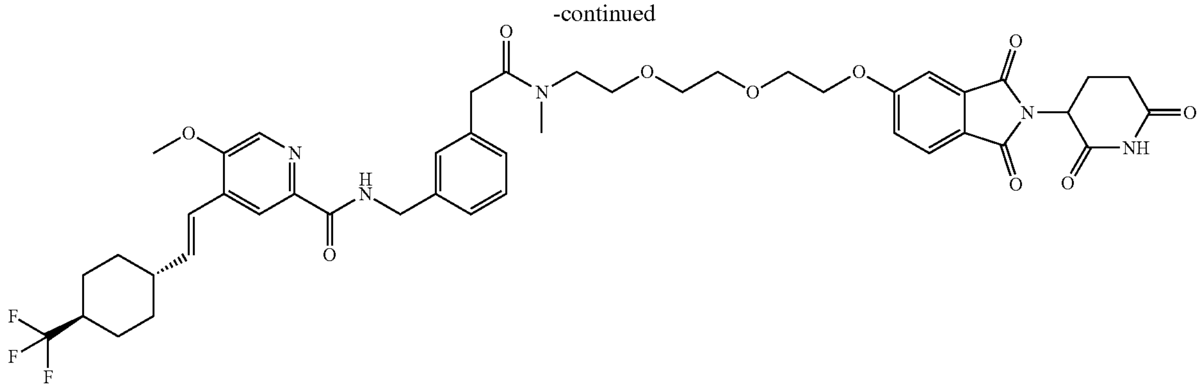

Step 1: 2-(2-(2-Hydroxyethoxy)ethoxy)ethyl 4-methylbenzenesulfonate

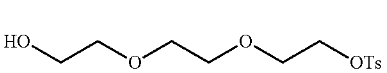 [SMILES: Cc1ccc(S(=O)(=O)OCCOCCOCCO)cc1]

The title compound (15 g, 37%) was furnished as a colorless oil. It was prepared from 2,2'-(ethane-1,2-diylbis(oxy))diethanol (20.0 g, 133.18 mmol) following the procedure outlined for Example 2, Step 1. LCMS (ESI): m/z 304.9 $(M+H)^+$.

Step 2: 2-(2-(2-(Methylamino)ethoxy)ethoxy)ethanol

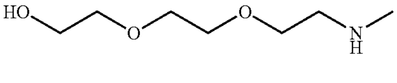

The title compound (4.5 g, 84%) was furnished as a colorless oil. It was prepared from 2-(2-(2-Hydroxyethoxy)ethoxy)ethyl 4-methylbenzenesulfonate (10 g, 32.86 mmol) following the procedure outlined for Example 1, Step 2. LCMS (ESI): m/z 163.9 $(M+H)^+$.

Step 3: tert-Butyl (2-(2-(2-hydroxyethoxy)ethoxy)ethyl)(methyl)carbamate

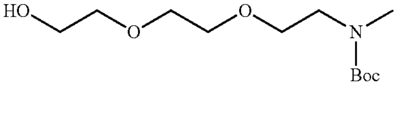 [SMILES: CN(CCOCCOCCO)C(=O)OC(C)(C)C]

The title compound (3.6 g, 64%) was furnished as a colorless oil. It was prepared from 2-[2-[2-(methylamino)ethoxy]ethoxy]ethanol (3.5 g, 21.44 mmol) following the procedure outlined for Example 1, Step 3. $^1H$ NMR (400 MHz, $CDCl_3$): δ 3.75-3.71 (m, 2H), 3.67-3.60 (m, 8H), 3.40 (br s, 2H), 2.91 (s, 3H), 1.45 (s, 9H).

Step 4: 2,2,5-Trimethyl-4-oxo-3,8,11-trioxa-5-aza-tridecan-13-yl 4-methylbenzenesulfonate

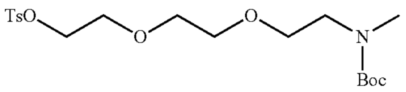 [SMILES: Cc1ccc(S(=O)(=O)OCCOCCOCCN(C)C(=O)OC(C)(C)C)cc1]

The title compound (4.15 g, 73%) was furnished as a colorless oil. It was prepared from tert-butyl (2-(2-(2-hydroxyethoxy)ethoxy)ethyl)(methyl)carbamate (3.60 g, 13.67 mmol) following the procedure outlined for Example 1, Step 4. LCMS (ESI): m/z 440.1 $(M+Na)^+$.

Step 5: tert-Butyl(2-(2-(2-((2-(2,6-dioxopiperidin-3-yl)-1,3-dioxoisoindolin-5-yl)oxy)ethoxy)ethoxy)ethyl)(methyl)carbamate

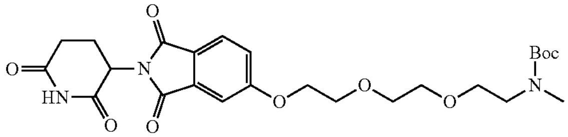 [SMILES: CN(CCOCCOCCOc1ccc2c(c1)C(=O)N(C1CCC(=O)NC1=O)C2=O)C(=O)OC(C)(C)C]

The title compound (139 mg, 37%) was furnished as a yellow oil. It was prepared from 2,2,5-trimethyl-4-oxo-3,8,11-trioxa-5-azatridecan-13-yl-4-methylbenzenesulfonate (300 mg, 0.72 mmol) following the procedure outlined for Example 1, Step 5. LCMS (ESI): m/z 542.1 $(M+Na)^+$.

Step 6: 2-(2,6-Dioxopiperidin-3-yl)-5-(2-(2-(2-(methylamino)ethoxy)ethoxy)ethoxy)isoindoline-1,3-dione hydrochloride

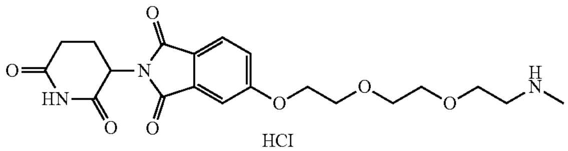

The title compound (78.9 mg, quant.) was furnished as a white oil. It was prepared from tert-butyl (2-(2-(2-((2-(2,6-dioxopiperidin-3-yl)-1,3-dioxoisoindolin-5-yl)oxy)ethoxy)ethoxy)ethyl)(methyl)carbamate (90 mg, 0.17 mmol) following the procedure outlined for Example 1, Step 6. LCMS (ESI): m/z 420.2 $(M+H)^+$.

Step 7: N-(3-(2-((2-(2-(2-((2-(2,6-Dioxopiperidin-3-yl)-1,3-dioxoisoindolin-5-yl)oxy)ethoxy)ethoxy)ethyl)(methyl)amino)-2-oxoethyl)benzyl)-5-methoxy-4-((E)-2-(trans-4-trifluoromethyl)cyclohexyl)vinyl)picolinamide

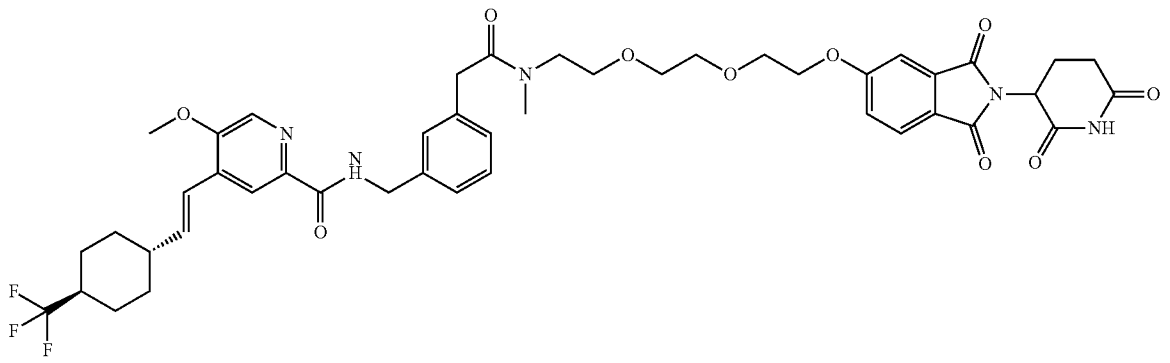 [SMILES: COc1cnc(C(=O)NCc2cccc(CC(=O)N(C)CCOCCOCCOc3ccc4c(c3)C(=O)N(C3CCC(=O)NC3=O)C4=O)c2)cc1/C=C/[C@H]1CC[C@H](C(F)(F)F)CC1]

The title compound (21.4 mg, 43%) was furnished as a white solid. It was prepared from 2-(2,6-dioxopiperidin-3-yl)-5-(2-(2-(2-(methylamino)ethoxy)ethoxy)ethoxy)isoindoline-1,3-dione hydrochloride (90 mg, 0.17 mmol) following the procedure outlined for Example 1, Step 7. It was purified by prep-TLC (10% MeOH in DCM). $^1$H NMR (400 MHz, DMSO-$d_6$): δ 11.09 (s, 1H), 9.03 (d, J=6.0 Hz, 1H), 8.32 (s, 1H), 8.04 (s, 1H), 7.80 (t, J=8.4 Hz, 1H), 7.41 (d, J=9.6 Hz, 1H), 7.36-7.28 (m, 1H), 7.26-7.18 (m, 1H), 7.17-7.11 (m, 2H), 7.05 (t, J=8.4 Hz, 1H), 6.63-6.53 (m, 2H), 5.13-5.10 (m, 1H), 4.45 (d, J=3.2 Hz, 2H), 4.27 (d, J=3.6 Hz, 2H), 3.99 (s, 3H), 3.76 (s, 2H), 3.68 (s, 1H), 3.64 (s, 1H), 3.59-3.52 (m, 3H), 3.51-3.47 (m, 3H), 2.98, 2.86 (s, 3H total), 2.64-2.56 (m, 4H), 2.22-2.20 (m, 2H), 2.04-2.02 (m, 1H), 1.93-1.86 (m, 4H), 1.34-1.23 (m, 5H). LCMS (ESI): m/z 878.4 (M+H)$^+$.

Example 7

Preparation of N-(3-(20-((2-(2,6-Dioxopiperidin-3-yl)-1,3-dioxoisoindolin-5-yl)oxy)-3-methyl-2-oxo-6,9,12,15,18-pentaoxa-3-azaicosyl)benzyl)-5-methoxy-4-((E)-2-(trans-4-(trifluoromethyl)cyclohexyl)vinyl)picolinamide The general reaction scheme was as follows:

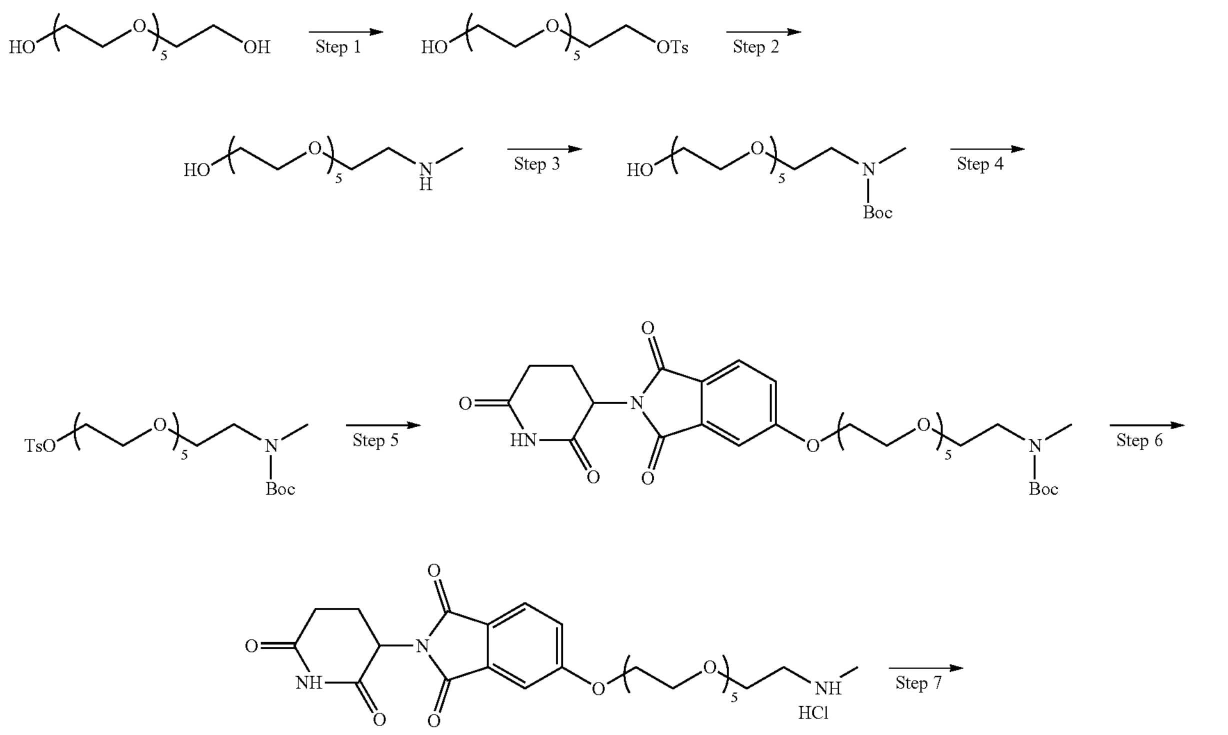

-continued

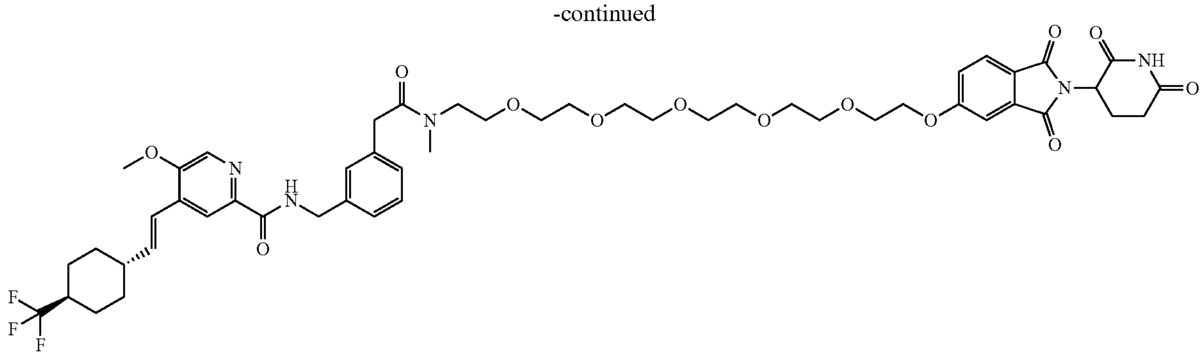

Step 1: 17-Hydroxy-3,6,9,12,15-pentaoxaheptadecyl 4-methylbenzenesulfonate

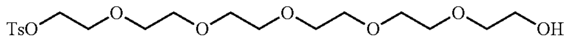 [SMILES: Cc1ccc(S(=O)(=O)OCCOCCOCCOCCOCCOCCO)cc1]

The title compound (6.5 g, 84%) was furnished as a colorless oil. It was prepared from 3,6,9,12,15-pentaoxaheptadecane-1,17-diol (5.0 g, 17.71 mmol) following the procedure outlined for Example 1, Step 1. LCMS (ESI): m/z 437.2 $(M+H)^+$.

Step 2: 5,8,11,14,17-Pentaoxa-2-azanonadecan-19-ol

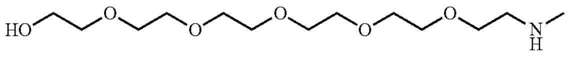 [SMILES: CNCCOCCOCCOCCOCCOCCO]

The title compound (4.0 g, 91%) was furnished as a colorless oil. It was prepared from 17-hydroxy-3,6,9,12,15-pentaoxaheptadecyl 4-methylbenzenesulfonate (6.5 g, 14.89 mmol) following the procedure outlined for Example 1, Step 2. $^1H$ NMR (400 MHz, $CDCl_3$): δ 3.83-3.78 (m, 2H), 3.75-3.72 (m, 2H), 3.66-3.61 (m, 18H), 3.59-3.56 (m, 2H), 3.28-3.22 (m, 2H), 2.77 (s, 3H).

Step 3: tert-Butyl (17-hydroxy-3,6,9,12,15-pentaoxaheptadecyl)(methyl)carbamate

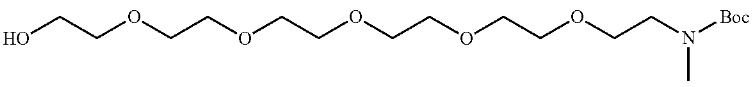 [SMILES: CN(CCOCCOCCOCCOCCOCCO)C(=O)OC(C)(C)C]

The title compound (1.9 g, 47%) was furnished as a yellow oil. It was prepared from 5,8,11,14,17-pentaoxa-2-azanonadecan-19-ol (3.0 g, 10.16 mmol) following the procedure outlined for Example 1, Step 3. $^1H$ NMR (400 MHz, $CDCl_3$): δ 3.74-3.71 (m, 2H), 3.69-3.58 (m, 20H), 3.39 (s, 2H), 2.91 (s, 3H), 1.45 (s, 9H).

Step 4: 2,2,5-Trimethyl-4-oxo-3,8,11,14,17,20-hexaoxa-5-azadocosan-22-yl 4-methylbenzenesulfonate

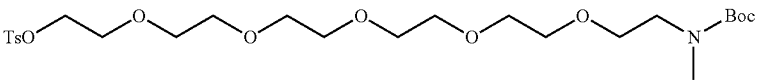 [SMILES: Cc1ccc(S(=O)(=O)OCCOCCOCCOCCOCCOCCN(C)C(=O)OC(C)(C)C)cc1]

The title compound (1.7 g, 64%) was furnished as a colorless oil. It was prepared from tert-butyl (17-hydroxy-3,6,9,12,15-pentaoxaheptadecyl)(methyl)carbamate (1.9 g, 4.8 mmol) following the procedure outlined for Example 1, Step 4. LCMS (ESI): m/z 450.6 (M−100+H)$^+$.

Step 5: tert-Butyl (17-((2-(2,6-dioxopiperidin-3-yl)-1,3-dioxoisoindolin-5-yl)oxy)-3,6,9,12,15-pentaoxaheptadecyl)(methyl)carbamate

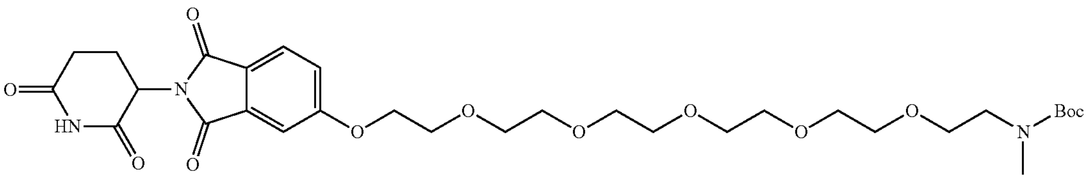 [SMILES: CN(CCOCCOCCOCCOCCOCCOc1ccc2c(c1)C(=O)N(C1CCC(=O)NC1=O)C2=O)C(=O)OC(C)(C)C]

The title compound (260 mg, 73%) was furnished as a colorless oil. It was prepared from 2,2,5-trimethyl-4-oxo-3,8,11,14,17,20-hexaoxa-5-azadocosan-22-yl 4-methylbenzenesulfonate (300 mg, 0.55 mmol) following the procedure outlined for Example 1, Step 5. LCMS (ESI): m/z 552.2 (M−100+H)$^+$.

Step 6: 5-(5,8,11,14,17-Pentaoxa-2-azanonadecan-19-yloxy)-2-(2,6-dioxopiperidin-3-yl)isoindoline-1,3-dione hydrochloride

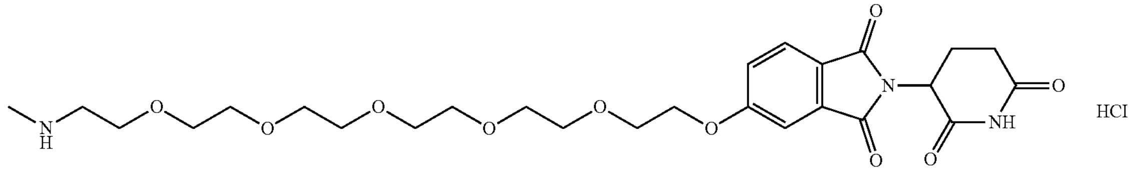

The title compound (220 mg, 94%) was furnished as a yellow solid. It was prepared from tert-butyl (17-((2-(2,6-dioxopiperidin-3-yl)-1,3-dioxoisoindolin-5-yl)oxy)-3,6,9,12,15-pentaoxaheptadecyl)(methyl)carbamate (260 mg, 0.40 mmol) following the procedure outlined for Example 1, Step 6. LCMS (ESI): m/z 552.2 (M+H)$^+$.

Step 7: N-(3-(20-((2-(2,6-Dioxopiperidin-3-yl)-1,3-dioxoisoindolin-5-yl)oxy)-3-methyl-2-oxo-6,9,12,15,18-pentaoxa-3-azaicosyl)benzyl)-5-methoxy-4-((E)-2-(trans-4-(trifluoromethyl)cyclohexyl)vinyl)picolinamide

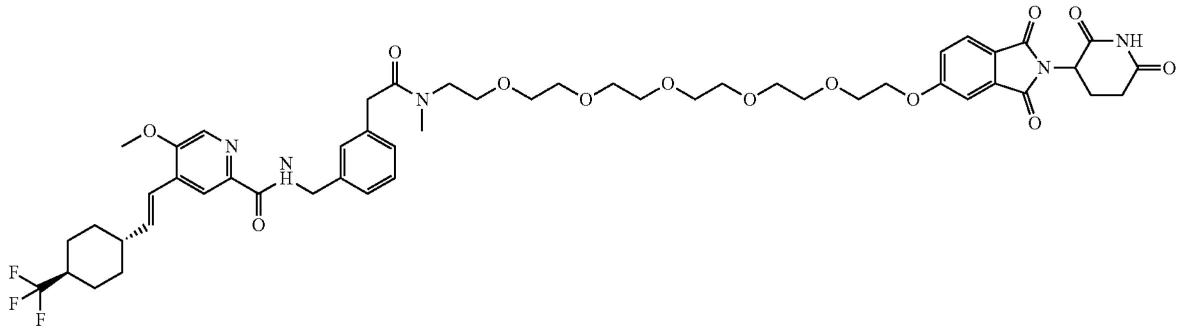 [SMILES: COc1cnc(C(=O)NCc2cccc(CC(=O)N(C)CCOCCOCCOCCOCCOCCOc3ccc4c(c3)C(=O)N(C3CCC(=O)NC3=O)C4=O)c2)cc1/C=C/[C@H]1CC[C@H](C(F)(F)F)CC1]

The title compound (24 mg, 22%) was furnished as a white solid. It was prepared from 5-(5,8,11,14,17-pentaoxa-2-azanonadecan-19-yloxy)-2-(2,6-dioxopiperidin-3-yl)isoindoline-1,3-dione hydrochloride (68 mg, 0.12 mmol) following the procedure outlined for Example 1, Step 7. It was purified by prep-HPLC (Boston Green ODS 150*30 mm*5 um, water-ACN, 55-75%). $^1$H NMR (400 MHz, DMSO-$d_6$): δ 11.10 (s, 1H), 9.07 (s, 1H), 8.29 (s, 1H), 8.02 (s, 1H), 7.78 (d, J=8.4 Hz, 1H), 7.40 (s, 1H), 7.32 (d, J=8.0 Hz, 1H), 7.19-7.16 (m, 1H), 7.11 (t, J=7.2 Hz, 2H), 7.02 (t, J=6.8 Hz, 1H), 6.58-6.53 (m, 2H), 5.10-5.06 (m, 1H), 4.42 (d, J=6.0 Hz, 2H), 4.24 (s, 2H), 3.95 (s, 3H), 3.73 (s, 2H), 3.64-3.60 (m, 4H), 3.44-3.41 (m, 16H), 3.37-3.36 (m, 2H), 2.94, 2.77 (s, 3H total), 2.85-2.82 (m, 1H), 2.57-2.55 (m, 1H), 2.20-2.17 (m, 2H), 2.04-1.99 (m, 1H), 1.86-1.82 (m, 4H), 1.34-1.21 (m, 5H). LCMS (ESI): m/z 1010.6 $(M+H)^+$.

Example 8

Preparation of N-(3-(2-((3-((2-(2,6-Dioxopiperidin-3-yl)-1,3-dioxoisoindolin-5-yl)oxy)propyl)(methyl)amino)-2-oxoethyl)benzyl)-5-methoxy-4-((E)-2-(trans-4-(trifluoromethyl)cyclohexyl)vinyl)picolinamide The general reaction scheme was as follows:

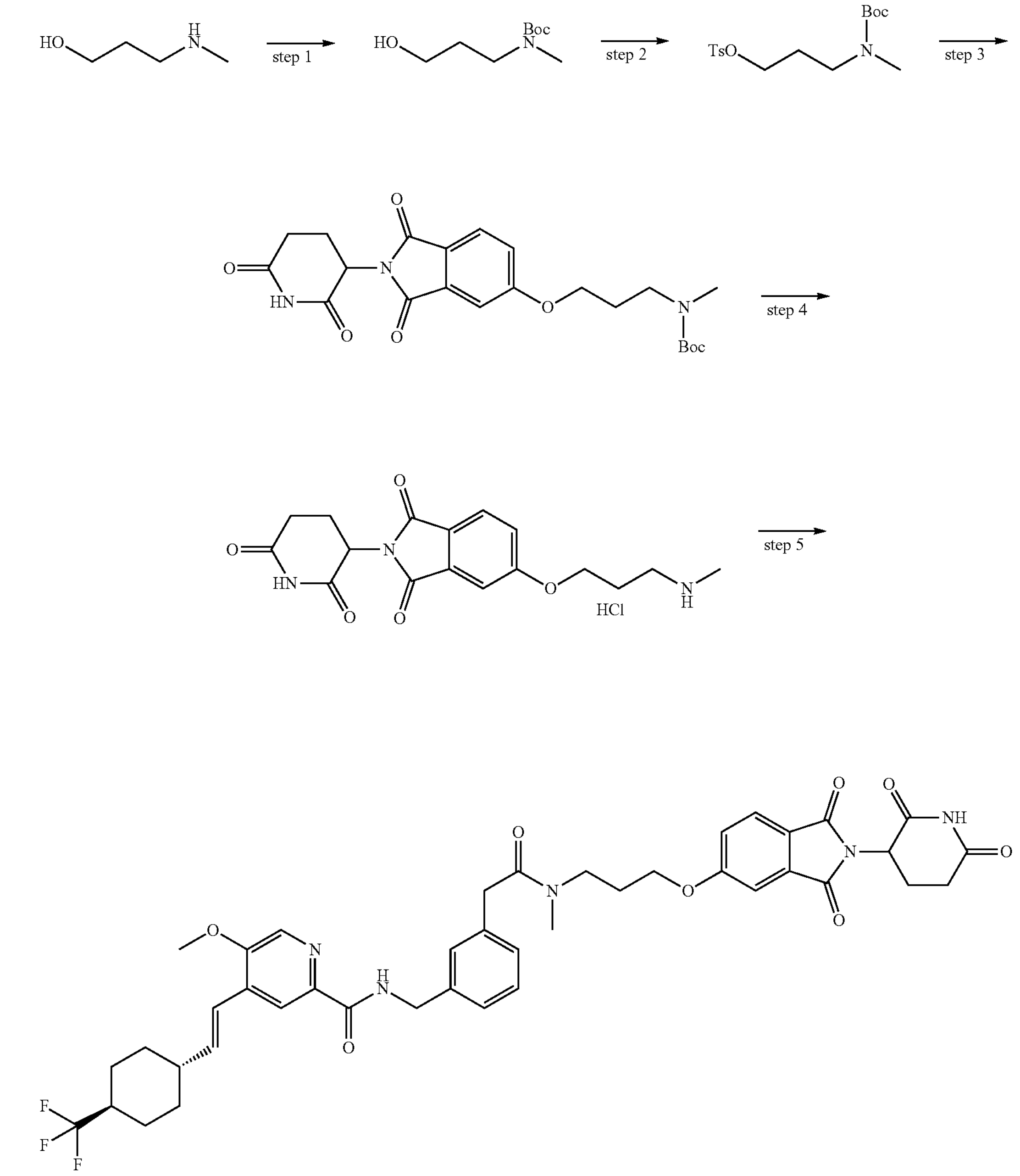

Step 1: tert-Butyl (3-hydroxypropyl)(methyl)carbamate

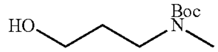

The title compound (5 g, 47%) was furnished as a colorless oil. It was prepared from 3-(methylamino)propan-1-ol (5 g, 56.09 mmol) following the procedure outlined for Example 1, Step 3. $^1$H NMR (400 MHz, $CDCl_3$): δ 3.80 (br s, 1H), 3.35 (m, 2H), 3.34 (m, 2H), 2.79 (s, 3H), 1.64 (m, 2H), 1.42 (s, 9H).

Step 2: 3-((tert-Butoxycarbonyl)(methyl)amino)propyl 4-methylbenzenesulfonate

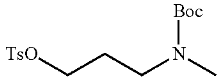

To a solution of tert-butyl (3-hydroxypropyl)(methyl) carbamate (2 g, 10.57 mmol) in DCM (7.5 mL) were added KI (439 mg, 2.64 mmol) and $Ag_2O$ (3.67 g, 15.85 mmol) at 0° C. Then TsCl (2.4 g, 12.68 mmol) in DCM (22 mL) was added dropwise. The resulting reaction mixture was stirred at 40° C. for 16 hours. The reaction mixture was then filtered and the filtrate was concentrated under reduced pressure. The residue was purified by column chromatography on silica gel (0-5% MeOH in DCM) to afford the title compound (630 mg, 17%) as a colorless oil. LCMS (ESI): m/z 244.0 $(M-100+H)^+$.

Step 3: tert-Butyl (3-((2-(2,6-dioxopiperidin-3-yl)-1,3-dioxoisoindolin-5-yl)oxy)propyl)(methyl)carbamate

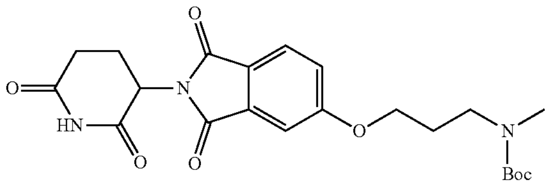 [SMILES: CN(CCCOc1ccc2c(c1)C(=O)N(C1CCC(=O)NC1=O)C2=O)C(=O)OC(C)(C)C]

The title compound (120 mg, 31%) was furnished as a colorless oil. It was prepared from 3-((tert-butoxycarbonyl)(methyl)amino)propyl 4-methylbenzenesulfonate (300 mg, 0.87 mmol) following the procedure outlined for Example 1, Step 5. $^1$H NMR (400 MHz, $CDCl_3$): δ 8.03 (s, 1H), 7.79 (d, J=8.0 Hz, 1H), 7.34 (d, J=2.4 Hz, 1H), 7.20 (dd, J=2.0, 8.4 Hz, 1H), 4.97 (dd, J=5.2, 12.4 Hz, 1H), 4.11 (t, J=6.0 Hz, 2H), 3.44 (t, J=6.8 Hz, 2H), 2.89 (s, 3H), 2.86-2.79 (m, 2H), 2.20-2.02 (m, 4H), 1.44 (s, 9H).

Step 4: 2-(2,6-Dioxopiperidin-3-yl)-5-(3-(methylamino)propoxy)isoindoline-1,3-dione hydrochloride

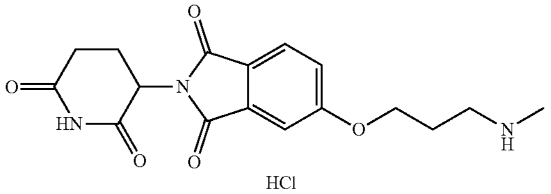 [SMILES: CNCCCOc1ccc2c(c1)C(=O)N(C1CCC(=O)NC1=O)C2=O ; Cl]

The title compound (85 mg, 83%) was furnished as a yellow oil. It was prepared from tert-butyl (3-((2-(2,6-dioxopiperidin-3-yl)-1,3-dioxoisoindolin-5-yl)oxy)propyl)(methyl)carbamate (120 mg, 0.270 mmol) following the procedure outlined for Example 1, Step 6. LCMS (ESI): m/z 346.1 $(M+H)^+$.

Step 5: N-(3-(2-((3-((2-(2,6-Dioxopiperidin-3-yl)-1,3-dioxoisoindolin-5-yl)oxy)propyl)(methyl)amino)-2-oxoethyl)benzyl)-5-methoxy-4-((E)-2-(trans-4-(trifluoromethyl)cyclohexyl)vinyl)picolinamide

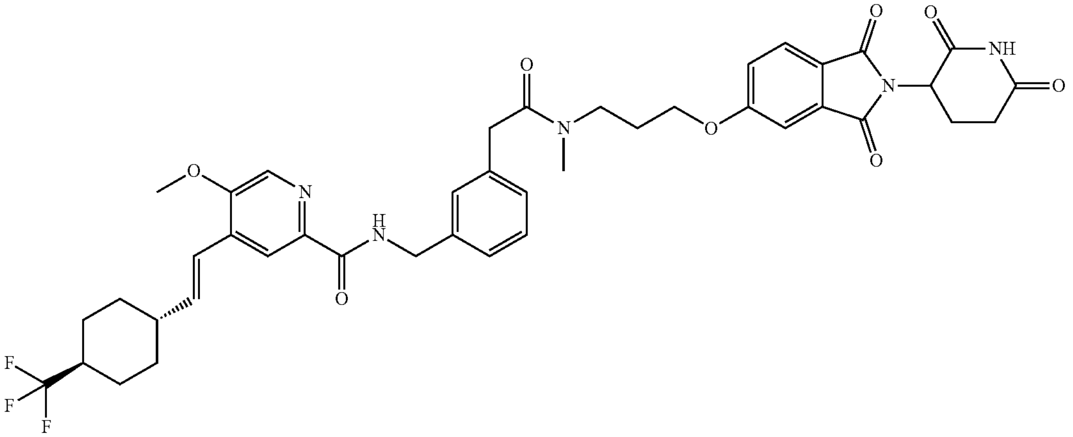 [SMILES: COc1cnc(C(=O)NCc2cccc(CC(=O)N(C)CCCOc3ccc4c(c3)C(=O)N(C3CCC(=O)NC3=O)C4=O)c2)cc1/C=C/[C@H]1CC[C@H](C(F)(F)F)CC1]

The title compound (29.1 mg, 14%) was furnished as a yellow solid. It was prepared from 2-(2,6-dioxopiperidin-3-yl)-5-(3-(methylamino)propoxy)isoindoline-1,3-dione hydrochloride (85 mg, 0.22 mmol) following the procedure outlined for Example 1, Step 7. It was purified by column chromatography on silica gel (100% EtOAc). $^1$H NMR (400 MHz, DMSO-$d_6$): δ 11.11 (s, 1H), 9.07-9.06 (m, 1H), 8.31 (d, J=6.0 Hz, 1H), 8.03 (d, J=7.2 Hz, 1H), 7.82-7.80 (m, 1H), 7.41-7.33 (m, 1H), 7.32-7.26 (m, 1H), 7.24-7.18 (m, 1H), 7.16-7.12 (m, 2H), 7.06-7.05 (m, 1H), 6.59-6.54 (m, 2H), 5.12 (dd, J=13.2, 5.2 Hz, 1H), 4.46-4.41 (m, 2H), 4.14-4.05 (m, 2H), 3.98 (s, 3H), 3.65 (s, 2H), 3.53-3.47 (m, 1H), 3.45-3.39 (m, 2H), 2.96, 2.81 (s, 3H total), 2.62-2.60 (m, 1H), 2.20-2.18 (s, 2H), 2.08-1.97 (m, 2H), 1.92-1.89 (m, 6H), 1.25-1.23 (m, 4H). LCMS (ESI): m/z 804.2 (M+H)$^+$.

Example 9

Preparation of N-(3-(2-((7-((2-(2,6-Dioxopiperidin-3-yl)-1,3-dioxoisoindolin-5-yl)oxy)heptyl)(methyl)amino)-2-oxoethyl)benzyl)-5-methoxy-4-((E)-2-(trans-4-(trifluoromethyl)cyclohexyl)vinyl)picolinamide The general reaction scheme was as follows:

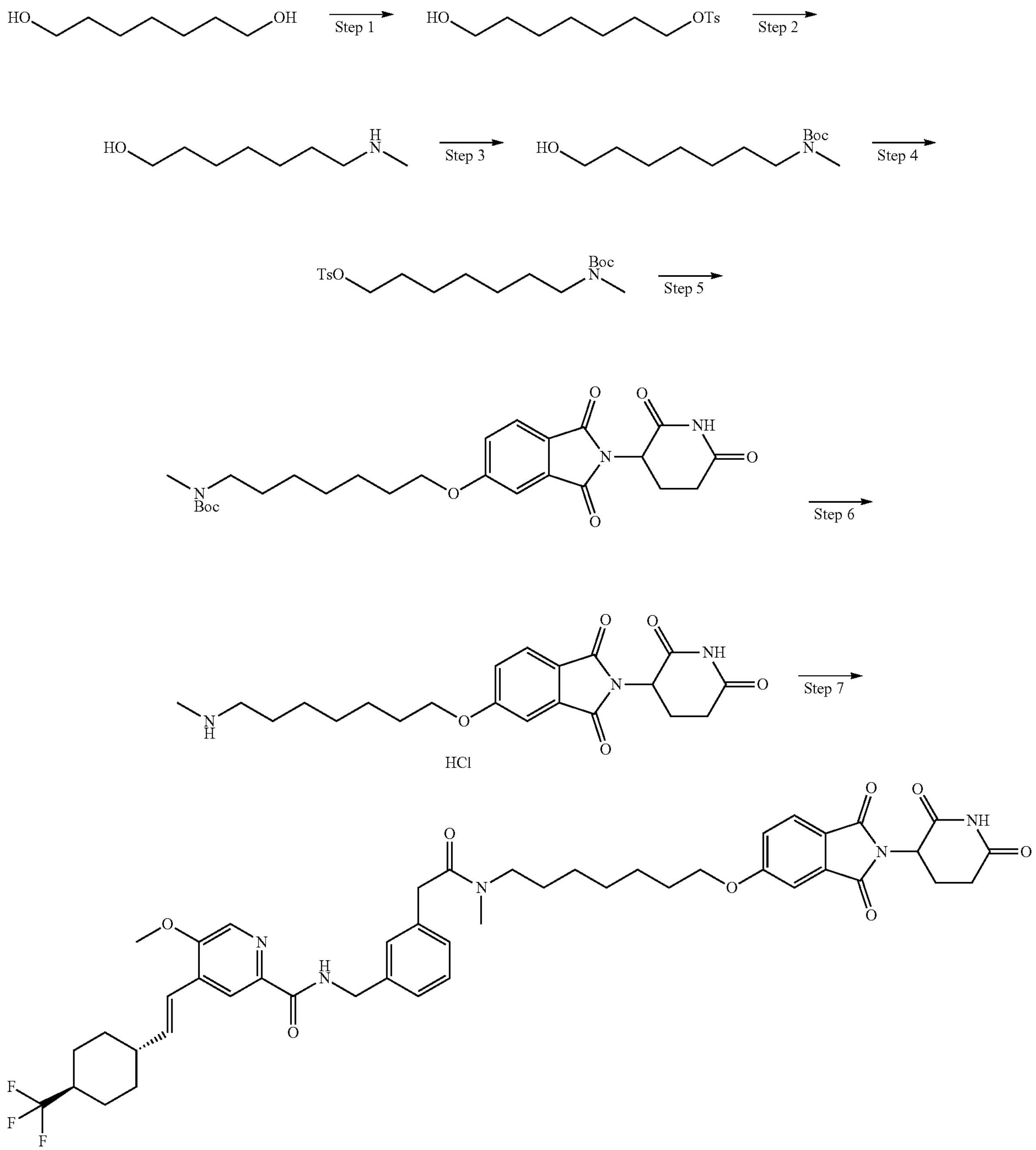

Step 1: 7-Hydroxyheptyl 4-methylbenzenesulfonate

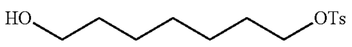 [SMILES: Cc1ccc(S(=O)(=O)OCCCCCCCO)cc1]

The title compound (6.2 g, 57%) was furnished as a colorless oil. It was prepared from heptane-1,7-diol (5.0 g, 37.82 mmol) following the procedure outlined for Example 1, Step 1. LCMS (ESI): m/z 308.9 $(M+Na)^+$.

Step 2: 7-(Methylamino)heptan-1-ol

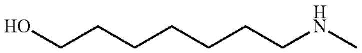

The title compound (3.1 g, 99%) was furnished as a colorless oil. It was prepared from 7-hydroxyheptyl 4-methylbenzenesulfonate (6.2 g, 21.65 mmol) following the procedure outlined for Example 1, Step 2. LCMS (ESI): m/z 146.0 $(M+H)^+$.

Step 3: tert-Butyl (7-hydroxyheptyl)(methyl)carbamate

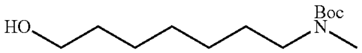 [SMILES: CN(CCCCCCCO)C(=O)OC(C)(C)C]

The title compound (400 mg, 47%) was furnished as colorless oil. It was prepared from 7-(methylamino)heptan-1-ol (500 mg, 3.44 mmol) following the procedure outlined for Example 1, Step 3. LCMS (ESI): m/z 146.0 $(M-100+H)^+$.

Step 4: 7-((tert-Butoxycarbonyl)(methyl)amino)heptyl 4-methylbenzenesulfonate

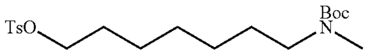 [SMILES: Cc1ccc(S(=O)(=O)OCCCCCCCN(C)C(=O)OC(C)(C)C)cc1]

The title compound (600 mg, 92%) was furnished as a colorless oil. It was prepared from tert-butyl (7-hydroxyheptyl)(methyl)carbamate (400 mg, 1.63 mmol) following the procedure outlined for Example 1, Step 4. LCMS (ESI): m/z 422.1 $(M+Na)^+$.

Step 5: tert-Butyl (7-((2-(2,6-dioxopiperidin-3-yl)-1,3-dioxoisoindolin-5-yl)oxy)heptyl)(methyl)carbamate

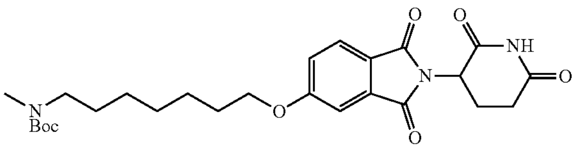 [SMILES: CN(CCCCCCCOc1ccc2c(c1)C(=O)N(C1CCC(=O)NC1=O)C2=O)C(=O)OC(C)(C)C]

The title compound (350 mg, 93%) was furnished as a yellow oil. It was prepared from 7-((tert-butoxycarbonyl)(methyl)amino)heptyl 4-methylbenzenesulfonate (300 mg, 0.75 mmol) following the procedure outlined for Example 1, Step 5. LCMS (ESI): m/z 524.1 $(M+Na)^+$.

Step 6: 2-(2,6-Dioxopiperidin-3-yl)-5-((7-(methylamino)heptyl)oxy)isoindoline-1,3-dione hydrochloride

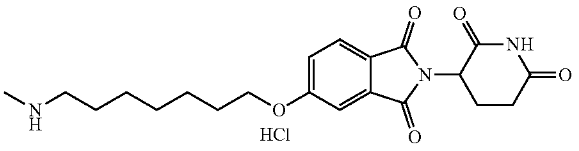 [SMILES: CNCCCCCCCOc1ccc2c(c1)C(=O)N(C1CCC(=O)NC1=O)C2=O ; Cl]

The title compound (300 mg, 98%) was furnished as a yellow oil. It was prepared from tert-butyl (7-((2-(2,6-dioxopiperidin-3-yl)-1,3-dioxoisoindolin-5-yl)oxy) heptyl)(methyl)carbamate (350 mg, 0.7 mmol) following the procedure outlined for Example 1, Step 6. LCMS (ESI): m/z 402.1 $(M+H)^+$.

Step 7: N-(3-(2-((7-((2-(2,6-Dioxopiperidin-3-yl)-1,3-dioxoisoindolin-5-yl)oxy)heptyl)(methyl)amino)-2-oxoethyl)benzyl)-5-methoxy-4-((E)-2-(trans-4-(trifluoromethyl)cyclohexyl)vinyl)picolinamide

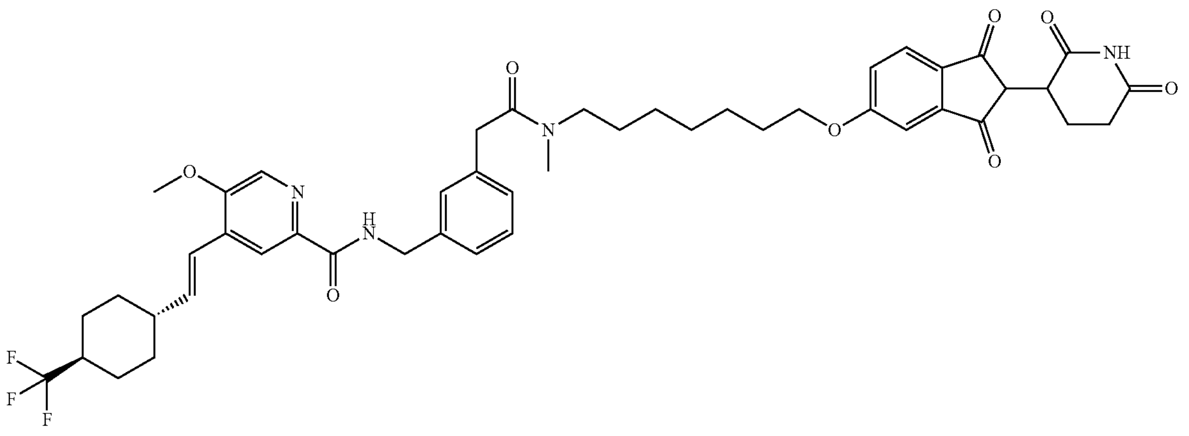

The title compound (40.3 mg, 42%) was furnished as a white solid. It was prepared from 2-(2,6-dioxopiperidin-3-yl)-5-((7-(methylamino)heptyl)oxy)isoindoline-1,3-dione hydrochloride (55 mg, 0.13 mmol) following the procedure outlined for Example 1, Step 7. It was purified by prep-HPLC (Boston Green ODS 150*30 mm*5 um, water-ACN, 70-90%). $^1$H NMR (400 MHz, DMSO-$d_6$): δ 11.12 (s, 1H), 9.09 (t, J=6.0 Hz, 1H), 8.33 (s, 1H), 8.05 (s, 1H), 7.81 (d, J=8.4 Hz, 1H), 7.40 (s, 1H), 7.34-7.30 (m, 1H), 7.25-7.20 (m, 1H), 7.15 (d, J=7.2 Hz, 2H), 7.08 (t, J=6.0 Hz, 1H), 6.59-6.53 (m, 2H), 5.13-5.09 (m, 1H), 4.45 (d, J=5.2 Hz, 2H), 4.15-4.10 (m, 2H), 3.99 (s, 3H), 3.63 (s, 2H), 3.27-3.21 (m, 2H), 2.91, 2.76 (s, 3H total), 2.90-2.84 (m, 1H), 2.61-2.57 (m, 1H), 2.21-2.20 (s, 2H), 2.05-2.02 (m, 1H), 1.94-1.83 (m, 4H), 1.70-1.67 (m, 2H), 1.41-1.23 (m, 11H), 1.17-1.14 (m, 2H). LCMS (ESI): m/z 860.5 (M+H)$^+$.

Example 10

Preparation of N-(3-(2-((5-((2-(2,6-Dioxopiperidin-3-yl)-1,3-dioxoisoindolin-5-yl)oxy)pentyl)(methyl)amino)-2-oxoethyl)benzyl)-5-methoxy-4-((E)-2-(trans-4-(trifluoromethyl)cyclohexyl)vinyl)picolinamide The general reaction scheme was as follows:

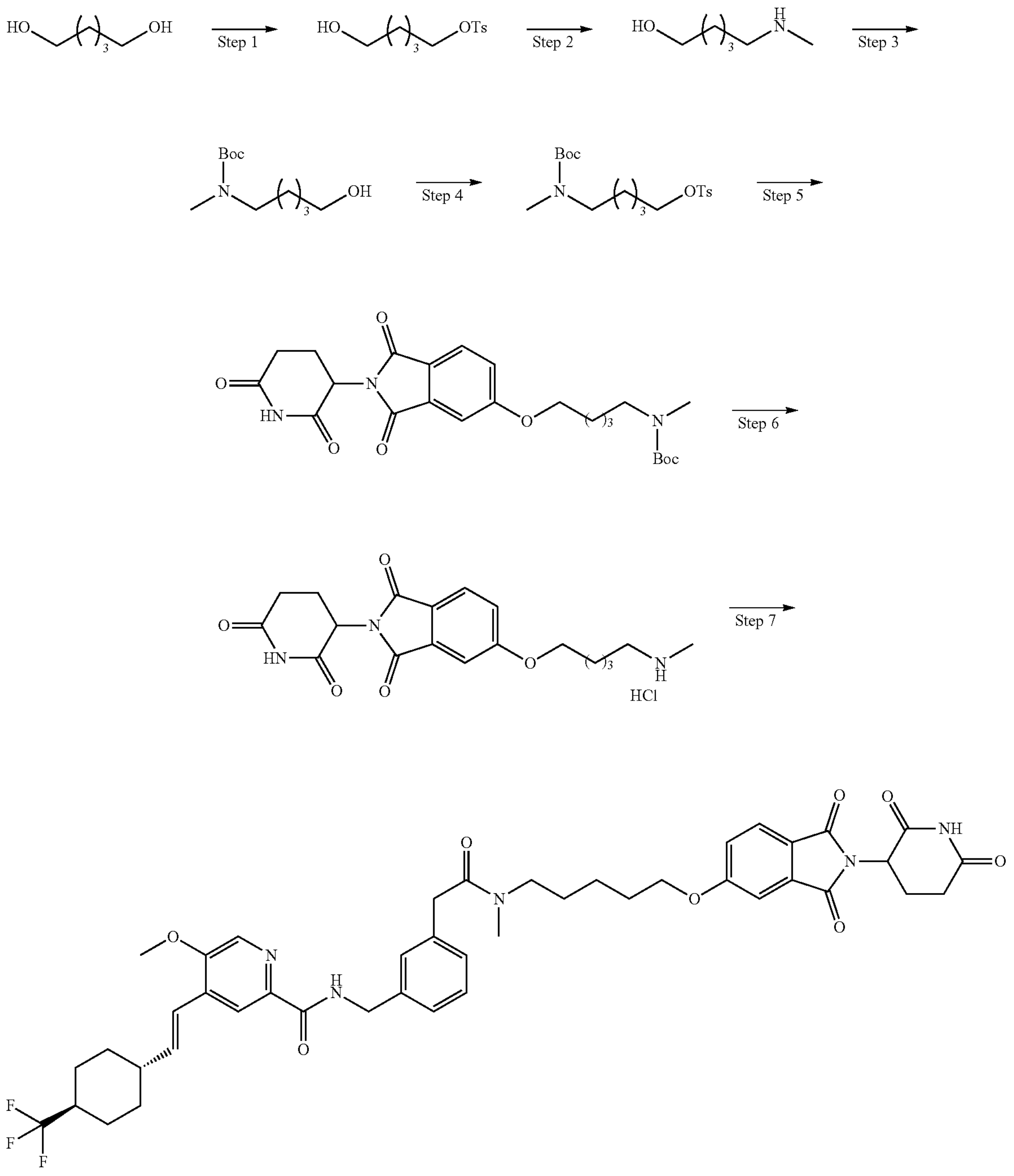

Step 1: 5-Hydroxypentyl 4-methylbenzenesulfonate

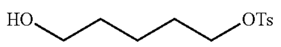

The title compound (3 g, 61%) was furnished as a colorless oil. It was prepared from 1,5-pentanediol (2.0 g, 19.2 mmol) following the procedure outlined for Example 1, Step 1. LCMS (ESI): m/z 280.9 $(M+Na)^+$.

Step 2: 5-(Methylamino)pentan-1-ol

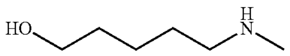

The title compound (1.3 g, 96%) was furnished as a colorless oil. It was prepared from 5-hydroxypentyl 4-methylbenzenesulfonate (3.0 g, 11.61 mmol) following the procedure outlined for Example 1, Step 2.

Step 3: tert-Butyl (5-hydroxypentyl)(methyl)carbamate

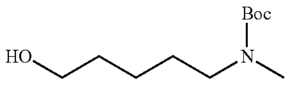

The title compound (900 mg, 37%) was furnished as a colorless oil. It was prepared from 5-(methylamino)pentan-1-ol (1.3 g, 11.09 mmol) following the procedure outlined for Example 1, Step 3. $^1$H NMR (400 MHz, $CDCl_3$): δ 3.63 (t, J=6.4 Hz, 2H), 3.20 (br s, 2H), 2.82 (s, 3H), 1.62-1.49 (m, 4H), 1.44 (s, 9H), 1.38-1.30 (m, 2H).

Step 4: 5-((tert-Butoxycarbonyl)(methyl)amino)pentyl 4-methylbenzenesulfonate

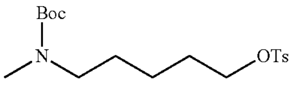 [SMILES: Cc1ccc(S(=O)(=O)OCCCCCN(C)C(=O)OC(C)(C)C)cc1]

The title compound (1.34 g, 87%) was furnished as a colorless oil. It was prepared from tert-butyl (5-hydroxypentyl)(methyl)carbamate (900 mg, 4.14 mmol) following the procedure outlined for Example 1, Step 4. $^1$H NMR (400 MHz, $CDCl_3$): δ 7.78 (d, J=8.4 Hz, 2H), 7.34 (d, J=8.0 Hz, 2H), 4.03-4.00 (m, 2H), 3.17-3.13 (m, 2H), 2.79 (s, 3H), 2.45 (s, 3H), 1.70-1.63 (m, 2H), 1.48-1.46 (m, 2H), 1.43 (s, 9H), 1.33-1.29 (m, 2H). LCMS (ESI): m/z 394.1 $(M+Na)^+$.

Step 5: tert-Butyl (5-((2-(2,6-dioxopiperidin-3-yl)-1,3-dioxoisoindolin-5-yl)oxy)pentyl)(methyl)carbamate

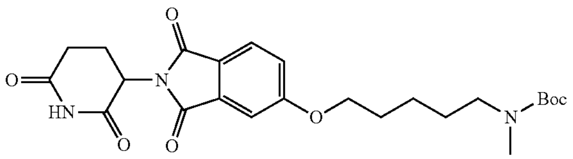

The title compound (254 mg, 66%) was furnished as a yellow oil. It was prepared from 5-((tert-butoxycarbonyl)(methyl)amino)pentyl 4-methylbenzenesulfonate (300 mg, 0.81 mmol) following the procedure outlined for Example 1, Step 5. LCMS (ESI): m/z 496.2 $(M+Na)^+$.

Step 6: 2-(2,6-Dioxopiperidin-3-yl)-5-((5-(methylamino)pentyl)oxy)isoindoline-1,3-dione hydrochloride

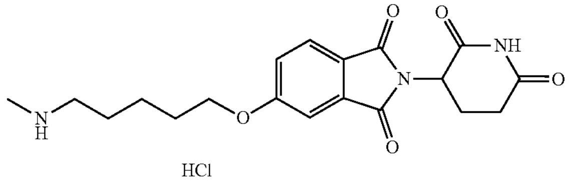 [SMILES: CNCCCCCOc1ccc2c(c1)C(=O)N(C1CCC(=O)NC1=O)C2=O ; Cl]

The title compound (200 mg, 91%) was furnished as a white oil. It was prepared from tert-butyl (5-((2-(2,6-dioxopiperidin-3-yl)-1,3-dioxoisoindolin-5-yl)oxy)pentyl)(methyl)carbamate (254 mg, 0.54 mmol) following the procedure outlined for Example 1, Step 6. LCMS (ESI): m/z 374.1 $(M+H)^+$.

Step 7: N-(3-(2-((5-((2-(2,6-Dioxopiperidin-3-yl)-1,3-dioxoisoindolin-5-yl)oxy)pentyl)(methyl)amino)-2-oxoethyl)benzyl)-5-methoxy-4-((E)-2-(trans-4-(trifluoromethyl)cyclohexyl)vinyl)picolinamide

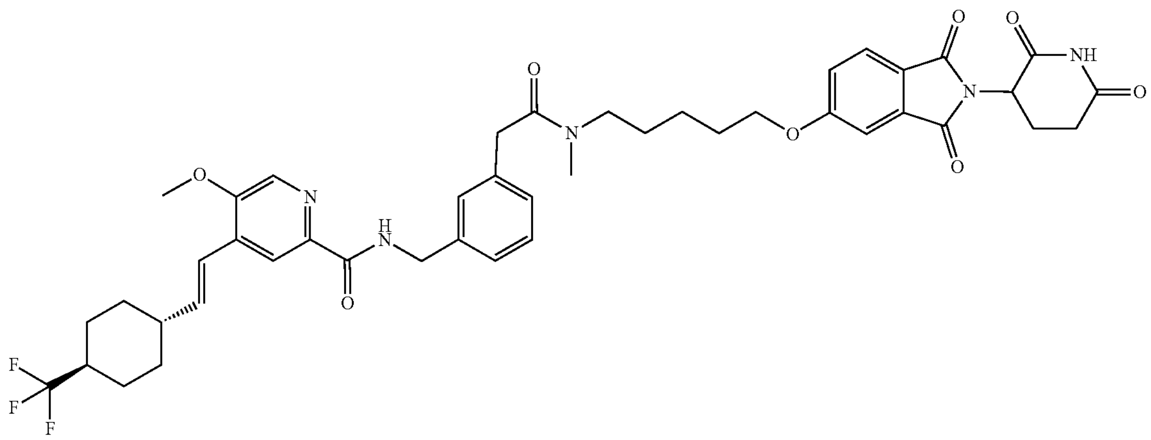 [SMILES: COc1cnc(C(=O)NCc2cccc(CC(=O)N(C)CCCCCOc3ccc4c(c3)C(=O)N(C3CCC(=O)NC3=O)C4=O)c2)cc1/C=C/[C@H]1CC[C@H](C(F)(F)F)CC1]

The title compound (19 mg, 4%) was furnished as a white solid. It was prepared from 2-(2,6-dioxopiperidin-3-yl)-5-((5-(methylamino)pentyl)oxy)isoindoline-1,3-dione hydrochloride (200 mg, 0.54 mmol) following the procedure outlined for Example 1, Step 7. It was purified by prep-HPLC (Welch Xtimate C18 150*30 mm*5 um, water (0.225% FA)-ACN, 60-80%). $^1$H NMR (400 MHz, $CDCl_3$): δ 8.25-8.19 (m, 2H), 8.11-8.09 (m, 1H), 8.03 (s, 1H), 7.78 (d, J=8.4 Hz, 1H), 7.32 (s, 1H), 7.25 (s, 1H), 7.19-7.16 (m, 2H), 6.66 (d, J=16.0 Hz, 1H), 6.54-6.47 (m, 1H), 4.99-4.94 (m, 1H), 4.64 (d, J=6.0 Hz, 2H), 4.08-4.01 (m, 2H), 3.99-3.97 (m, 3H), 3.74-3.70 (m, 2H), 3.42 (t, J=7.2 Hz, 1H), 3.34-3.28 (m, 1H), 2.99, 2.95 (s, 3H total), 2.95-2.73 (m, 4H), 2.24-2.12 (m, 2H), 2.06-1.94 (m, 5H), 1.88-1.76 (m, 2H), 1.53-1.32 (m, 5H), 1.30-1.19 (m, 2H). LCMS (ESI): m/z 832.5 $(M+H)^+$.

Example 11

Preparation of N-(3-(2-((5-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-5-oxopentyl)amino)-2-oxoethyl)benzyl)-5-methoxy-4-((E)-2-(trans-4-(trifluoromethyl)cyclohexyl)vinyl)picolinamide The general reaction scheme was as follows:

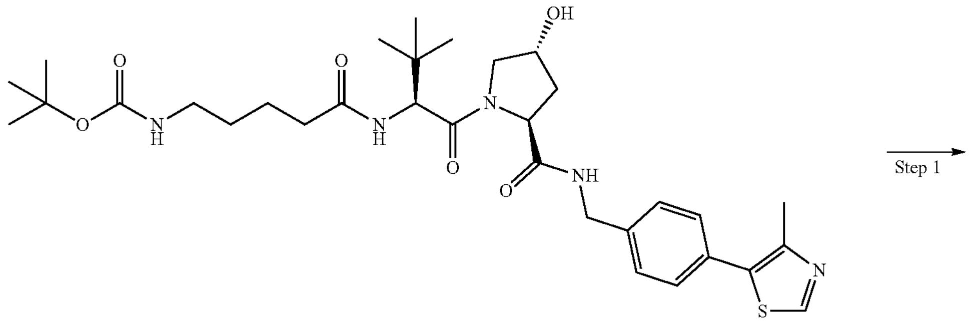

-continued

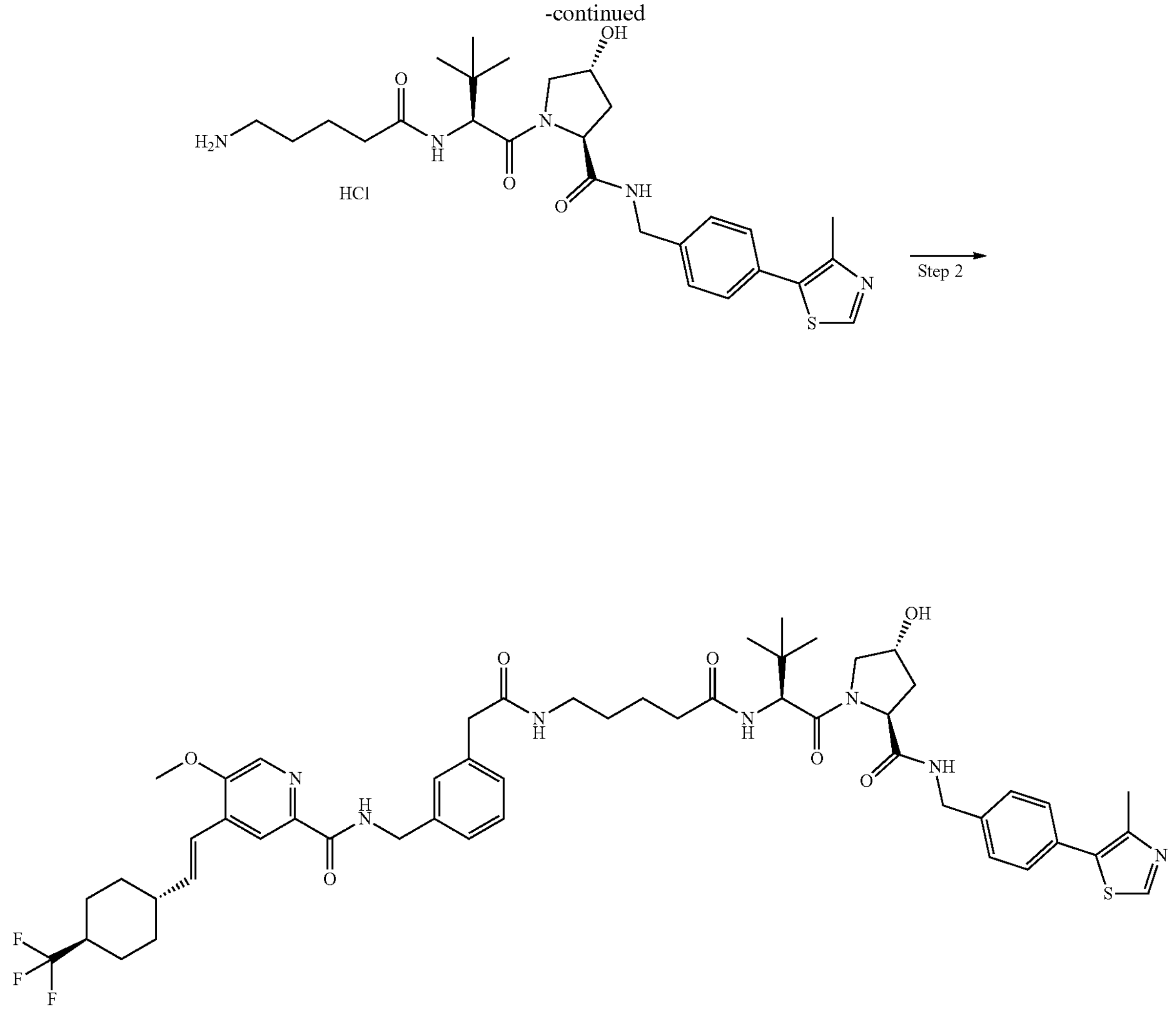

Step 1: (2S,4R)-1-((S)-2-(5-Aminopentanamido)-3,3-dimethylbutanoyl)-4-hydroxy-N-(4-(4-methylthiazol-5-yl)benzyl)pyrrolidine-2-carboxamide hydrochloride

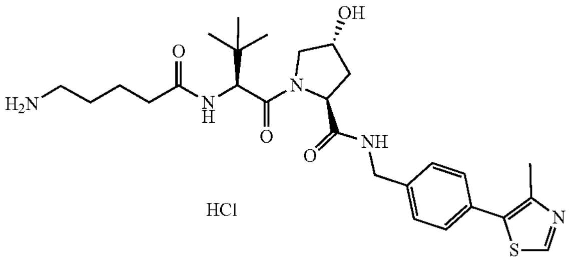 [SMILES: Cc1ncsc1-c1ccc(CNC(=O)[C@@H]2C[C@@H](O)CN2C(=O)[C@@H](NC(=O)CCCCN)C(C)(C)C)cc1 ; Cl]

To a solution of tert-butyl (5-(((S)-1-((2S,4R)-4-hydroxy-2-((4-(4-methylthiazol-5-yl) benzyl)carbamoyl)pyrrolidin-1-yl)-3,3-dimethyl-1-oxobutan-2-yl)amino)-5-oxopentyl) carbamate (300.0 mg, 0.4800 mmol) in 1,4-dioxane (1.5 mL) was added 4 M HCl in 1,4-dioxane (6 mL, 24 mmol). After stirring at room temperature for 2 hours, the reaction mixture was concentrated to afford the title compound (200 mg, 74%) as a yellow oil. LCMS (ESI): m/z 530.2 $(M+H)^+$.

Step 2: N-(3-(2-((5-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-5-oxopentyl)amino)-2-oxoethyl)benzyl)-5-methoxy-4-((E)-2-(trans-4-(trifluoromethyl)cyclohexyl)vinyl) picolinamide

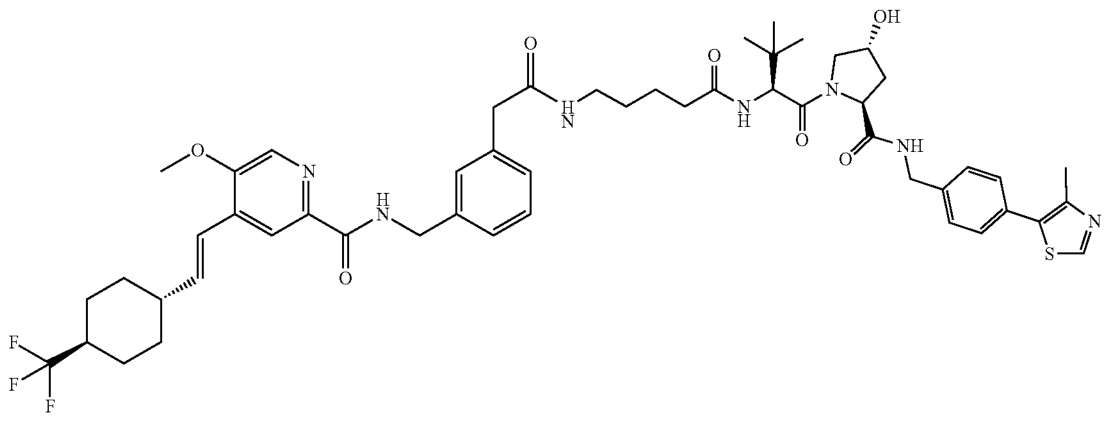 [SMILES: COc1cnc(C(=O)NCc2cccc(CC(=O)NCCCCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]

To a mixture of (2S,4R)-1-((S)-2-(5-aminopentanamido)-3,3-dimethylbutanoyl)-4-hydroxy-N-(4-(4-methylthiazol-5-yl)benzyl)pyrrolidine-2-carboxamide hydrochloride (85.6 mg, 0.15 mmol) and 2-(3-((5-methoxy-4-((E)-2-(trans-4-(trifluoromethyl)cyclohexyl)vinyl)picolinamido)methyl) phenyl)acetic acid (60 mg, 0.13 mmol) in DCM (2 mL) was added DIPEA (0.06 mL, 0.38 mmol) and $T_3P$ (160 mg, 0.25 mmol) at room temperature. Then the resulting mixture was stirred at 40° C. for 1 hour. The reaction was quenched by adding water (10 mL) at 0° C. The layers were separated, the aqueous solution was extracted with DCM (30 mL×2). The combined organic layer was washed with brine (20 mL×2), dried over $Na_2SO_4$ and concentrated. The residue was purified by prep-HPLC (Boston Green ODS 150*30 mm*5 um, water (0.075% TFA)-CAN, 55-75%) to afford the title compound (43.1 mg, 33%) as a white solid. $^1H$ NMR (400 MHz, $CD_3OD$): δ 9.08-9.03 (m, 1H), 8.31 (s, 1H), 8.22 (d, J=7.2 Hz, 1H), 7.48 (d, J=8.0 Hz, 2H), 7.42 (d, J=8.0 Hz, 2H), 7.30-7.23 (m, 3H), 7.22-7.18 (m, 1H), 6.73 (d, J=16.4 Hz, 1H), 6.63-6.57 (m, 1H), 4.62-4.57 (m, 6H), 4.37-4.34 (m, 1H), 4.04 (s, 3H), 3.93-3.87 (m, 1H), 3.81-3.78 (m, 1H), 3.48 (s, 2H), 3.16 (t, J=6.8 Hz, 2H), 2.49 (s, 3H), 2.29-2.18 (m, 4H), 2.11-2.07 (m, 1H), 1.99-1.95 (m, 4H), 1.61-1.57 (m, 2H), 1.53-1.40 (m, 4H), 1.39-1.35 (m, 3H), 1.03 (s, 9H). LCMS (ESI): m/z 495.1 $(M/2+H)^+$.

Example 12

Preparation of N-(3-(2-((7-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl) amino)-7-oxoheptyl)amino)-2-oxoethyl)benzyl)-5-methoxy-4-((E)-2-(trans-4-(trifluoromethyl) cyclohexyl)vinyl)picolinamide The general reaction scheme was as follows:

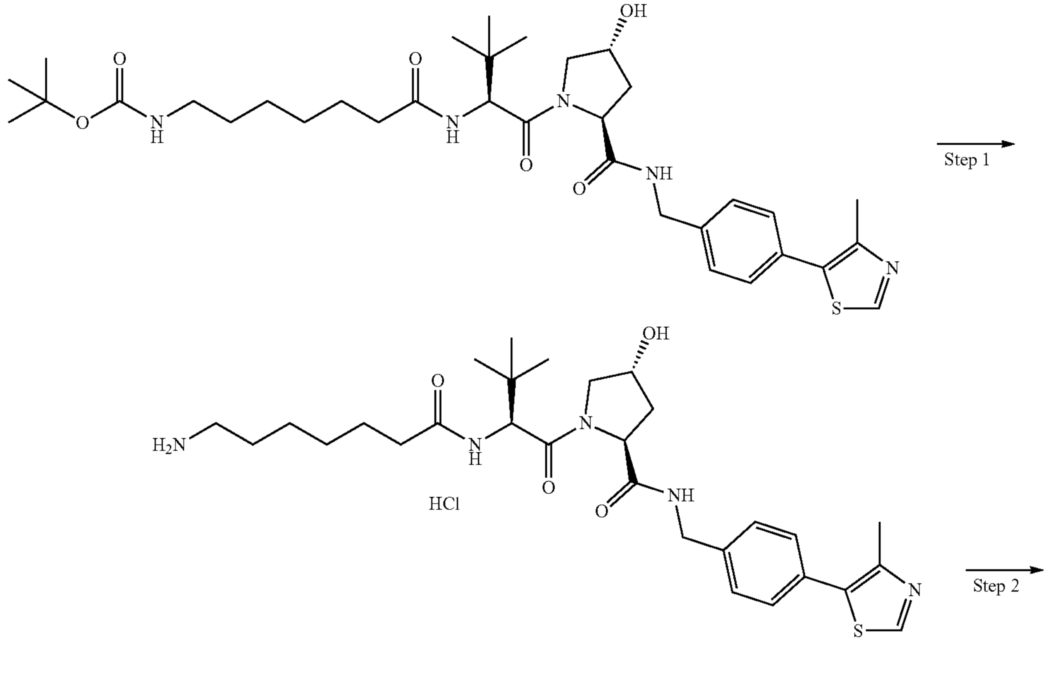

-continued

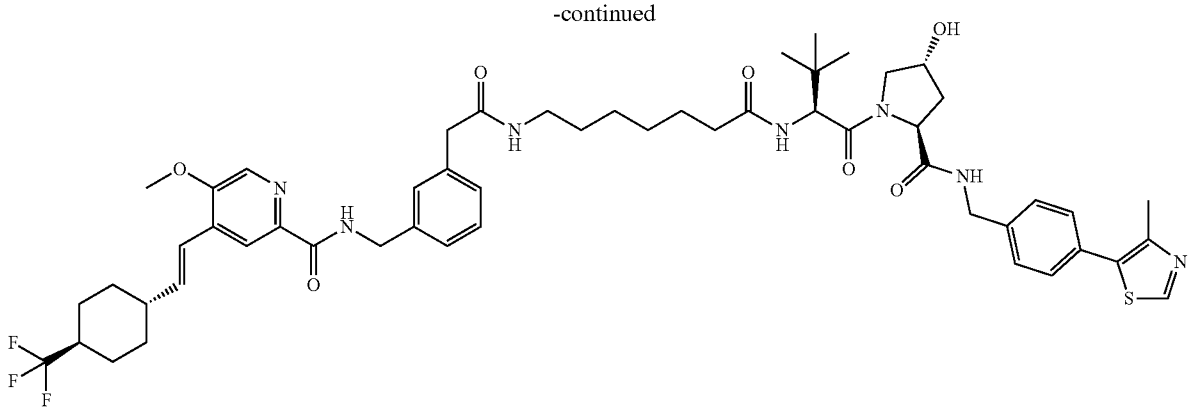

Step 1: (2S,4R)-1-((S)-2-(7-Aminoheptanamido)-3,3-dimethylbutanoyl)-4-hydroxy-N-(4-(4-methylthiazol-5-yl)benzyl)pyrrolidine-2-carboxamide hydrochloride

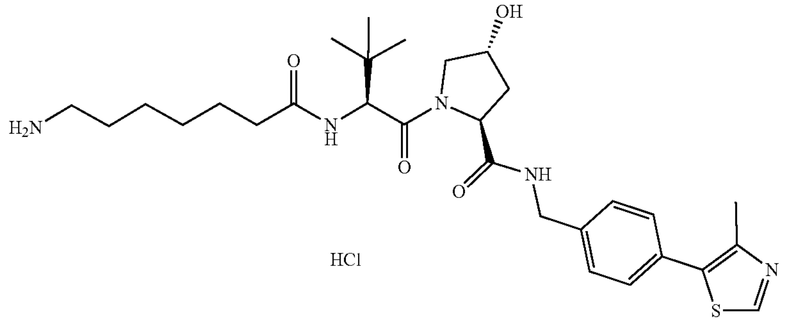 [SMILES: Cc1ncsc1-c1ccc(CNC(=O)[C@@H]2C[C@@H](O)CN2C(=O)[C@@H](NC(=O)CCCCCCN)C(C)(C)C)cc1 ; Cl]

The title compound (140 mg, 78%) was furnished as a yellow oil. It was prepared from tert-butyl (7-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl) amino)-7-oxoheptyl)carbamate (200 mg, 0.30 mmol) following the procedure outlined for Example 11, Step 1. LCMS (ESI): m/z 580.2 $(M+Na)^+$.

Step 2: N-(3-(2-((7-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-7-oxoheptyl)amino)-2-oxoethyl)benzyl)-5-methoxy-4-((E)-2-(trans-4-(trifluoromethyl)cyclohexyl)vinyl) picolinamide

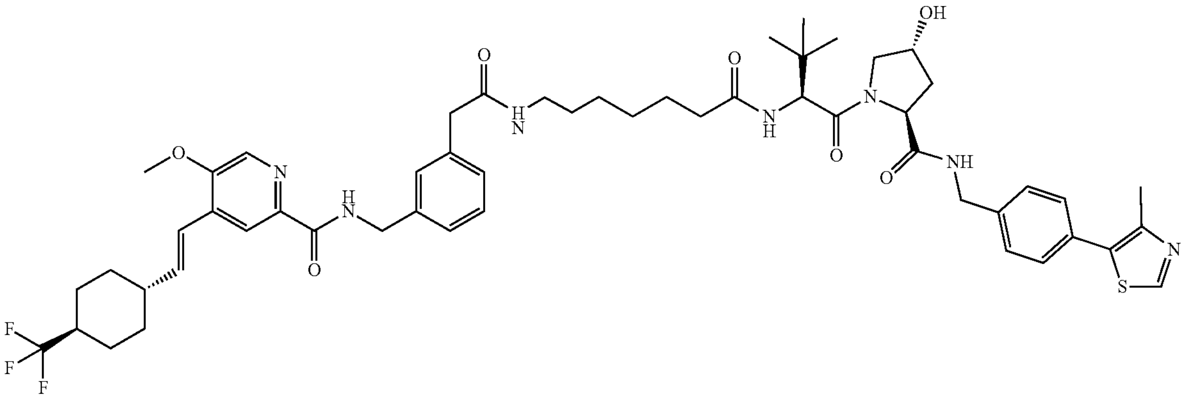 [SMILES: COc1cnc(C(=O)NCc2cccc(CC(=O)NCCCCCCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]

The title compound (65.3 mg, 38%) was furnished as a white solid. It was prepared from (2S,4R)-1-((S)-2-(7-aminoheptanamido)-3,3-dimethylbutanoyl)-4-hydroxy-N-(4-(4-methylthiazol-5-yl)benzyl)pyrrolidine-2-carboxamide hydrochloride (120 mg, 0.20 mmol) following the procedure outlined for Example 11, Step 2. It was purified by prep-HPLC (Boston Green ODS 150*30 mm*5 um, water (0.075% TFA)-CAN, 56-76%). $^1H$ NMR (400 MHz, $CD_3OD$): δ 9.14 (s, 1H), 8.31 (s, 1H), 8.25 (s, 1H), 7.48 (d, J=8.0 Hz, 2H), 7.42 (d, J=8.0 Hz, 2H), 7.30-7.23 (m, 3H), 7.19 (d, J=6.8 Hz, 1H), 6.74 (d, J=16.0 Hz, 1H), 6.63 (dd, J=16.0, 6.4 Hz, 1H), 4.63 (s, 1H), 4.95-4.59 (m, 5H), 4.35 (d, J=15.2 Hz, 1H), 4.04 (s, 3H), 3.94-3.89 (m, 1H), 3.83-3.78 (m, 1H), 3.47 (s, 2H), 3.14 (t, J=6.8 Hz, 2H), 2.49 (s, 3H), 2.26-2.18 (m, 4H), 2.11-2.06 (m, 1H), 1.99-1.47 (m, 4H), 1.60-1.53 (m, 2H), 1.47-1.40 (m, 4H), 1.38-1.26 (m, 7H), 1.03 (s, 9H). LCMS (ESI): m/z 1017.0 $(M+H)^+$.

Example 13

Preparation of N-(3-(2-((9-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-9-oxononyl)amino)-2-oxoethyl)benzyl)-5-methoxy-4-((E)-2-(trans-4-(trifluoromethyl)cyclohexyl)vinyl)picolinamide The general reaction scheme was as follows:

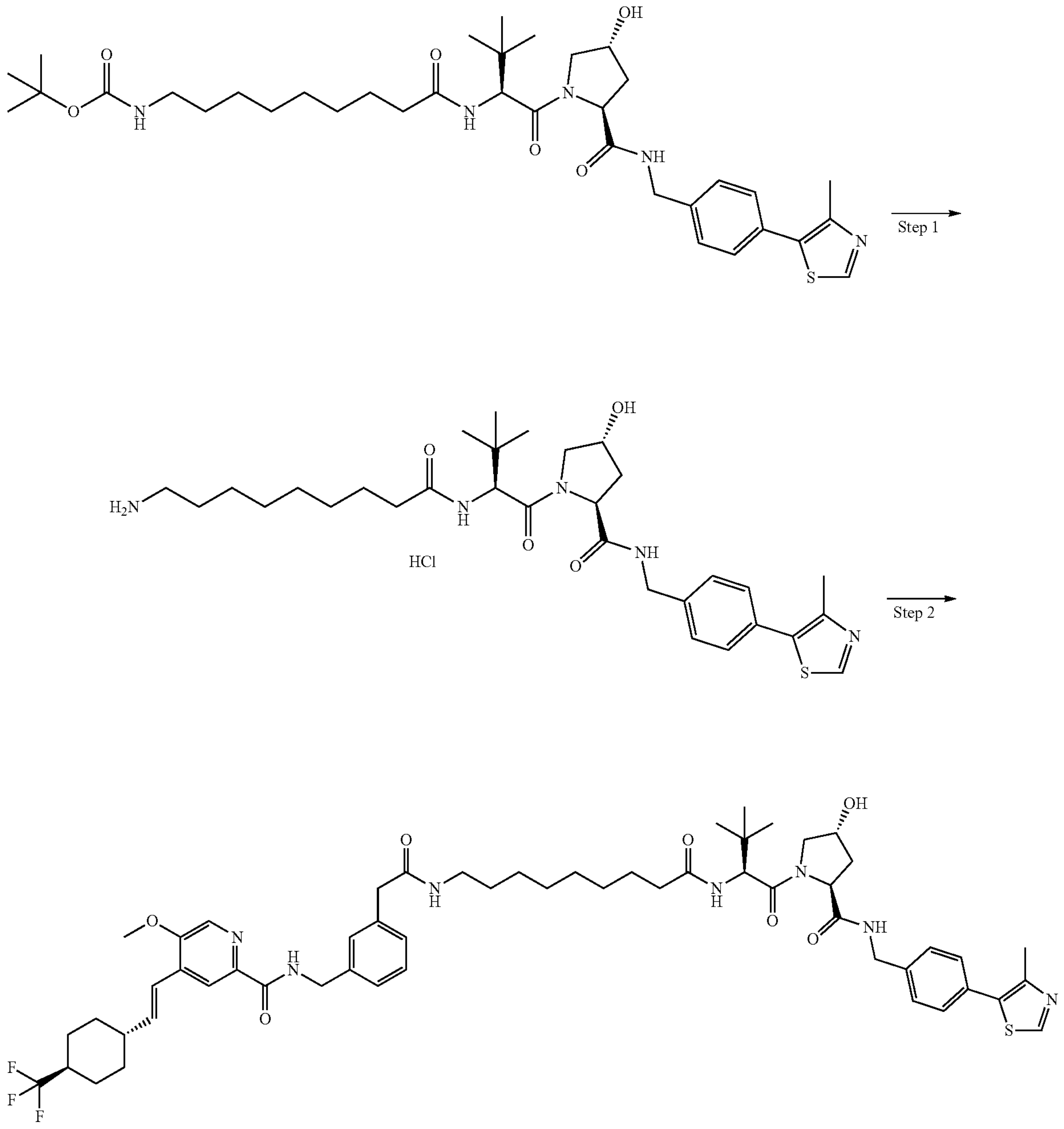

Step 1: (2S,4R)-1-((S)-2-(9-Aminononanamido)-3,3-dimethylbutanoyl)-4-hydroxy-N-(4-(4-methylthiazol-5-yl)benzyl)pyrrolidine-2-carboxamide hydrochloride The title compound (270 mg, 990%) was furnished as a yellow oil. It was prepared from tert-butyl (9-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl) amino)-9-oxononyl)carbamate (300 mg, 0.44 mmol) following the procedure outlined for Example 11, Step 1. LCMS (ESI): m/z 586.3 $(M+H)^+$.

Step 2: N-(3-(2-((9-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-9-oxononyl)amino)-2-oxoethyl)benzyl)-5-methoxy-4-((E)-2-(trans-4-(trifluoromethyl)cyclohexyl)vinyl) picolinamide

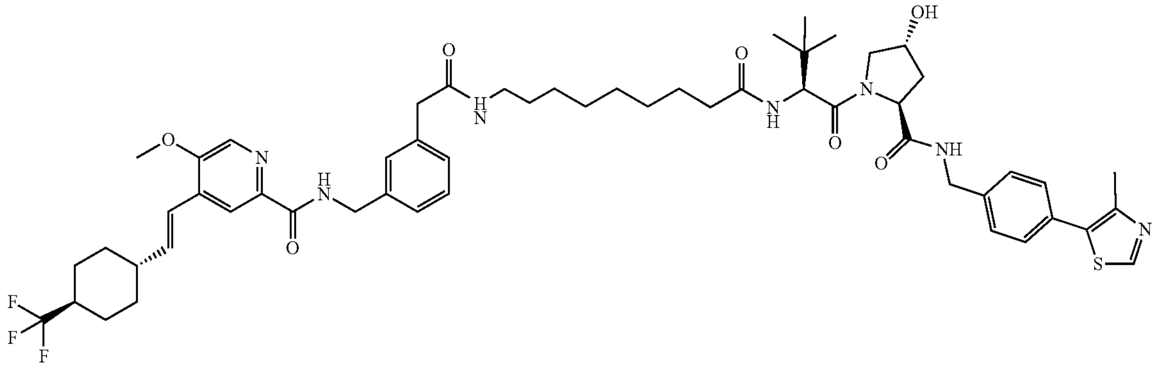 [SMILES: COc1cnc(C(=O)NCc2cccc(CC(=O)NCCCCCCCCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]

The title compound (23 mg, 20%) was furnished as a white solid. It was prepared from (2S,4R)-1-((S)-2-(9-aminononanamido)-3,3-dimethylbutanoyl)-4-hydroxy-N-(4-(4-methylthiazol-5-yl)benzyl)pyrrolidine-2-carboxamide hydrochloride (78.4 mg, 0.13 mmol) following the procedure outlined for Example 11, Step 2. It was purified by prep-HPLC (Boston Green ODS 150*30 mm*5 um, water (0.075% TFA)-CAN, 55-85%). $^1H$ NMR (400 MHz, $CD_3OD$): δ 9.06 (s, 1H), 8.30 (s, 1H), 8.22 (s, 1H), 7.47 (d, J=8.4 Hz, 2H), 7.42 (d, J=8.4 Hz, 2H), 7.29-7.23 (m, 3H), 7.20-7.18 (m, 1H), 6.73 (d, J=16.4 Hz, 1H), 6.62 (dd, J=16.4, 6.8 Hz, 1H), 4.63-4.49 (m, 6H), 4.33 (d, J=15.6 Hz, 1H), 4.01 (s, 3H), 3.89-3.87 (m, 1H), 3.79-3.75 (m, 1H), 3.45 (s, 2H), 3.11 (t, J=6.8 Hz, 2H), 2.48 (s, 3H), 2.26-2.18 (m, 4H), 2.10-2.05 (m, 1H), 2.02-1.92 (m, 4H), 1.58-1.56 (m, 2H), 1.41-1.39 (m, 4H), 1.31-1.24 (m, 11H), 1.01 (s, 9H). LCMS (ESI): m/z 1044.9 $(M+H)^+$.

Example 14

Preparation of N-(3-((S)-13-((2S,4R)-4-Hydroxy-2-((4-(4-methylthiazol-5-yl)benzyl)carbamoyl)pyrrolidine-1-carbonyl)-14,14-dimethyl-2,11-dioxo-6,9-dioxa-3,12-diazapentadecyl)benzyl)-5-methoxy-4-((E)-2-(trans-4-(trifluoromethyl)cyclohexyl)vinyl) picolinamide The general reaction scheme was as follows:

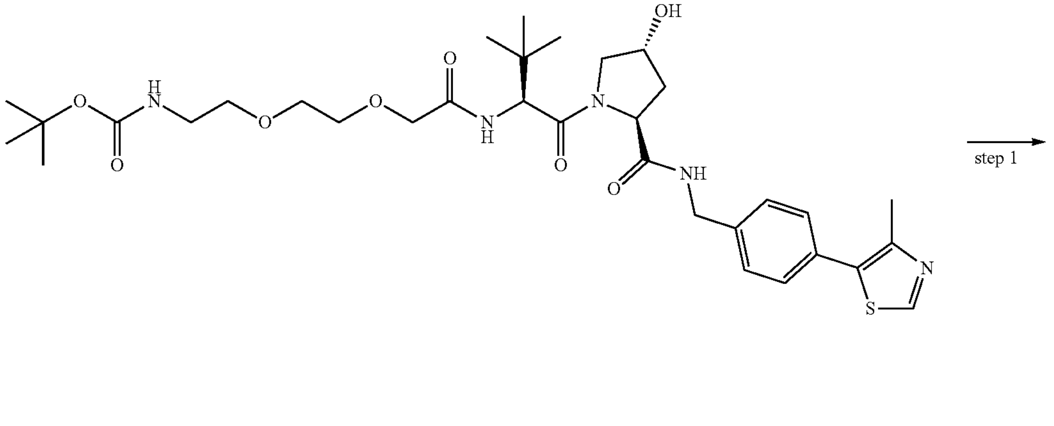

-continued

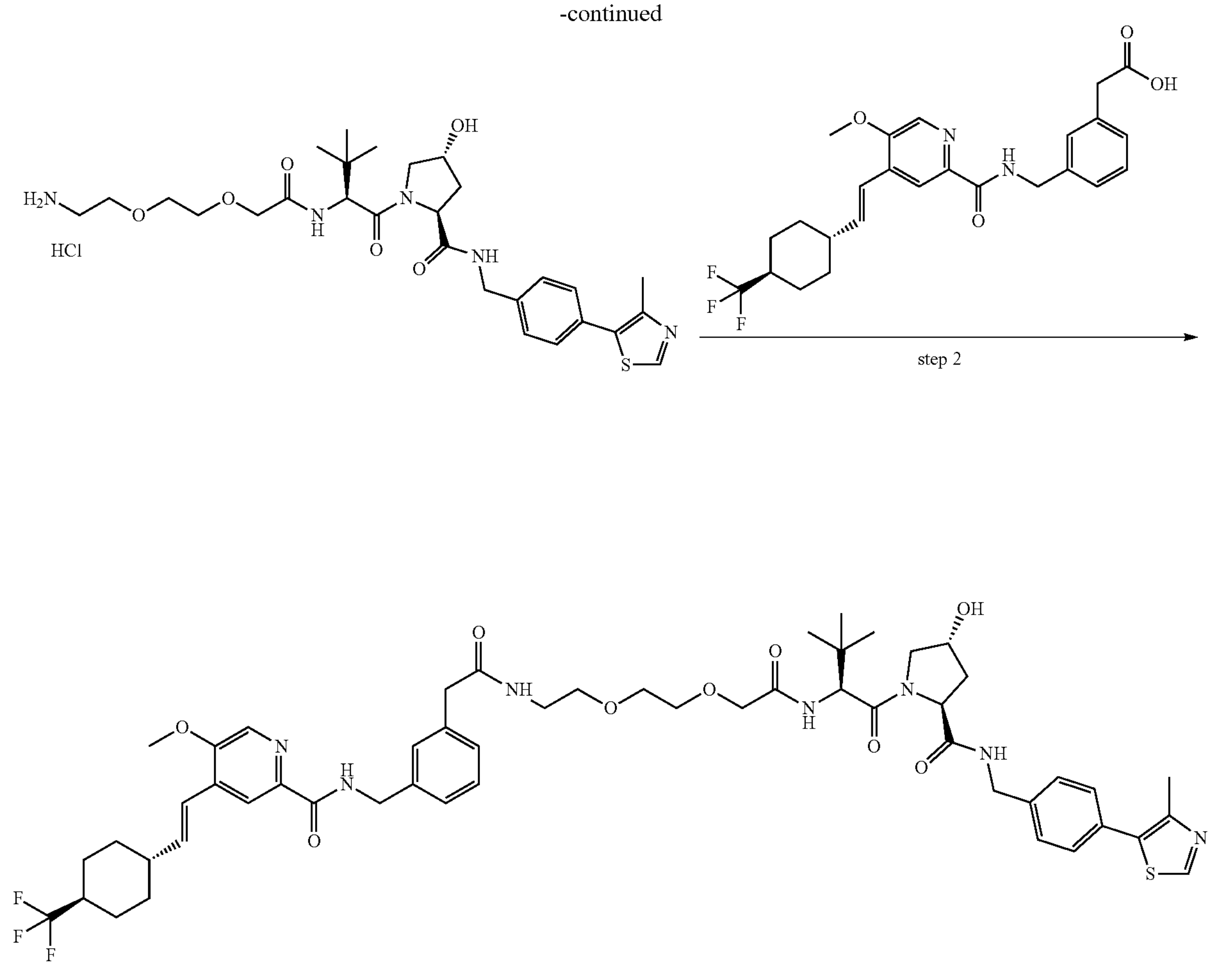

Step 1: (2S,4R)-1-((S)-2-(2-(2-(2-Aminoethoxy) ethoxy)acetamido)-3,3-dimethylbutanoyl)-4-hydroxy-N-(4-(4-methylthiazol-5-yl)benzyl)pyrrolidine-2-carboxamide hydrochloride

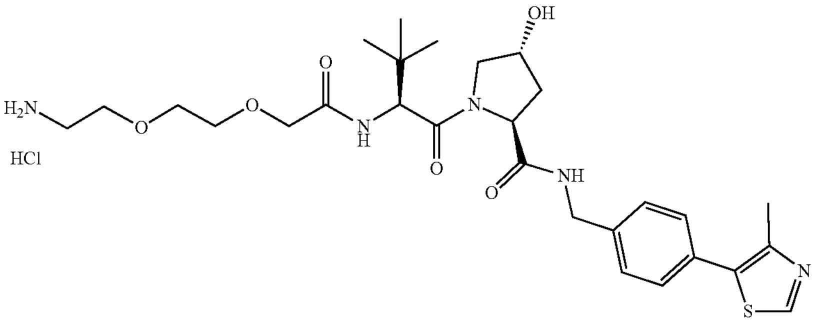 [SMILES: Cl ; Cc1ncsc1-c1ccc(CNC(=O)[C@@H]2C[C@@H](O)CN2C(=O)[C@@H](NC(=O)COCCOCCN)C(C)(C)C)cc1]

The title compound (272 mg, quant.) was furnished as a white solid. It was prepared from tert-butyl (2-(2-(2-(((S)-1-((2S,4R)-4-hydroxy-2-((4-(4-methylthiazol-5-yl)benzyl) carbamoyl)pyrrolidin-1-yl)-3,3-dimethyl-1-oxobutan-2-yl) amino)-2-oxoethoxy)ethoxy)ethyl)carbamate (300 mg, 0.44 mmol) following the procedure outlined for Example 11, Step 1. LCMS (ESI): m/z 576.3 $(M+H)^+$.

Step 2: N-(3-((S)-13-((2S,4R)-4-Hydroxy-2-((4-(4-methylthiazol-5-yl)benzyl)carbamoyl)pyrrolidine-1-carbonyl)-14,14-dimethyl-2,11-dioxo-6,9-dioxa-3,12-diazapentadecyl)benzyl)-5-methoxy-4-((E)-2-(trans-4-(trifluoromethyl)cyclohexyl)vinyl)picolinamide

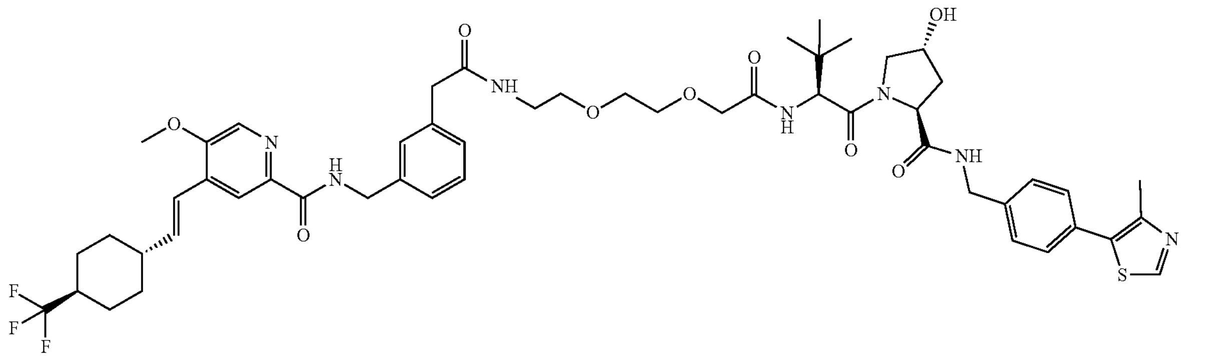 [SMILES: COc1cnc(C(=O)NCc2cccc(CC(=O)NCCOCCOCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]

The title compound (11.8 mg, 10%) was furnished as a white solid. It was prepared from (2S,4R)-1-((S)-2-(2-(2-(2-Aminoethoxy)ethoxy)acetamido)-3,3-dimethylbutanoyl)-4-hydroxy-N-(4-(4-methylthiazol-5-yl)benzyl)pyrrolidine-2-carboxamide hydrochloride (77 mg, 0.13 mmol) following the procedure outlined for Example 11, Step 2. It was purified by prep-HPLC (Welch Xtimate C18 150*30 mm*5 um, water (0.225% FA)-CAN, 55-85%). $^1H$ NMR (400 MHz, DMSO-$d_6$): δ 9.06 (t, J=5.6 Hz, 1H), 8.96 (s, 1H), 8.57 (t, J=5.6 Hz, 1H), 8.32 (s, 1H), 8.15-8.07 (m, 1H), 8.04 (s, 1H), 7.44 (d, J=10.0 Hz, 1H), 7.37-7.35 (m, 4H), 7.23-7.09 (m, 4H), 6.64-6.53 (m, 2H), 5.17 (d, J=3.2 Hz, 1H), 4.58 (d, J=9.2 Hz, 1H), 4.49-4.41 (m, 3H), 4.38-4.29 (m, 2H), 4.28-4.21 (m, 1H), 3.98 (s, 3H), 3.96 (s, 2H), 3.70-3.64 (m, 1H), 3.63-3.57 (m, 3H), 3.52-3.51 (m, 2H), 3.44-3.41 (m, 4H), 3.22-3.11 (m, 2H), 2.45-2.41 (m, 3H), 2.22-2.20 (m, 2H), 2.11-2.01 (m, 1H), 1.96-1.82 (m, 5H), 1.36-1.23 (m, 4H), 0.98-0.89 (m, 9H). LCMS (ESI): m/z 1034.6 $(M+H)^+$.

Example 15

Preparation of N-(3-((S)-16-((2S,4R)-4-Hydroxy-2-((4-(4-methylthiazol-5-yl)benzyl)carbamoyl)pyrrolidine-1-carbonyl)-17,17-dimethyl-2,14-dioxo-6,9,12-trioxa-3,15-diazaoctadecyl)benzyl)-5-methoxy-4-((E)-2-(trans-4-(trifluoromethyl)cyclohexyl)vinyl)picolinamide The general reaction scheme was as follows:

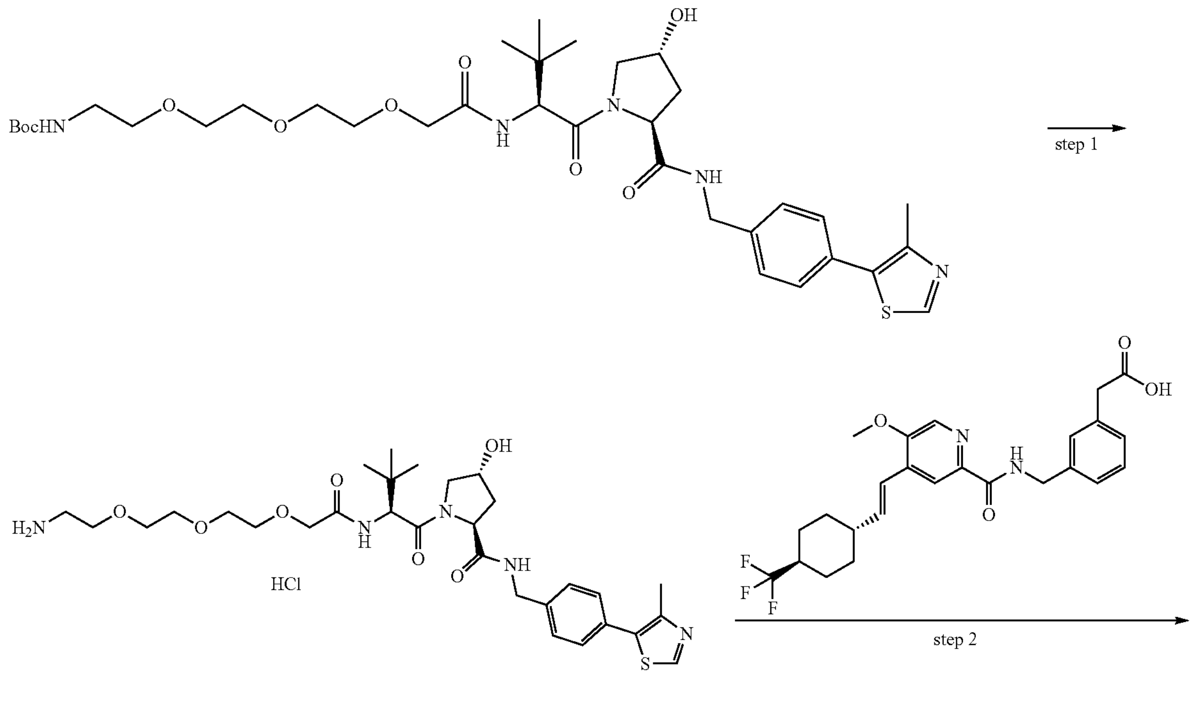

-continued

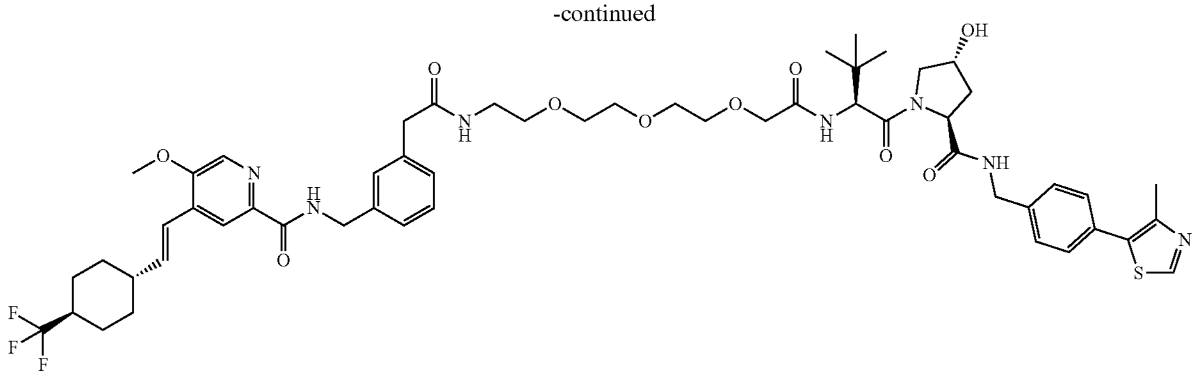

Step 1: (2S,4R)-1-((S)-14-amino-2-(tert-butyl)-4-oxo-6,9,12-trioxa-3-azatetradecan-1-oyl)-4-hydroxy-N-(4-(4-methylthiazol-5-yl)benzyl)pyrrolidine-2-carboxamide hydrochloride

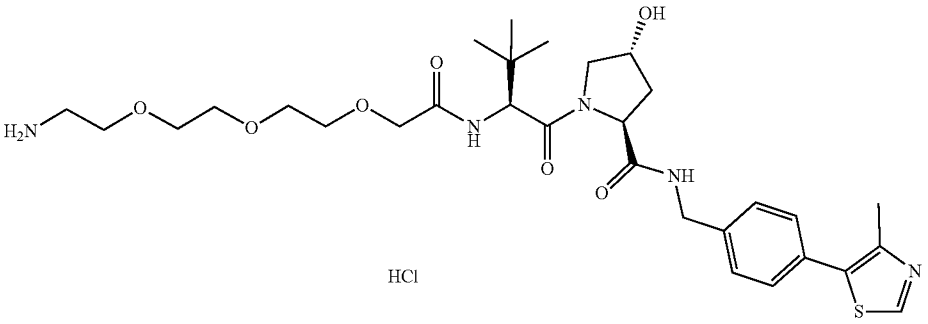 [SMILES: Cc1ncsc1-c1ccc(CNC(=O)[C@@H]2C[C@@H](O)CN2C(=O)[C@@H](NC(=O)COCCOCCOCCN)C(C)(C)C)cc1 ; Cl]

HCl

The title compound (273 mg, quant.) was furnished as a white solid. It was prepared from tert-butyl ((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)carbamate (300 mg, 0.42 mmol) following the procedure outlined for Example 11, Step 1. LCMS (ESI): m/z 620.3 $(M+H)^+$.

Step 2: N-(3-((S)-16-((2S,4R)-4-Hydroxy-2-((4-(4-methylthiazol-5-yl)benzyl)carbamoyl)pyrrolidine-1-carbonyl)-17,17-dimethyl-2,14-dioxo-6,9,12-trioxa-3,15-diazaoctadecyl)benzyl)-5-methoxy-4-((E)-2-(trans-4-(trifluoromethyl)cyclohexyl)vinyl)picolinamide

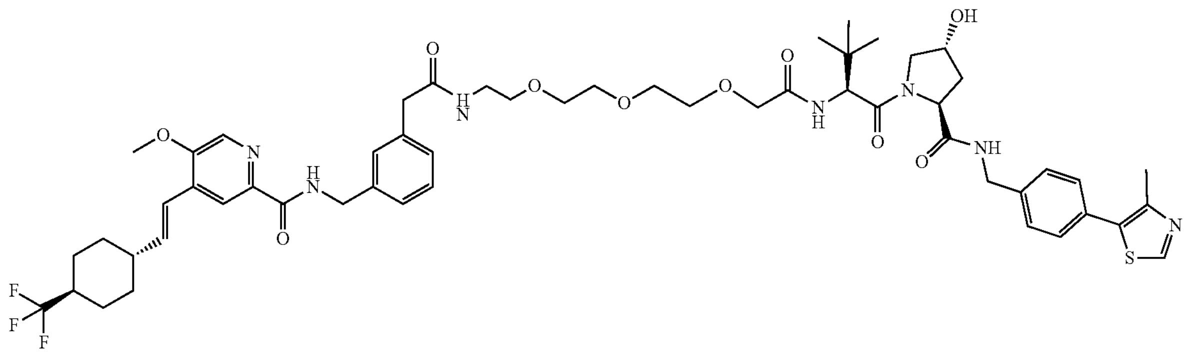 [SMILES: COc1cnc(C(=O)NCc2cccc(CC(=O)NCCOCCOCCOCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]

The title compound (30.4 mg, 27%) was furnished as a white solid. It was prepared from (2S,4R)-1-((S)-14-amino-2-(tert-butyl)-4-oxo-6,9,12-trioxa-3-azatetradecan-1-oyl)-4-hydroxy-N-(4-(4-methylthiazol-5-yl)benzyl)pyrrolidine-2-carboxamide hydrochloride (103 mg, 0.16 mmol) following the procedure outlined for Example 11, Step 2. It was purified by prep-HPLC (Welch Xtimate C18 150*30 mm*5 um, water (0.2% FA)-ACN, 53-93%). $^1$H NMR (400 MHz, DMSO-$d_6$): δ 9.07 (t, J=6.4 Hz, 1H), 8.99-8.94 (m, 1H), 8.59 (t, J=5.6 Hz, 1H), 8.33 (s, 1H), 8.14-8.05 (m, 2H), 7.45-7.35 (m, 5H), 7.23-7.10 (m, 4H), 6.64-6.53 (m, 2H), 5.16 (br s, 1H), 4.56 (d, J=9.6 Hz, 1H), 4.48-4.40 (m, 3H), 4.40-4.32 (m, 2H), 4.28-4.21 (m, 1H), 3.99 (s, 3H), 3.96 (s, 2H), 3.69-3.65 (m, 1H), 3.63-3.58 (m, 3H), 3.57-3.50 (m, 6H), 3.49-3.46 (m, 4H), 3.16 (q, J=5.6 Hz, 2H), 2.45-2.41 (m, 3H), 2.29-2.15 (m, 2H), 2.10-2.02 (m, 1H), 1.97-1.80 (m, 5H), 1.38-1.21 (m, 4H), 0.97-0.89 (m, 9H). LCMS (ESI): m/z 1078.6 (M+H)$^+$.

Example 16

Preparation of N-(3-((S)-19-((2S,4R)-4-Hydroxy-2-((4-(4-methylthiazol-5-yl)benzyl)carbamoyl)pyrrolidine-1-carbonyl)-20,20-dimethyl-2,17-dioxo-6,9,12,15-tetraoxa-3,18-diazahenicosyl)benzyl)-5-methoxy-4-((E)-2-(trans-4-(trifluoromethyl)cyclohexyl)vinyl)picolinamide The general reaction scheme was as follows:

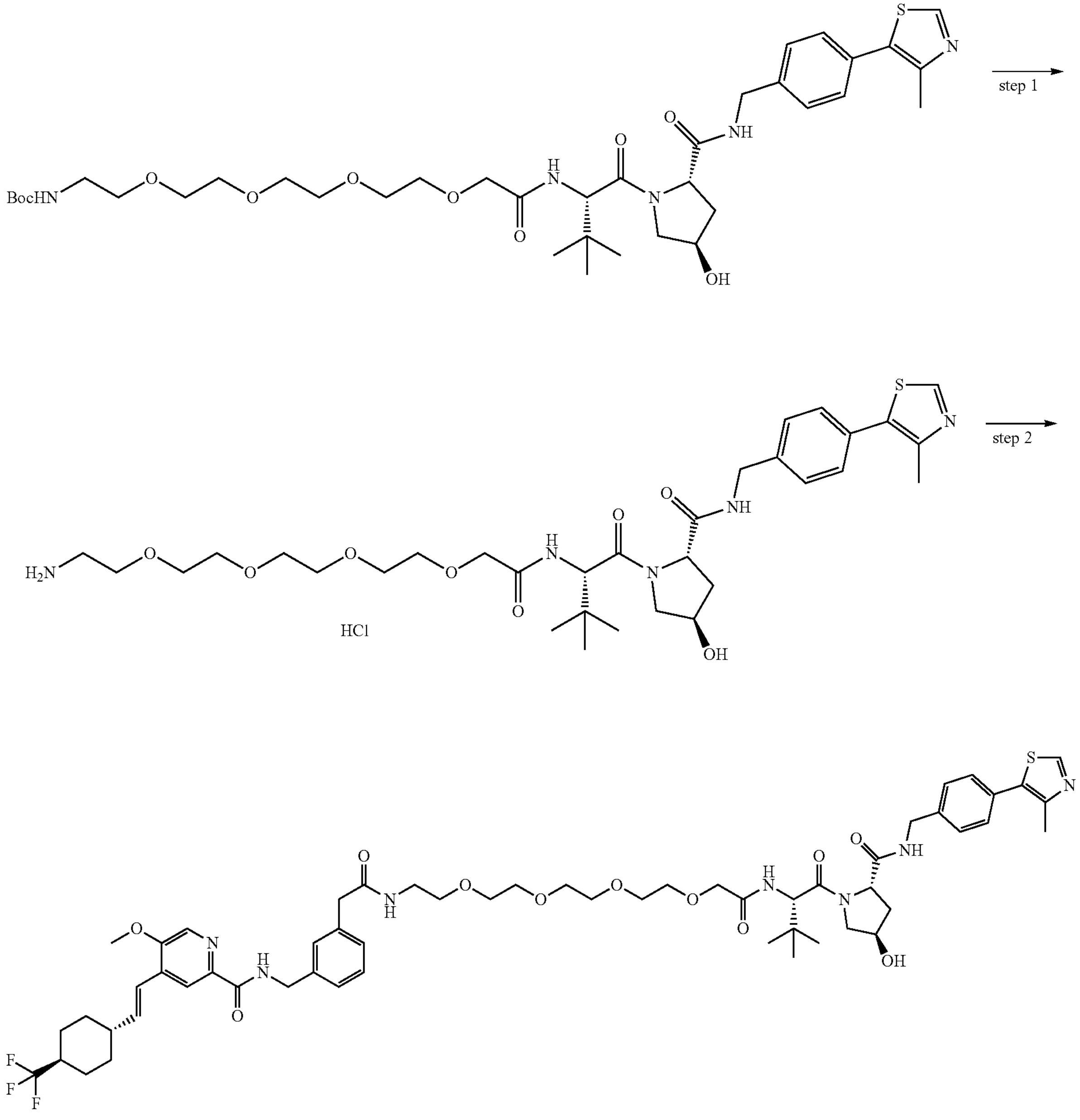

Step 1: (2S,4R)-1-((S)-17-Amino-2-(tert-butyl)-4-oxo-6,9,12,15-tetraoxa-3-azaheptadecan-1-oyl)-4-hydroxy-N-(4-(4-methylthiazol-5-yl)benzyl)pyrrolidine-2-carboxamide hydrochloride

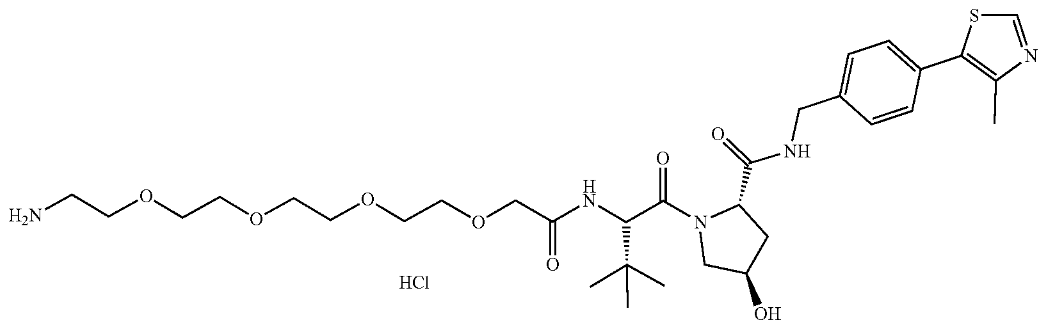

The title compound (300 mg, 99%) was furnished as a yellow solid. It was prepared from tert-butyl ((S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecyl)carbamate (330 mg, 0.43 mmol) following the procedure outlined for Example 11, Step 1. LCMS (ESI): m/z 664.3 $(M+H)^+$.

Step 2: N-(3-((S)-19-((2S,4R)-4-Hydroxy-2-((4-(4-methylthiazol-5-yl)benzyl)carbamoyl)pyrrolidine-1-carbonyl)-20,20-dimethyl-2,17-dioxo-6,9,12,15-tetraoxa-3,18-diazahenicosyl)benzyl)-5-methoxy-4-((E)-2-(trans-4-(trifluoromethyl)cyclohexyl)vinyl)picolinamide

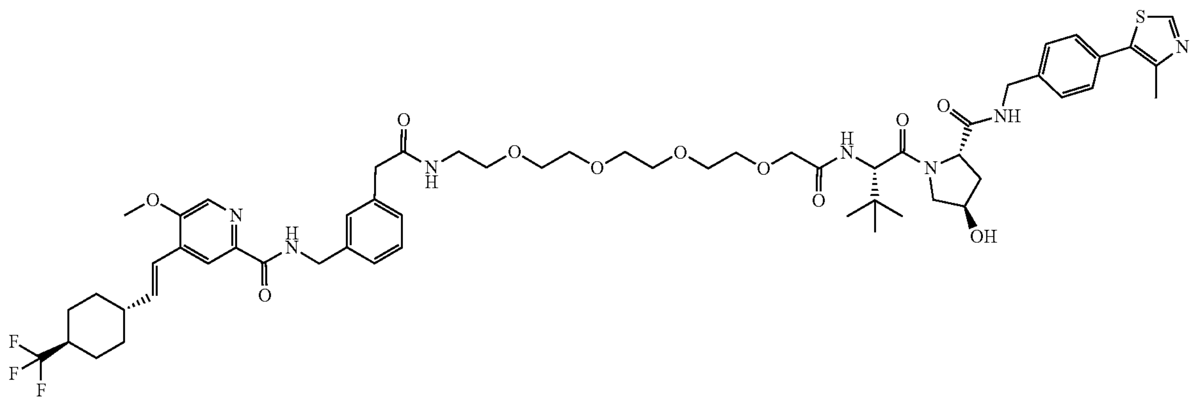 [SMILES: COc1cnc(C(=O)NCc2cccc(CC(=O)NCCOCCOCCOCCOCC(=O)N[C@H](C(=O)N3C[C@H](O)C[C@H]3C(=O)NCc3ccc(-c4scnc4C)cc3)C(C)(C)C)c2)cc1/C=C/[C@H]1CC[C@H](C(F)(F)F)CC1]

The title compound (69 mg, 57%) was furnished as a white solid. It was prepared from (2S,4R)-1-((S)-17-amino-2-(tert-butyl)-4-oxo-6,9,12,15-tetraoxa-3-azaheptadecan-1-oyl)-4-hydroxy-N-(4-(4-methylthiazol-5-yl)benzyl)pyrrolidine-2-carboxamide hydrochloride (88 mg, 0.13 mmol) following the procedure outlined for Example 11, Step 2. It was purified by prep-HPLC (Welch Xtimate C18 150*30 mm*5 um, water (0.235% FA)-ACN, 60-90%). $^1H$ NMR (400 MHz, $CD_3OD$): δ 8.86 (s, 1H), 8.29 (s, 1H), 8.13 (s, 1H), 7.46-7.38 (m, 4H), 7.29-7.18 (m, 4H), 6.70 (d, J=16.0 Hz, 1H), 6.54 (dd, J=16.0, 6.8 Hz, 1H), 4.69 (s, 1H), 4.61-4.55 (m, 5H), 4.50-4.48 (m, 2H), 4.36-4.34 (m, 1H), 4.04-4.00 (m, 4H), 3.91-3.75 (m, 2H), 3.70-3.46 (m, 17H), 2.47 (s, 3H), 2.26-2.20 (m, 1H), 2.09-2.08 (m, 2H), 2.02-1.99 (m, 4H), 1.44-1.27 (m, 5H), 1.01 (s, 9H). LCMS (ESI): m/z 562.1 $(M/2+H)^+$.

Example 17
Preparation of N-(3-((S)-22-((2S,4R)-4-Hydroxy-2-((4-(4-methylthiazol-5-yl)benzyl)carbamoyl)pyrrolidine-1-carbonyl)-23,23-dimethyl-2,20-dioxo-6,9,12,15,18-pentaoxa-3,21-diazatetracosyl)benzyl)-5-methoxy-4-((E)-2-(trans-4-(trifluoromethyl)cyclohexyl)vinyl)picolinamide
The general reaction scheme was as follows:
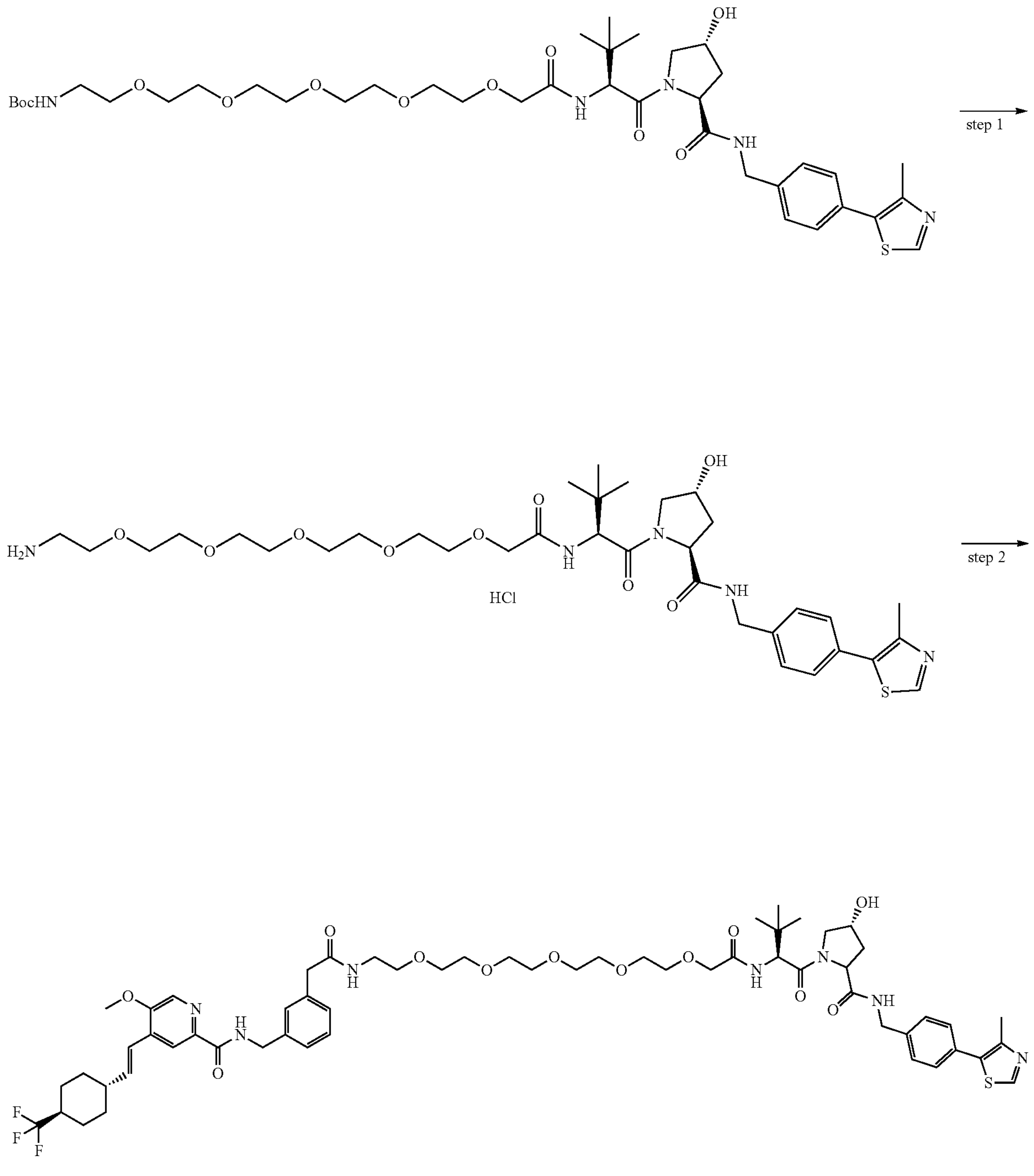

Step 1: (2S,4R)-1-((S)-20-Amino-2-(tert-butyl)-4-oxo-6,9,12,15,18-pentaoxa-3-azaicosan-1-oyl)-4-hydroxy-N-(4-(4-methylthiazol-5-yl)benzyl)pyrrolidine-2-carboxamide hydrochloride

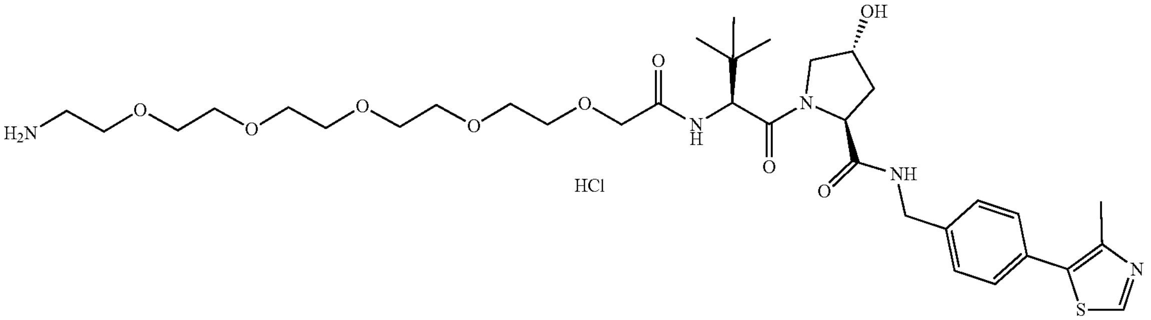 [SMILES: Cc1ncsc1-c1ccc(CNC(=O)[C@@H]2C[C@@H](O)CN2C(=O)[C@@H](NC(=O)COCCOCCOCCOCCOCCN)C(C)(C)C)cc1 ; Cl]

The title compound (270 mg, 98%) was furnished as a yellow solid. It was prepared from tert-butyl ((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosyl)carbamate (300 mg, 0.37 mmol) following the procedure outlined for Example 11, Step 1. LCMS (ESI): m/z 708.4 $(M+H)^+$.

Step 2: N-(3-((S)-22-((2S,4R)-4-Hydroxy-2-((4-(4-methylthiazol-5-yl)benzyl)carbamoyl)pyrrolidine-1-carbonyl)-23,23-dimethyl-2,20-dioxo-6,9,12,15,18-pentaoxa-3,21-diazatetracosyl)benzyl)-5-methoxy-4-((E)-2-(trans-4-(trifluoromethyl)cyclohexyl)vinyl)picolinamide

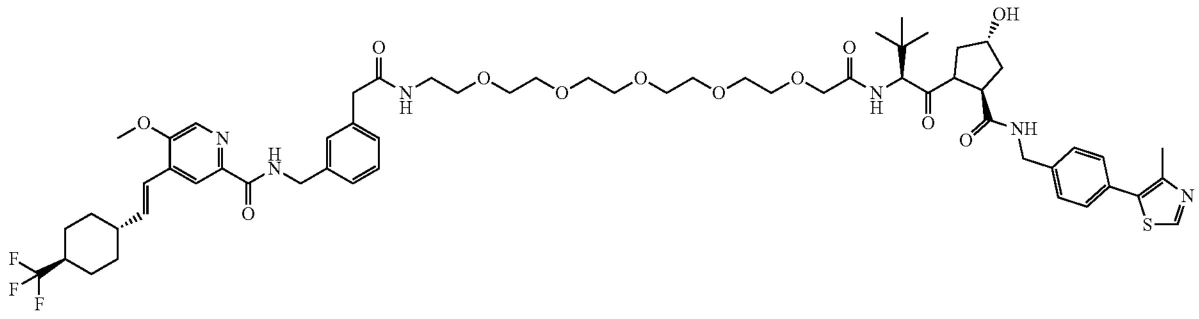

The title compound (37 mg, 22%) was furnished as a white solid. It was prepared from (2S,4R)-1-((S)-20-Amino-2-(tert-butyl)-4-oxo-6,9,12,15,18-pentaoxa-3-azaicosan-1-oyl)-4-hydroxy-N-(4-(4-methylthiazol-5-yl)benzyl)pyrrolidine-2-carboxamide hydrochloride (100 mg, 0.13 mmol) following the procedure outlined for Example 11, Step 2. It was purified by HPLC (Welch Xtimate C18 150*30 mm*5 um, water (0.225% FA)-ACN, 59-79%). $^1$H NMR (400 MHz, $CD_3OD$): δ 8.84 (s, 1H), 8.27 (s, 1H), 8.11 (s, 1H), 7.45-7.37 (m, 4H), 7.29-7.17 (m, 4H), 6.68 (d, J=16.4 Hz, 1H), 6.52 (dd, J=16.4, 7.2 Hz, 1H), 4.67 (s, 1H), 4.56 (s, 1H), 4.48-4.46 (m, 1H), 4.33-4.31 (m, 1H), 4.01-3.98 (m, 4H), 3.87-3.82 (m, 1H), 3.80-3.76 (m, 1H), 3.66-3.62 (m, 4H), 3.60 (s, 2H), 3.55-3.51 (m, 4H), 3.49-3.44 (m, 4H), 3.31-3.28 (m, 12H), 2.46-2.43 (m, 3H), 2.23-2.16 (m, 2H), 2.10-2.05 (m, 1H), 2.03-1.92 (m, 4H), 1.45-1.26 (m, 5H), 1.01 (s, 9H). LCMS (ESI): m/z 584.1 $(M/2+H)^+$.

Example 18
Preparation of N-(3-(17-((5-((S)-1-((S)-2-Cyclohexyl-2-((S)-2-(methylamino)propanamido)acetyl) pyrrolidine-2-carboxamido)-4-phenylthiazol-2-yl) amino)-3-methyl-2,17-dioxo-6,9,12,15-tetraoxa-3-azaheptadecyl)benzyl)-5-methoxy-4-((E)-2-(trans-4-(trifluoromethyl)cyclohexyl)vinyl)picolinamide
The general reaction scheme was as follows:
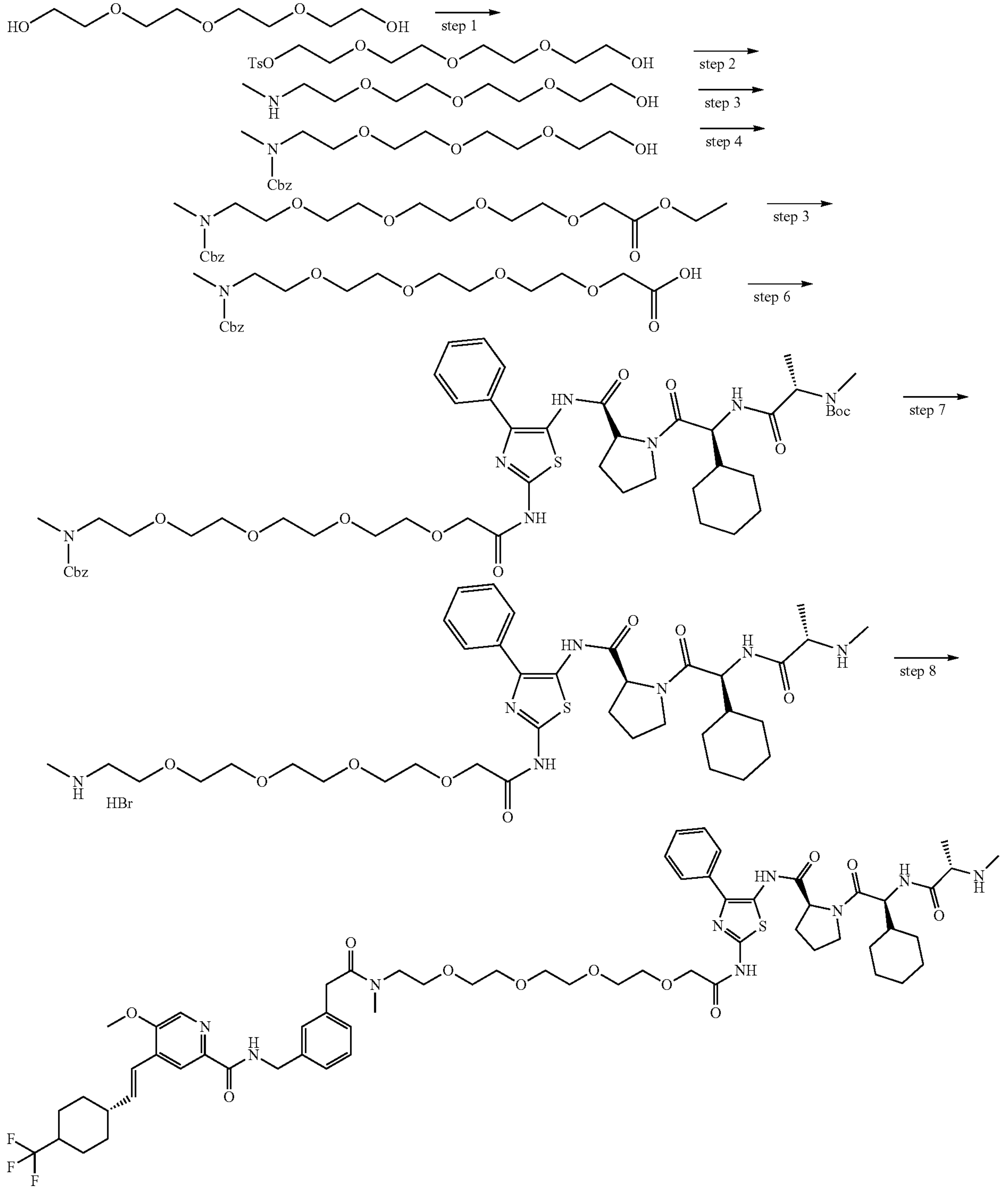

Step 1: 2-(2-(2-(2-Hydroxyethoxy)ethoxy)ethoxy) ethyl 4-methylbenzenesulfonate

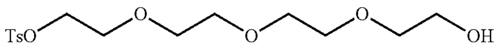 [SMILES: Cc1ccc(S(=O)(=O)OCCOCCOCCOCCO)cc1]

To a solution of 2,2'-((oxybis(ethane-2,1-diyl))bis(oxy)) diethanol (8.0 g, 41.19 mmol) in DCM (40 mL) were added KI (1.71 g, 10.3 mmol) and $Ag_2O$ (11.45 g, 49.43 mmol) at 0° C. Then a solution of TsCl (8.64 g, 45.31 mmol) in DCM (45 mL) was added dropwise at 0° C. The resulting mixture was stirred at room temperature for 16 hours. Then the reaction mixture was filtered, the filtrate was concentrated. The residue was purified by column chromatography on silica gel (0-2% MeOH in DCM) to afford the title compound (5.6 g, 39%) as a colorless oil. $^1$H NMR (400 MHz, $CDCl_3$): δ 7.80 (d, J=8.4 Hz, 2H), 7.35 (d, J=8.4 Hz, 2H), 4.19-4.13 (m, 2H), 3.74-3.56 (m, 14H), 2.45 (s, 3H).

Step 2: 5,8,11-Trioxa-2-azatridecan-13-ol

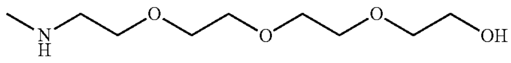

To a solution of 2-(2-(2-(2-hydroxyethoxy)ethoxy) ethoxy)ethyl 4-methylbenzenesulfonate (5.6 g, 16.07 mmol) in EtOH (4 mL) was added 33% $MeNH_2$ in EtOH solution (11.76 mL, 241.1 mmol) dropwise at 0° C. The reaction was stirred at 60° C. for 16 hours. After cooling to room temperature, the reaction mixture was concentrated. The residue was purified by column chromatography on silica gel (0-10% MeOH in DCM) to afford the title compound (3.3 g, quant.) as a colorless oil.

Step 3: Benzyl (2-(2-(2-(2-hydroxyethoxy)ethoxy) ethoxy)ethyl)(methyl)carbamate

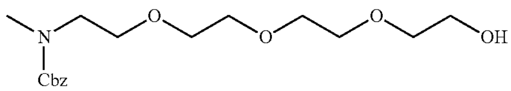 [SMILES: CN(CCOCCOCCOCCO)C(=O)OCc1ccccc1]

To a solution of 5,8,11-trioxa-2-azatridecan-13-ol (3.3 g, 16.07 mmol) in DMF (5 mL) was added Cbz-OSu (8.0 g, 32.15 mmol) and $Et_3N$ (3.36 mL, 24.11 mmol) at room temperature. The resulting mixture was stirred at 40° C. for 2 hours. Then the reaction mixture was diluted with EtOAc (30 mL), washed with brine (50 mL×3), dried over $Na_2SO_4$ and concentrated. The residue was purified by column chromatography on silica gel (0-3% MeOH in DCM) to afford the title compound (4.1 g, 75%) as a yellow oil. $^1$H NMR (400 MHz, $CDCl_3$):

δ 7.39-7.28 (m, 5H), 5.13 (s, 2H), 3.71-3.70 (m, 2H), 3.67-3.56 (m, 12H), 3.48-3.47 (m, 2H), 3.00 (s, 3H).

Step 4: Ethyl 4-methyl-3-oxo-1-phenyl-2,7,10,13, 16-pentaoxa-4-azaoctadecan-18-oate

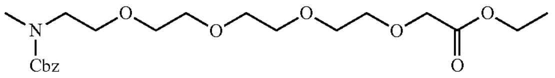 [SMILES: CCOC(=O)COCCOCCOCCOCCN(C)C(=O)OCc1ccccc1]

To a suspension of NaH (60% in mineral oil, 576 mg, 24.02 mmol) in THF (20 mL) was added benzyl N-[2-[2-[2-(2-hydroxyethoxy)ethoxy]ethoxy]ethyl]-N-methyl-carbamate (4.1 g, 12.01 mmol) at 0° C. The reaction mixture was stirred at 0° C. for 30 minutes. Then ethyl 2-bromoacetate (4.08 mL, 36.03 mmol) was added at 0° C. and the resulting mixture was stirred at room temperature for 16 hours. The reaction was then quenched by the dropwise addition of water (1 mL) at 0° C. The reaction mixture was diluted with water (50 mL) and extracted with EtOAc (60 mL×2). The combined organic layer was washed with brine (50 mL×2), dried over $Na_2SO_4$ and concentrated. The residue was purified by column chromatography on silica gel (0-80% EtOAc in petroleum ether) to afford the title compound (3.2 g, 62%) as a yellow oil. $^1$H NMR (400 MHz, $CDCl_3$): δ 7.39-7.27 (m, 5H), 5.13 (s, 2H), 4.21 (q, J=7.2 Hz, 2H), 4.14-4.12 (m, 2H), 3.75-3.67 (m, 4H), 3.66-3.55 (m, 10H), 3.48-3.46 (m, 2H), 3.00 (s, 3H), 1.29-1.26 (m, 3H).

Step 5: 4-Methyl-3-oxo-1-phenyl-2,7,10,13,16-pentaoxa-4-azaoctadecan-18-oic acid

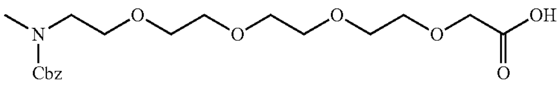 [SMILES: CN(CCOCCOCCOCCOCC(=O)O)C(=O)OCc1ccccc1]

To a solution of ethyl 4-methyl-3-oxo-1-phenyl-2,7,10, 13,16-pentaoxa-4-azaoctadecan-18-oate (3.3 g, 7.75 mmol) in THF (10 mL) and water (10 mL) was added lithium hydroxide monohydrate (929 mg, 22.14 mmol) at room temperature. The resulting mixture was stirred at room temperature for 3 hours. Then the reaction mixture was diluted with EtOAc (30 mL), extracted by water (30 mL×3). The aqueous layer was adjusted pH to 3-4 with 2M HCl, extracted by EtOAc (30 mL×3). The combined organic layer was dried over $Na_2SO_4$ and concentrated to give the title compound (2.8 g, 91%) as a yellow oil. $^1$H NMR (400 MHz, $CDCl_3$): δ 7.38-7.28 (m, 5H), 5.13 (s, 2H), 4.16 (s, 2H), 3.76-3.72 (m, 2H), 3.70-3.58 (m, 12H), 3.49-3.48 (m, 2H), 3.00 (s, 3H).

Step 6: tert-Butyl N-[(1S)-2-[[(1S)-2-[(2S)-2-[[2-[[2-[2-[2-[2-[2-[benzyloxycarbonyl(methyl)amino]ethoxy]ethoxy]ethoxy]ethoxy]acetyl]amino]-4-phenyl-thiazol-5-yl]carbamoyl]pyrrolidin-1-yl]-1-cyclohexyl-2-oxo-ethyl]amino]-1-methyl-2-oxo-ethyl]-N-methyl-carbamate

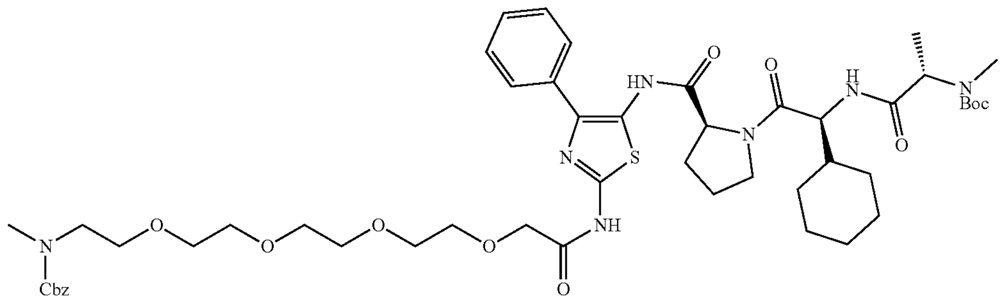

To a mixture of tert-butyl ((S)-1-(((S)-2-((S)-2-((2-amino-4-phenylthiazol-5-yl)carbamoyl)pyrrolidin-1-yl)-1-cyclohexyl-2-oxoethyl)amino)-1-oxopropan-2-yl)(methyl)carbamate (300 mg, 0.49 mmol), 4-methyl-3-oxo-1-phenyl-2,7,10,13,16-pentaoxa-4-azaoctadecan-18-oic acid (293 mg, 0.73 mmol) and DIPEA (316 mg, 2.45 mmol) in DCM (6 mL) was added $T_3P$ (623 mg, 0.98 mmol) at room temperature. Then the reaction mixture was stirred at 40° C. for 1 hour. The reaction was quenched by adding water (10 mL) at 0° C. The layers were separated and the aqueous solution was extracted with DCM (10 mL×2). The combined organic layer was washed with brine (20 mL×2), dried over $Na_2SO_4$ and concentrated. The residue was purified by column chromatography on silica gel (0-100% EtOAc in petroleum ether) to afford the title compound (370 mg, 76%) as a yellow oil. LCMS (ESI): m/z 994.7 $(M+H)^+$.

Step 7: (S)—N-(2-(5,8,11,14-Tetraoxa-2-azahexadecanamido)-4-phenylthiazol-5-yl)-1-((S)-2-cyclohexyl-2-((S)-2-(methylamino)propanamido)acetyl)pyrrolidine-2-carboxamide hydrogen bromide

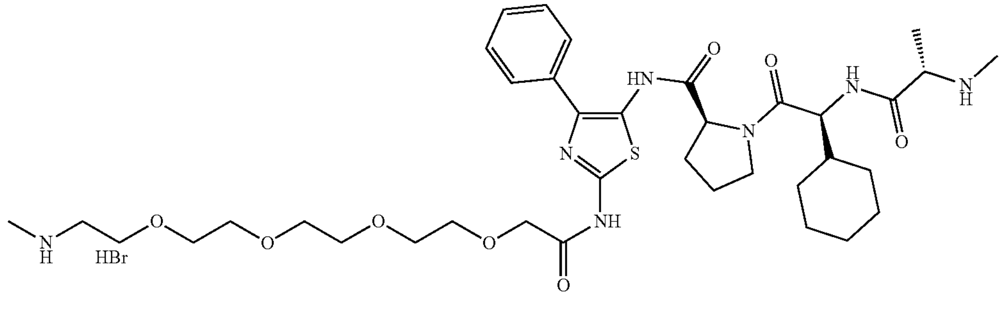

To a a solution of tert-butyl N-[(1S)-2-[[(1S)-2-[(2S)-2-[[2-[[2-[2-[2-[2-[2-[benzyloxycarbonyl(methyl)amino]ethoxy]ethoxy]ethoxy]ethoxy]acetyl]amino]-4-phenyl-thiazol-5-yl]carbamoyl]pyrrolidin-1-yl]-1-cyclohexyl-2-oxo-ethyl]amino]-1-methyl-2-oxo-ethyl]-N-methyl-carbamate (40 mg, 0.04 mmol) in DCM (1 mL) was added 33% HBr in AcOH (0.1 mL). The resulting mixture was stirred at room temperature for 1 hour. Then the reaction mixture was concentrated under reduced pressure to afford the title compound (30.6 mg, 90%) as a light yellow solid. LCMS (ESI): m/z 760.5 $(M+H)^+$.

Step 8: N-(3-(17-((5-((S)-1-((S)-2-Cyclohexyl-2-((S)-2-(methylamino)propanamido)acetyl)pyrrolidine-2-carboxamido)-4-phenylthiazol-2-yl)amino)-3-methyl-2,17-dioxo-6,9,12,15-tetraoxa-3-azaheptadecyl)benzyl)-5-methoxy-4-((E)-2-(trans-4-(trifluoromethyl)cyclohexyl)vinyl)picolinamide

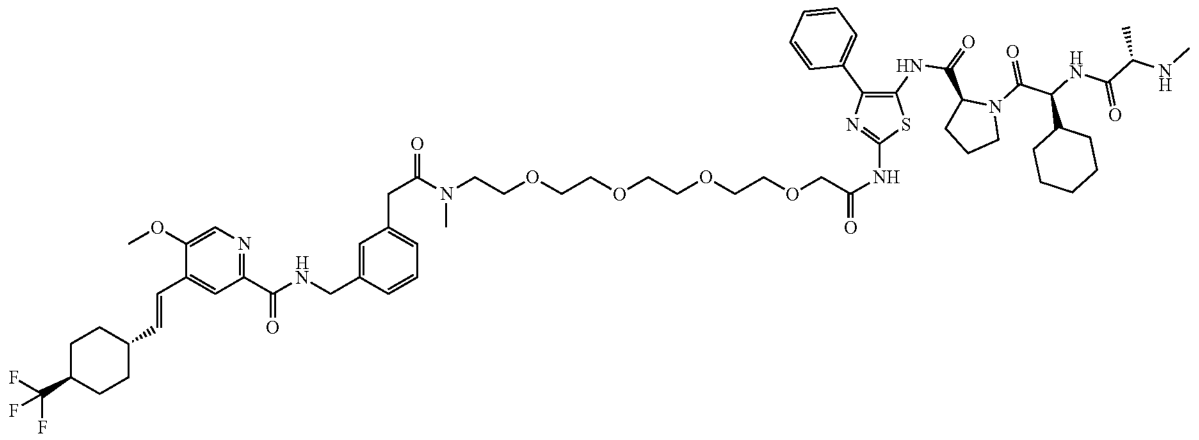 [SMILES: CN[C@@H](C)C(=O)N[C@H](C(=O)N1CCC[C@H]1C(=O)Nc1sc(NC(=O)COCCOCCOCCOCCN(C)C(=O)Cc2cccc(CNC(=O)c3cc(/C=C/[C@H]4CC[C@H](C(F)(F)F)CC4)c(OC)cn3)c2)nc1-c1ccccc1)C1CCCCC1]

To a mixture of (S)—N-(2-(5,8,11,14-tetraoxa-2-azahexadecanamido)-4-phenylthiazol-5-yl)-1-((S)-2-cyclohexyl-2-((S)-2-(methylamino)propanamido)acetyl)pyrrolidine-2-carboxamide hydrogen bromide (30.6 mg, 0.04 mmol), 2-(3-((5-methoxy-4-((E)-2-(trans-4-(trifluoromethyl)cyclohexyl)vinyl)picolinamido)methyl)phenyl)acetic acid (15 mg, 0.03 mmol) and DIPEA (0.03 mL, 0.16 mmol) in DCM (1 mL) was added $T_3P$ (40 mg, 0.06 mmol) at room temperature. The reaction mixture was stirred for 1 hour at 40° C. The reaction was quenched by adding water (4 mL) at 0° C. The layers were separated, the aqueous solution was extracted with DCM (5 mL×3). The combined organic layer was washed with brine (20 mL×2), dried over $Na_2SO_4$ and concentrated. The residue was purified by prep-HPLC (Welch Xtimate C18 150*40 mm*10 um, water (0.2% FA)-ACN, 36-66%) to afford the title compound (11.9 mg, 30%) as a white solid. $^1H$ NMR (400 MHz, $CD_3OD$): δ=8.28 (s, 1H), 8.13 (s, 1H), 7.75 (d, J=7.2 Hz, 2H), 7.42 (t, J=7.6 Hz, 2H), 7.36-7.30 (m, 1H), 7.28-7.18 (m, 3H), 7.12-7.10 (m, 1H), 6.69 (d, J=16.0 Hz, 1H), 6.53 (dd, J=16.0, 6.8 Hz, 1H), 4.52-4.50 (m, 1H), 4.22 (d, J=14.0 Hz, 2H), 4.00 (s, 3H), 3.95-3.94 (m, 1H), 3.79 (s, 1H), 3.77-3.62 (m, 10H), 3.56-3.44 (m, 10H), 3.02, 2.90 (s, 3H total), 2.48 (s, 3H), 2.31-1.89 (m, 11H), 1.86-1.62 (m, 6H), 1.44-1.02 (m, 13H). LCMS (ESI): m/z 610.4 $(M/2+H)^+$.

Example 19

Preparation of N-(3-(20-((5-((S)-1-((S)-2-Cyclohexyl-2-((S)-2-(methylamino)propanamido)acetyl)pyrrolidine-2-carboxamido)-4-phenylthiazol-2-yl)amino)-3-methyl-2,20-dioxo-6,9,12,15,18-pentaoxa-3-azaicosyl)benzyl)-5-methoxy-4-((E)-2-(trans-4-(trifluoromethyl)cyclohexyl)vinyl)picolinamide The general reaction scheme was as follows:

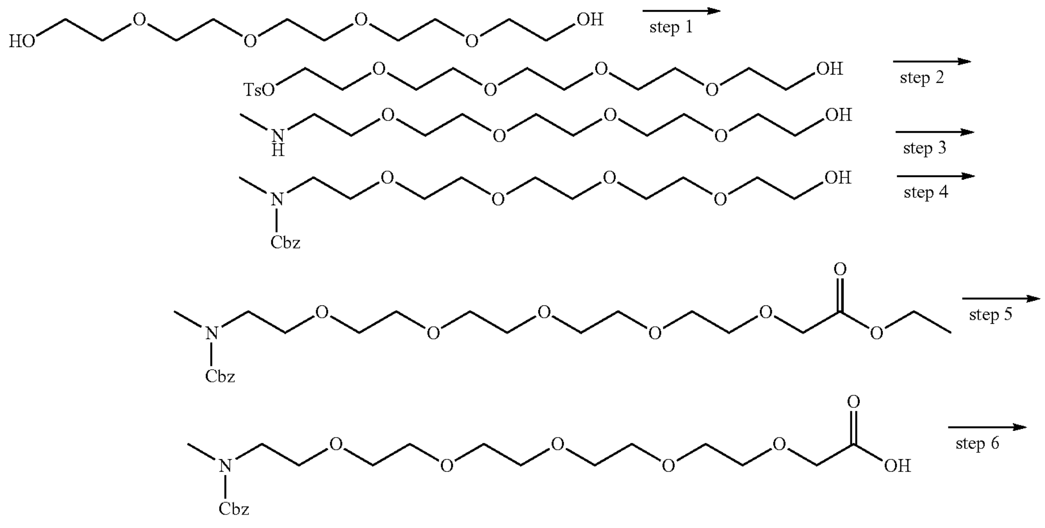

-continued

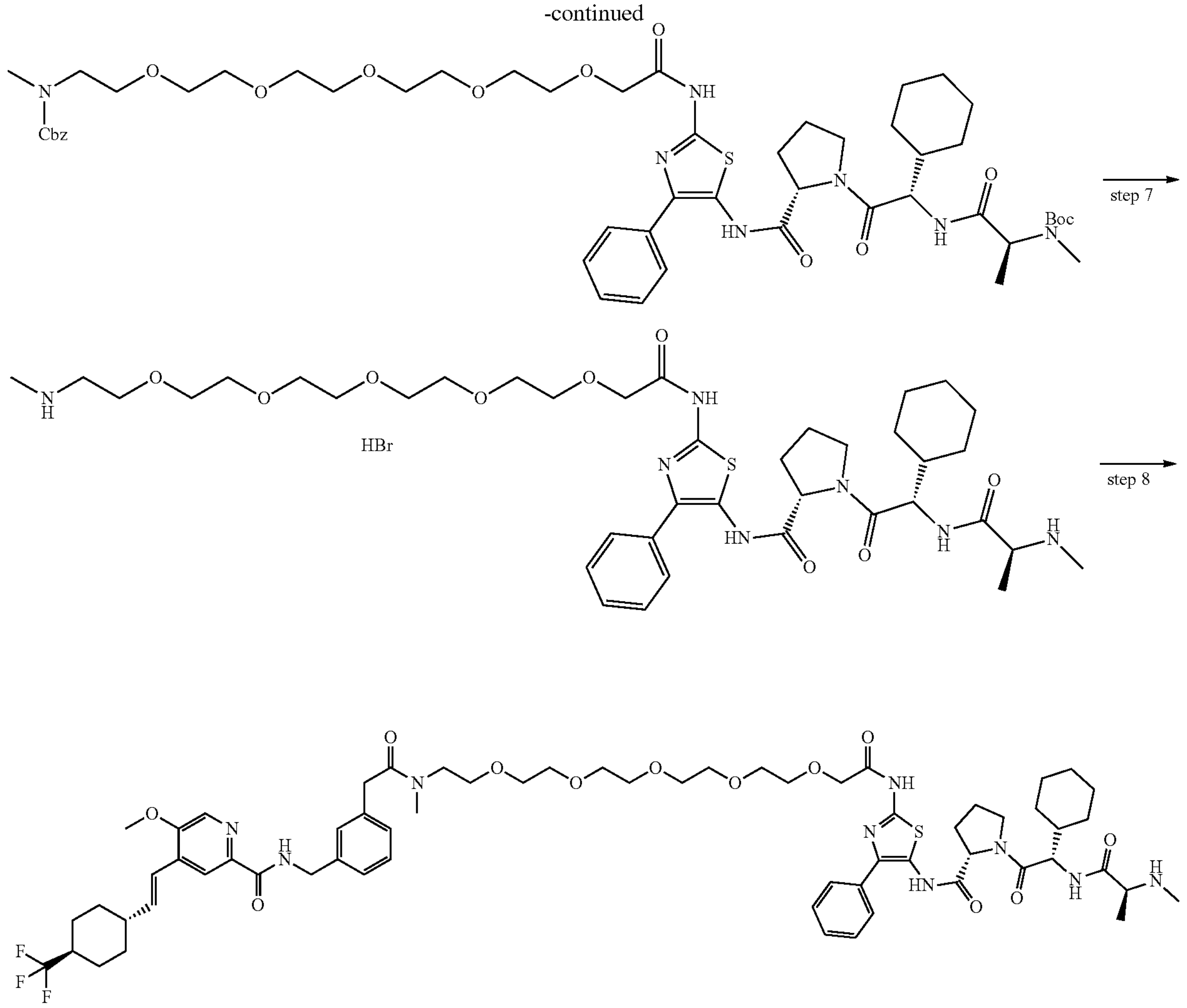

Step 1: 14-Hydroxy-3,6,9,12-tetraoxatetradecyl 4-methylbenzenesulfonate

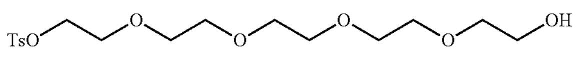 [SMILES: Cc1ccc(S(=O)(=O)OCCOCCOCCOCCOCCO)cc1]

The title compound (3.06 g, 37%) was furnished as a colorless oil. It was prepared from 3,6,9,12-tetraoxatetradecane-1,14-diol (5.0 g, 20.98 mmol) following the procedure outlined for Example 18, Step 1. LCMS (ESI): m/z 393.2 $(M+H)^+$.

Step 2: 5,8,11,14-Tetraoxa-2-azahexadecan-16-ol

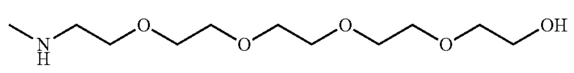 [SMILES: CNCCOCCOCCOCCOCCO]

The title compound (1.96 g, 100%) was furnished as a colorless oil. It was prepared from 14-hydroxy-3,6,9,12-tetraoxatetradecyl 4-methylbenzenesulfonate (3.06 g, 7.8 mmol) following the procedure outlined for Example 18, Step 2.

Step 3: Benzyl (14-hydroxy-3,6,9,12-tetraoxatetradecyl)(methyl)carbamate

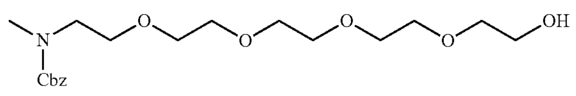 [SMILES: CN(CCOCCOCCOCCOCCO)C(=O)OCc1ccccc1]

The title compound (1.12 g, 37%) was furnished as a colorless oil. It was prepared from 5,8,11,14-tetraoxa-2-azahexadecan-16-ol (1.96 g, 7.8 mmol) following the procedure outlined for Example 18, Step 3. $^1H$ NMR (400 MHz, $CDCl_3$): δ 7.39-7.28 (m, 5H), 5.13 (s, 2H), 3.75-3.70 (m, 2H), 3.68-3.56 (m, 16H), 3.48 (br s, 2H), 3.00 (s, 3H). LCMS (ESI): m/z 386.2 $(M+H)^+$.

Step 4: Ethyl 4-methyl-3-oxo-1-phenyl-2,7,10,13,16,19-hexaoxa-4-azahenicosan-21-oate

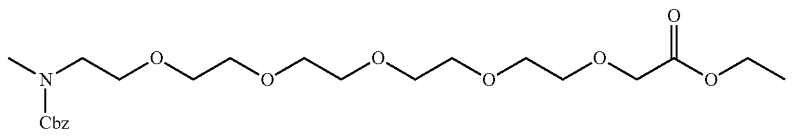 [SMILES: CCOC(=O)COCCOCCOCCOCCOCCN(C)C(=O)OCc1ccccc1]

The title compound (1.06 g, 77%) was furnished as a yellow oil. It was prepared from benzyl (14-hydroxy-3,6,9,12-tetraoxatetradecyl)(methyl)carbamate (1.12 g, 2.91 mmol) following the procedure outlined for Example 18, Step 4. $^1H$ NMR (400 MHz, $CDCl_3$): δ 7.39-7.27 (m, 5H), 5.12 (s, 2H), 4.21 (q, J=7.2 Hz, 2H), 4.16-4.11 (m, 2H), 3.74-3.67 (m, 4H), 3.66-3.56 (m, 14H), 3.51-3.43 (m, 2H), 3.00 (s, 3H), 1.28 (t, J=7.2 Hz, 3H).

Step 5: 4-Methyl-3-oxo-1-phenyl-2,7,10,13,16,19-hexaoxa-4-azahenicosan-21-oic acid

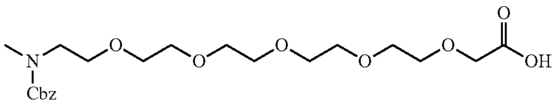 [SMILES: CN(CCOCCOCCOCCOCCOCC(=O)O)C(=O)OCc1ccccc1]

The title compound (850 mg, 85%) was furnished as a yellow oil. It was prepared from ethyl 4-methyl-3-oxo-1-phenyl-2,7,10,13,16,19-hexaoxa-4-azahenicosan-21-oate (1.06 g, 2.25 mmol) following the procedure outlined for Example 18, Step 5. LCMS (ESI): m/z 444.3 $(M+H)^+$.

Step 6: tert-Butyl N-[(1S)-2-[[(1S)-2-[(2S)-2-[[2-[[2-[2-[2-[2-[2-[2-[Benzyloxycarbonyl(methyl)amino]ethoxy]ethoxy]ethoxy]ethoxy]ethoxy]acetyl]amino]-4-phenyl-thiazol-5-yl]carbamoyl]pyrrolidin-1-yl]-1-cyclohexyl-2-oxo-ethyl]amino]-1-methyl-2-oxo-ethyl]-N-methyl-carbamate

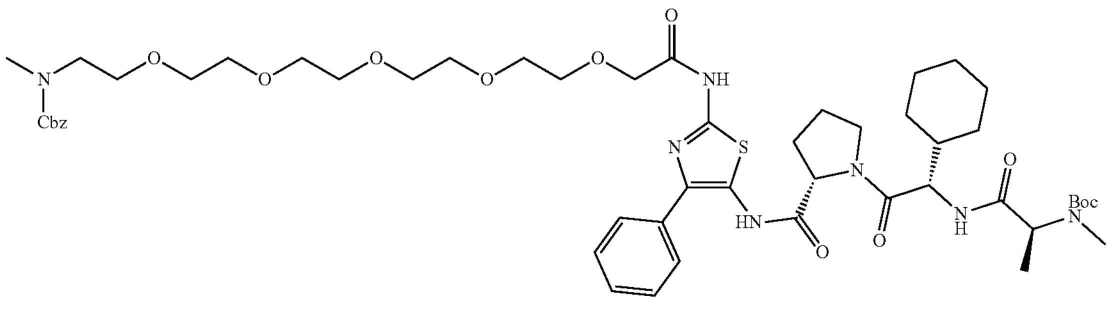

The title compound (340 mg, 67%) was furnished as a yellow oil. It was prepared from 4-methyl-3-oxo-1-phenyl-2,7,10,13,16,19-hexaoxa-4-azahenicosan-21-oic acid (282 mg, 0.64 mmol) following the procedure outlined for Example 18, Step 6. LCMS (ESI): m/z 1038.7 $(M+H)^+$.

Step 7: (S)—N-(2-(5,8,11,14,17-Pentaoxa-2-azanonadecanamido)-4-phenylthiazol-5-yl)-1-((S)-2-cyclohexyl-2-((S)-2-(methylamino)propanamido)acetyl)pyrrolidine-2-carboxamide hydrobromide

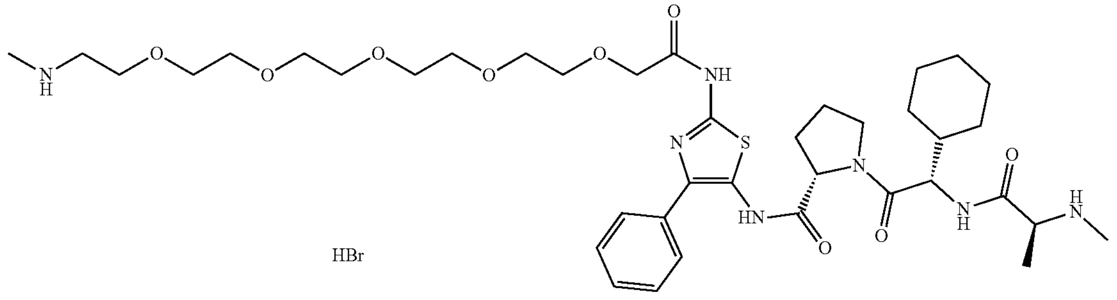

HBr

The title compound (68 mg, quant.) was furnished as a yellow oil. It was prepared from tert-butyl N-[(1S)-2-[[(1S)-2-[(2S)-2-[[2-[[2-[2-[2-[2-[2-[2-[benzyloxycarbonyl (methyl)amino]ethoxy]ethoxy]ethoxy]ethoxy]ethoxy] acetyl]amino]-4-phenyl-thiazol-5-yl]carbamoyl]pyrrolidin-1-yl]-1-cyclohexyl-2-oxo-ethyl]amino]-1-methyl-2-oxo-ethyl]-N-methyl-carbamate (80 mg, 0.08 mmol) following the procedure outlined for Example 18, Step 7. LCMS (ESI): m/z 804.6 $(M+H)^+$.

Step 8: N-(3-(20-((5-((S)-1-((S)-2-Cyclohexyl-2-((S)-2-(methylamino)propanamido)acetyl)pyrrolidine-2-carboxamido)-4-phenylthiazol-2-yl)amino)-3-methyl-2,20-dioxo-6,9,12,15,18-pentaoxa-3-azaicosyl)benzyl)-5-methoxy-4-((E)-2-(trans-4-(trifluoromethyl)cyclohexyl)vinyl)picolinamide

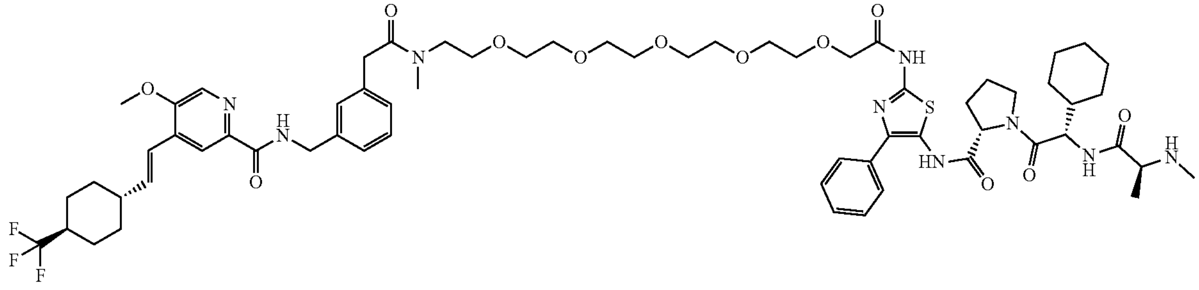 [SMILES: CN[C@@H](C)C(=O)N[C@H](C(=O)N1CCC[C@H]1C(=O)Nc1sc(NC(=O)COCCOCCOCCOCCOCCN(C)C(=O)Cc2cccc(CNC(=O)c3cc(/C=C/[C@H]4CC[C@H](C(F)(F)F)CC4)c(OC)cn3)c2)nc1-c1ccccc1)C1CCCCC1]

The title compound (17.4 mg, 21%) was furnished as a white solid. It was prepared from (S)—N-(2-(5,8,11,14,17-pentaoxa-2-azanonadecanamido)-4-phenylthiazol-5-yl)-1-((S)-2-cyclohexyl-2-((S)-2-(methylamino)propanamido) acetyl)pyrrolidine-2-carboxamide hydrobromide (68 mg, 0.08 mmol) following the procedure outlined for Example 18, Step 8. It was purified by prep-HPLC (Welch Xtimate C18 150*25 mm*5 um, water (0.2% FA)-ACN, 36-66%). $^1H$ NMR (400 MHz, $CD_3OD$): δ 8.28 (s, 1H), 8.13 (s, 1H), 7.76-7.74 (m, 2H), 7.42 (t, J=6.8 Hz, 2H), 7.36-7.30 (m, 1H), 7.29-7.20 (m, 3H), 7.12 (t, J=6.8 Hz, 1H), 6.69 (d, J=16.0 Hz, 1H), 6.53 (dd, J=16.0, 6.8 Hz, 1H), 4.52-4.43 (m, 1H), 4.23 (d, J=4.8 Hz, 2H), 4.00 (s, 3H), 3.95-3.94 (m, 1H), 3.81 (s, 1H), 3.76-3.64 (m, 10H), 3.57-3.51 (m, 13H), 3.48-3.47 (m, 1H), 3.04, 2.91 (s, 3H total), 2.44 (s, 3H), 2.29-1.89 (m, 11H), 1.87-1.60 (m, 6H), 1.47-1.00 (m, 13H). LCMS (ESI): m/z 632.1 $(M/2+H)^+$.

Example 20
Preparation of N-(3-(23-((5-((S)-1-((S)-2-Cyclohexyl-2-((S)-2-(methylamino)propanamido)acetyl)pyrrolidine-2-carboxamido)-4-phenylthiazol-2-yl)amino)-3-methyl-2,23-dioxo-6,9,12,15,18,21-hexaoxa-3-azatricosyl)benzyl)-5-methoxy-4-((E)-2-(trans-4-(trifluoromethyl)cyclohexyl)vinyl)picolinamide formate
The general reaction scheme was as follows:
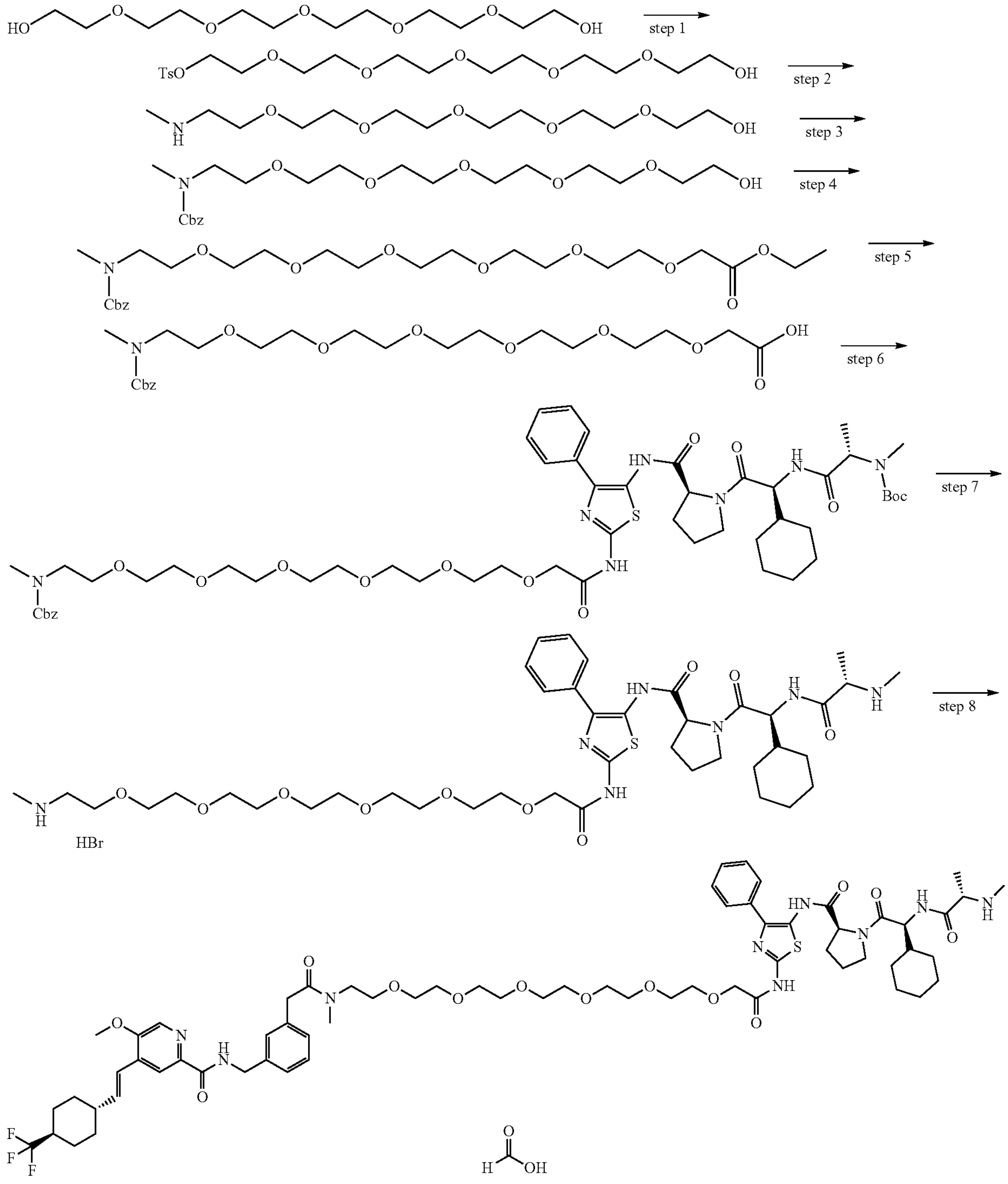

Step 1: 17-Hydroxy-3,6,9,12,15-pentaoxaheptadecyl 4-methylbenzenesulfonate

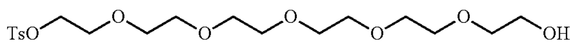 [SMILES: Cc1ccc(S(=O)(=O)OCCOCCOCCOCCOCCOCCO)cc1]

The title compound (5.0 g, 32%) was furnished as a colorless oil. It was prepared from 3,6,9,12,15-pentaoxaheptadecane-1,17-diol (10.0 g, 35.42 mmol) following the procedure outlined for Example 18, Step 1. LCMS (ESI): m/z 437.3 $(M+H)^+$.

Step 2: 5,8,11,14,17-Pentaoxa-2-azanonadecan-19-ol

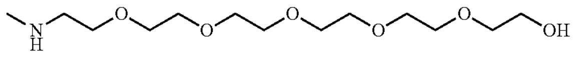 [SMILES: CNCCOCCOCCOCCOCCOCCO]

The title compound (2.9 g, quant.) was furnished as a colorless oil. It was prepared from 17-hydroxy-3,6,9,12,15-pentaoxaheptadecyl 4-methylbenzenesulfonate (4.4 g, 10.08 mmol) following the procedure outlined for Example 18, Step 2. LCMS (ESI): m/z 296.1 $(M+H)^+$.

Step 3: Benzyl (17-hydroxy-3,6,9,12,15-pentaoxaheptadecyl)(methyl)carbamate

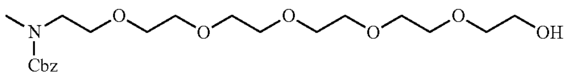 [SMILES: CN(CCOCCOCCOCCOCCOCCO)C(=O)OCc1ccccc1]

The title compound (1.2 g, 58%) was furnished as a colorless oil. It was prepared from 5,8,11,14,17-pentaoxa-2-azanonadecan-19-ol (1.0 g, 4.82 mmol) following the procedure outlined for Example 18, Step 3. $^1$H NMR (400 MHz, $CDCl_3$): δ 7.35-7.29 (m, 5H), 5.12 (s, 2H), 3.71-3.70 (m, 2H), 3.68-3.57 (m, 20H), 3.47-3.46 (m, 2H), 3.00 (s, 3H).

Step 4: Ethyl 4-methyl-3-oxo-1-phenyl-2,7,10,13,16,19,22-heptaoxa-4-azatetracosan-24-oate

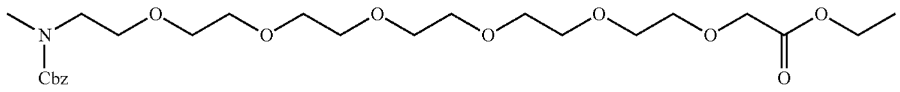 [SMILES: CCOC(=O)COCCOCCOCCOCCOCCOCCN(C)C(=O)OCc1ccccc1]

The title compound (400 mg, 28%) was furnished as a yellow oil. It was prepared from benzyl (17-hydroxy-3,6,9,12,15-pentaoxaheptadecyl)(methyl)carbamate (1.2 g, 2.79 mmol) following the procedure outlined for Example 18, Step 4. $^1$H NMR (400 MHz, $CDCl_3$): δ 7.38-7.29 (m, 5H), 5.13 (s, 2H), 4.22 (q, J=7.2 Hz, 2H), 4.15 (s, 2H), 3.78-3.72 (m, 2H), 3.71-3.68 (m, 2H), 3.67-3.61 (m, 16H), 3.48-3.47 (m, 2H), 3.00 (s, 3H), 1.72 (s, 2H), 1.29 (t, J=7.2 Hz, 3H).

Step 5: 4-Methyl-3-oxo-1-phenyl-2,7,10,13,16,19,22-heptaoxa-4-azatetracosan-24-oic acid

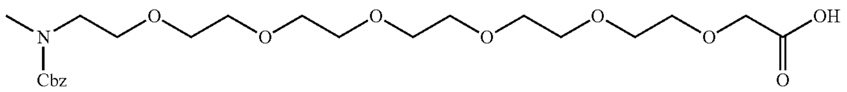 [SMILES: CN(CCOCCOCCOCCOCCOCCOCC(=O)O)C(=O)OCc1ccccc1]

The title compound (378 mg, quant.) was furnished as a yellow oil. It was prepared from ethyl 4-methyl-3-oxo-1-phenyl-2,7,10,13,16,19,22-heptaoxa-4-azatetracosan-24-oate (400 mg, 0.780 mmol) following the procedure outlined for Example 18, Step 5. LCMS (ESI): m/z 488.3 $(M+H)^+$.

Step 6: tert-Butyl N-[(1S)-2-[[(1S)-2-[(2S)-2-[[2-[[2-[2-[2-[2-[2-[2-[2-[benzyloxycarbonyl(methyl)amino]ethoxy]ethoxy]ethoxy]ethoxy]ethoxy]ethoxy]acetyl]amino]-4-phenyl-thiazol-5-yl]carbamoyl]pyrrolidin-1-yl]-1-cyclohexyl-2-oxo-ethyl]amino]-1-methyl-2-oxo-ethyl]-N-methyl-carbamate

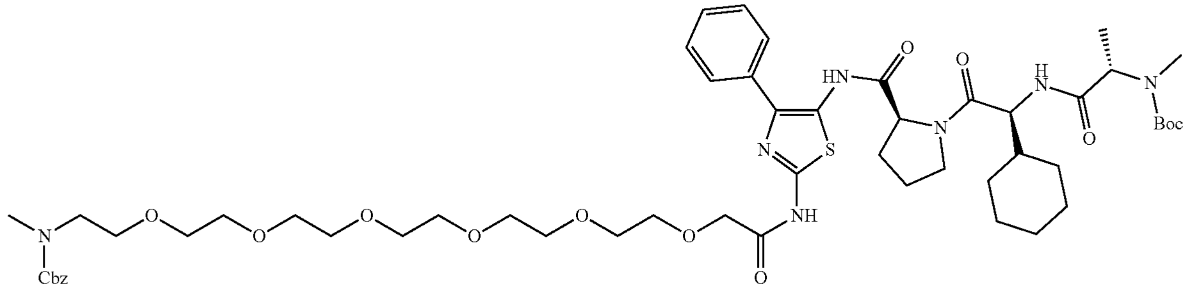

The title compound (205 mg, 39%) was furnished as a yellow oil. It was prepared from 4-methyl-3-oxo-1-phenyl-2,7,10,13,16,19,22-heptaoxa-4-azatetracosan-24-oic acid (358 mg, 0.73 mmol) following the procedure outlined for Example 18, Step 6. LCMS (ESI): m/z 1082.7 (M+H)+.

Example 21

Preparation of N-(3-(2-((4-((5-((S)-1-((S)-2-Cyclohexyl-2-((S)-2-(methylamino)propanamido)acetyl)pyrrolidine-2-carboxamido)-4-phenylthiazol-2-yl)amino)-4-oxobutyl)(methyl)amino)-2-oxoethyl)benzyl)-5-methoxy-4-((E)-2-(trans-4-(trifluoromethyl)cyclohexyl)vinyl)picolinamide The general reaction scheme was as follows:

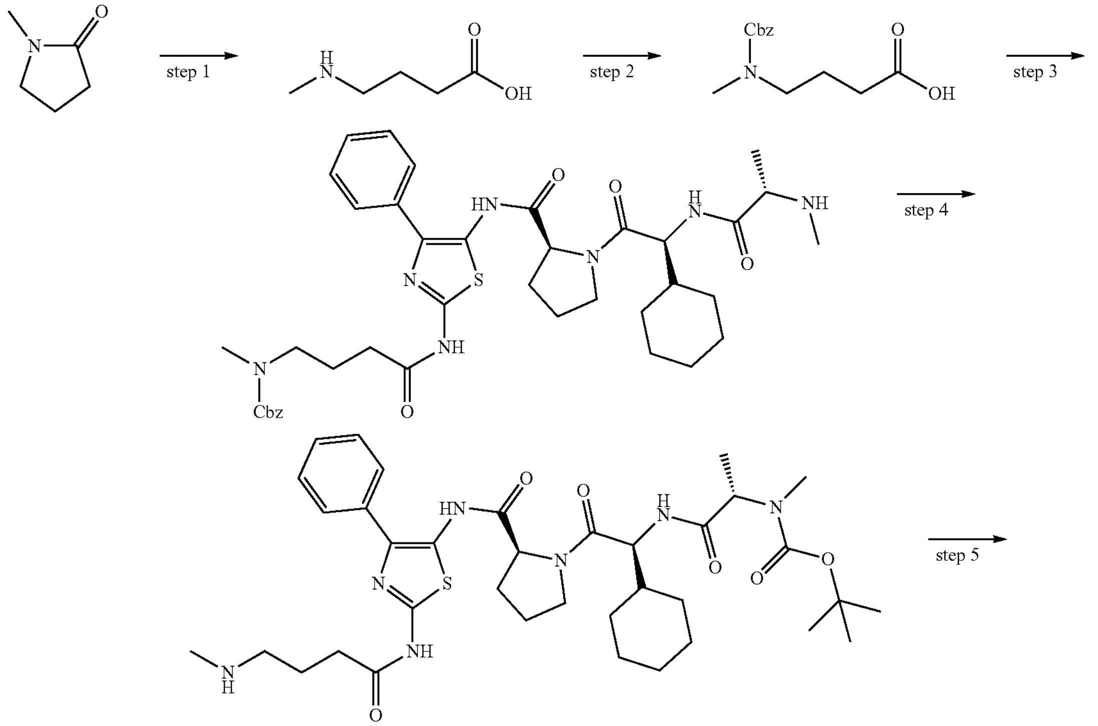

-continued

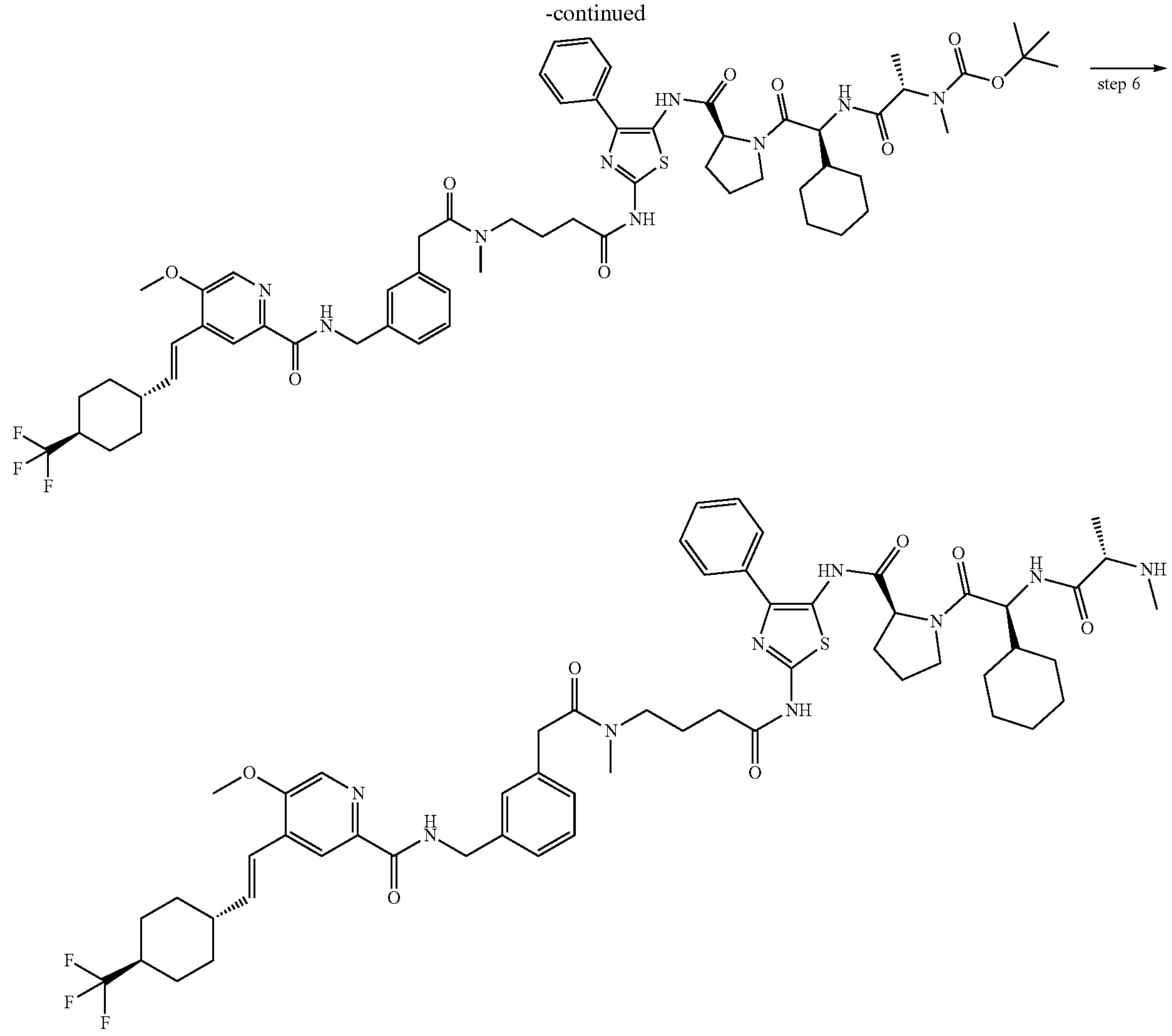

Step 1: 4-(Methylamino)butanoic acid

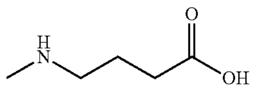

To a solution of 1-methyl-2-pyrrolidinone (2.0 g, 20.18 mmol) in $H_2O$ (22 mL) was added barium hydroxide octahydrate (3.89 mg, 12.32 mmol) at room temperature. The heterogenous mixture was heated at 110° C. for 3 hours and then cooled to 0° C. and saturated with $CO_2$ gas. The resulting white precipitate was collected by filtration and washed with ice-cold water. The clear filtrates were evaporated to dryness to afford the title compound (1.01 g, 43%) as a white solid. $^1$H NMR (400 MHz, DMSO-$d_6$): δ 2.77-2.68 (m, 2H), 2.39 (s, 3H), 2.22-2.14 (m, 2H), 2.08 (s, 1H), 1.65-1.59 (m, 2H).

Step 2: 4-(((Benzyloxy)carbonyl)(methyl)amino)butanoic acid

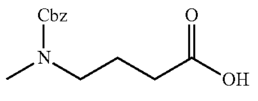 [SMILES: CN(CCCC(=O)O)C(=O)OCc1ccccc1]

To a solution of 4-(methylamino)butanoic acid (200 mg, 1.71 mmol) in DMF (5 mL) was added $Et_3N$ (259 mg, 2.56 mmol) and N-(Benzyloxycarbonyloxy)succinimide (511 mg, 2.05 mmol) at room temperature. The reaction mixture was stirred for 16 hours at room temperature. After that, EtOAc (40 mL) was added. The organic layer was washed with water (40 mL×2), dried over anhydrous $Na_2SO_4$, filtered and concentrated. The residue was purified by column chromatography on silica gel (0-10% MeOH in DCM) to afford the title compound (300 mg, 70%) as a colorless oil. LCMS (ESI): m/z 252.1 (M+H)$^+$.

Step 3: tert-Butyl N-[(1S)-2-[[(1S)-2-[(2S)-2-[[2-[4-[benzyloxycarbonyl(methyl)amino]butanoylamino]-4-phenyl-thiazol-5-yl]carbamoyl]pyrrolidin-1-yl]-1-cyclohexyl-2-oxo-ethyl]amino]-1-methyl-2-oxo-ethyl]-N-methyl-carbamate

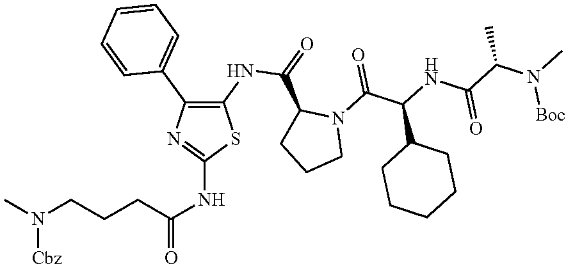

The title compound (500 mg, 37%) was furnished as a white solid. It was prepared from 4-(((Benzyloxy)carbonyl)(methyl)amino)butanoic acid (400 mg, 1.59 mmol) following the procedure outlined for Example 18, Step 6. LCMS (ESI): m/z 846.4 (M+H)+.

Step 4: tert-Butyl((S)-1-(((S)-1-cyclohexyl-2-((S)-2-((2-(4-(Methylamino)butanamido)-4-phenylthiazol-5-yl)carbamoyl)pyrrolidin-1-yl)-2-oxoethyl)amino)-1-oxopropan-2-yl)(methyl)carbamate

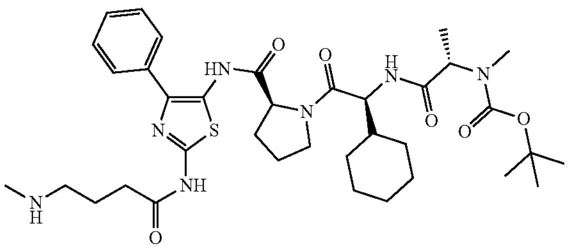 [SMILES: CNCCCC(=O)Nc1nc(-c2ccccc2)c(NC(=O)[C@@H]2CCCN2C(=O)[C@@H](NC(=O)[C@H](C)N(C)C(=O)OC(C)(C)C)C2CCCCC2)s1]

To a solution of tert-butyl N-[(1S)-2-[[(1S)-2-[(2S)-2-[[2-[4-[benzyloxycarbonyl(methyl)amino]butanoylamino]-4-phenyl-thiazol-5-yl]carbamoyl]pyrrolidin-1-yl]-1-cyclohexyl-2-oxo-ethyl]amino]-1-methyl-2-oxo-ethyl]-N-methyl-carbamate (119 mg, 0.14 mmol) in MeOH (5 mL) was added 10% Pd/C (75 mg, 0.07 mmol) at room temperature. The reaction mixture was stirred at room temperature under hydrogen atmosphere (15 psi) for 16 hours. Then the reaction mixture was filtered, the filtrate was concentrated. The residue was purified by prep-TLC (10% MeOH in DCM) to afford the title compound (30 mg, 30%) as a white solid. LCMS (ESI): m/z 712.4 (M+H)+.

Step 5: tert-Butyl((S)-1-(((S)-1-cyclohexyl-2-((S)-2-((2-(4-(2-(3-((5-Methoxy-4-((E)-2-(trans-4-(trifluoromethyl)cyclohexyl)vinyl)picolinamido)methyl)phenyl)-N-methylacetamido)butanamido)-4-phenylthiazol-5-yl)carbamoyl)pyrrolidin-1-yl)-2-oxoethyl)amino)-1-oxopropan-2-yl)(methyl)carbamate

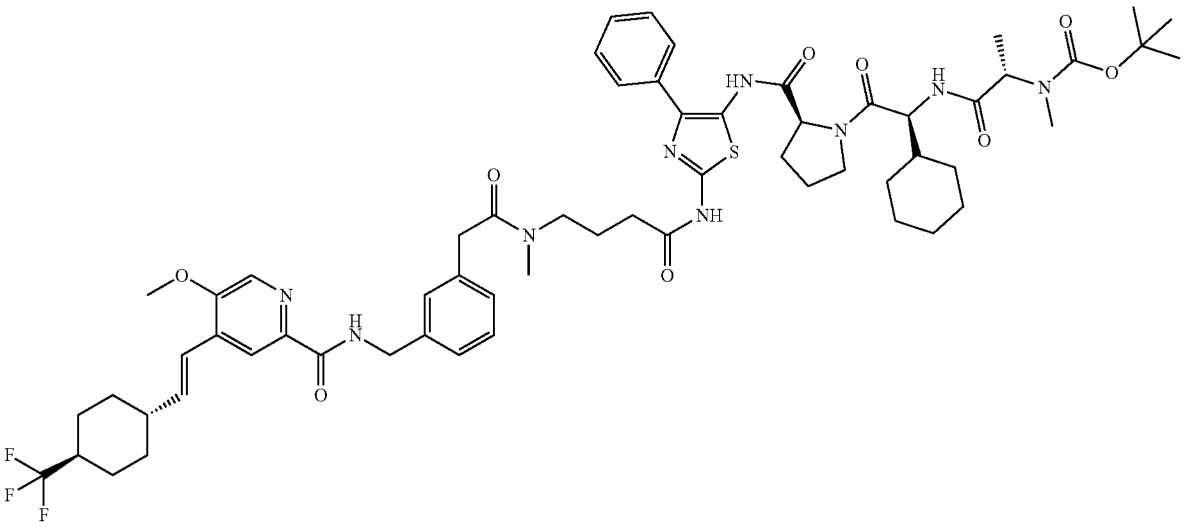 [SMILES: COc1cnc(C(=O)NCc2cccc(CC(=O)N(C)CCCC(=O)Nc3nc(-c4ccccc4)c(NC(=O)[C@@H]4CCCN4C(=O)[C@@H](NC(=O)[C@H](C)N(C)C(=O)OC(C)(C)C)C4CCCCC4)s3)c2)cc1/C=C/[C@H]1CC[C@H](C(F)(F)F)CC1]

To a mixture of tert-butyl((S)-1-(((S)-1-cyclohexyl-2-((S)-2-((2-(4-(Methylamino)butanamido)-4-phenylthiazol-5-yl)carbamoyl)pyrrolidin-1-yl)-2-oxoethyl)amino)-1-oxopropan-2-yl)(methyl)carbamate (24.6 mg, 0.03 mmol), 2-(3-((5-methoxy-4-((E)-2-(trans-4-(trifluoromethyl)cyclohexyl)vinyl)picolinamido)methyl)phenyl)acetic acid (15 mg, 0.03 mmol) and DIPEA (0.02 mL, 0.09 mmol) in DCM (2 mL) was added $T_3P$ (40 mg, 0.06 mmol). The resulting mixture was stirred at 40° C. for 1 hour. Then the reaction mixture was concentrated. The residue was purified by prep-TLC (10% MeOH in DCM) to afford the title compound (20 mg, 54%) as a white solid. LCMS (ESI): m/z 1170.7 $(M+H)^+$.

Step 6: N-(3-(2-((4-((5-((S)-1-((S)-2-Cyclohexyl-2-((S)-2-(methylamino)propanamido)acetyl)pyrrolidine-2-carboxamido)-4-phenylthiazol-2-yl)amino)-4-oxobutyl)(methyl)amino)-2-oxoethyl)benzyl)-5-methoxy-4-((E)-2-(trans-4-(trifluoromethyl)cyclohexyl)vinyl)picolinamide

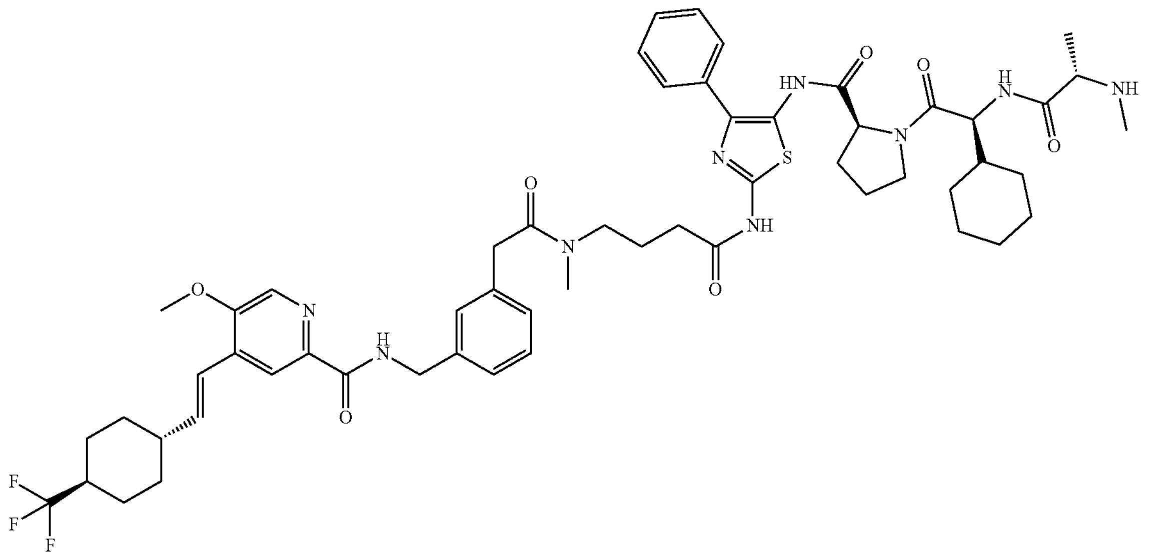 [SMILES: CN[C@@H](C)C(=O)N[C@H](C(=O)N1CCC[C@H]1C(=O)Nc1sc(NC(=O)CCCN(C)C(=O)Cc2cccc(CNC(=O)c3cc(/C=C/[C@H]4CC[C@H](C(F)(F)F)CC4)c(OC)cn3)c2)nc1-c1ccccc1)C1CCCCC1]

To a stirred solution of tert-butyl((S)-1-(((S)-1-cyclohexyl-2-((S)-2-((2-(4-(2-(3-((5-Methoxy-4-((E)-2-(trans-4-(trifluoromethyl)cyclohexyl)vinyl)picolinamido)methyl)phenyl)-N-methylacetamido)butanamido)-4-phenylthiazol-5-yl)carbamoyl)pyrrolidin-1-yl)-2-oxoethyl)amino)-1-oxopropan-2-yl)(methyl)carbamate (16 mg, 0.01 mmol) in 1,4-dioxane (1 mL) was added 4 M HCl in 1,4-dioxane (1 mL, 4 mmol) and the mixture was stirred at room temperature for 2 hours. Then the reaction mixture was concentrated. The residue was purified by prep-HPLC (Welch Xtimate C18 150*30 mm*5 um, water (0.225% FA)-ACN, 38-58%) to afford the title compound (8 mg, 50%) as a white solid. $^1H$ NMR (400 MHz, $CD_3OD$): δ 8.23 (d, J=12.8 Hz, 1H), 8.10 (d, J=8.8 Hz, 1H), 7.72 (d, J=8.0 Hz, 2H), 7.39 (t, J=7.6 Hz, 2H), 7.33-7.28 (m, 1H), 7.21-7.14 (m, 3H), 7.12-7.08 (m, 1H), 6.67-6.59 (m, 1H), 6.51-6.43 (m, 1H), 4.60-4.52 (m, 6H), 3.97-3.94 (m, 4H), 3.79-3.68 (m, 3H), 3.43-3.36 (m, 3H), 3.00, 2.89 (s, 3H total), 2.42-2.32 (m, 6H), 2.13 (m, 6H), 1.99-1.86 (m, 4H), 1.79 (m, 6H), 1.38-1.35 (m, 2H), 1.27-1.25 (m, 9H). LCMS (ESI): m/z 1070.7 $(M+H)^+$.

Example 22

His-tagged TEAD proteins are pre-incubated with TEAD project compounds for 30 minutes at room temperature. Biotinylated lipid pocket probes are then added to the TEAD/Compound mixture and incubated for 60 minutes at room temperature. The lipid pocket probe competes with the test compound for the TEAD lipid pocket until equilibrium is reached. After 60 minutes, Europium labelled anti-His (Perkin Elmer #ADO 110) and XL665 labelled streptavidin (CIS Bio 610SAXAC) are added to the TEAD/test compound/lipid pocket mixture and incubated for 30 minutes. TR-FRET values are then measured using an EnVision multi-label plate reader (Perkin Elmer Cat #2104-1A.) If the lipid pocket probe binds to TEAD as expected, a TR-FRET signal results from the proximity of Tani-His Eu and XL665. If a TEAD lipid pocket binder such as binds and displaces the lipid pocket probe, the disruption of the TEAD:probe interaction results in a decrease in TR-FRET signal. The potency of compounds as TEAD lipid pocket binders is determined by $IC_{50}$ value generated using a non-linear 4 parameter curve fit. This assay format enables more sensitive determinations of lipid pocket affinity than the aforementioned TEAD lipid pocket FP assay due to the decreased concentration of TEAD protein required for the TR-FRET assay format.

The results for compounds 1 to 21 are presented in Table 3 below.

TABLE 3

| Compound | Lipid HTRF TEAD1 $IC_{50}$[uM] | Lipid HTRF TEAD2 $IC_{50}$[uM] | Lipid HTRF TEAD3 $IC_{50}$[uM] | Lipid HTRF TEAD4 $IC_{50}$[uM] |
|---|---|---|---|---|
| 1 | 0.65 | 0.23 | 6.00 | 0.09 |
| 2 | 5.75 | 1.15 | 18.85 | 0.40 |
| 3 | 0.30 | 0.13 | 4.80 | 0.06 |
| 4 | 0.28 | 0.20 | 1.83 | 0.07 |
| 5 | 0.51 | 0.18 | 4.00 | 0.11 |
| 6 | 1.15 | 0.18 | 30.00 | 0.07 |
| 7 | 0.36 | 0.11 | 2.00 | 0.06 |

TABLE 3-continued

| Compound | Lipid HTRF TEAD1 $IC_{50}$[uM] | Lipid HTRF TEAD2 $IC_{50}$[uM] | Lipid HTRF TEAD3 $IC_{50}$[uM] | Lipid HTRF TEAD4 $IC_{50}$[uM] |
|---|---|---|---|---|
| 8 | 0.72 | 0.29 | 8.20 | 0.18 |
| 9 | 1.30 | 0.65 | 5.37 | 0.32 |
| 10 | 18.83 | 4.80 | 50.00 | 0.47 |
| 11 | 0.70 | 0.37 | 2.53 | 0.17 |
| 12 | 1.32 | 0.69 | 5.90 | 0.28 |
| 13 | 0.98 | 0.46 | 4.03 | 0.22 |
| 14 | 0.72 | 0.41 | 3.83 | 0.17 |
| 15 | 0.60 | 0.38 | 3.63 | 0.17 |
| 16 | 0.35 | 0.16 | 2.57 | 0.06 |
| 17 | 0.28 | 0.09 | 1.50 | 0.04 |
| 18 | 0.60 | 0.49 | 4.80 | 0.14 |
| 19 | 0.54 | 0.36 | 4.10 | 0.14 |
| 20 | 0.51 | 0.34 | 4.30 | 0.13 |
| 21 | 1.30 | 1.00 | 6.20 | 0.43 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It is to be understood that the invention is not limited to the particular embodiments and aspects of the disclosure described above, as variations of the particular embodiments and aspects may be made and still fall within the scope of the appended claims. All documents cited to or relied upon herein are expressly incorporated by reference.

What is claimed is:

1. A compound selected from the group consisting of:

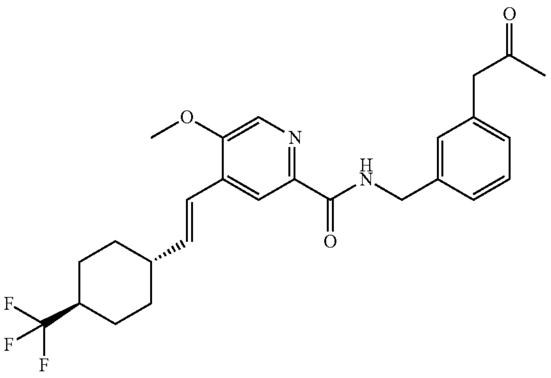

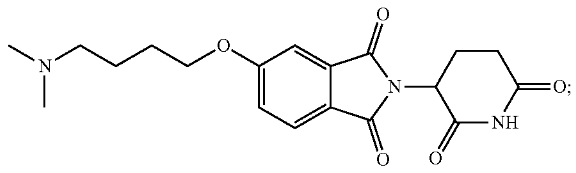

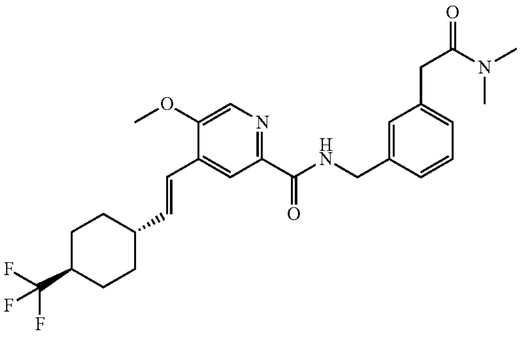

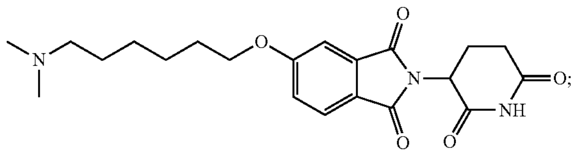

-continued

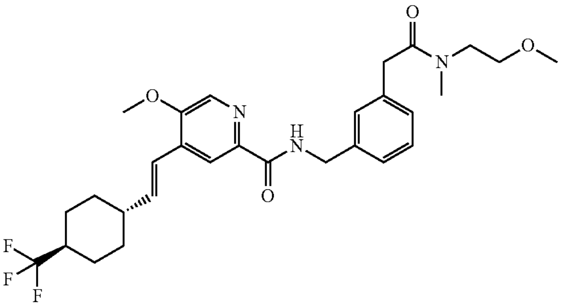

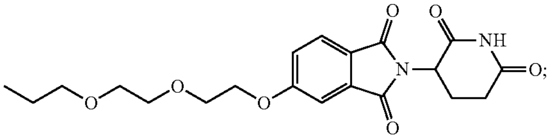

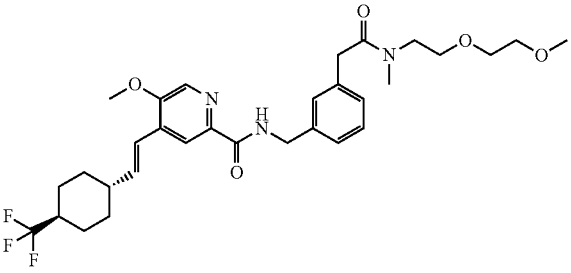

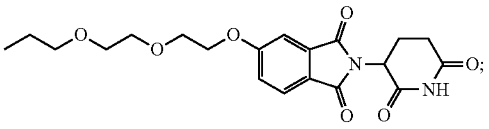

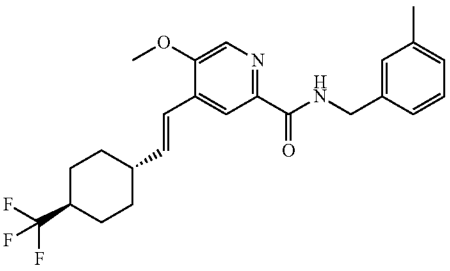

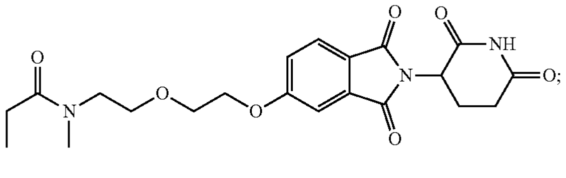

-continued
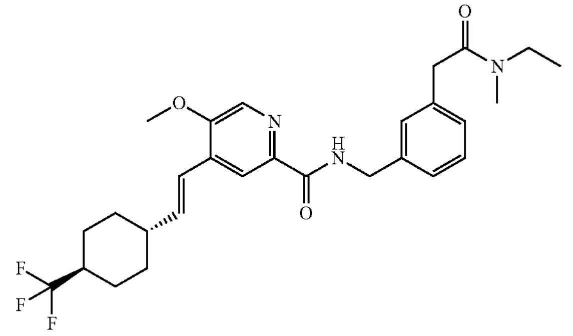
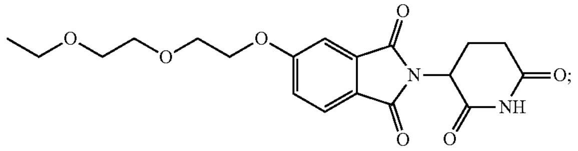
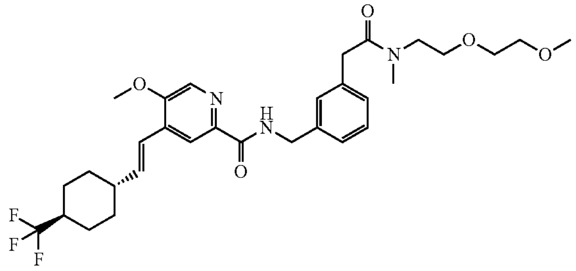
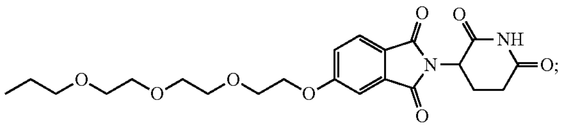
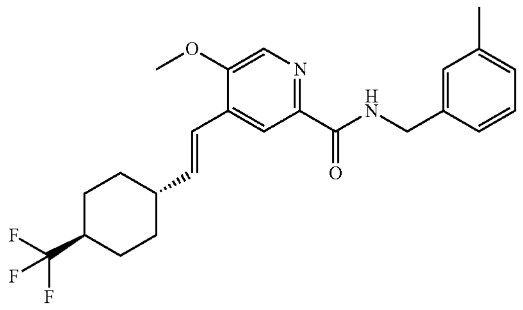
-continued
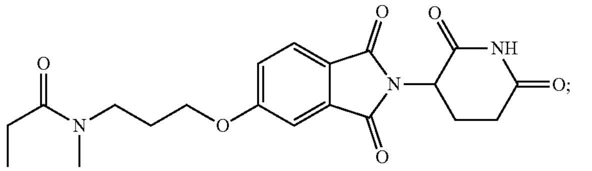
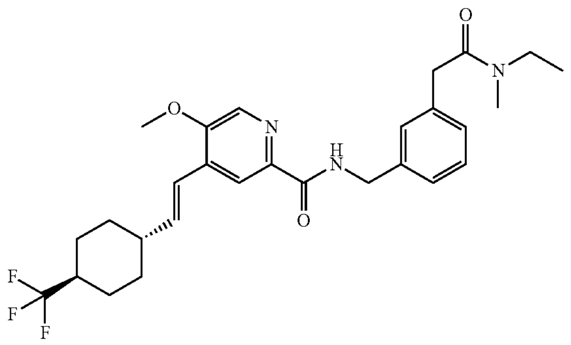
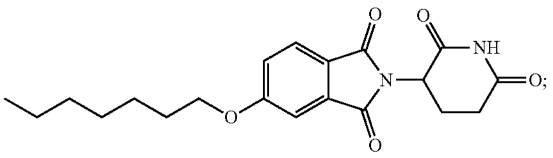
and
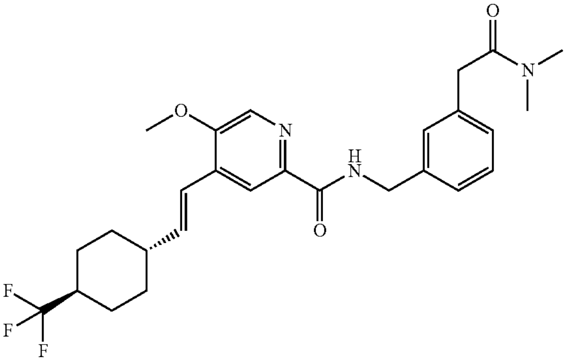
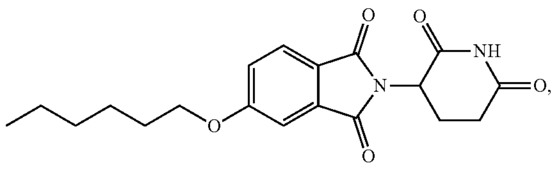
or a stereoisomer or pharmaceutically acceptable salt thereof.

2. A compound selected from the group consisting of:
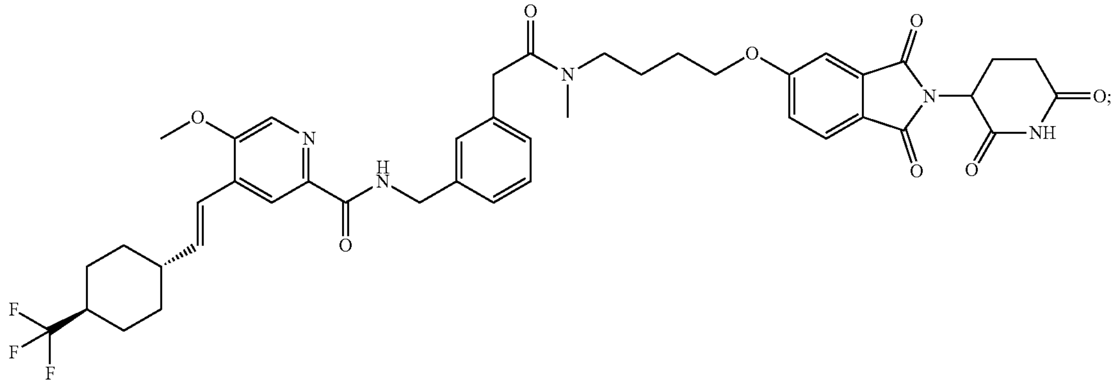
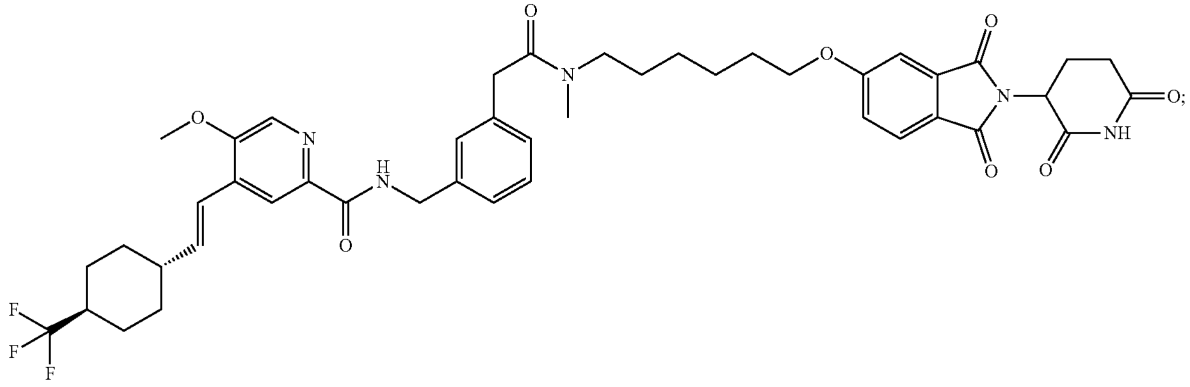
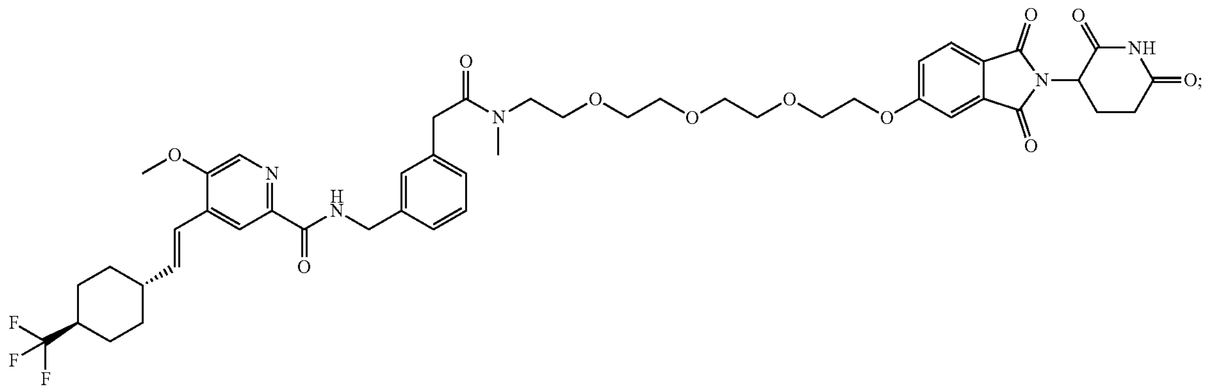
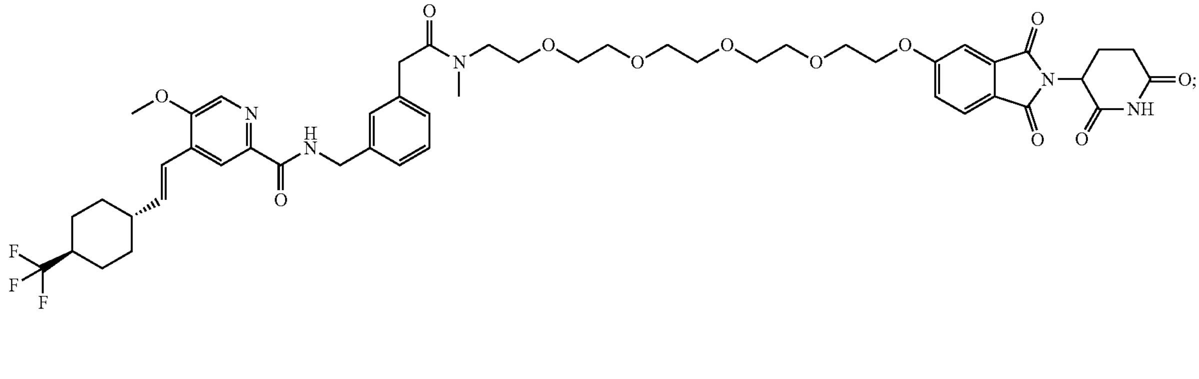

-continued
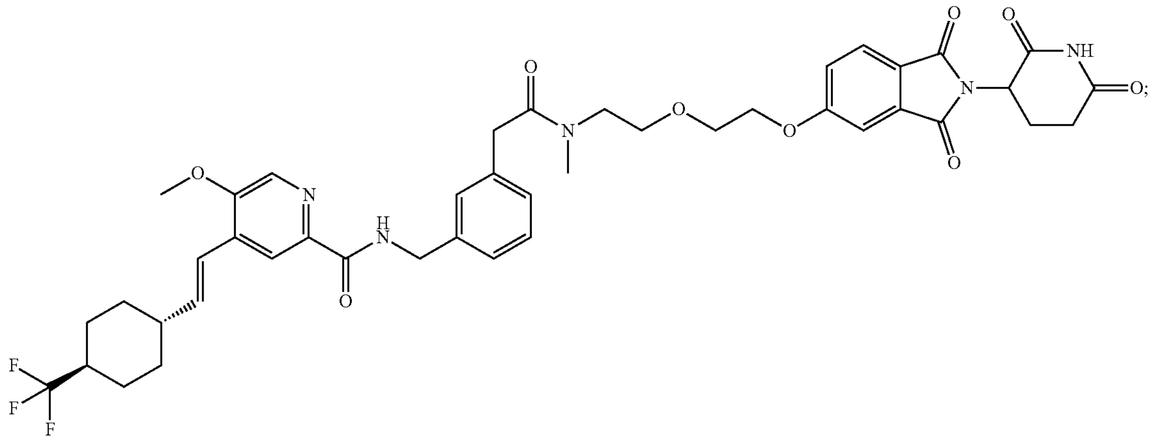
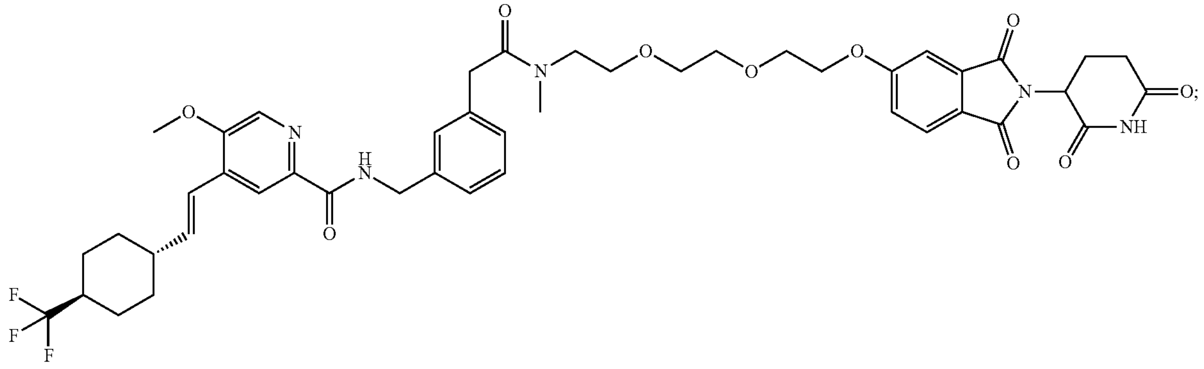
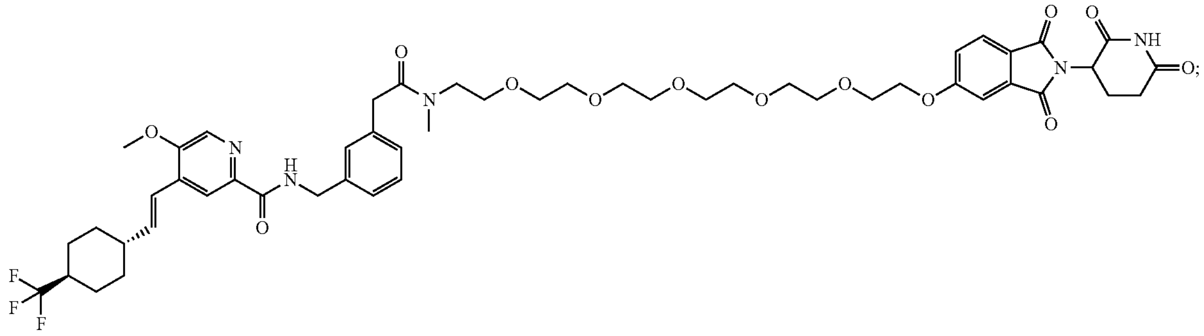
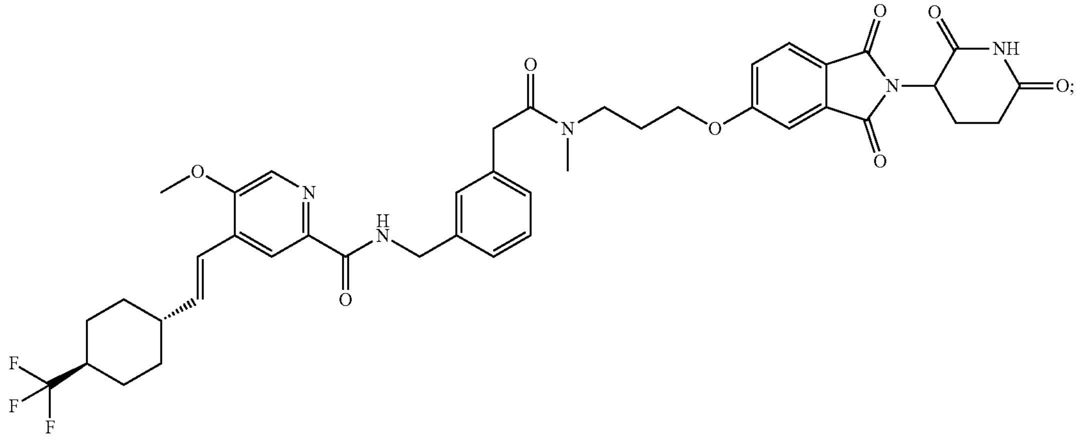

-continued
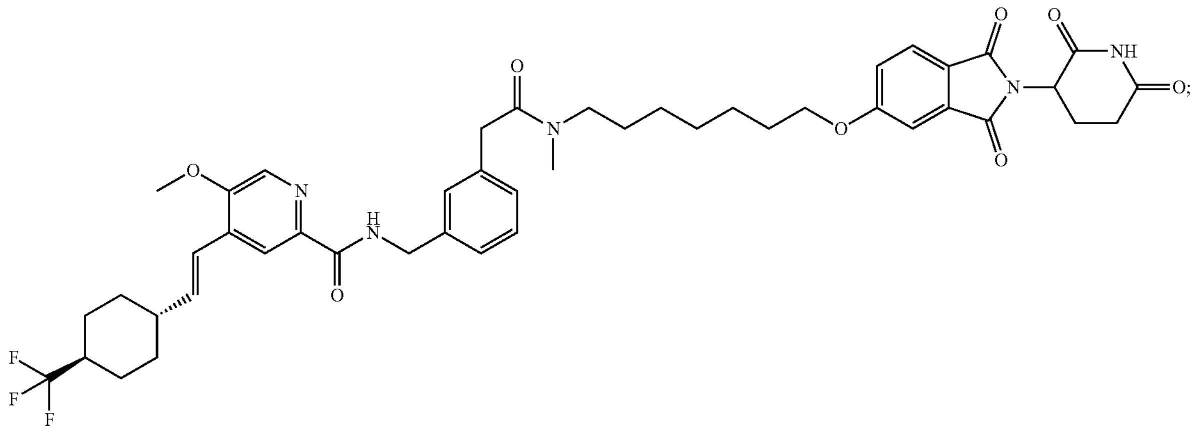
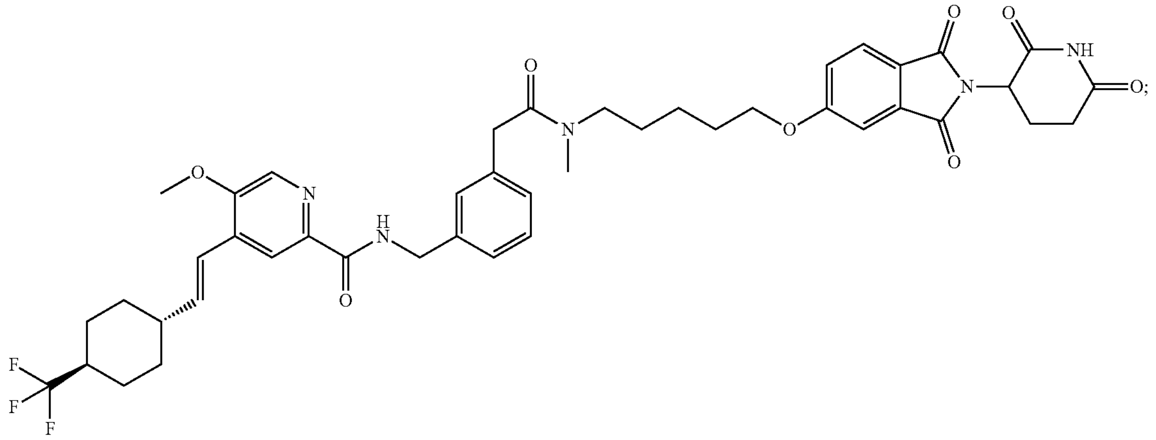
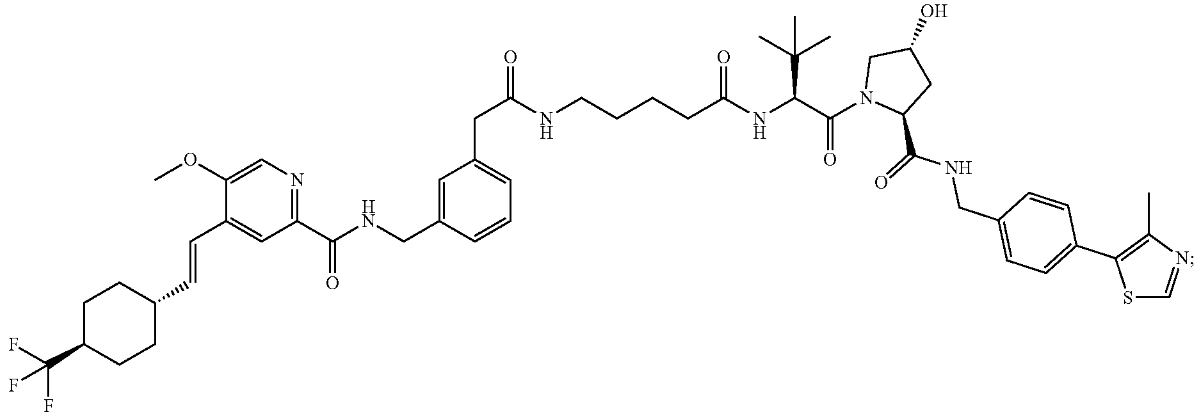
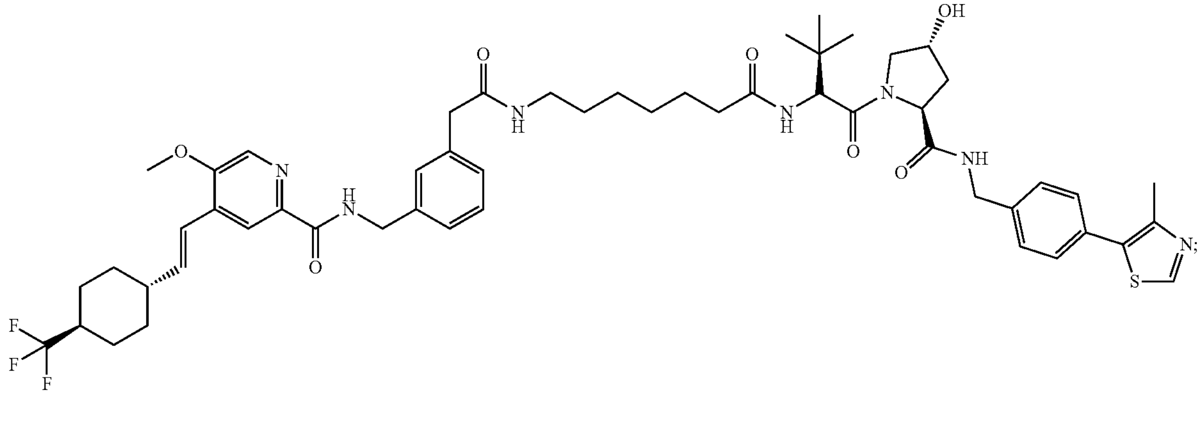

-continued
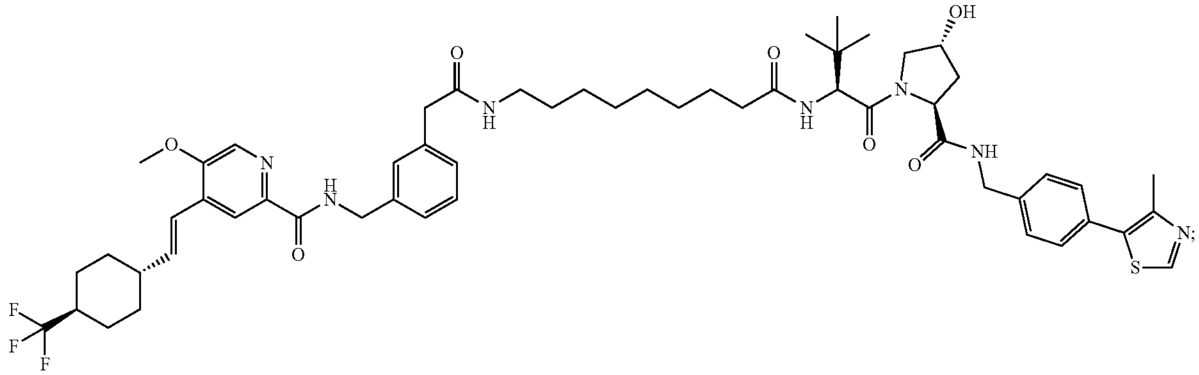
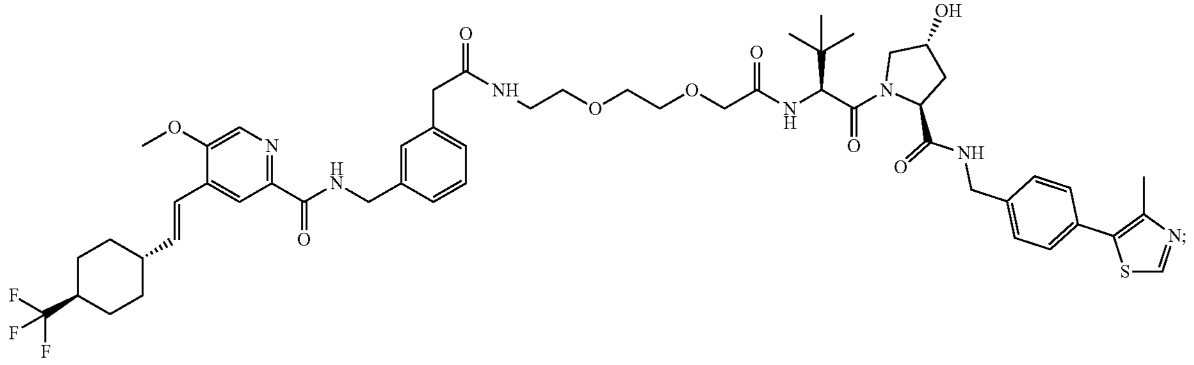
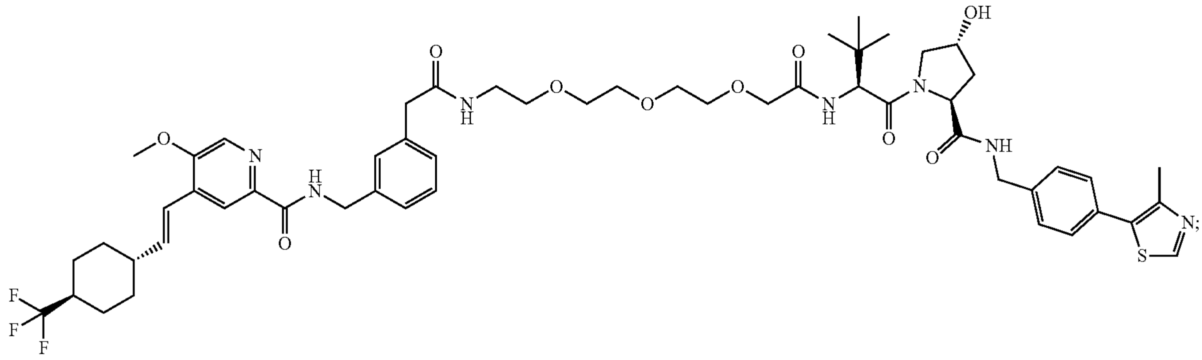
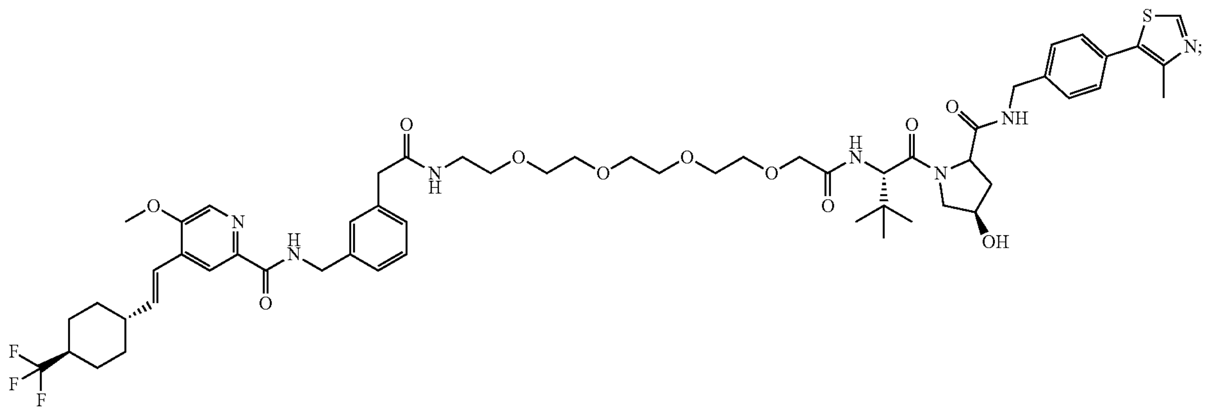

-continued
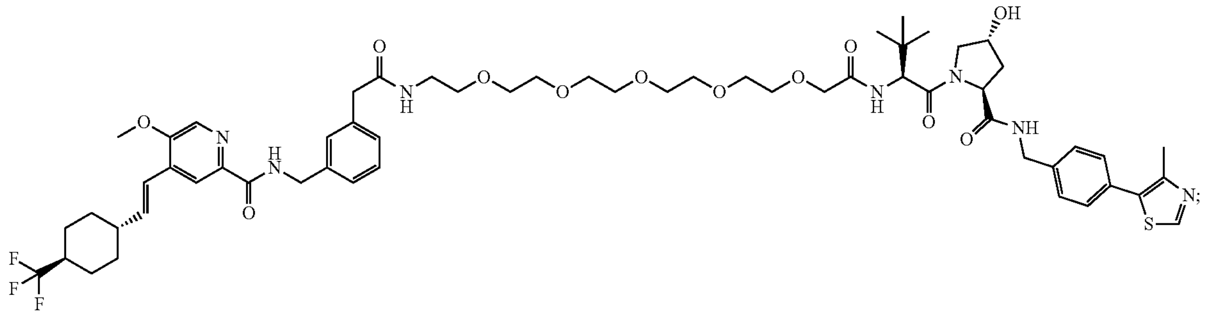
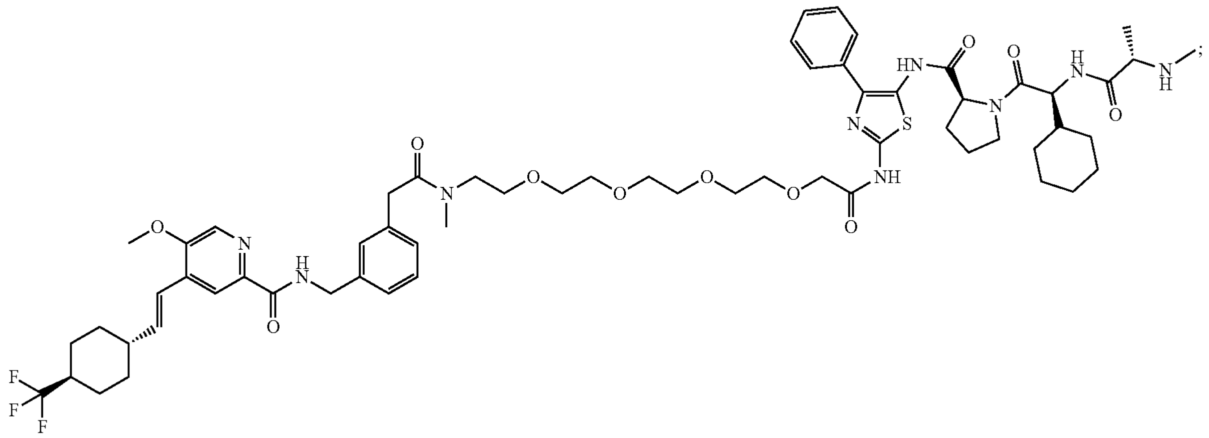
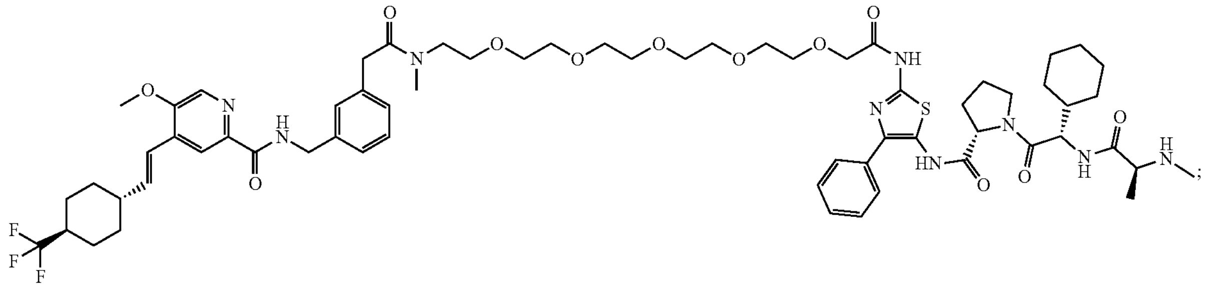
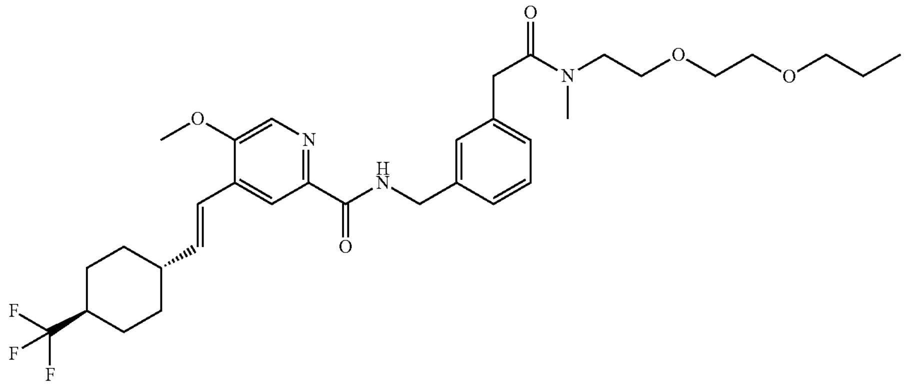

-continued

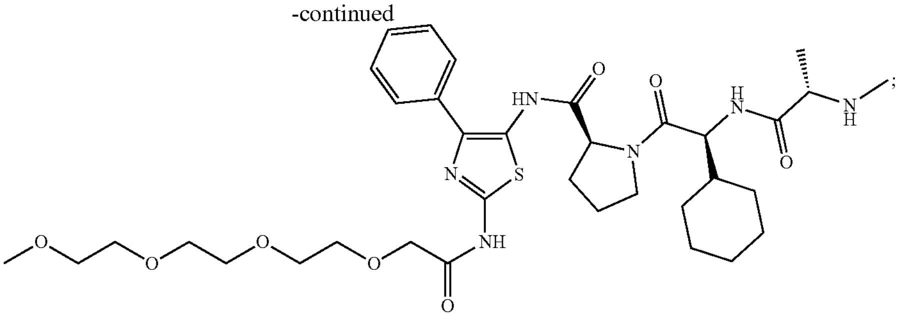

; and

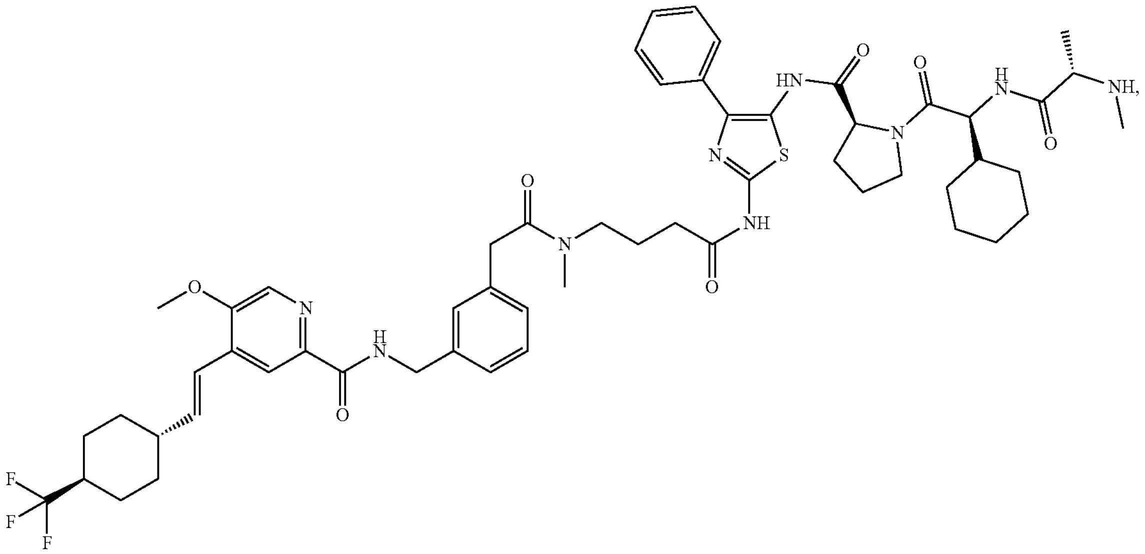 [SMILES: CN[C@@H](C)C(=O)N[C@H](C(=O)N1CCC[C@H]1C(=O)Nc1sc(NC(=O)CCCN(C)C(=O)Cc2cccc(CNC(=O)c3cc(/C=C/[C@H]4CC[C@H](C(F)(F)F)CC4)c(OC)cn3)c2)nc1-c1ccccc1)C1CCCCC1]

, or a stereoisomer or pharmaceutically acceptable salt thereof.

3. A pharmaceutical composition, comprising a compound of claim 1, or a stereoisomer or pharmaceutically acceptable salt thereof, and a pharmaceutically acceptable carrier, diluent, or excipient.

4. A method for treating cancer in a mammal, comprising administering a compound of claim 1, or a stereoisomer or pharmaceutically acceptable salt thereof, to the mammal.

5. A method for modulating TEAD activity, comprising contacting TEAD with a compound of claim 1, or a stereoisomer or pharmaceutically acceptable salt thereof.

6. A method for treating a disease or condition mediated by TEAD activity in a mammal, comprising administering a compound of claim 1, or a stereoisomer or pharmaceutically acceptable salt thereof, to the mammal.

7. The method of claim 6, wherein the disease or condition is a hyperproliferative disorder.

8. A method of degrading a TEAD protein, comprising contacting the TEAD protein with a compound of claim 1.

9. A ternary complex, comprising
a compound of claim 1;
a TEAD protein; and
a ubiquitin ligase.

10. A pharmaceutical composition, comprising a compound of claim 2, or a stereoisomer or pharmaceutically acceptable salt thereof, and a pharmaceutically acceptable carrier, diluent, or excipient.

11. A method for treating cancer in a mammal, comprising administering a compound of claim 2, or a stereoisomer or pharmaceutically acceptable salt thereof, to the mammal.

12. A method for modulating TEAD activity, comprising contacting TEAD with a compound of claim 2, or a stereoisomer or pharmaceutically acceptable salt thereof.

13. A method for treating a disease or condition mediated by TEAD activity in a mammal, comprising administering a compound of claim 2, or a stereoisomer or pharmaceutically acceptable salt thereof, to the mammal.

14. The method of claim 13, wherein the disease or condition is a hyperproliferative disorder.

15. A method of degrading a TEAD protein, comprising contacting the TEAD protein with a compound of claim 2.

* * * * *

SEQUENCE LISTING

```
Sequence total quantity: 18
SEQ ID NO: 1            moltype = AA  length = 440
FEATURE                 Location/Qualifiers
source                  1..440
                        mol_type = protein
                        organism = synthetic construct
                        note = Description of Artificial Sequence: Synthetic
                         polypeptide
SEQUENCE: 1
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                              440

SEQ ID NO: 2            moltype = AA  length = 214
FEATURE                 Location/Qualifiers
source                  1..214
                        mol_type = protein
                        organism = synthetic construct
                        note = Description of Artificial Sequence: Synthetic
                         polypeptide
SEQUENCE: 2
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 3            moltype = AA  length = 447
FEATURE                 Location/Qualifiers
source                  1..447
                        mol_type = protein
                        organism = synthetic construct
                        note = Description of Artificial Sequence: Synthetic
                         polypeptide
SEQUENCE: 3
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                      447

SEQ ID NO: 4            moltype = AA  length = 218
FEATURE                 Location/Qualifiers
source                  1..218
                        mol_type = protein
                        organism = synthetic construct
```

-continued

```
                         note = Description of Artificial Sequence: Synthetic
                          polypeptide
SEQUENCE: 4
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 5             moltype = AA  length = 10
FEATURE                  Location/Qualifiers
source                   1..10
                         mol_type = protein
                         organism = synthetic construct
                         note = Description of Artificial Sequence: Synthetic peptide
SEQUENCE: 5
GFTFSDSWIH                                                         10

SEQ ID NO: 6             moltype = AA  length = 18
FEATURE                  Location/Qualifiers
source                   1..18
                         mol_type = protein
                         organism = synthetic construct
                         note = Description of Artificial Sequence: Synthetic peptide
SEQUENCE: 6
AWISPYGGST YYADSVKG                                                18

SEQ ID NO: 7             moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 7
RHWPGGFDY                                                          9

SEQ ID NO: 8             moltype = AA  length = 11
FEATURE                  Location/Qualifiers
source                   1..11
                         mol_type = protein
                         organism = synthetic construct
                         note = Description of Artificial Sequence: Synthetic peptide
SEQUENCE: 8
RASQDVSTAV A                                                       11

SEQ ID NO: 9             moltype = AA  length = 7
FEATURE                  Location/Qualifiers
source                   1..7
                         mol_type = protein
                         organism = synthetic construct
                         note = Description of Artificial Sequence: Synthetic peptide
SEQUENCE: 9
SASFLYS                                                            7

SEQ ID NO: 10            moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 10
QQYLYHPAT                                                          9

SEQ ID NO: 11            moltype = AA  length = 118
FEATURE                  Location/Qualifiers
source                   1..118
                         mol_type = protein
                         organism = synthetic construct
                         note = Description of Artificial Sequence: Synthetic
                          polypeptide
SEQUENCE: 11
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSS    118

SEQ ID NO: 12            moltype = AA  length = 108
FEATURE                  Location/Qualifiers
source                   1..108
                         mol_type = protein
                         organism = synthetic construct
                         note = Description of Artificial Sequence: Synthetic
```

-continued

```
                          polypeptide
SEQUENCE: 12
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR               108

SEQ ID NO: 13           moltype = AA  length = 447
FEATURE                 Location/Qualifiers
source                  1..447
                        mol_type = protein
                        organism = synthetic construct
                        note = Description of Artificial Sequence: Synthetic
                         polypeptide
SEQUENCE: 13
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                    447

SEQ ID NO: 14           moltype = AA  length = 214
FEATURE                 Location/Qualifiers
source                  1..214
                        mol_type = protein
                        organism = synthetic construct
                        note = Description of Artificial Sequence: Synthetic
                         polypeptide
SEQUENCE: 14
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                            214

SEQ ID NO: 15           moltype = AA  length = 449
FEATURE                 Location/Qualifiers
source                  1..449
                        mol_type = protein
                        organism = synthetic construct
                        note = Description of Artificial Sequence: Synthetic
                         polypeptide
SEQUENCE: 15
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                  449

SEQ ID NO: 16           moltype = AA  length = 216
FEATURE                 Location/Qualifiers
source                  1..216
                        mol_type = protein
                        organism = synthetic construct
                        note = Description of Artificial Sequence: Synthetic
                         polypeptide
SEQUENCE: 16
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                          216

SEQ ID NO: 17           moltype = AA  length = 450
FEATURE                 Location/Qualifiers
source                  1..450
                        mol_type = protein
                        organism = synthetic construct
                        note = Description of Artificial Sequence: Synthetic
                         polypeptide
SEQUENCE: 17
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPSRE  360
```

-continued

```
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                   450

SEQ ID NO: 18           moltype = AA  length = 215
FEATURE                 Location/Qualifiers
source                  1..215
                        mol_type = protein
                        organism = synthetic construct
                        note = Description of Artificial Sequence: Synthetic
                         polypeptide
SEQUENCE: 18
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215
```